US007919495B2

(12) United States Patent
Ishii et al.

(10) Patent No.: US 7,919,495 B2
(45) Date of Patent: Apr. 5, 2011

(54) PYRIDYL NON-AROMATIC NITROGEN-CONTAINING HETEROCYCLIC-1-CARBOXYLATE COMPOUND

(75) Inventors: Takahiro Ishii, Tokyo (JP); Takashi Sugane, Tokyo (JP); Jun Maeda, Tokyo (JP); Fumie Narazaki, Tokyo (JP); Akio Kakefuda, Tokyo (JP); Kentaro Sato, Tokyo (JP); Tatsuhisa Takahashi, Tokyo (JP); Takatoshi Kanayama, Tokyo (JP); Chikashi Saitoh, Tokyo (JP); Jotaro Suzuki, Tokyo (JP); Chisato Kanai, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 790 days.

(21) Appl. No.: 11/816,508

(22) PCT Filed: Feb. 16, 2006

(86) PCT No.: PCT/JP2006/302698
§ 371 (c)(1),
(2), (4) Date: Aug. 16, 2007

(87) PCT Pub. No.: WO2006/088075
PCT Pub. Date: Aug. 24, 2006

(65) Prior Publication Data
US 2008/0306046 A1 Dec. 11, 2008

(30) Foreign Application Priority Data

Feb. 17, 2005 (JP) .............................. P. 2005-040197
Oct. 18, 2005 (JP) .............................. P. 2005-303065

(51) Int. Cl.
*A61K 31/496* (2006.01)
*A61K 31/4545* (2006.01)
*C07D 401/12* (2006.01)
*C07D 401/14* (2006.01)
*C07D 413/12* (2006.01)
*C07D 413/14* (2006.01)
*C07D 417/14* (2006.01)

(52) U.S. Cl. ......... 514/253.05; 514/253.06; 514/253.13; 514/316; 514/318; 544/131; 544/363; 544/364; 544/365; 544/360; 546/187; 546/194; 540/575

(58) Field of Classification Search .................. None
See application file for complete search history.

(56) References Cited

U.S. PATENT DOCUMENTS

| 5,870,472 | A | 2/1999 | Chang et al. |
| 7,585,886 | B2 * | 9/2009 | Hachiya et al. ............... 514/423 |
| 2003/0166644 | A1 | 9/2003 | Ebdrup et al. |
| 2004/0102450 | A1 | 5/2004 | Ewing et al. |
| 2004/0186148 | A1 | 9/2004 | Shankar et al. |
| 2005/0182130 | A1 | 8/2005 | Abouabdellah et al. |
| 2006/0160819 | A1 | 7/2006 | Hansen et al. |
| 2006/0160820 | A1 | 7/2006 | Hansen et al. |
| 2006/0160826 | A1 | 7/2006 | Ebdrup et al. |
| 2006/0247290 | A1 | 11/2006 | Abouabdellah et al. |
| 2006/0293310 | A1 | 12/2006 | Abouabdellah et al. |
| 2007/0021405 | A1 | 1/2007 | Abouabdellah et al. |
| 2007/0021424 | A1 | 1/2007 | Abouabdellah et al. |
| 2007/0027141 | A1 | 2/2007 | Abouabdellah et al. |
| 2007/0219187 | A1 | 9/2007 | Bessis et al. |

FOREIGN PATENT DOCUMENTS

| CA | 2184919 | 7/1996 |
| CA | 2370411 | 8/2002 |
| EP | 0 477 903 | 4/1992 |
| JP | 4-261157 A | 9/1992 |
| JP | 9-510974 A | 11/1997 |
| JP | 9-511764 A | 11/1997 |
| JP | 2001-503778 A | 5/1998 |
| JP | 2002-541109 A | 12/2002 |
| JP | 2003-192659 | 9/2003 |
| WO | WO 95/26337 | 10/1995 |
| WO | WO 96/21648 | 7/1996 |
| WO | WO 98/20893 | 5/1998 |
| WO | WO 99/37304 | 7/1999 |
| WO | WO 00/59510 | 10/2000 |
| WO | WO 01/07436 A2 | 2/2001 |
| WO | WO 02/43762 A3 | 6/2002 |
| WO | WO 03/051841 A2 | 6/2003 |
| WO | WO 03/055848 A2 | 7/2003 |
| WO | WO 03/065989 A2 | 8/2003 |
| WO | WO 2004/020430 A2 | 3/2004 |
| WO | WO 2004/033422 A2 | 4/2004 |
| WO | WO 2004/085385 A2 | 10/2004 |
| WO | WO 2004/111004 A1 | 12/2004 |
| WO | WO 2004/111007 A1 | 12/2004 |

(Continued)

OTHER PUBLICATIONS

Seierstad et al. J.Med. Chem. vol. 51, p. 7327-7343 (2008).*
James D. Leggett, et al. "*Oleamide is a selective endogenous agonist of rat and human $CB_1$ cannabinoid receptors*," British Journal of Pharmacology (2004) 141, pp. 253-262, 2004 Nature Publishing Group.
Indonesian Office Action dated Nov. 2, 2010 (2 pgs.); English translations dated Feb. 11, 2010 (2 pgs.).
Chinese Office Action, issued in CN Application No. 200680004214.X on Feb. 12, 2010 (4 pages).

(Continued)

*Primary Examiner* — Emily Bernhardt
(74) *Attorney, Agent, or Firm* — Finnegan, Henderson, Farabow, Garrett & Dunner, LLP

(57) ABSTRACT

To provide a compound usable for treatment of diseases associated with fatty acid amide hydrolase (FAAH), especially for treatment of urinary frequency and urinary incontinence, overactive bladder and/or pain.
We have found that a novel pyridyl non-aromatic nitrogen-containing heterocyclic-1-carboxylate derivative and its pharmaceutically acceptable salt has a potent FAAH-inhibitory activity. Further, the pyridyl non-aromatic nitrogen-containing heterocyclic-1-carboxylate derivative of the present invention has an excellent effect for increasing an effective bladder capacity, an excellent effect for relieving urinary frequency and an excellent anti-allodynia effect, and is therefore usable for treatment of urinary frequency and urinary incontinence, overactive bladder and/or pain.

15 Claims, No Drawings

FOREIGN PATENT DOCUMENTS

| WO | WO 2004/111032 A1 | 12/2004 |
| --- | --- | --- |
| WO | WO 2005/044797 A1 | 5/2005 |
| WO | WO 2005/070910 A2 | 8/2005 |
| WO | WO 2005/077898 A1 | 8/2005 |
| WO | WO 2005/090322 A1 | 9/2005 |
| WO | WO 2005/090347 A1 | 9/2005 |

OTHER PUBLICATIONS

Korean Office Action, issued in KN Application No. 10-2007-7020924 on Mar. 15, 2010 (5 pages).

Korean Office Action, issued in KN Application No. 10-2009-7011570 on Mar. 15, 2010 (5 pages).

Korean Office Action, issued in KN Application No. 10-2009-7011569 on Mar. 15, 2010 (5 pages).

Robert B. Angier et al., "Antiviral Agents. I. Analogs and Derivatives of 2-Diethylaminoethyl 4-Methylpiperazine-1-carboxylate", Organic Chemical Research Section, Lederle Laboratories Division, American Cyanamid Co., Pearl River, NY 10965, vol. 11, pp. 720-729. J. Med. Chem. (1968).

Franze Effenberger et al., "2(1*H*)-Pyridon als Austrittsgruppe bei Acylierungsreaktionen-Anwendungen in der Peptidchemie", Chem. Ber. 118, 468-482 (1985).

Franze Effenberger et al., "2(1*H*)-Pyridon als Austrittsgruppe bei Acylierungsreaktionen-Anwendungen in der Peptidchemie", Chem. Ber. 118, 468-482 (1985).

P.H. Reggio, "Endocannabinoid structure-activity relationships for interaction at the cannabinoid receptors", Prostaglandins, Leukotrienes and Essential Fatty Acids, vol. 66, pp. 143-160, (2002).

M. Montero et al., "Calcineurin-independent inhibition of mitochondrial $Ca^{2+}$ uptake by cyclosporin A", British Journal of Pharmacology (2004) 141, 263-268.

Benjamin F. Cravatt et al., "Molecular characterization of an enzyme that degrades neuromodulatory fatty-acid amides", Nature, vol. 384, Nov. 1996, pp. 83-87.

Christopher J. Fowler et al., "Fatty acid amide hydrolase: biochemistry, pharmacology, and therapeutic possibilities for an enzyme hydrolyzing anandamide, 2-arachidonoylglycerol, palmitoylethanolamide, and oleamide", Biochemical Pharmacology 62 (2001 pp. 517-526.

Roger G. Pertwee, "Pharmacology of Cannabinoid Receptor Ligands", Current Medicinal Chemistry, 1999, vol. 6, No. 8, pp. 635-664.

Natalia Dmitrieva et al., "Contrasting Effects of WIN 55212-2 on Motility of the Rat Bladder and Uterus", The Journal of Neuroscience, Aug. 15, 2002, 22(16): 7147-7153.

Siân I. Jaggar et al., "The anti-hyperalgesic actions of the cannabinoid anandamide and the putative CB2 receptor agonist palmitoylethanolamide in visceral and somatic inflammatory pain", Pain 76 (1998, pp. 189-199.

Satish Kathuria et al., "Modulation of anxiety through blockade of anandamide hydrolysis", Nature Medicine, vol. 9, No. 1, Jan. 2003, pp. 76-81.

Japanese Office Action, issued in JP Application No. P2007-503689 on May 24, 2010 (3 pages).

Non-Final Office Action issued in U.S. Appl. No. 12/543,690, Date Mailed: May 27, 2010.

Abstract of Zhumal Prikladnoi Khimii, 1995, pp. 675-679, vol. 68(4), Prozorovskii et al.

Non-Final Office Action issued in U.S. Appl. No. 12/543,659, Date Mailed: Jul. 9, 2010.

Second Chinese Office Action, issued in CN Application No. 200680004214.X on Sep. 20, 2010, (2 pages).

Japanese Office Action (Decision of Refusal), issued in JP Application No. P2007-503689 on Sep. 22, 2010 (2 pages).

Korean Office Action (Notice of Preliminary Rejection), issued in KR Application No. 10-2009-7011569 on Nov. 13, 2010 (3 pages).

Korean Office Action (Notice of Preliminary Rejection), issued in KR Application No. 10-2009-7011570 on Nov. 13, 2010 (3 pages).

Korean Office Action (Notice of Preliminary Rejection), issued in KR Application No. 10-2007-7020924 on Nov. 13, 2010 (3 pages).

Canadian Office Action, issued in CA Application No. 2,598,294 on Dec. 13, 2010, (4 pages).

\* cited by examiner

PYRIDYL NON-AROMATIC NITROGEN-CONTAINING HETEROCYCLIC-1-CARBOXYLATE COMPOUND

This application is a 371 of PCT/JP2006/302698, filed Feb. 16, 2006.

TECHNICAL FIELD

The present invention relates to a pyridyl non-aromatic nitrogen-containing heterocyclic-1-carboxylate derivative or its pharmaceutically acceptable salt, serving as a medicine, especially as a remedy for urinary frequency and urinary incontinence, a remedy for overactive bladder and/or a remedy for pain having a fatty acid amide hydrolase (hereinafter referred to as FAAH)-inhibitory activity. The present invention also relates to a screening method for an FAAH activity inhibitor serving as a remedy for urinary frequency and urinary incontinence, a remedy for overactive bladder and/or a remedy for pain; and to a pharmaceutical composition for treatment of urinary frequency and urinary incontinence, for treatment of overactive bladder and/or for treatment of pain that contains the substance obtained according to the screening method of the present invention or contains a substance which inhibits the activity of fatty acid amide hydrolase.

BACKGROUND ART

Fatty acid amide hydrolase (FAAH) is known to hydrolyze endocannabinoid to inactivate it (see Non-Patent References 1 to 4). Endocannabinoid is a generic term for a biological substance that acts on a cannabinoid receptor to exhibit its physiological activity. Typical endocannabinoids are anandamide, palmitoyl ethanolamide, oleamide, 2-arachidonoyl glycerol; and they are known to be hydrolyzed by FAAH to lose their activity. Δ9-tetrahydrocannabinol that is considered as the active ingredient of *Cannabis* (marijuana) is known to activate a cannabinoid receptor (see Non-Patent Reference 5).

In mammals, two types of cannabinoid receptor CB1 and CB2 have heretofore been known. CB1 is expressed in central and peripheral nervous systems, and when activated, it exhibits its mental action and analgesic action. CB2 is expressed in immune systems, and when activated, it exhibits its antiinflammatory action and analgesic (and antiinflammatory) action.

On the other hand, in a cystitic rat model, a cannabinoid receptor agonist increases the bladder capacity and the urination threshold (Non-Patent Reference 6 and Non-Patent Reference 7); and the side effects of hallucination, delusion, tachycardia, orthostatic hypotension to be observed in administration of a cannabinoid receptor agonist to animals are not observed when an FAAH inhibitor is administered thereto (Non-Patent Reference 8). From these, the FAAH inhibitor is expected as a remedy for urinary frequency and urinary incontinence, a remedy for overactive bladder and/or a remedy for pain.

As compounds having an FAAH-inhibitory activity, known are compounds capable of serving as analgesic, antianxiety, antiepileptic, antidepressant, antiemetic, cardiovascular agent or antiglaucomatous agent [C1-4 alkyl or polycyclic aromatic ester derivatives of aromatic ring or phenyl-substituted aliphatic hydrocarbon-carbamic acids (Patent Reference 1) and phenyl cyclohexylcarbamate (Patent Reference 2)]. Dioxane-2-alkylcarbamate derivatives, which are compounds having an FAAH-inhibitory activity, are described as a remedy for urinary incontinence, one embodiment of a large number of disorders listed therein (Patent Reference 3). However, Patent Reference 3 does not disclose experimental results to support the remedial effect for treatment of urinary frequency and urinary incontinence and/or for treatment of overactive bladder, not disclosing any suggestion for it. 4-Aminopyridyl piperidine-1-carboxylate, a type of pyridyl non-aromatic nitrogen-containing heterocyclic-1-carboxylates, is described as an acetylcholine esterase inhibitor (Non-Patent Reference 9); however, the reference describes nothing about the compound to be a remedy for urinary frequency and urinary incontinence and/or a remedy for overactive bladder.

Patent Reference 1: WO2003/065989
Patent Reference 2: WO2004/033422
Patent Reference 3: JP-A 2003-192659
Non-Patent Reference 1: Prostaglandins Leukotrienes and Essential Fatty Acids, (England), 2002, Vol. 66, pp. 143-160
Non-Patent Reference 2: British Journal of Pharmacology (England), 2004, Vol. 141, pp. 253-262
Non-Patent Reference 3: Nature (England), 1996, Vol. 384, pp. 83-87
Non-Patent Reference 4: Biochemical Pharmacology, (USA), 2001, Vol. 62, pp. 517-526
Non-Patent Reference 5: Current Medicinal Chemistry (USA), 1999, Vol. 6, pp. 635-664
Non-Patent Reference 6: The Journal of Neuroscience, 2002, Vol. 22, pp. 7147-7153
Non-Patent Reference 7: Pain, 1998, Vol. 76, pp. 189-199
Non-Patent Reference 8: Nature Medicine, (England), 2003, Vol. 9, pp. 76-81
Non-Patent Reference 9: Journal of Pharmaceutical Science, 1992, Vol. 81, pp. 380-385

DISCLOSURE OF THE INVENTION

Problems to be Solved by the Invention

An object of the present invention is to provide a remedy for urinary frequency and urinary incontinence, a remedy for overactive bladder and/or a remedy for pain, which are free from or are relieved from cannabinoid-like side effects and a problem of addiction. Other objects are to provide a method for screening for an FAAH activity-inhibiting substance, or that is, a remedy for urinary frequency and urinary incontinence, a remedy for overactive bladder and/or a remedy for pain; and to provide a pharmaceutical composition for treatment of urinary frequency and urinary incontinence, for treatment of overactive bladder and/or for treatment of pain, which contains the substance obtained according to the screening method of the present invention or a substance capable of inhibiting the activity of a fatty acid amide hydrolase.

Means for Solving the Problems

The present inventors have assiduously studied for producing a compound having an FAAH-inhibitory activity, and as a result, have found out novel pyridyl nitrogen-containing heterocyclic-1-carboxylate derivatives.

In addition, the present inventors have found for the first time that, when a compound having an FAAH-inhibitory activity is administered to a rat suffering from urinary frequency induced by cyclophosphamide, then the effective bladder capacity of the rat increases, and have further found that the compound having an FAAH-inhibitory activity has an excellent therapeutical effect in a pain model rat, therefore providing a screening method for a remedy for urinary frequency and urinary incontinence, a remedy for overactive bladder and/or a remedy for pain by selecting an FAAH inhibitor, and have thus completed the present invention.

Specifically, the present invention relates to the following:

[1] A pyridyl non-aromatic nitrogen-containing heterocyclic-1-carboxylate derivative of a general formula (I), and its pharmaceutically acceptable salt:

[Chemical Formula 1]

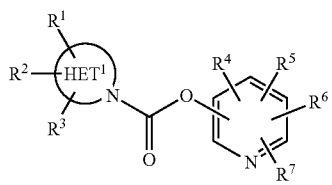

(I)

[the symbols in formula (I) have the following meanings:
$HET^1$ represents a 5- to 7-membered non-aromatic nitrogen-containing hetero ring,
$R^1$, $R^2$ and $R^3$ are the same or different, each representing
  (1) H,
  (2) OH,
  (3) optionally-esterified carboxyl,
  (4) cyano,
  (5) lower alkyl-CO—,
  (6) oxo (=O),
  (7) a formula $[R^{101}—(O)m1]m2-[ALK^1$ optionally substituted with OH]—(O)n1-,
    (m1 and n1 are the same or different, each indicating 0 or 1, m2 is from 1 to 5,
    $ALK^1$ represents lower alkylene, lower alkenylene or lower alkynylene,
    $R^{101}$ represents
      (i) H,
      (ii) $Ar^{1a}$ optionally substituted with at least one substituent selected from the group consisting of:
        (a) $H_2N$—,
        (b) halo,
        (c) cyano,
        (d) optionally-esterified carboxyl,
        (e) a group $R^{1011a}R^{1012a}N$—CO—,
        (f) $HET^2$,
        (g) $Ar^{1a}$ optionally substituted with halo, cyano, OH, lower alkyl-O— or lower alkyl,
          $Ar^{1a}$ represents aryl,
        (h) lower alkyl,
        (j) OH,
        (k) lower alkyl-O— optionally substituted with $Ar^{1a}$ or halo-$Ar^{1a}$,
        (l) $HET^2$-CO— optionally substituted with halo, $Ar^{1a}$ or $HETAr^{1a}$,
          $HET^2$ represents nitrogen-containing hetero ring,
          $HETAr^{1a}$ represents nitrogen-containing heteroaryl,
        (s) $HET^2$-$CONR^{1011a}$—,
        (t) $H_2NCONH$—, and
        (u) optionally-esterified carboxyl-$ALK^{2a}$,
          $ALK^{2a}$ represents lower alkyl or lower alkenyl,
      (iii) $ALK^{2a}$ optionally substituted with a group $R^{1011a}R^{1012a}N$ or $Ar^{1a}$,
        $R^{1011a}$ and $R^{1012a}$ are the same or different, each representing
          (a) H,
          (b) cALK,
            cALK represents a cycloalkyl,
          (c) $ALK^{2a}$ optionally substituted with halo, cALK, OH, lower alkyl-O— or $Ar^{1a}$, or
          (d) $Ar^{1a}$—$SO_2$— optionally substituted with halo,
      (iv) $HET^2$ optionally substituted with at least one substituent selected from the group consisting of
        (a) $ALK^{2a}$ optionally substituted with $Ar^{1a}$ or halo-$Ar^{1a}$,
        (b) $Ar^{1a}$,
        (c) $HETAr^{1a}$ optionally substituted with lower alkyl,
        (d) $Ar^{1a}$—CO— or halo-$Ar^{1a}$—CO—,
      (v) cALK optionally substituted with $ALK^{2a}$,
      or
      (vi) optionally-esterified carboxyl,
    (in this, when m2 is from 2 to 5, then $[R^{101}—(O)m1]$'s may be the same or different),
  (8) a group $R^{102}$-$ALK^1$-$N(R^{103})$—CO—,
    ($R^{102}$ represents
      (i) H,
      (ii) cALK,
      (iii) $HETAr^{1a}$, or
      (iv) $Ar^{1a}$ optionally substituted with at least one substituent selected from the group consisting of
        (a) HO,
        (b) $ALK^{2a}$—O—
        (c) cALK-$ALK^1$—O—,
        (d) cALK—$Ar^{1a}$-$ALK^1$—O—, and
        (e) $Ar^{1a}$-$ALK^1$—O—,
    $R^{103}$ represents
      (i) H,
      (ii) cALK,
      (iii) $ALK^{2a}$ optionally substituted with at least one substituent selected from the group consisting of
        (a) $HET^2$,
        (b) $Ar^{1a}$, and
        (c) halo-$Ar^{1a}$,
      (iv) $HETAr^{1a}$, or
      (v) $Ar^{1a}$—[CO]m1 optionally substituted with at least one substituent selected from the group consisting of
        (a) cALK,
        (b) $H_2N$,
        (c) a group $R^{1011a}R^{1012a}N$—CO—, or
        (d) $ALK^{2a}$),
  (9) a group $R^{104a}R^{105a}N$—[CO]m1$ALK^1$—,
    ($R^{104a}$ and $R^{105a}$ are the same or different, each representing a group $R^{103}$),
  (10) a group $R^{106}$-$ALK^3$-$L^1$-,
    ($R^{106}$ represents
      (i) a group $R^{101}$—(O)m1-,
      (ii) a group $R^{104a}R^{105a}N$—
      (iii) a group $ALK^{2a}$—CONH—, or
      (iv) a group $Ar^{1a}$—CONH—,
    $ALK^3$ represents lower alkylene, lower alkenylene or cycloalkylene,
    $L^1$- represents —C(=O)— or —$SO_2$—),
  (11) $ALK^{2a}$—CONH— optionally substituted with $Ar^{1a}$,
  (12) $Ar^{1a}$ substituted with halo,

(13) a group [$R^{107}$—(O)m1]m2-$Ar^2$—(O)n1-,
($Ar^2$ represents arylene,
$R^{107}$ represents
  (i) H,
  (ii) halo,
  (iii) $ALK^{2a}$ optionally substituted with at least one substituent selected from the group consisting of
    (a) HO,
    (b) cALK,
    (c) $HET^2$,
    (d) $Ar^{1a}$ optionally substituted with halo, lower alkyl, lower alkyl-O—, a group $R^{1011a}R^{1012a}$N—[CO]p-, cyano or optionally-esterified carboxyl,
    (e) optionally-esterified carboxyl,
    (f) $HET^2$-[CO]p- optionally substituted with a group $R^{1011a}R^{1012a}$N—[CO]p-, and
    (g) a group $R^{1011a}R^{1012a}$N—[CO]p-,
    p indicates 0 or 1,
  (iv) a group $R^{1011a}R^{1012a}$N—[CO]p-, or
  (v) a group $R^{1011a}R^{1012a}$N—[CO]p-$Ar^{1a}$,
  in this, when m2 is from 2 to 5, then [$R^{107}$—(O)m1]'s may be the same or different, and further the group [$R^{107}$—(O)m1]m2 may be methylenedioxy to form a ring),
(14) a group [$R^{107}$—(O)m1]m2-$Ar^2$—N($R^{103}$)—CO—,
(in this, when m2 is from 2 to 5, then [$R^{107}$—(O)m1]'s may be the same or different),
(15) a group [$R^{1011a}R^{1012a}$N—[CO]m1]m2-$Ar^2$—(O)n1-,
(in this, when m2 is from 2 to 5, then [$R^{1011a}R^{1012a}$N—[CO]m1]'s may be the same or different),
(16) a group [$R^{108}$]m2-$Ar^2$-$L^2$-,
[$R^{108}$ represents
  (i) H,
  (ii) halo,
  (iii) HO,
  (iv) cALK-O—,
  (v) a group $R^{109}$-$ALK^1$—(O)m1-,
    ($R^{109}$ represents
      (a) H,
      (b) cALK,
      (c) $Ar^{1a}$ optionally substituted with at least one substituent selected from the group consisting of
        (1') halo,
        (2') cyano,
        (3') $NO_2$,
        (4') $ALK^{2a}$ optionally substituted with halo,
        (5') HO,
        (6') $ALK^{2a}$—O— optionally substituted with halo,
        (7') optionally-esterified carboxyl, or
        (8') a group $R^{104a}R^{105a}$N—,
      (d) $HETAr^{1a}$, or
      (e) a group $R^{104a}R^{105a}$N—[CO]m1-),
  (vi) a group $R^{1013}R^{1014}$N—,
    $R^{1013}$ and $R^{1014}$ are the same or different, each representing
      (i) H,
      (ii) $ALK^{2a}$,
      (iii) cALK-$ALK^1$—, or
      (iv) $Ar^{1a}$-$ALK^1$— optionally substituted with at least one substituent selected from the group consisting of
        (1') halo,
        (2') cyano,
        (3') $ALK^{2a}$ optionally substituted with halo,
        (4') $ALK^{2a}$—O— optionally substituted with halo,
  (vii) $HET^2$-(O)m1- optionally substituted with lower alkyl,
$L^2$ represents —CO— or —S(O)$_q$—,
q indicates 0, 1 or 2,
in this, when m2 is from 2 to 5, then [$R^{108}$]'s may be the same or different],
(17) a group [$R^{101}$]m2-$Ar^2$—CONH—,
(in this, when m2 is from 2 to 5, then [$R^{101}$]'s may be the same or different),
(18) a group [$R^{111}$]m2-HETAr$^2$—(O)m1-,
($R^{111}$ represents
  (i) H,
  (ii) halo,
  (iii) oxo (=O), or
  (iv) a group $R^{103a}$—(O)n1-,
    $R^{103a}$ represents
      (i) H,
      (ii) cALK,
      (iii) $ALK^{2a}$ optionally substituted with at least one substituent selected from the group consisting of
        (a) $HET^2$,
        (b) $Ar^{1a}$,
        (c) cALK and
        (d) halo-$Ar^{1a}$,
      (iv) $HETAr^{1a}$, or
      (v) $Ar^{1a}$ optionally substituted with at least one substituent selected from the group consisting of
        (a) cALK, (b) $H_2$N, and (c) a group $R^{1011a}R^{1012a}$N—CO—,
    HETAr$^2$ represents nitrogen-containing heteroarylene,
    in this, when m2 is from 2 to 5, then [$R^{111}$]'s may be the same or different),
(19) a formula [$R^{112}$]m2-HETAr$^2$—N($R^{103}$)—CO—,
($R^{112}$ represents
  (i) H,
  (ii) cALK,
  (iii) $ALK^{2a}$, or
  (iv) $Ar^{1a}$ optionally substituted with at least one substituent selected from the group consisting of
    (a) halo,
    (b) HO,
    (c) $ALK^{2a}$—O—, and
    (d) $Ar^{1a}$-$ALK^1$—O—,
  in this, when m2 is from 2 to 5, then [$R^{112}$]'s may be the same or different,
(20) a formula [$R^{108}$]m2-HETAr$^2$-$L^2$-,
(in this, when m2 is from 2 to 5, then [$R^{108}$]'s may be the same or different), provided that, when any one group of $R^1$, $R^2$ and $R^3$ is a group [$R^{111}$]m2-HETAr$^2$—(O)m1- and when m1 is 0, then the remaining groups of $R^1$, $R^2$ and $R^3$ are H;
$R^4$, $R^5$, $R^6$ and $R^7$ are the same or different, each representing
(1) H,
(2) halo,
(3) optionally-esterified carboxyl,
(4) HO,
(5) a group $R^{113}$-$ALK^4$—(O)m3-,
($ALK^4$ represents lower alkylene, lower alkenylene, or lower alkynylene, m3 indicates 0 or 1,
$R^{113}$ represents
  (i) H,
  (ii) HO,
  (iii) lower alkyl-O— optionally substituted with optionally-esterified carboxyl,
  (iv) optionally-esterified carboxyl,
  (v) lower alkyl-CO—O—, or (vi) a group $R^{104b}R^{105b}N-[CO]m3-(R^{104b}$ and $R^{105b}$ are the same or different, each representing a group $R^{103}$), (6) $R^{114}R^{115}N(R^{114}$ and $R^{115}$ are the same or different, each representing
  (i) H, or
  (ii) $ALK^{2b}$ optionally substituted with a group $R^{104b}R^{105b}N$,
  $ALK^{2b}$ represents lower alkyl or lower alkenyl), (7) a group $R^{116}-(ALK^4)n2-N(R^{117})-CO-$,
(n2 indicates 0 or 1,
$R^{116}$ represents
  (i) H,
  (ii) HO,
  (iii) lower alkyl-O—,
  (iv) optionally-esterified carboxyl,
  (v) a group $R^{104b}R^{105b}N-[CO]m3-$,
  (vi) $Ar^{1b}$ optionally substituted with (a) OH or (b) $ALK^{2b}-O-$,
  $Ar^{1b}$ represents aryl,
  (vii) $HET^3$ optionally substituted with a group $R^{104b}R^{105b}N-[CO]m3-$ or optionally-esterified carboxyl,
  $HET^3$ represents nitrogen-containing hetero ring,
  (viii) $Ar^{1b}$ optionally substituted with a group $R^{104b}R^{105b}N-[CO]m3-$, or
  (ix) $SO_3H$),
$R^{117}$ represents (i) H or (ii) $ALK^{2b}$ optionally substituted with $Ar^{1b}$, (8) $Ar^{1b}$ optionally substituted with at least one substituent selected from the group consisting of optionally-esterified carboxyl and a group $R^{1011b}R^{1012b}N-[(CO)]m3-$,
$R^{1011b}$ and $R^{1012b}$ are the same or different, each representing
  (i) H,
  (ii) cALK,
  (iii) $ALK^{2b}$ optionally substituted with halo, cALK, OH, lower alkyl-O— or $Ar^{1b}$, or
  (iv) $Ar^{1b}-SO_2-$ optionally substituted with halo, (9) $HET^3$ optionally substituted with optionally-esterified carboxyl,

(10) $HET^3-CO-$ optionally substituted with at least one substituent selected from the group consisting of $ALK^{2b}$ and a group $R^{104b}R^{105b}N-[CO]m3-$, or

(11) cyano,
provided that 4-aminopyridin-3-yl piperidine-1-carboxylate is excluded—the same shall be applied hereinunder].

[2] The compound of [1], represented by a general formula (II):

[Chemical Formula 2]

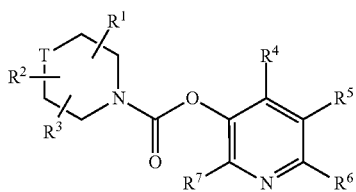

(II)

[in formula (II), $R^1$ to $R^7$ have the same meanings as in [1],
T represents $CH_2$, NH, $NHCH_2$ or O,
and this includes a case where the hydrogen in T is substituted with $R^1$ to $R^3$—the same shall be applied hereinunder].

[3] The compound of [2], wherein $R^1$ to $R^3$ are the same or different, each representing a group $[R^{101}-(O)m1]m2-[ALK^1$ optionally substituted with OH$]-(O)n1-$, a group $R^{102}-ALK^1-N(R^{103})-CO-$, a group $R^{106}-ALK^3-L^1-$, a group $[R^{107}-(O)m1]m2-Ar^2-(O)n1-$, a group $[R^{107}-(O)m1]m2-Ar^2-N(R^{103})-CO-$, or a group $[R^{108}]m2-Ar^2-L^2-$.

[4] A pyridyl non-aromatic nitrogen-containing heterocyclic-1-carboxylate derivative of a general formula (III) and its pharmaceutically acceptable salt:

[Chemical Formula 3]

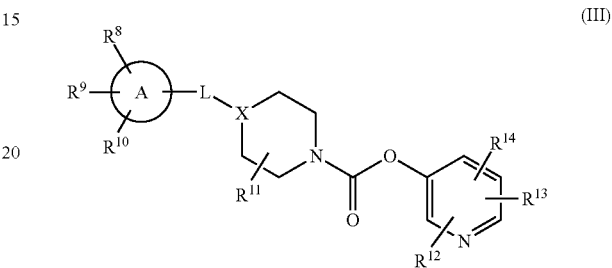

(III)

[the symbols in formula (III) have the following meanings:
ring A represents benzene ring, cyclopentane ring, cyclohexane ring, cycloheptane ring, or 5- to 7-membered nitrogen-containing hetero ring;
L represents single bond, lower alkylene, lower alkenylene, $-N(R^{15})-C(=O)-$, $-C(=O)-N(R^{15})-$, -(lower alkenylene)-C(=O)—, —O—, or —C(=O)—,
$R^{15}$ represents H, or lower alkyl,
X represents CH, or N,
$R^8$ to $R^{10}$ are the same or different, each representing
  a group selected from the following group G,
  aryl optionally substituted with the same or different groups selected from the following group G,
  nitrogen-containing heteroaryl optionally substituted with the same or different groups selected from the following group G,
  $R^{16}$-(lower alkylene)-O—,
  $R^{16}$-(lower alkylene)-N($R^{15}$)—, or
  $R^{17}R^{18}N-C(=O)-$,
$R^{16}$ represents
  aryl optionally substituted with the same or different groups selected from the following group G,
  nitrogen-containing heteroaryl optionally substituted with the same or different groups selected from the following group G, or
  3- to 8-membered cycloalkyl,
$R^{17}$ and $R^{18}-$ are the same or different, each representing H, lower alkyl, or 3- to 8-membered cycloalkyl,
(further, $R^{17}$ and $R^{18}$ may form, together with the N atom bonding thereto, 3- to 8-membered nitrogen-containing hetero ring),
the group G includes H, halo, —CN, $-CF_3$, lower alkyl, or —O-lower alkyl,
$R^{11}$ represents H, lower alkyl, or oxo (=O),
$R^{12}$ to $R^{14}$ are the same or different, each representing H, lower alkyl, $-C(=O)-O$-(lower alkyl), $-CO_2H$, or $-CONH_2$].

[5] The compound of [4], wherein the ring A is benzene ring, cyclohexane ring, piperidine ring, or piperazine ring.

[6] The compound of [5], wherein $R^9$, $R^{10}$, $R^{11}$, $R^{12}$ and $R^{13}$ are H.

[7] A pyridyl non-aromatic nitrogen-containing heterocyclic-1-carboxylate of a general formula (IV) and its pharmaceutically acceptable salt:

[Chemical Formula 4]

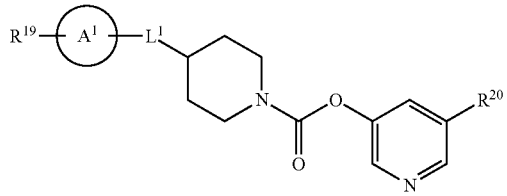

(IV)

[the symbols in formula (IV) have the following meanings:
ring $A^1$ represents benzene ring, piperidine ring or piperazine ring;
$L^1$ represents lower alkylene, lower alkenylene, —N($R^{15}$)—C(=O)—, or —O—;
$R^{15}$ represents H, or lower alkyl,
$R^{19}$ represents
  a group selected from the following group G,
  nitrogen-containing heteroaryl optionally substituted with the same or different groups selected from the following group G,
  $R^{16}$-(lower alkylene)-O—, or $R^{17}R^{18}$N—C(=O)—,
$R^{16}$ represents
  aryl optionally substituted with the same or different groups selected from the following group G,
  nitrogen-containing heteroaryl optionally substituted with the same or different groups selected from the following group G, or
  3- to 8-membered cycloalkyl,
$R^{17}$ and $R^{18}$ are the same or different, each representing H, or lower alkyl,
(further, $R^{17}$ and $R^{18}$ may form, together with the N atom bonding thereto, 5- or 6-membered nitrogen-containing hetero ring),
the group G includes H, halo, —CN, —$CF_3$, lower alkyl, or —O-lower alkyl,
$R^{20}$ represents H, —C(=O)—O-(lower alkyl), —$CO_2$H, or —$CONH_2$].

[8] A pyridyl non-aromatic nitrogen-containing heterocyclic-1-carboxylate of a general formula (V) and its pharmaceutically acceptable salt:

[Chemical Formula 5]

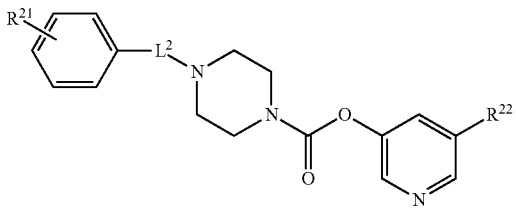

(V)

[the symbols in formula (V) have the following meanings:
$L^2$ represents lower alkylene, lower alkenylene, or -(lower alkenylene)-C(=O)—,
$R^{21}$ represents H, halo, —CN, —$CF_3$, lower alkyl, or —O-lower alkyl, $R^{22}$ represents H, —C(=O)—O-(lower alkyl), —$CO_2$H or —$CONH_2$].

[9] The compound of [1] selected from the following group:
pyridin-3-yl 4-{4-[(3-fluorobenzyl)oxy]phenoxy}piperidine-1-carboxylate,
5-{[(4-{4-[(3-fluorobenzyl)oxy]phenoxy}piperidin-1-yl)carbonyl]oxy}nicotinic acid,
5-({[4-(2-phenylethyl)piperidin-1-yl]carbonyl}oxy)nicotinic acid,
5-[({4-[4-(2-cyclohexylethoxy)phenoxy]piperidin-1-yl}carbonyl)oxy]nicotinic acid,
5-[({4-[(E)-2-phenylvinyl]piperidin-1-yl}carbonyl)oxy]nicotinic acid,
5-{[(4-[3-[1-(6-methylpyridin-2-yl)piperidin-4-yl]propyl}piperidin-1-yl)carbonyl]oxy}nicotinic acid,
5-(aminocarbonyl)pyridin-3-yl 4-{2-[3-(aminocarbonyl)phenyl]ethyl}piperidine-1-carboxylate,
5-(aminocarbonyl)pyridin-3-yl 4-(2-{3-[(dimethylamino)carbonyl]phenyl}ethyl)piperidine-1-carboxylate,
5-(aminocarbonyl)pyridin-3-yl 4-{2-[3-(piperidin-1-ylcarbonyl)phenyl]ethyl}piperidine-1-carboxylate,
5-(aminocarbonyl)pyridin-3-yl 4-{2-[3-(pyrrolidin-1-ylcarbonyl)phenyl]ethyl}piperidine-1-carboxylate,
pyridin-3-yl 4-[(2E)-3-phenylprop-2-enoyl]piperazine-1-carboxylate,
pyridin-3-yl 4-(anilinocarbonyl)piperidine-1-carboxylate,
5-(aminocarbonyl)pyridin-3-yl 4-(2-phenylethyl)piperidine-1-carboxylate, pyridin-3-yl 4-(2-phenylethyl)piperazine-1-carboxylate,
5-(methoxycarbonyl)pyridin-3-yl 4-(2-phenylethyl)piperazine-1-carboxylate,
5-(aminocarbonyl)pyridin-3-yl 4-[2-(3-fluorophenyl)ethyl]piperidine-1-carboxylate,
5-(aminocarbonyl)pyridin-3-yl 4-[2-(3-cyanophenyl)ethyl]piperidine-1-carboxylate.
[10] A pharmaceutical composition comprising the compound of [1] as an active ingredient thereof.
[11] The pharmaceutical composition of [10], which is an FAAH inhibitor.
[12] The pharmaceutical composition of [10], which is a medicament for treatment of urinary frequency, urinary incontinence and/or overactive bladder.
[13] The pharmaceutical composition of [10], which is a medicament for treatment of pain.
[14] Use of the compound of [1] for the manufacture of an FAAH inhibitor or a medicament for treatment of urinary frequency, urinary incontinence and/or overactive bladder.
[15] Use of the compound of [1] for the manufacture of an FAAH inhibitor or a medicament for treatment of pain.
[16] A method for treating urinary frequency, urinary incontinence and/or overactive bladder, comprising administering a therapeutically effective amount of the compound of [1] to a patient.
[17] A method for treating pain, comprising administering a therapeutically effective amount of the compound of [1] to a patient.
[18] A screening method for a remedy for urinary frequency and urinary incontinence, a remedy for overactive bladder and/or a remedy for pain, comprising (1) a step of contacting a test substance with a polypeptide, which contains (a) an amino acid sequence represented by SEQ ID NO:2, SEQ ID NO:4, SEQ ID NO:6 or SEQ ID NO:8, (b) an amino acid sequence derived from the amino acid sequence represented by SEQ ID NO:2, SEQ ID NO:4, SEQ ID NO:6 or SEQ ID NO:8 through deletion, substitution and/or insertion of from 1 to 10 amino acids therein, (c) an amino acid sequence having a homology of at least 70% to the amino acid sequence represented by SEQ ID NO:2, SEQ ID NO:4, SEQ ID NO:6 or SEQ ID NO:8, or (d) an amino acid sequence of the entire amino acid sequence encoded by a polynucleotide represented by SEQ ID NO:1, SEQ ID NO:3, SEQ ID NO:5 or SEQ ID NO:7 or by a polynucleotide capable of hybridizing with its complementary sequence under a stringent condition, or its part not having at least the transmembrane region-containing amino terminal region thereof, and which may hydrolyze a substrate, (2) a step of analyzing the polypeptide for its activity change, and (3) a step of selecting a substance capable of inhibiting the polypeptide activity, (wherein the "substrate" with which FAAH or functional FAAH is contacted may be any and every endocannabinoid capable of being hydrolyzed by FAAH or functional FAAH; and concretely, it includes anandamide, palmitoylethanolamide, 2-arachidonoyl glycerol, and oleamide; and the substrate labeled with $^3$H or $^{14}$C, as well as a mixture of the labeled substrate and the unlabeled substrate may be used— the same shall be applied hereinunder).

[19] A screening method for a remedy for urinary frequency and urinary incontinence, a remedy for overactive bladder and/or a remedy for pain, comprising (1) a step of contacting a test substance with a polypeptide, which contains (a) an amino acid sequence represented by SEQ ID NO:2, SEQ ID NO:4, SEQ ID NO:6 or SEQ ID NO:8, (b) an amino acid sequence derived from the amino acid sequence represented by SEQ ID NO:2, SEQ ID NO:4, SEQ ID NO:6 or SEQ ID NO:8 through deletion, substitution and/or insertion of from 1 to 10 amino acids therein, (c) an amino acid sequence having a homology of at least 70% to the amino acid sequence represented by SEQ ID NO:2, SEQ ID NO:4, SEQ ID NO:6 or SEQ ID NO:8, or (d) an amino acid sequence of the entire amino acid sequence encoded by a polynucleotide represented by SEQ ID NO:1, SEQ ID NO:3, SEQ ID NO:5 or SEQ ID NO:7 or by a polynucleotide capable of hybridizing with its complementary sequence under a stringent condition, or its part not having at least the transmembrane region-containing amino terminal region thereof, and which may hydrolyze a substrate, in the presence of a substrate of the polypeptide, (2) a step of measuring the amount of the hydrolyzed product converted from the substrate, and (3) a step of selecting a substance capable of inhibiting the hydrolysis of the substrate.

[20] A screening method for a remedy for urinary frequency and urinary incontinence, a remedy for overactive bladder and/or a remedy for pain, comprising (1) a step of contacting a test substance with a cell or a tissue expressing a polypeptide, which contains (a) an amino acid sequence represented by SEQ ID NO:2, SEQ ID NO:4, SEQ ID NO:6 or SEQ ID NO:8, (b) an amino acid sequence derived from the amino acid sequence represented by SEQ ID NO:2, SEQ ID NO:4, SEQ ID NO:6 or SEQ ID NO:8 through deletion, substitution and/or insertion of from 1 to 10 amino acids therein, (c) an amino acid sequence having a homology of at least 70% to the amino acid sequence represented by SEQ ID NO:2, SEQ ID NO:4, SEQ ID NO:6 or SEQ ID NO:8, or (d) an amino acid sequence of the entire amino acid sequence encoded by a polynucleotide represented by SEQ ID NO:1, SEQ ID NO:3, SEQ ID NO:5 or SEQ ID NO:7 or by a polynucleotide capable of hybridizing with its complementary sequence under a stringent condition, or its part not having at least the transmembrane region-containing amino terminal region thereof, and which may hydrolyze a substrate, or with a lysate or a homogenate of the cell or the tissue, in the presence of a substrate of the polypeptide, (2) a step of measuring the amount of the hydrolyzed product converted from the substrate, and (3) a step of selecting a substance capable of inhibiting the hydrolysis of the substrate.

[21] A screening method for a remedy for urinary frequency and urinary incontinence, a remedy for overactive bladder and/or a remedy for pain, comprising (1) a step of contacting a test substance with a fatty acid amide hydrolase, (2) a step of analyzing the enzyme for its activity change, and (3) a step of selecting a substance capable of inhibiting the activity of the enzyme.

Outcomes of the Invention

The pharmacological tests of Examples 438 to Example 442 have confirmed the effectiveness of the compounds of the present invention. For example, typical compounds shown in Table 64 have an excellent FAAH-inhibitory effect; typical compounds shown in Example 441 are useful as a remedy for urinary frequency and urinary incontinence, and a remedy for overactive bladder; and typical compounds shown in Example 442 are useful as a remedy for pain. In addition, the compounds of the present invention are highly stable in aqueous solutions, and have excellent properties as medicines.

The invention described in Patent Reference 2 is useful as analgesic, antianxiety, antiepileptic, antidepressant, antiemetic, cardiovascular agent or antiglaucomatous agent; however, the present inventors have found that the present invention is useful for a remedy for urinary frequency and urinary incontinence and/or a remedy for overactive bladder, differing from Patent Reference 2. Further, the compounds of the present invention have an excellent FAAH-inhibitory effect, and are therefore useful for remedies for (1) neuropsychiatric disorders (e.g., anxiety, depression, epilepsy), (2) brain disorders, neurodegenerative disorders (e.g., head injury, cerebral ischemia, dementia), (3) immunological and inflammatory diseases, (4) vomiting, (5) eating disorders, (6) irritable bowel syndrome, ulcerative colitis, (7) hypertension, (8) glaucoma, or (9) sleep disorders. In addition, the compounds are free from or are relieved from cannabinoid-like side effects and a problem of addiction.

Further, according to the screening method of the present invention, a remedy for urinary frequency and urinary incontinence, a remedy for overactive bladder and/or a remedy for pain that are free from or are relieved from cannabinoid-like side effects and a problem of addiction can be selected on the basis of inhibition of FAAH activity. The substances obtained according to the screening method and the FAAH activity-inhibitory substances may produce pharmaceutical compositions useful for treatment of urinary frequency and urinary incontinence, for treatment of overactive bladder and/or for treatment of pain.

BEST MODE FOR CARRYING OUT THE INVENTION

The present invention is described in detail hereinunder.
The compounds of the present invention are described in detail hereinunder.

DEFINITIONS

Unless otherwise specifically indicated, the term "lower" in the definition of the structural formulae in this description means a linear or branched carbon chain having from 1 to 6 carbon atoms.

"Lower alkyl" includes, for example, methyl, ethyl, propyl, isopropyl, butyl, isobutyl, sec-butyl, tert-butyl, pentyl, isopentyl, neopentyl, tert-pentyl, hexyl, isohexyl; preferably methyl, ethyl, propyl, butyl, tert-butyl.

"Lower alkenyl" means an aliphatic hydrocarbon group having at least one double bond, including, for example, vinyl, propenyl, allyl, isopropenyl, 1,3-butadienyl, hexenyl.

"Cycloalkyl" means a mono- to tri-cyclic aliphatic saturated hydrocarbon ring group having from 3 to 14 carbon atoms, including, for example, cyclopropyl, cyclobutyl, cyclopentyl, cyclohexyl, cycloheptyl, cyclooctyl, bicycloheptyl, bicyclooctyl, tricyclododecanyl, bicyclo[2.2.1]heptyl, bicyclo[2.2.2]octyl, preferably cyclopropyl, cyclobutyl, cyclopentyl, cyclohexyl, cycloheptyl, cyclooctyl.

"Aryl" means a mono- to tri-cyclic aromatic hydrocarbon ring group having from 6 to 14 carbon atoms, in which the phenyl may be condensed with cycloalkyl. For example, it includes phenyl, indenyl, naphthyl, anthryl, phenanthryl, indanyl, tetrahydronaphthyl, preferably phenyl, naphthyl.

"Heterocyclic" means a 4- to 16-membered, monocyclic, bicyclic or tricyclic, saturated or unsaturated ring having from 1 to 4 hetero atoms selected from N, S and O. The heterocyclic group may be crosslinked or spiro-structured. The unsaturated ring includes an aromatic ring (heteroaryl) and a non-aromatic ring. The monocyclic group includes azetidinyl, oxetanyl, pyrrolidinyl, 1,3-dioxolanyl, pyrazolidinyl, piperazinyl, piperidyl, piperazinyl, morpholinyl, thiomorpholinyl, furyl, thienyl, pyrrolyl, imidazolyl, pyrazolyl, thiazolyl, oxazolyl, pyridyl, pyrazinyl, pyrimidinyl, triazolyl, thiadiazolyl, pyridazinyl, oxadiazolyl, tetrazolyl; the bicyclic group includes indolyl, isoindolyl, 3,4-methylenedioxyphenyl, 3,4-ethylenedioxyphenyl, benzofuranyl, benzothienyl, benzothiadiazolyl, benzothiazolyl, benzimidazolyl, indolyl, isoindolyl, quinolyl, isoquinolyl, 1,2,3,4-tetrahydroquinolyl, 1,2,3,4-tetrahydroisoquinolyl, decahydroisoquinolyl, quinoxalinyl; the tricyclic group includes carbazolyl, acridinyl, phenothiazinyl. The crosslinked heterocyclic group includes quinuclidinyl, 2,5-diazabicyclo[2.2.1]heptyl, 8-azabicyclo[3.2.1]octyl, 7-azabicyclo[2.2.1]heptyl. The spiro-structured heterocyclic group includes 1,4-dioxa-8-azaspiro[4,5]decanyl.

"Nitrogen-containing heteroaryl" means a 4- to 10-membered, mono- or bi-cyclic aromatic nitrogen-containing heteroaryl, having from 1 to 4 nitrogen atoms of the above-mentioned heterocyclic group. It includes, for example, pyrrolyl, imidazolyl, thiazolyl, pyrazolyl, triazolyl, tetrazolyl, pyridyl, pyridazinyl, pyrimidinyl, pyrazinyl, indolyl, isoindolyl, benzimidazolyl, benzopyrazolyl, quinolyl, isoquinolyl, quinoxalinyl, preferably imidazolyl, thiazolyl, pyridyl, benzimidazolyl, quinolyl.

"Nitrogen-containing saturated heterocyclic group" means a 3- to 10-membered, mono- or bi-cyclic nitrogen-containing heterocycloalkyl group, having from 1 to 3 nitrogen atoms of the above-mentioned heterocyclic group. It includes, for example, aziridinyl, azetidinyl, pyrrolidinyl, piperidyl, piperazinyl, morpholinyl, hexahydroazepinyl, 1,4-diazepinyl, 1,4-oxazepinyl, quinuclidinyl, 2,5-diazabicyclo[2.2.1]heptyl, azabicyclooctyl (e.g., azabicyclo[3.2.1]octyl), diazabicyclooctyl, azabicyclononyl, azabicyclodecanyl, 1,4-dioxa-8-azaspiro[4,5]decanyl, preferably pyrrolidinyl, piperidyl, piperazinyl, morpholinyl, hexahydroazepinyl, 1,4-diazepinyl, 1,4-oxazepinyl, quinuclidinyl, 2,5-diazabicyclo[2.2.1]heptyl, azabicyclo[3.2.1]octyl.

"Nitrogen-containing hetero ring" means the above-mentioned nitrogen-containing heteroaryl group, the above-mentioned nitrogen-containing saturated heterocyclic group, or a condensed group of nitrogen-containing heteroaryl and nitrogen-containing heterocycloalkyl. Preferably, it is pyrrolidinyl, piperidyl, piperazinyl, morpholinyl, hexahydroazepinyl, azabicyclo[3.2.1]octyl, 1,4-dioxa-8-azaspiro[4.5]decanyl, imidazolyl, pyridyl, quinolyl.

"Non-aromatic nitrogen-containing hetero ring" means a nitrogen-containing saturated heterocyclic group and an unsaturated nitrogen-containing heterocyclic group except the nitrogen-containing heteroaryl of the above-mentioned nitrogen-containing heterocyclic group. Preferably, it is a 5- to 7-membered non-aromatic nitrogen-containing heterocyclic group.

"Lower alkylene", "lower alkenylene", "cycloalkylene", "arylene" and "nitrogen-containing heteroarylene" are divalent groups derived from the above-mentioned lower alkyl, lower alkenyl, cycloalkyl, aryl and nitrogen-containing heteroaryl, by removing any one hydrogen atom from them.

"Esterified carboxyl" means lower alkyl-O—CO—, aryl-lower alkyl-O—CO—, or —H$_2$N—CO-aryl-lower alkyl-O—CO—.

"Halo" means a halogen group, concretely including fluoro, chloro, bromo, iodo, preferably fluoro, chloro.

"Optionally substituted" means "unsubstituted" or "substituted with the same or different, 1 to 5 substituents".

Depending on the type of the substituent therein, the compound (I) of the present invention may have optical isomers (optically-active isomers, diastereomers) or geometric isomers. Accordingly, the compound (I) of the present invention includes mixtures or isolated compounds of these optical isomers or geometric isomers.

The compound (I) of the present invention may form pharmaceutically acceptable salts such as acid-addition salts or salts with bases. For example, the salts includes acid addition salts with an inorganic acid such as hydrochloric acid, hydrobromic acid, hydroiodic acid, sulfuric acid, nitric acid, phosphoric acid; or an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid; as well as salts with an inorganic base such as sodium, potassium, magnesium, calcium, aluminium; or an organic base such as methylamine, ethylamine, monoethanolamine, diethanolamine, triethanolamine, cyclohexylamine, lysine, ornithine. Further, the compound (I) or its pharmaceutically acceptable salt of the present invention may form hydrates, solvates with ethanol or the like, and crystalline polymorphs.

Further, the compound (I) of the present invention includes all compounds capable of being metabolized in living bodies to be converted into the compound (I) or its pharmaceutically acceptable salt of the present invention, that is, prodrugs. The group to form prodrugs of the compound (I) of the present invention includes those described in Prog. Med., 5:2157-2161 (1985), and those described in "PHARMACEUTICAL RESEARCH and DEVELOPMENT", VOLUME 7 Drug Design, pp. 163-198 by Hirokawa Publishing, 1990. Concretely, they are groups capable of being converted into primary amine or secondary amine, or HO—, HO—CO— or the like in the present invention through hydrolysis or solvolysis or under a physiological condition. Prodrugs of HO— are, for example, optionally-substituted lower alkyl-CO—O—, optionally-substituted aryl-CO—O—, optionally-substituted heteroaryl-CO—O—, RO—CO-optionally-substituted lower alkylene-CO—O— (R means H— or lower alkyl—the same shall be applied hereinunder), RO—CO-optionally-substituted lower alkenylene-CO—O—, RO—CO-lower alkylene-O-lower alkylene-CO—O—, RO—CO—CO—O—, ROS(=O)$_2$-optionally-substituted lower alkenylene-CO—, phthalidyl-O—, 5-methyl-1,3-dioxolen-2-on-4-yl-methyloxy.

"Urinary frequency" as referred to in this description indicates a condition where the urination frequency has increased over a normal range. "Urinary incontinence" means a involuntary urination that is problematic in a social and sanitary life.

"Overactive bladder" as referred to in this description indicates a syndrome to be diagnosed by a subjective symptom such as urinary frequency or urgency (Neurourology and Urodynamics, USA, 2002, Vol. 21, pp. 167-178). The pathogenic cause includes, for example, neuropathy (for example, caused by neurogenic bladder, cerebral infarction), lower urinary tract obstruction (e.g., benign prostatic hypertrophy) and aging; and as the pathogenic mechanism common to these, hyperactivity of capsaicin-sensitive afferent neuron.

Overactive bladder may be treated by relieving the condition of urinary frequency, urinary incontinence and urgency. This is obvious, for example, from the fact that administration of an anticholinergic agent, oxybutynin hydrochloride (Japan Standard Product Classification Number 87259; by Aventis Pharma) to a patient suffering from overactive bladder, at a dose of from 2 to 3 mg/once and three times a day may relieve the condition of urinary frequency, urinary incontinence and urgency, and the administration is therefore effective for treatment of overactive bladder.

The presence of the effect for treatment of urinary frequency and urinary incontinence and/or the effect for treatment of overactive bladder may be confirmed by methods known to those skilled in the art or by modified methods from them. For example, a pathologic model induced by administration of from 50 to 200 mg of cyclophosphamide (CPA) to rat, guinea pig, dog or the like is frequently used in this technical field (Ozawa et al., The Journal of Urology, Vol. 162, pp. 2211-2216, 1999; Boucher et al., The Journal of Urology, Vol. 164, pp. 203-208, 2000). This is a pathologic model that accompanies hemorrhagic cystitis, and since capsaicin-sensitive afferent neuron participates in the pathogenic mechanism of urinary frequency, it may be considered that this model may be a suitable pathologic model for various types of overactive bladder including neuropathic bladder (Carlo Alberto Maggi et al., Journal of the Autonomic Nervous System, Vol. 38, pp. 201-208, 1992). A urinary frequency condition may be confirmed by the decrease in the effective bladder capacity. To the pathologic model animal, an effective dose of a pharmaceutical composition is administered orally, intraperitoneally or intravenously, once or plural times; and when the effective bladder capacity of the animal has increased, then the effect of the pharmaceutical composition for treatment of urinary frequency and urinary incontinence and/or for treatment of overactive bladder may be confirmed.

"Pain" as referred to in this description is a generic term for neuropathic pain, nociceptive pain and inflammatory pain, of which "neuropathic pain" means pain caused by peripheral or central nervous system dysfunction and includes diabetic neuropathic pain, cancer pain, trigeminal neuralgia, phantom pain, postherpetic pain and thalamic pain. The essential clinical symptom of neuropathic pain includes pain as if clutched, pain as if scorched, hyperalgesia and allodynia.

Nonsteroidal antiinflammatory drugs and narcotic analgesics such as morphine that are ordinary analgesics are known to be weakly effective for neuropathic pain. In a medical site, an antiepileptic such as gabapentin, and an antiarrhythmic such as mexiletine are used for pain relief, but their analgesic potency is not sufficient.

The presence of the effect for treatment of neuropathic pain may be confirmed by methods known to those skilled in the art or by modified methods from them. For example, using an L5/L6 spinal nerve ligated rat that is produced according to partial modification of a Kim and Chung's method (Pain, Vol. 50, pp. 355-363, 1992), the ameliorating effect of a compound for significant reduction in the response threshold to tactile stimulation (allodynia) is evaluated, and based on it, the effect of the tested compound for treatment of neuropathic pain may be confirmed.

The compound of the present invention includes those effective for urinary frequency and urinary incontinence as well as overactive bladder; those effective for pain, especially for neuropathic pain; and those effective for both the two.

[Production Methods]

The compound and its pharmaceutically acceptable salt of the present invention can be produced by applying various known production methods, utilizing the characteristics based on its basic skeleton of the compound or the type of the substituent therein.

Depending on the type of a functional group in the compound, it may often be effective in point of its production technology to substitute the functional group with a suitable protective group (capable of being readily converted into the functional group) in a stage of its starting material or intermediate. The functional group includes, for example, an amino group, a hydroxyl group and a carboxyl group; and their protective groups are, for example, those described in "Protective Groups in Organic Synthesis (2nd Ed)" by Greene & Wuts. These may be suitably selected and used depending on the reaction conditions.

In this method, the protective groups is removed if necessary after it has been introduced and the reaction carried out, in order to produce the desired compound.

Typical production methods for the compounds of the present invention and their intermediates are described below. (The abbreviations given in the following description are as follows:

DMF: N,N-dimethylformamide,

DMSO: dimethylsulfoxide,

THF: tetrahydrofuran,

TFA: trifluoroacetic acid,

Tol: toluene,

EtOAc: ethyl acetate,

DCE: 1,2-dichloroethane,

TEA: triethylamine)

Typical production methods for the compounds of the present invention described below, to which, however, the present invention should not be limited.

In case where a similar substituent exists in a site of the compound of the present invention except that in the reaction formula in the production method for the compound, the compound that is encompassed within the scope of the present invention may be readily produced through substituent modification.

Production Method 1 (Carbamate Formation):

[Chemical Formula 6]

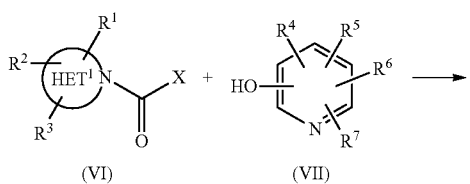

-continued

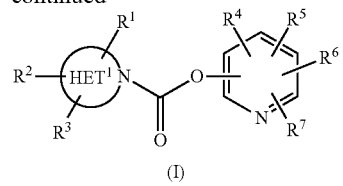

(In the formula, X represents a leaving group advantageous to the reaction, and the same shall be applied hereinunder.)

This reaction is for esterification of a ketone derivative of a general formula (VI) and a reaction-corresponding amount of a hydroxypyridine derivative of a general formula (VII), in a solvent inert to the reaction, with stirring with cooling or at room temperature or with heating. The leaving group X includes, for example, a halogen atom, a lower alkoxy group, a phenoxy group, an imidazolyl group. The inert solvent includes, for example, DMF, dimethylacetamide, THF, dioxane, dimethoxyethane, diethoxyethane, benzene, Tol, xylene and their mixed solvents. For promoting the reaction, a base (e.g., sodium, sodium hydride, sodium methoxide, sodium ethoxide) is preferably added to the reaction mixture.

Production Method 2 (Carbamate Formation):

[Chemical Formula 7]

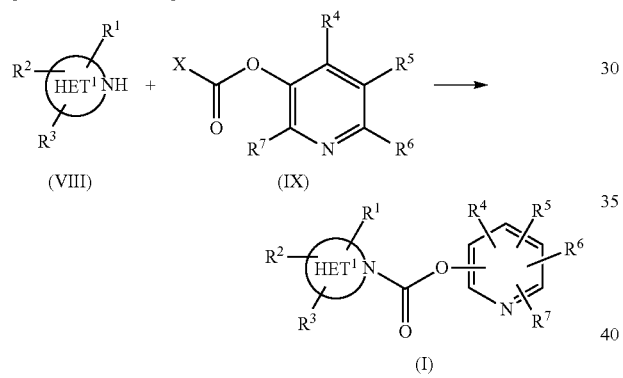

This reaction is conducted by stirring a nitrogen-containing heterocyclic compound of a general formula (VIII) and a reaction-corresponding amount of a pyridine derivative of a general formula (IX) in a solvent inert to the reaction, with cooling or at room temperature or with heating. For promoting the reaction, a base (e.g., sodium, sodium hydride, sodium methoxide, sodium ethoxide, TEA, pyridine) is preferably added to the reaction mixture.

Production Method 3 (Hydrolysis):

A compound (1-3) of the present invention having a carboxyl group can be obtained through hydrolysis of the corresponding compound having an esterified carboxyl group, for example, according to deprotection described in "Protective Groups in Organic Synthesis (2nd Ed)" by Greene & Wuts.

[Chemical Formula 8]

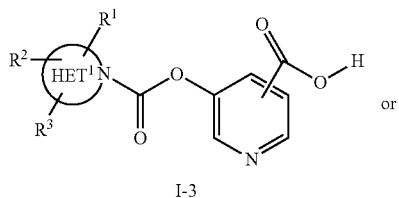

(In the formula, the group ROCO— means an esterified carboxyl group, and the same shall be applied hereinunder.)

Production Method 4 (Amidation):

[Chemical Formula 9]

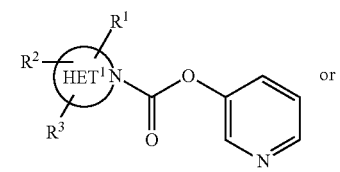

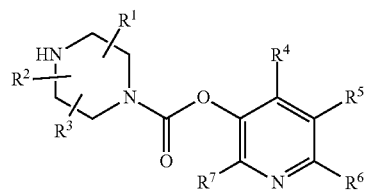

The compound (I-3) or the compound where $R^1$ is a carboxylic acid may react with an amine, and the compound where $R^1$ is an amine may react with a carboxylic acid, thereby various amide compounds can be obtained. When the nitrogen-containing heterocyclic compound is piperidine, then it may be reacted with a carboxylic acid or a sulfonic acid compound or their reactive derivative to produce various types of amide compounds. The reaction may be conducted in the presence of a condensing agent (e.g., dicyclohexylcarbodiimide (DCC), diisopropylcarbodiimide (DIPC), 1-ethyl-3-(3-dimethylaminopropyl)carbodiimide (WSC), 1,1'-carbonylbis-1H-imidazole (CDI)) and optionally further in the presence of an additive (e.g., N-hydroxysuccinimide (HONSu) 1-hydroxybenzotriazole (HOBt), dimethylaminopyridine (DMAP)). The reactive derivative of the carboxylic acid or the sulfonic acid compound includes acid halides, acid anhydrides, active esters. The reaction may also be conducted, for example, according to the methods described in "Jikken Kagaku koza (Courses in Experimental Chemistry, 4th Ed)", Vol. 22, edited by the Chemical Society of Japan, Maruzen, 1992.

Production Method 5 (Coupling Reaction):

[Chemical Formula 10]

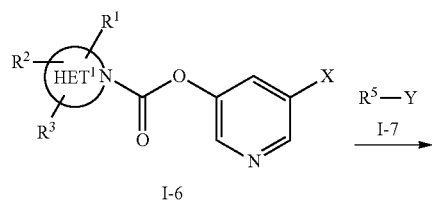

(In the formula, the symbols have the following meanings. X represents halogen or —O—SO$_2$CF$_3$, and Y represents —B(OH)$_2$, dialkylboron, dialkoxyboron or trialkyltin. X may be —B(OH)$_2$, dialkylboron, dialkoxyboron or trialkyltin, and Y may be halogen or —O—SO$_2$CF$_3$.)

Two aromatic rings, or that is, a combination of a compound (I-6) and a compound (I-7), are reacted preferably in the presence of a transition metal catalyst and a suitable additive, thereby producing a biaryl compound (I-8). Typical methods for it are described in "Jikken Kagaku koza (Courses in Experimental Chemistry, 4th Ed)", Vol. 25, Organic Synthesis VII, pp. 353-366, pp. 396-427, 1991 (Maruzen). The transition metal catalyst preferred for use herein includes various palladium complexes such as tetrakis(triphenylphosphine)palladium, and various nickel complexes such as dibromobis(triphenylphosphine)nickel. The additive also preferred for use herein includes triphenylphosphine, sodium carbonate, zinc; and these may be suitably selected depending on the method to which they are applied. In general, the reaction is conducted in a solvent at room temperature or with heating. Apart from the reaction described herein, also preferably used is a reaction for biaryl structure formation, for example, a reaction of a halogenated aryl compound with an aryl-Grignard reagent in the presence of a suitable transition metal catalyst.

(Production Methods for Starting Compounds)

The starting compounds to be used for producing the compounds of the present invention may be known compounds or may be produced by optionally processing known compounds according to the above-mentioned production methods, or according to methods well known to those skilled in the art (J. March, ADVANCED ORGANIC CHEMISTRY (John WILEY & SONS (1992)) (for example, acylation, alkylation, urea formation, oxidation, reduction (preferably, COMPREHENSIVE ORGANIC SYNTHESIS 8 REDUCTION (Pergamon Press) (1991)), halogenation).

Production Method (i):
Mitsunobu Reaction:

A starting compound (X) may be produced through Mitsunobu reaction of alcohols of general formulae (XI) and (XII). This reaction is conducted by stirring the compounds (XI) and (XII) in the presence of an equivalent or excessive amount of triphenylphosphine and diethyl azodicarboxylate, in an inert solvent as in the production method 1, under cooling to heating conditions.

[Chemical Formula 11]

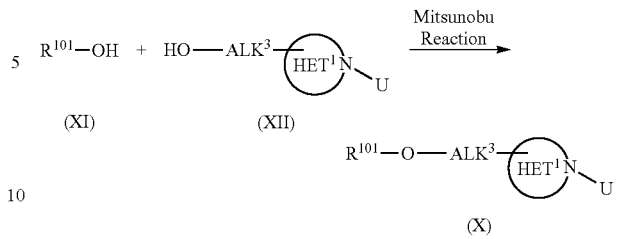

(In the formula, the symbols have the following meanings:
U represents an amino-protective group,
ALK$^3$ represents ALK$^1$ optionally substituted with HO, and the same shall be applied hereinunder.)

Production Method (ii):
Substitution Reaction:

This reaction is alkylation. A primary amine, a secondary amine, an alcohol, a thiol, a primary amide or a secondary amide is reacted with a reaction-corresponding amount of a compound having a leaving group, in a solvent inert to the reaction, in an equivalent ratio of the two, or in such a ratio that any one of the two is excessive, with stirring under cooling to heating conditions. As the case may be, the reaction may be conducted advantageously in the presence of a base (e.g., inorganic base such as potassium carbonate, sodium carbonate, cesium carbonate; organic base such as TEA, diisopropylethylamine; metal alkoxide such as potassium tert-butoxide, sodium tert-butoxide; sodium hydride, lithium hydride) and an additive (tetra-n-butylammonium iodide, potassium iodide, sodium iodide) for smoothly promoting the reaction. The solvent inert to the reaction includes, for example, dichloromethane, DCE, chloroform, benzene, Tol, xylene, ether, THF, dioxane, EtOAc, ethanol, methanol, 2-propanol, acetonitrile, DMF, N,N-dimethylacetamide, N-methylpyrrolidone, dimethylimidazolidinone, DMSO, acetone, methyl ethyl ketone, water, as well as their homogeneous or heterogeneous mixed solvents. The solvent may be suitably selected depending on various reaction conditions employed.

[Chemical Formula 12]

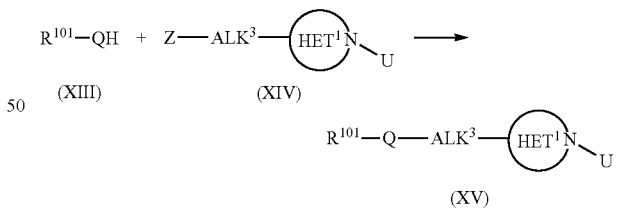

[In the formula, the symbols have the following meanings:
Q represents O, S or NH,
Z represents a leaving group (e.g., Cl, Br, I or OMs).]

Production Method (iii):

This production method comprises reacting an aldehyde or ketone of a general formula (XVI) with a Wittig reagent or a Horner-Emmons reagent of a general formula (XVII), thereby producing a compound (XVI).

This reaction is conducted in the presence of an equivalent or excessive amount of a base (e.g., organic base such as TEA, diisopropylethylamine; inorganic base such as potassium carbonate, sodium carbonate, cesium carbonate), by stirring the compound (XVI) and the compound (XVII) in the above-mentioned inert solvent, in an equivalent ratio of the two, or in such a ratio that any one of the two is excessive, under cooling to heating conditions. As the case may be, an additive (e.g., tetra-n-butylammonium iodide, potassium iodide) may be advantageously added to the system for smoothly promoting the reaction.

[Chemical Formula 13]

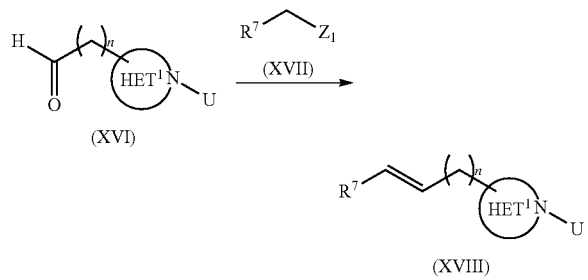

$Z_1$ represents a group used in a Wittig reagent or a Horner-Emmons reagent (e.g., phosphonium salt, or phosphorous diester), n indicates 0 or 1.

[1] Screening Method of the Present Invention:

Fatty acid amide hydrolase (hereinafter this may be referred to as FAAH) includes enzymes having an activity of hydrolyzing anandamide, palmitoylethanolamide, oleamide, and/or 2-arachidonoyl glycerol, and so far as they are identified as those of the same molecule species, they may be derived from any species, for example, from mammals such as human (GenBank Accession Number NM_001441), mouse (GenBank Accession Number NM_010173), rat (GenBank Accession Number NM_024132), porcine (GenBank Accession Number AB027132), rabbit, sheep, chicken, dog, cat, hamster, squirrel, bear, deer, monkey. In addition, it is not limited to a natural polypeptide, but may include artificially-produced mutants.

Regarding (a) a polypeptide which contains an amino acid sequence of the entire amino acid sequence represented by SEQ ID NO:2, SEQ ID NO:4, SEQ ID NO:6 or SEQ ID NO:8 or a part of the amino acid sequence not having at least the transmembrane region-containing amino terminal region thereof, and which may hydrolyze anandamide, palmitoylethanolamide, oleamide, and/or 2-arachidonoyl glycerol;

(b) a polypeptide which contains an amino acid sequence of the entire amino acid sequence derived from the amino acid sequence represented by SEQ ID NO:2, SEQ ID NO:4, SEQ ID NO:6 or SEQ ID NO:8 through deletion, substitution and/or insertion of from 1 to 10, preferably from 1 to 7, more preferably from 1 to 5 amino acids therein, or a part of the amino acid sequence not having at least the transmembrane region-containing amino acid terminal region thereof, and which may hydrolyze anandamide, palmitoylethanolamide, oleamide, and/or 2-arachidonoyl glycerol;

(c) a polypeptide which contains an amino acid sequence having a homology of at least 70%, preferably at least 80%, more preferably at least 90%, most preferably at least 95% to the amino acid sequence represented by SEQ ID NO:2, SEQ ID NO:4, SEQ ID NO:6 or SEQ ID NO:8, and which may hydrolyze anandamide, palmitoylethanolamide, oleamide, and/or 2-arachidonoyl glycerol;

(d) a polypeptide which contains an amino acid sequence of the entire amino acid sequence encoded by a polynucleotide represented by SEQ ID NO:1, SEQ ID NO:3, SEQ ID NO:5 or SEQ ID NO:7 or by a polynucleotide capable of hybridizing with its complementary sequence under a stringent condition, or its part not having at least the transmembrane region-containing amino terminal region thereof, and which may hydrolyze anandamide, palmitoylethanolamide, oleamide, and/or 2-arachidonoyl glycerol;

the above (a) to (d) are generically referred to as a generic term "functional FAAH".

The above-mentioned "transmembrane region-containing amino terminal region" as referred to in this description means an amino terminal region that includes the extracellular region at an amino terminal, and a transmembrane region buried in the cell membrane sandwiched between the extracellular region and the intracellular region. The existence and the site of the transmembrane region may be predicted from the amino acid sequence of the protein, using a protein membrane structure prediction program, TMpred, PSORT, SOSUI. Concretely, the "transmembrane region-containing amino terminal region" is, for example, the region of from the first to the 30th in SEQ ID NO:2, and the region of from the first to the 29th in SEQ ID NO:6. It is known that the polypeptide represented by the 30th to 579th amino acids in SEQ ID NO:6 excluding the region of from the 1st to the 29th in SEQ ID NO:6 also has the same enzymatic activity as that of the polypeptide from which the region is not excluded (Matthew et al., Biochemistry, Vol. 37, pp. 15177-15178, 1998).

The "homology" as referred to in this description means the values identities obtained by the use of the parameters prepared in default through search with Clustal V program (Higgins & Sharp, Gene, Vol. 73, pp. 237-244, 1998; Thompson et al., Nucleic Acid Res., Vol. 22, pp. 4673-7680, 1994). The parameters are as follows:

As pairwise alignment parameters,
K tuple 1
Gap Penalty 3
Window 5
Diagonals Saved 5.

The above-mentioned "stringent condition" for hybridization as referred to in this description means a condition not causing any unspecific binding. Concretely, for example, the hybridization is effected in a solution comprising 50% formamide, 5×SSC (0.75 M NaCl, 0.075 M sodium citrate, pH 7), 5×Denhardt's solution (0.1% Ficoll 400, 0.1% polyvinylpyrrolidone, 0.1% BSA), modified salmon sperm DNA (50 g/ml), 0.1% SDS, and 10% dextran sulfate, under a temperature condition of from 37 to 42° C. for about 12 to 18 hours, and then optionally after pre-washed, this is washed with a washing solution (0.2×SSC, 0.1% SDS) under a temperature condition of from 50 to 60° C.

The above-mentioned "hydrolysis of anandamide, palmitoyl ethanolamide, oleamide and/or 2-arachidonoyl glycerol" as referred to in this description concretely means that, according to the method described in Examples 1 to 4, anandamide (N-arachidonoyl ethanolamine) is decomposed into arachidonic acid and ethanolamine; palmitoyl ethanolamide (N-palmitoyl ethanolamine) is into palmitic acid and ethanolamine; oleamide (cis-9,10-octadecenamide) is into oleic acid and ammonia, and 2-arachidonoyl glycerol is into arachidonic acid and glycerol, through hydrolysis in a buffer having a pH of from 7 to 9 at 4° C. to 37° C. for 30 minutes to 90 minutes.

The screening method of the present invention includes a screening method for a remedy for urinary frequency and urinary incontinence, a remedy for overactive bladder and/or a remedy for pain, comprising (1) a step of contacting a test substance with FAAH or functional FAAH, (2) a step of analyzing it for the activity of FAAH or functional FAAH, and (3) a step of selecting a substance that inhibits the activity of FAAH or functional FAAH.

(1) Step of Contacting Test Substance with FAAH or Functional FAAH:

For contacting a test substance with FAAH or functional FAAH, the test substance may be added to any of the following:

- a) a cell or a tissue expressing FAAH or functional FAAH,
- b) a transformant transformed with an expression vector containing a polynucleotide that encodes FAAH or functional FAAH,
- c) a lysate or a homogenate of a) or b),
- d) a purified product of FAAH or functional FAAH purified from c), and incubated for a predetermined period of time; or
- e) a tissue homogenate or blood of a test animal to which the test substance has been administered may be used.

a) Cell or Tissue Expressing FAAH or Functional FAAH:

Concretely, the cell expressing FAAH or functional FAAH includes neurons, glial cells, epithelial cells, endothelial cells, lymphocytes, macrophages, platelets, mast cells, monocytes, dendritic cells, hepatocytes, renal cells, enterocytes, pancreatic cells, uterine cells, placental cells, bladder cells, prostatic cells, keratinization cells, and muscular cells. So far as they express FAAH or functional FAAH, these cells may be derived from any species; and for example, herein employable are cells derived from mammals such as human, mouse, rat, porcine, rabbit, sheep, chicken, dog, cat, hamster, squirrel, bear, deer, monkey.

For the cells, usable are established cell lines; and cells peeled from or isolated from animal tissues may also be used. The established cell lines usable herein include human bladder epithelial cancer-derived cell line 5673 cells, human prostatic cancer-derived cell line PC-3 cells, rat basophilic leukemia cell line RBL-2H3 cells, rat neuroblastoma cell line N18TG2 cells, rat glioma cell line C6 cells, rat macrophage cell line J774 cells, rat adrenal medulla-derived pheochromocytoma cell line PC-12 cells, human monocytic cell line U937 cells, human breast cancer cell line MFC-7 cells, human breast cancer cell line EFM-19 cells, human colon cancer-derived cell line CaCo-2 cells (these cell lines are available from American Type Culture Collection (ATCC)), human epidermal keratinocyte cell line HaCaT cells, and human neuroblastoma cell line CHP100 cells. Preferred are human bladder epithelial cancer-derived cell line 5673 cells, and rat basophilic leukemia cell line RBL-2H3 cells.

The tissue expressing FAAH or functional FAAH concretely includes brain, bladder, prostate, kidney, liver, testis, muscle, vessel, pancreas, digestive tube, lung, uterus, placenta, skin, lymphocyte, platelet, macrophage, monocyte, mast cell, and prostate. Preferably used are brain, liver and monocyte. So far as they express FAAH or functional FAAH, these tissues may be derived from any species. For example, tissues derived from mammals such as human, mouse, rat, porcine, rabbit, sheep, chicken, dog, cat, hamster, squirrel, bear, deer, monkey may be used.

For determining whether or not a cell or a tissue expresses FAAH or functional FAAH, a cell or tissue extract may be used and analyzed through western blotting, using an antibody capable of detecting the intended polypeptide, or through PCR (polymerase chain reaction) using primers capable of specifically detecting a polynucleotide that encodes the intended polypeptide. In addition, a lysate or a homogenate of a cell or a tissue is reacted with a substrate such as anandamide, palmitoyl ethanolamide, oleamide, and/or 2-arachidonoyl glycerol, in a buffer having a pH of from 7 to 9 at 4° C. to 37° C. for 30 minutes to 90 minutes, whereupon the system is determined whether or not the substrate is hydrolyzed for the intended determination.

b) Transformant Transformed with Expression Vector Containing Polynucleotide that Encodes FAAH or Functional FAAH:

A polynucleotide that encodes FAAH or functional FAAH may be isolated from a cDNA library through screening by PCR or hybridization, using primers and a probe planned and synthesized on the basis of the information of known amino acid sequences and base sequences.

The fragment that contains the isolated polynucleotide is inserted into a suitable expression vector, and it may be transfected into a host cell of eukaryote or prokaryote; and in the host cell, the polypeptide encoded by the transfected polynucleotide may be thus expressed. The expression vector may be any known one suitably selected depending on the host cell, for which, in addition, also usable is a vector plasmid suitably selected depending on the host cell and having a suitable promoter and a phenotype expression-related sequence introduced thereinto. Also usable is an expression vector with a specific sequence introduced thereinto in such a manner that the polypeptide encoded by the inserted polynucleotide may be expressed as fused with glutathion-S-transferase (GST) or with a tag such as Flag or His. In case where one cell is transformed with some different types of polynucleotides at the same time, then one expression vector to be used may be so planned that it includes such different types of polynucleotides, or those polynucleotides may be separately in different expression vectors. Alternatively, a cell with a chromosomal DNA having the constitution of the type may be produced and it may be used.

The expression vector with a desired polynucleotide introduced thereinto may be given to a host cell according to a DEAE-dextran method (Luthman et al., Nucleic Acids Res., Vol. 11, pp. 1295-1308, 1983), a calcium phosphate-DNA coprecipitation method (Graham et al., Virology, Vol. 52, pp. 456-457, 1973), a method of using a commercially-available transfection reagent, Lipofectamine 2000 (by Invitrogen) or FeGENE 6 (by Roche Molecular Biochemicals), or an electroporation method (Neumann et al., EMBO J., Vol. 1, pp. 841-845, 1982) for intended transformation. In case where *E. coli* is used as the host cell, a competent cell of *E. coli* is formed with coexistence with $CaCl_2$, $MgCl_2$ or RbCl according to a Hanahan's method (Hanahan et al., Mol. Biol. Vol. 166, pp. 557-580, 1983), and an expression vector with the desired polynucleotide introduced thereinto is given thereto for transformation of the cell.

c) Lysate or Homogenate of a) or b):

A cell homogenate may be prepared by washing a cell a few times with a buffer, and then homogenized using a Potter-Elvehjem homogenizer or the like thereby giving a uniform solution. A tissue homogenate may be prepared by adding a buffer cooled with ice to a tissue in an amount of from 5 to 10 volume times the weight of the tissue, homogenizing it using a Potter-Elvehjem homogenizer in ice thereby giving a uniform solution, and then further ultrasonically homogenizing it for a few seconds. The buffer may be Tris buffer (50 mM Tris-HCl (pH 8.0), 1 mM EDTA) or Hepes buffer (1 mM EDTA, 100 mM NaCl, 12.5 mM Hepes, pH 8.0). For example, the test methods of Example 438 and Example 439 are applicable to the case. A lysate of *E. coli* transformed with an expression vector that contains an FAAH or functional FAAH-encoding polynucleotide may be prepared by collecting cells of *E. coli* through centrifugation and then dissolving them in a lysis buffer (for example, 20 mM Tris-HCl (pH 8.0), 500 mM NaCl, 10% glycerol, 0.2 mM EDTA, 0.5 mM DTT, 10 mM imidazole, 1% n-octyl-β-D-glucopyranoside).

d) Purified Product of FAAH or Functional FAAH Purified from c):

A purified product of FAAH or functional FAAH may be prepared from a) a cell or tissue expressing FAAH or functional FAAH or b) a lysate or a homogenate of a transformant transformed with an expression vector that contains an FAAH or functional FAAH-encoding polynucleotide, according to an ordinary purification method of affinity chromatography, electrochromatography, gel filtration chromatography, ion-exchange chromatography or partition chromatography.

Concretely, the purification is as follows: A cell or tissue expressing FAAH or functional FAAH is homogenized in a solvent containing sucrose, and then subjected to centrifugation and ultra-high-speed centrifugation to obtain a microsome fraction, thereafter this is dissolved in a solvent containing Triton-X and further centrifuged for deposit removal, and the resulting protein-lysate is processed in a high-performance protein liquid chromatography (FPLC) system (by Pharmacia) (Ueda et al., J. Biol. Chem., Vol. 270, pp. 23813-23827, 1995).

Alternatively, E. coli transformed so as to express a His tag-fused FAAH or functional FAAH is dissolved in a lysis buffer, then ultrasonically processed and centrifuged (e.g., at 10000×g for 20 minutes), and the resulting supernatant is mixed with a resin previously equilibrated with the lysis buffer and having a high affinity with His tag, at a low temperature for at least 12 hours. Then, the resin is washed, and the His tag-fused FAAH or functional FAAH is released from the resin to obtain its purified product.

For contacting a test substance with the above-mentioned cell or tissue, or the cell or tissue-lysate or homogenate prepared in the manner as above, or the purified FAAH or functional FAAH product, employable is a method of incubation for a predetermined period of time, with adding or not adding a test substance to them. Concretely, a test substance is dissolved in a solution suitably selected depending on its solubility therein, such as distilled water or dimethyl sulfoxide (DMSO), and is added to the above-mentioned cell or tissue, or the cell or tissue-lysate or homogenate, or the purified FAAH or functional FAAH product to be from 0.003 nM to 10 µM. The cell or tissue sample is incubated in a $CO_2$ incubator at 37° C. for 30 to 60 minutes; and the others are at 4° C. to 37° C. for 30 to 90 minutes, thereby attaining the intended contact with the test substance.

e) Tissue Homogenate or Blood of Test Animal Administered with Test Substance:

When a test substance is administered to a test animal, then the test substance may be contacted with the FAAH or functional FAAH existing in the tissue or the blood of the test animal. The test animal includes, for example, mammals such as mouse, rat, dog. A test substance may be administered to the test animal as follows: A test substance is suspended or dissolved in a carrier generally used in accordance with the property of the test substance, such as physiological saline water, dimethylformamide solution or 10% methyl cellulose solution, and it may be administered to a test animal orally, subcutaneously, intraperitoneally or intravenously. After the administration, the tissue is taken out, and the tissue is homogenized according to the method described in the above c), thereby preparing a tissue homogenate. Concretely, for example, from 1 to 3 mg/kg of a test substance is orally administered to a 9-week age rat, and its brain, liver or monocyte taken out of it after 30 minutes is homogenized to prepare the tissue homogenate Alternatively, from 0.3 to 3 mg/kg of a test substance is intravenously administered to a 13 to 18-month age dog, and its brain, liver or monocyte taken out of it after 30 minutes is homogenized to prepare the tissue homogenate. More concretely, for example, the tissue homogenate may be prepared according to the method described in Example 440. Blood may be collected from the heart or the descending aorta of a test animal to which the test substance has been administered.

(2) Step of Analyzing FAAH or Functional FAAH Activity Change:

For analyzing the FAAH or functional FAAH activity change, employable is a method of determining the change in the enzymatic activity of FAAH or functional FAAH based on the presence or absence of contact with a test substance. The enzymatic activity of FAAH or functional FAAH may be determined by contacting FAAH or functional FAAH with a substrate for a predetermined period of time, and measuring the amount of the decomposed product of the substrate. Alternatively, it may also be determined by measuring the amount of endocannabinoid that is an endogenous substrate for FAAH contained in a tissue or blood of a test animal.

For analyzing the test substance-dependent enzymatic activity change, a substrate is contacted with FAAH or functional FAAH for a predetermined period of time in the presence or absence of a test substance, and the ratio of the amount of the decomposed product of the substrate in the presence of the test substance to the amount of the decomposed product of the substrate in the absence of the test substance is obtained for the intended analysis.

Alternatively, FAAH or functional FAAH previously contacted with a test substance, and FAAH or functional FAAH not contacted with a test substance are separately contacted with a substrate for a predetermined period of time, and the ratio of the amount of the decomposed product of the substrate by the FAAH or functional FAAH previously contacted with the test substance to the amount of the decomposed product of the substrate by the FAAH or functional FAAH not contacted with the test substance is obtained whereby the test substance-dependent enzymatic activity change may be determined.

Further, the test substance-dependent enzymatic activity change may also be determined by measuring the amount of endocannabinoid in the tissue or blood of a test animal before and after administration of a test substance to the test animal, followed by obtaining the ratio of the endocannabinoid amount after the test substance administration to the endocannabinoid amount before the test substance administration; or by measuring the amount of endocannabinoid in the tissue or blood of a test animal administered or not administered with a test substance, followed by obtaining the ratio of the endocannabinoid amount in the tissue or blood of the test animal administered with the test substance to the endocannabinoid amount in the tissue or blood of the test animal not administered with the test substance, whereby the test substance-dependent enzymatic activity change may be determined.

FAAH and functional FAAH may be contacted with a substrate under the condition mentioned below, in accordance with the condition of the FAAH or functional FAAH.

For contacting the FAAH or functional FAAH expressed in the cell or tissue of a) or b) in the above (1) with a substrate, there may be employed a method of adding the substrate to the cultured cell or tissue in a buffer having a pH of from 7 to 9, and reacting them in a $CO_2$ incubator at 37° C. or room temperature preferably for 30 to 60 minutes. The reaction may be stopped by transferring the cell or tissue onto ice to rapidly cool it, whereupon an FAAH inhibitor may be contacted with it at its sufficient concentration; or by adding a 1:1

(by volume) solution of chloroform and methanol thereto. The cell or tissue is lysed or homogenized according to the method described in the above (1)c), thereby producing a lysate or a homogenate thereof.

For contacting FAAH or functional FAAH in the lysate or homogenate of a cell or tissue in c) or e) in the above (1), with a substrate, there may be employed a method of adding the substrate to the lysate or homogenate that has been diluted with a buffer having a pH of from 7 to 9 so as to have a protein concentration of preferably from 10 to 100 µg/ml, and reacting them under a temperature condition of from 4° C. to 37° C. The reaction time may be suitably defined depending on the condition such as the amount of the enzyme added, the amount of the substrate added and the reaction temperature. For example, when they are reacted at room temperature, the reaction time may be from 30 to 90 minutes.

For contacting the purified FAAH or functional FAAH in the above (1) d) with a substrate, there may be employed a method of adding the substrate to a lysate or a homogenate that has been diluted with a buffer having a pH of from 7 to 9, and reacting them under a temperature condition of from 4° C. to 37° C. The reaction time may be suitably defined depending on the condition such as the amount of the enzyme added, the amount of the substrate added and the reaction temperature. For example, when they are reacted at room temperature, the reaction time may be from 30 to 90 minutes.

For measuring the amount of the decomposed product of a substrate, the unreacted substrate and the decomposed product in the enzyme reaction solution are separated from each other, and the amount of the decomposed product may be measured. For separating the unreacted substrate from the decomposed product, the water-solubility of the decomposed product, ethanolamine may be utilized. For example, a 1:1 (by volume) solution of chloroform and methanol is added to the enzyme reaction solution in an amount of 2 times the reaction solution, followed by stirring, and then centrifuged, whereby the decomposed product containing in the upper layer, water/ethanol layer may be separated from the unreacted substrate contained in the lower layer, chloroform layer. Alternatively, the system may be mixed with a liquid scintillation cocktail agent of no water absorbability whereby the fat-soluble unreacted radioactive substrate may be taken into the cocktail agent and the decomposed product may be thereby separated from the unreacted substrate. Still alternatively, the unreacted substrate may be separated from the decomposed product through thin-layer chromatography or high-performance liquid chromatography.

In case where a $^3$H- or $^{14}$C-labeled substrate, or a mixture of a labeled substrate and an unlabeled substrate is used, the amount of the decomposed product or the amount of the unreacted substrate may be measured with a liquid scintillation counter, or it may be recorded as an X-ray latent image on an imaging plate and may be measured with an image plate reader.

In case where an unlabeled substrate is used, the absorbance at 205 nm of the system may be monitored through high-performance liquid chromatography, and the amount of the decomposed product or the amount of the unreacted substrate may be thereby measured (Lang et al., Anal. Biochem., Vol. 238, pp. 40-45, 1996).

When the amount of the unreacted substrate is measured, then amount of the unreacted substrate may be subtracted from the amount of the substrate added before the reaction, and the amount of the decomposed product may be thereby obtained. Alternatively, the amount of the decomposed product of the substrate measured in a buffer alone not containing FAAH or functional FAAH, as a control, may be subtracted from the amount of the decomposed product of the substrate with FAAH or functional FAAH, whereby the net amount of the decomposed product of the substrate with FAAH or functional FAAH may be obtained.

The amount of endocannabinoid in a tissue homogenate may be measured, for example, by homogenizing a sample tissue with a 2:1:1 (by volume) solution of chloroform, methanol and 50 mM Tris (pH 8.0), followed by measuring the amount of the endocannabinoid contained in the organic layer (chloroform layer) through liquid chromatography/isotope dilution mass spectrometry (Cravatt et al., Proc., Natl. Acad. Sci. USA, Vol. 98, pp. 9371-9376, 2001).

The amount of endocannabinoid in blood may be measured, for example, as follows: Plasma is separated from a blood sample, and the protein in the plasma is removed through centrifugation along with the same amount of acetone (−20° C.) added thereto. Acetone is evaporated by a nitrogen jet applied to the system, and a 1:2 (by volume) solution of methanol and chloroform is added to it, and the amount of endocannabinoid contained in the organic layer (chloroform layer) is measured through liquid chromatography/isotope dilution mass spectrometry (Giuffraida et al., Eur. J. Pharmacol., Vol. 408, pp. 161-168, 2000).

(3) Step of Selecting Substance that Inhibits the Activity of FAAH or Functional FAAH:

A substance that inhibits the activity of FAAH or functional FAAH may be selected as follows: A test substance is contacted with FAAH or functional FAAH, this is compared with a case not contacted with the test substance, and a substance that decreases the amount of the decomposed product of the substrate may be selected.

Concretely, a test substance is contacted with FAAH or functional FAAH, and this is compared with a case not contacted with a test substance. In this, the substance with which the amount of the decomposed product of the enzyme decreases preferably to ½ or less may be screened for a remedy for urinary frequency and urinary incontinence, a remedy for overactive bladder and/or a remedy for pain.

Alternatively, a test substance having a different concentration is contacted with FAAH or functional FAAH; and based on the amount of the decomposed product of the substrate not contacted with the test substance, as 100%, the relative value (%) of the decomposed product of the substrate contacted with the test substance having a different concentration is obtained; or based on the amount of the decomposed product of the substrate not contacted with the test substance, as 100%, and based on the amount of the decomposed product of the substrate in a case where a known FAAH inhibitor having a sufficient concentration is contacted with FAAH or functional FAAH for a sufficient period of time, as 0%, the relative value (%) of the amount of the decomposed product of the substrate contacted with the test substance having a different concentration is obtained. In an inhibition curve drawn on a graph in which the relative value (%) of the decomposed product of the substrate is on the vertical axis and the concentration of the test substance is on the horizontal axis, the concentration of the test substance that gives a relative value, 50%, of the decomposed product of the substrate ($IC_{50}$ value) is computed; and the substance of which the $IC_{50}$ value is preferably at most 1 µM, more preferably at most 100 nM is screened for a remedy for urinary frequency and urinary incontinence, a remedy for overactive bladder and/or a remedy for pain. For example, the tests of Example 438 to Example 440 are referred to.

Still alternatively, a test substance is administered to a test animal, and the amount of endocannabinoid in the tissue or blood of the animal is compared with each other before and after the test substance administration; and the substance that increases the amount preferably to 1.5 times may be selected for a substance that inhibits the activity of FAAH or functional FAAH, or that is, the substance may be screened for a remedy for urinary frequency and urinary incontinence, a remedy for overactive bladder and/or a remedy for pain.

[2] Test Substance:

Not specifically defined, the test substance for use in the screening method of the present invention includes, for example, commercially-available products (including peptides), various known compound registered in Chemical File (including peptides), compound groups obtained according to combinatorial chemistry technology (Terrett et al., J. Steele. Tetrahedron, Vol. 51, pp. 8135-8173, 1995), microorganisms-derived culture supernatants, plant or sea life-derived natural components, animal tissue extracts, as well as compounds (including peptides) produced through chemical or biological modification of the compounds (including peptides) selected according to the screening method of the present invention.

[3] Pharmaceutical Composition for Treatment of Urinary Frequency and Urinary Incontinence, for Treatment of Overactive Bladder and/or for Treatment of Pain:

As the active ingredient of the pharmaceutical composition of the present invention, usable is a substance that inhibits the activity of FAAH or functional FAAH, in which the inhibitor substance may be selected, for example, according to the screening method of the present invention.

The pharmaceutical composition of the present invention is not limited to a pharmaceutical composition that contains, as the active ingredient thereof, the substance obtained according to the screening method of the present invention, but may include any and every pharmaceutical composition for treatment of urinary frequency and urinary incontinence, for treatment of overactive bladder and/or for treatment of pain that contains, as the active ingredient thereof, a substance to inhibit the activity of FAAH or functional FAAH; and preferably, this is a pharmaceutical composition for treatment of urinary frequency and urinary incontinence, for treatment of overactive bladder and/or for treatment of pain.

The effect for treatment of urinary frequency and urinary incontinence, the effect for treatment of overactive bladder and/or the effect for treatment of pain may be confirmed in the manner as above.

The composition containing, as the active ingredient thereof, a substance that inhibits the activity of FAAH or functional FAAH, for example, DNA, protein (including antibody or antibody fragment), peptide or any other compound may be prepared as a pharmaceutical composition using pharmaceutically acceptable carrier, excipient and/or any other additive generally used in preparation of pharmaceutical compositions, depending on the type of the active ingredient therein.

The administration of the composition can be accompanied by, for example, oral administration via tablets, pills, capsules, granules, fine granules, powders or oral liquids; or parenteral administration via injections such as intravenous, intramuscular or intraarticular injections, suppositories, endermic preparations or intramucosal preparations. Especially for peptides that are digested in stomach, parenteral administration such as intravenous injection is preferred.

The solid composition for oral administration may comprise a mixture of at least one or more active ingredients and at least one inert diluents, for example, lactose, mannitol, glucose, microcrystalline cellulose, hydroxypropyl cellulose, starch, polyvinylpyrrolidone or magnesium aluminometasilicate. In addition to inert diluents, the solid composition may contain other additives, in an ordinary manner, for example, lubricants, disintegrators, stabilizers, solubilizers or solubilization assisting agents. The tablets and pills may be optionally coated with sugar or with gastric or enteric coat film.

The liquid composition for oral administration includes, for example, emulsions, solutions, suspensions, syrups and elixirs, and may contain ordinary inert diluents, for example, purified water or ethanol. In addition to inert diluents, the liquid composition may also contain, for example, moistening agents, suspending agents, sweeteners, aromatics or antiseptics.

Injections for parenteral administration includes aseptic aqueous or non-aqueous solutions, suspensions or emulsions. The aqueous solutions or suspensions may contain, for example, distilled water for injection or physiological saline, as a diluent. The diluents for the non-aqueous solutions or suspensions includes, for example, propylene glycol, polyethylene glycol, vegetable oil (e.g., olive oil), alcohols (e.g., ethanol) or Polysorbate 80. Such compositions may further contain moistening agents, emulsifiers, dispersants, stabilizers, solubilizers or solubilization assisting agents, or antiseptics. Such compositions may be sterilized, for example, by filtration through a bacteria retaining filter, or through addition of a germicide thereto, or through irradiation. If desired, a germ-free solid composition may be prepared, and before use, it may be dissolved in germ-free water or in any other germ-free medium for injection.

The dose of the composition may be suitably determined depending on the intensity of the activity of the active ingredient, or that is, the substance obtained according to the screening method of the present invention, and on the symptom, the age and the sex of the subject for its administration.

For example, in oral administration, the dose may be generally from about 0.1 to 100 mg/day, preferably from 0.1 to 50 mg/day to an adult (body weight of 60 kg). In parenteral administration, the injection dose may be from 0.01 to 50 mg/day, preferably from 0.01 to 10 mg/day.

EXAMPLES

The present invention is described in more detail with reference to the following Examples. The compounds of the present invention should not be limited to the compounds described in the following Examples. Production methods of starting compounds are shown in Reference Examples. Some compounds of the present invention may also be starting compounds for others; and for convenience sake, their production methods may be given herein as Reference Examples. The chemical structural formulae and the physicochemical properties of the compounds obtained in Reference Examples are shown in Tables 1 to 15. The chemical structural formulae of the compounds obtained in Examples are shown in Table 16 to Table 34; and the physicochemical properties thereof are in Tables 35 to 63. The structures of other compounds of the present invention are shown in Tables 65 to 73. These compounds may be readily produced according to the above-mentioned production methods or the methods described in the following Reference Examples and Examples, or according to methods self-obvious to those skilled in the art, or according to modifications of those methods.

When commercially-available kits are used, the written instructions attached thereto may be referred to.

The abbreviations given in this descriptions are as follows:
Rex: Reference Example
Ex: Example
Str: structural formula
DAT: physicochemical properties
¹H-NMR δ(ppm), solvent: nuclear magnetic resonance spectrum
In the physicochemical data of the compounds of Examples;
DMSO: DMSO-d6
MS m/z: mass spectral data
Com: compound
NC: cyano
Ph: phenyl
Me: methyl
diMe: dimethyl
Et: ethyl
Pr: propyl
iPr: isopropyl
Bu: butyl
tBu: tert-butyl
iBu: isobutyl
Pen: pentyl
Hex: hexyl
Hep: heptyl
Oct: octyl
cPr: cyclopropyl
cPen: cyclopentyl
cHex: cyclohexyl
cHep: cycloheptyl
cOct: cyclooctyl
Ac: acetyl
Cl: chloro
diCl: dichloro
CN: cyano
F: fluoro
diF: difluoro
FPh fluorophenyl
NCPh: cyanophenyl
diFPh: difluorophenyl
$O_2N$: nitro
MeO: methoxy
diMeO: dimethoxy
Br: bromo
diBr: dibromo
BrPh: bromophenyl
$F_3C$: trifluoromethyl
AcO: acetoxy
MeOCO or COOMe: methoxycarbonyl
tBuOCO or COOtBu: tert-butoxycarbonyl
HO: hydroxy
HOPh: hydroxyphenyl
$H_2N$: amino
PhCONH: benzoylamino
EtCONH: ethylcarbonylamino
$Me_2N$: dimethylamino
$Et_2N$: diethylamino
BIP2: 2-biphenyl
BIP3: 3-biphenyl
BIP4: 4-biphenyl
BIP5: 5-biphenyl
BIP6: 6-biphenyl
Thiop2: thiophen-2-yl
Thiop3: thiophen-3-yl
Thiop4: thiophen-4-yl
Thiop5: thiophen-5-yl
PYRR1: pyrrolidin-1-yl
PYRR2: pyrrolidin-2-yl
PYRR3: pyrrolidin-3-yl
PYRR4: pyrrolidin-4-yl
PYRR5: pyrrolidin-5-yl
Py2: pyridin-2-yl
Py3: pyridin-3-yl
Py4: pyridin-4yl
Py5: pyridin-5-yl
IM1: imidazol-1-yl
IM2: imidazol-2-yl
IM3: imidazol-3-yl
IM4: imidazol-4-yl
BenzIM1: benzimidazol-1-yl
BenzIM2: benzimidazol-2-yl
BenzIM3: benzimidazol-3-yl
BenzIM4: benzimidazol-4-yl
BenzIM5: benzimidazol-5-yl
BenzIM6: benzimidazol-6-yl
Pyrazi1: pyrazin-1-yl
Pyrazi2: pyrazin-2-yl
Pyrazi3: pyrazin-3-yl
Pyrazi4: pyrazin-4-yl
Pyrazi5: pyrazin-5-yl
Pyrazi6: pyrazin-6-yl
PIPE1: piperidin-1-yl
PIPE2: piperidin-2-yl
PIPE3: piperidin-3-yl
PIPE4: piperidin-4-yl
PIPE5: piperidin-5-yl
PIPE6: piperidin-6-yl
PIPERA: piperazine
PIPERA1: piperazin-1-yl
PIPERA2: piperazin-2-yl
PIPERA3: piperazin-3-yl
PIPERA4: piperazin-4-yl
PIPERA5: piperazin-5-yl
Pyrazo1: pyrazol-1-yl
Pyrazo2: pyrazol-2-yl
Pyrazo3: pyrazol-3-yl
Pyrazo4: pyrazol-4-yl
Pyrazo5: pyrazol-5-yl
Mo: morpholine
Mo2: morpholin-2-yl
Mo3: morpholin-3-yl
Mo4: morpholin-4-yl
Mo5: morpholin-5-yl
Azep: hexahydroazepine
Azep1: hexahydroazepin-1-yl
Azep2: hexyhydroazepin-2-yl
Azep3: hexyhydroazepin-3-yl
Azep4: hexyhydroazepin-4-yl
Thiaz2: thiazol-2-yl
Thiaz3: thiazol-3-yl
Thiaz4: thiazol-4-yl
Thiaz5: thiazol-5-yl
QUI1: quinolin-1-yl
QUI2: quinolin-2-yl
QUI3: quinolin-3-yl
QUI4: quinolin-4-yl
QUI5: quinolin-5-yl
QUI6: quinolin-6-yl
QUI7: quinolin-7-yl
QUI8: quinolin-8-yl
ISOQUI2: isoquinolin-2-yl
ISOQUI3: isoquinolin-3-yl
ISOQUI4: isoquinolin-4-yl
ISOQUI5: isoquinolin-5-yl
ISOQUI6: isoquinolin-6-yl ISOQUI7: isoquinolin-7-yl
ISOQUI8: isoquinolin-8-yl
NAPH1: naphthalen-1-yl
NAPH2: naphthalen-2-yl
NAPH3: naphthalen-3-yl
NAPH4: naphthalen-4-yl
NAPH5: naphthalen-5-yl
TEA: triethylamine
Sal: addition salt
HCl: hydrochloride
oxal: oxalate
fum: fumarate
p-tol: p-toluenesulfonate Reference Example 1

A THF (10 ml) solution containing phenol (471 mg) and diethyl azodicarboxylate (2.83 g, 40% Tol solution) was dropwise added to a THF (15 ml) solution containing tert-butyl 4-(hydroxymethyl)piperidine-1-carboxylate (1.57 g) and triphenylphosphine (1.70 g), at 0° C., followed by stirring at room temperature for 24 hours. Water (40 ml) was added to the reaction solution, followed by extraction with EtOAc. The organic layer was washed with an aqueous 1 M sodium hydroxide solution and saturated brine in that order, and then dried over anhydrous magnesium sulfate. The solvent was evaporated under reduced pressure, and the residue was purified by silica gel column chromatography (eluent; hexane:EtOAc=4:1 (v/v)) to obtain a colorless oil (1.14 g). The resulting compound was dissolved in EtOAc, a 4 M hydrogen chloride/EtOAc solution (9.6 ml) was added thereto, followed by stirring at room temperature for 5 hours to obtain 4-(phenoxymethyl)piperidine hydrochloride (680 mg) as colorless powder.

In the same manner as in Reference Example 1, the compounds of Reference Examples 2 to 27 were obtained.

Reference Example 28

Water (10 ml), sodium carbonate (4.76 g) and tetrakistriphenylphosphine palladium (866 mg) were added in that order to a dimethoxyethane (50 ml) solution containing 3-bromobenzamide (3.0 g) and (3-hydroxyphenyl)boronic acid (2.27 g), followed by stirring at 60° C. for 24 hours. The reaction solution was cooled, diluted with EtOAc, and the organic layer was washed with water and dried over anhydrous magnesium sulfate. The solvent was evaporated under reduced pressure, and the residue was purified by silica gel column chromatography (eluent: EtOAc) to obtain a pale yellow powder (2.74 g). Using the resulting compound and in the same manner as in Reference Example 1, the compound of Reference Example 28 was obtained.

Reference Example 29

A THF (80 ml) solution containing 4-(benzyloxy)phenol (8.0 g) and diethyl azodicarboxylate (26 ml, 40% Tol solution) was dropwise added to a THF (80 ml) solution containing tert-butyl 4-hydroxypiperidine-1-carboxylate (12 g) and triphenylphosphine (16 g) at 0° C., followed by stirring at room temperature for 24 hours. Water (40 ml) was added to the reaction solution, followed by extraction with EtOAc. The organic layer was washed with an aqueous 1 M sodium hydroxide solution and saturated brine in that order, and dried over anhydrous magnesium sulfate. The solvent was evaporated under reduced pressure, and the residue was purified by silica gel column chromatography (eluent: hexane:EtOAc=8:1 (v/v)) to obtain a colorless oil (12.4 g).

10% palladium-carbon (catalytic amount) was added to an ethanol (100 ml) solution containing the resulting compound (5.18 g), followed by stirring in a hydrogen gas atmosphere at room temperature under normal pressure for 16 hours. The catalyst was removed by filtration, and the resulting filtrate was concentrated under reduced pressure to obtain a pale brown solid (4.0 g).

1-(Bromomethyl)-3-fluorobenzene (2.5 ml) and potassium carbonate (2.8 g) were added to an acetonitrile (100 ml) solution containing the resulting compound (4.0 g), followed by heating at 80° C. for 22 hours. The solid matter was removed by filtration, the resulting filtrate was concentrated under reduced pressure, and the residue was purified by silica gel column chromatography (eluent: hexane:EtOAc=8:1 (v/v)) to obtain a colorless solid (5.15 g).

The resulting compound (5.15 g) was dissolved in EtOAc (20 ml), a 4 M hydrogen chloride/EtOAc solution (20 ml) was added thereto, followed by stirring at room temperature for 5 hours. Then, the solvent was evaporated under reduced pressure. The residue was dissolved in water, neutralized with an aqueous 1 M sodium hydroxide solution, and the solid formed was dried to obtain 4-{4-[(3-fluorobenzyl)oxy]phenoxy}piperidine (3.70 g).

In the same manner as in Reference Example 29, the compounds of Reference Examples 30 to 36 were obtained.

Reference Example 37

Diethyl azodicarboxylate (11 ml, 40% Tol solution) was dropwise added to a THF (30 ml) solution containing tert-butyl 4-hydroxypiperidine-1-carboxylate (4.6 g), triphenylphosphine (6.1 g) and 6-chloro-2-pyridinol (2.0 g) at 0° C., followed by stirring at room temperature for 24 hours. Water was added to the reaction solution, followed by extraction with EtOAc. The organic layer was washed with an aqueous 1 M sodium hydroxide solution, and dried over anhydrous magnesium sulfate. The solvent was evaporated under reduced pressure, and the residue was purified by silica gel column chromatography (eluent: hexane:EtOAc=10:1 (v/v)) to obtain tert-butyl 4-[(6-chloro-2-pyridinyl)oxy]-1-piperidinecarboxylate (3.8 g).

(3-Fluorophenyl)methanol (220 mg) and potassium tert-butoxide (200 mg) were added to a DMF (5 ml) solution containing tert-butyl 4-[(6-chloro-2-pyridinyl)oxy]-1-piperidinecarboxylate (500 mg), followed by heating at 100° C. for 30 minutes. Then, (3-fluorophenyl)methanol (220 mg) and potassium tert-butoxide (200 mg) were added thereto, followed by heating at 110° C. for 30 minutes. Water was added to the reaction solution, followed by extraction with EtOAc. The organic layer was washed with an aqueous saturated sodium hydrogencarbonate solution, and dried over anhydrous magnesium sulfate. The solvent was evaporated under reduced pressure, and the residue was purified by silica gel column chromatography (eluent: hexane:EtOAc=10:1 (v/v)) to obtain a white solid (420 mg).

The resulting compound (400 mg) was dissolved in EtOAc (5 ml), a 4 M hydrogen chloride/EtOAc solution (3 ml) was added thereto, followed by stirring overnight at room temperature. The precipitated solid was collected by filtration, washed with EtOAc, and dried under reduced pressure to obtain 2-[(3-fluorobenzyl)oxy]-6-(4-piperidinoxy)pyridine hydrochloride (310 mg).

In the same manner as in Reference Example 37, the compound of Reference Example 38 was obtained.

Reference Example 39

Water (4 ml), sodium carbonate (610 mg) and tetrakistriphenylphosphine palladium (110 mg) were added in that order to a Tol (10 ml) solution containing tert-butyl 4-[(6-chloro-2-pyridinyl)oxy]-1-piperidinecarboxylate (500 mg) and [3-(aminocarbonyl)phenyl]boronic acid (320 mg), followed by heating overnight at 100° C. The reaction solution was cooled and diluted with EtOAc. The organic layer was washed with an aqueous solution of anhydrous sodium hydrogencarbonate, and dried over anhydrous magnesium sulfate. The solvent was evaporated under reduced pressure, and the residue was purified by silica gel column chromatography (eluent: hexane:EtOAc=1:2 (v/v)) to obtain a pale yellow powder (590 mg).

The resulting compound (590 mg) was dissolved in EtOAc (5 ml), and a 4 M hydrogen chloride/EtOAc solution (5 ml) was added thereto, followed by stirring overnight at room temperature. The precipitated solid was collected by filtration, washed with EtOAc, and dried under reduced pressure to obtain 3-[6-(4-piperidinyloxy)-2-pyridinyl]benzamide hydrochloride (440 mg).

Reference Example 40

TEA (4.6 ml) and methanesulfonyl chloride (2.0 ml) were dropwise added to a methylene chloride (80 ml) solution containing tert-butyl 4-(2-hydroxyethyl)piperidine-1-carboxylate (5.0 g) at 0° C., followed by stirring at room temperature for 3 hours. An aqueous sodium hydrogencarbonate solution and methanol were added to the reaction solution, followed by stirring at room temperature for 30 minutes. This was extracted with chloroform, and the organic layer was washed with saturated brine, and dried over anhydrous magnesium sulfate. The solvent was evaporated under reduced pressure, and the residue was purified by silica gel column chromatography (eluent: chloroform:methanol=10:1 (v/v)) to obtain a colorless solid (6.1 g).

Sodium hydride (541 mg, 60% in oil) was added to a DMF (80 ml) solution containing the resulting compound (2.0 g) and phenylpropanol (1.3 g) at 0° C., followed by heating at 100° C. for 20 hours. The reaction solution was cooled, water was added thereto, followed by extraction with EtOAc. This was washed with an aqueous 1 M hydrochloric acid solution, an aqueous saturated sodium hydrogencarbonate solution and saturated brine in that order, and dried over anhydrous magnesium sulfate. The solvent was evaporated under reduced pressure, and the residue was purified by silica gel column chromatography (eluent: chloroform:methanol=20:1 (v/v)) to obtain a yellow oil (1.96 g).

The resulting compound (1.96 g) was dissolved in EtOAc (5 ml), and a 4 M hydrogen chloride/EtOAc solution (10 ml) was added thereto, followed by stirring at room temperature for 2 hours. The solid formed was collected by filtration and dried to obtain 4-[2-(3-phenylpropoxy)ethyl]piperidine hydrochloride (1.55 g).

Reference Example 41

TEA (2.30 ml) and methanesulfonyl chloride (1.22 ml) were dropwise added to a THF (40 ml) solution containing tert-butyl 4-hydroxypiperidine-1-carboxylate (3.02 g) at 0° C., followed by stirring at room temperature for 1 hour. EtOAc (50 ml) and water (50 ml) were added to the reaction solution. The organic layer was washed with aqueous 5% citric acid solution, an aqueous saturated sodium hydrogencarbonate solution and saturated brine in that order, and dried over anhydrous sodium sulfate. The solvent was evaporated under reduced pressure to obtain a pale orange oil. The resulting oil was dissolved in DMA (25 ml), and cesium carbonate (5.38 g) and 4-sulfanylphenol (1.89 g) were added thereto, followed by heating at 50° C. for 2 hours. The reaction solution was cooled, water was added thereto, followed by extraction with EtOAc. The organic layer was washed with an aqueous 1 M hydrochloric acid solution and saturated brine in that order, and dried over anhydrous sodium sulfate. The solvent was evaporated under reduced pressure, and the residue was purified by silica gel column chromatography (eluent: hexane:EtOAc=4:1 (v/v)) to obtain tert-butyl 4-[(4-hydroxyphenyl)sulfanyl]piperidine-1-carboxylate (3.40 g) as colorless powder.

1-(Bromomethyl)-3-fluorobenzene (0.436 ml) and potassium carbonate (670 mg) were added to an acetonitrile (15 ml) solution containing tert-butyl 4-[(4-hydroxyphenyl)sulfanyl]piperidine-1-carboxylate (1.00 g), followed by heating at 80° C. for 2 hours. The reaction solution was cooled, saturated brine was added thereto, followed by extraction with chloroform. The organic layer was dried over anhydrous sodium sulfate, the solvent was evaporated under reduced pressure, and the resulting residue was purified by silica gel column chromatography (eluent: hexane:EtOAc=8:1 (v/v)) to obtain tert-butyl 4-({4-[(3-fluorobenzyl)oxy]phenyl}sulfanyl)piperidine-1-carboxylate (1.50 g) as colorless powder.

Tert-butyl 4-({4-[(3-fluorobenzyl)oxy]phenyl}sulfanyl)piperidine-1-carboxylate (501 mg) was dissolved in EtOAc (5 ml), and a 4 M hydrogen chloride/EtOAc solution (3 ml) was added thereto, followed by stirring at room temperature for 3 hours. Then, the solvent was evaporated under reduced pressure. The residue was dissolved in water, neutralized with an aqueous 1 M sodium hydroxide solution, followed by extraction with chloroform. The organic layer was washed with saturated brine, dried over anhydrous sodium sulfate, and the solvent was evaporated under reduced pressure to obtain 4-({4-[(3-fluorobenzyl)oxy]phenyl}sulfanyl)piperidine (328 mg).

In the same manner as in Reference Example 41, the compound of Reference Example 42 was obtained.

Reference Example 43 mCPBA (1.64 g) was added to a chloroform (20 ml) solution containing tert-butyl 4-({4-[(3-fluorobenzyl)oxy]phenyl}sulfanyl)piperidine-1-carboxylate (1.50 g) obtained in the method of Reference Example 41, at 0° C., followed by stirring at room temperature for 17 hours. The solid was removed by filtration, and an aqueous 10% sodium sulfate solution was added to the filtrate, followed by extraction with chloroform. The organic layer was washed with an aqueous saturated sodium hydrogencarbonate solution, and dried over anhydrous sodium sulfate. The solvent was evaporated under reduced pressure, and the residue was purified by silica gel column chromatography (eluent: hexane:EtOAc=2:1 (v/v)) to obtain a colorless powder (1.58 g). The resulting powder (1.56 g) was dissolved in EtOAc (10 ml), a 4 M hydrogen chloride/EtOAc solution (8 ml) was added thereto, followed by stirring at room temperature for 2 hours. Then, the solid was collected by filtration and washed with EtOAc to obtain 4-({4-[(3-fluorobenzyl)oxy]phenyl}sulfonyl)piperidine hydrochloride (1.13 g) as colorless powder.

In the same manner as in Reference Example 43, the compounds of Reference Examples 44 to 46 were obtained.

Reference Example 47

A THF (5 ml) solution of tert-butyl 4-[(4-hydroxyphenyl)sulfanyl]piperidine-1-carboxylate (495 mg) obtained in the method of Reference Example 41 and diethyl azodicarboxylate (1.04 g, 40% Tol solution) were dropwise added to a THF (5 ml) solution containing cyclohexylmethanol and triphenylphosphine (629 mg), at 0° C., followed by stirring at room temperature for 24 hours. Water (40 ml) was added to the reaction solution, followed by extraction with EtOAc. The organic layer was washed with an aqueous 1 M sodium hydroxide solution and saturated brine in that order, and dried over anhydrous magnesium sulfate. The solvent was evaporated under reduced pressure, and the residue was purified by silica gel column chromatography (eluent: hexane:EtOAc=9:1 (v/v)) to obtain tert-butyl 4-{[4-(cyclohexylmethoxy)phenyl]sulfonyl}piperidine-1-carboxylate (744 mg) as pale yellow oil.

The resulting tert-butyl 4-{[4-(cyclohexylmethoxy)phenyl]sulfonyl}piperidine-1-carboxylate (635 mg) was dissolved in EtOAc (7 ml), and a 4 M hydrogen chloride/EtOAc solution (3.6 ml) was added thereto, followed by stirring at room temperature for 6 hours. The solid was collected by filtration and washed with EtOAc to obtain 4-{[4-(cyclohexylmethoxy)phenyl]sulfonyl}piperidine hydrochloride (485 mg) as colorless powder.

In the same manner as in Reference Example 47, the compound of Reference Example 48 was obtained.

Reference Example 49

Sodium hydride (355 mg, 60% in oil) and benzyl bromide (1.0 ml) were added to a THF (40 ml) solution containing tert-butyl 4-hydroxypiperidine-1-carboxylate (1.5 g), followed by heating at 60° C. for 13 hours. The reaction solution was cooled, water was added thereto, followed by extraction with EtOAc. This was washed with an aqueous 1 M hydrochloric acid solution, an aqueous saturated sodium hydrogencarbonate solution and saturated brine in that order, and dried over anhydrous magnesium sulfate. The solvent was evaporated under reduced pressure, and the residue was purified by silica gel column chromatography (eluent: hexane:EtOAc=10:1 (v/v)) to obtain a colorless oil (1.91 g).

The resulting compound (1.8 g) was dissolved in EtOAc (5 ml), and a 4 M hydrogen chloride/EtOAc solution (15 ml) was added thereto, followed by stirring at room temperature for 3 hours. The reaction solution was diluted with isopropyl ether, and the solid formed was collected by filtration and dried to obtain 4-(benzyloxy)piperidine hydrochloride (1.32 g).

In the same manner as in Reference Example 49, the compounds of Reference Examples 50 to 53 were obtained.

Reference Example 54

Diethyl azodicarboxylate (2.6 ml, 40% Tol solution) was dropwise added to a THF (10 ml) solution containing (3-fluorophenyl)methanol (730 mg), triphenylphosphine (1.5 g) and 6-chloro-3-pyridinol (500 mg) at 0° C., followed by stirring at room temperature for 24 hours. The reaction solution was diluted with EtOAc. The organic layer was washed with an aqueous saturated sodium hydrogencarbonate solution and dried over anhydrous magnesium sulfate. The solvent was evaporated under reduced pressure, and the residue was purified by silica gel column chromatography (eluent: hexane:EtOAc=8:1 (v/v)) to obtain a white solid (810 mg).

Tert-butyl 4-hydroxypiperidine-1-carboxylate (1.0 g) and potassium tert-butoxide (570 mg) were added to a DMF (10 ml) solution containing the resulting white solid (800 mg), followed by heating at 130° C. for 1 hour. Then, potassium tert-butoxide (400 mg) was added thereto, followed by further heating at 130° C. for 1 hour. The reaction solution was cooled to room temperature, diluted with EtOAc, washed with an aqueous saturated sodium hydrogencarbonate solution, and dried over anhydrous magnesium sulfate. The solvent was evaporated under reduced pressure, and the residue was purified by silica gel column chromatography (eluent: hexane:EtOAc=7:1 (v/v)) to obtain a white solid (350 mg).

The resulting compound (345 mg) was dissolved in EtOAc (3 ml), and a 4 M hydrogen chloride/EtOAc solution (2 ml) was added thereto, followed by stirring overnight at room temperature. The solid precipitated was collected by filtration, washed with EtOAc, and dried under reduced pressure to obtain 6-[(3-fluorobenzyl)oxy]-2-(4-piperidinoxy)pyridine hydrochloride (260 mg).

Reference Example 55

[1-(Tert-butoxycarbonyl)piperidin-4-yl]acetic acid (0.60 g) was dissolved in dimethylformamide (12 ml), and 1-[3-(dimethylamino)propyl]-3-ethylcarbodiimide hydrochloride (0.89 g), 1-hydroxybenzotriazole (0.50 g) and benzylamine (0.40 g) were added thereto, followed by stirring at room temperature for 15 hours. Water was added to the reaction solution and stirred for 1 hour. Then, sodium hydrogencarbonate solution was added thereto, followed by extraction with EtOAc. The organic layer was washed with 0.5 M hydrochloric acid and saturated brine in that order. The organic layer was dried over anhydrous magnesium sulfate, the solvent was evaporated under reduced pressure, and the residue was purified by silica gel column chromatography (eluent: hexane:EtOAc=1:2 (v/v)) to obtain a colorless powder (0.69 g).

The resulting compound (0.69 g) was dissolved in EtOAc (10 ml), and a 4 M hydrogen chloride/EtOAc solution (2.2 ml) was added thereto, followed by stirring at room temperature for 20 hours. The reaction solution was concentrated into a dry solid to obtain N-benzyl-2-piperidin-4-ylacetamide hydrochloride (0.62 g).

Reference Example 56

Phosphoric acid (7 ml) and diphosphorus pentoxide (14 g) were heated at 150° C. for 30 minutes, N-methylbenzene-1,2-diamine (1.3 g) and 4-piperidin-4-ylbutanoic acid hydrochloride (1.5 g) were added thereto, followed by heating at 120° C. for 3 hours. The reaction solution was poured into water, neutralized with aqueous sodium hydroxide solution, and then extracted with chloroform. The organic layer was dried over anhydrous magnesium sulfate, the solvent was evaporated under reduced pressure, and the residue was purified by silica gel column chromatography (eluent: chloroform:methanol:aqueous ammonia=10:1:0.1 (v/v/v)) to obtain 1-methyl-2-(3-piperidin-4-ylpropyl)-1H-benzimidazole (1.61 g).

Reference Example 57 and Reference Example 58

Potassium tert-butoxide (1.72 g) was added to a THF (30 ml) solution containing [4-(methoxycarbonyl)benzyl](triphenyl)phosphonium bromide (7.51 g) at 0° C., followed by stirring for 1 hour. A THF (20 ml) solution containing tert-butyl 4-formylpiperidine-1-carboxylate (Beilstein Registry No. 7704210, 2.96 g) was dropwise added to the reaction solution at 0° C., followed by stirring for 14 hours. Water was added to the reaction solution, followed by extraction with EtOAc. The organic layer was washed with saturated brine, and dried over anhydrous sodium sulfate. The solvent was evaporated under reduced pressure, and the residue was purified by silica gel column chromatography (eluent: hexane:EtOAc 9:1 (v/v)) to obtain a yellow oil (3.77 g).

The resulting compound (3.75 g) was dissolved in methanol (20 ml) and THF (10 ml), and an aqueous 1 M sodium hydroxide solution (16.3 ml) was added thereto, followed by stirring at 50° C. for 4 hours. The reaction solution was cooled, and the solvent was evaporated under reduced pressure. This was made acidic with 1 M hydrochloric acid added, and the solid precipitated was collected by filtration and washed with water to obtain a pale brown powder (2.82 g).

Ammonium chloride (2.26 g), 1-ethyl-3-(dimethylaminopropyl)carbodiimide hydrochloride (3.24 g), 1-hydroxybenzotriazole (1.14 g) and TEA (5.88 ml) were added to a DMF (30 ml) solution containing the resulting compound (2.80 g), followed by stirring at room temperature for 32 hours. Water was added to the reaction solution, and the solid precipitated was collected by filtration and washed with water to obtain a pale brown powder (2.61 g).

The resulting compound (2.58 g) was dissolved in EtOAc (15 ml), and a 4 M hydrogen chloride/EtOAc solution (15 ml) was added thereto, followed by stirring at room temperature for 8 hours. The solid formed was collected by filtration, washed with EtOAc, and dried to obtain 4-[(E)-2-piperidin-4-ylvinyl]benzamide hydrochloride (1.92 g) (Reference Example 57).

10% Palladium-carbon (catalytic amount) was added to a methanol (15 ml)/water (5 ml) solution containing 4-[(E)-2-piperidin-4-ylvinyl]benzamide hydrochloride (800 mg), followed by stirring in a hydrogen gas atmosphere at room temperature under normal pressure for 4 hours. The catalyst was removed by filtration, and the resulting filtrate was concentrated under reduced pressure. The resulting solid was recrystallized from ethanol/acetonitrile to obtain 4-(2-piperidin-4-ylethyl)benzamide hydrochloride (451 mg) (Reference Example 58).

Reference Example 59

Sodium triacetoxyborohydride (2.2 g) was added to a dichloromethane (30 ml) solution containing tert-butyl 4-(4-aminophenoxy)-1-piperidinecarboxylate (2.0 g, Beilstein Registry No. 9262581), cyclohexenecarbaldehyde (770 mg) and acetic acid (1.25 g), at 0° C., followed by stirring at room temperature for 2 hours. An aqueous saturated sodium hydrogencarbonate solution was added to the reaction solution, followed by extraction with chloroform. The organic layer was washed with an aqueous saturated sodium hydrogencarbonate solution, and dried over anhydrous magnesium sulfate. The solvent was evaporated under reduced pressure, and the resulting solid was recrystallized from EtOAc/hexane to obtain a pale brown crystal (2.0 g).

Sodium triacetoxyborohydride (1.1 g) was added to a dichloromethane (20 ml) solution containing the resulting crystal (970 mg), an aqueous 37% formaldehyde solution (0.94 ml) and acetic acid (0.75 g), at 0° C., followed by stirring at room temperature for 2 hours. An aqueous saturated sodium hydrogencarbonate solution was added to the reaction solution, followed by extraction with chloroform. The organic layer was washed with an aqueous saturated sodium hydrogencarbonate solution, and dried over anhydrous magnesium sulfate. The solvent was evaporated under reduced pressure, and the resulting oil was dissolved in EtOAc (15 ml). A 4 M hydrogen chloride/EtOAc solution (5 ml) was added thereto, followed by stirring overnight at room temperature. The solid precipitated was collected by filtration, washed with EtOAc, and dried under reduced pressure to obtain N-(cyclohexylmethyl)-N-methyl-4-(4-piperidinyloxy)aniline hydrochloride (820 mg).

Reference Example 60

In an argon stream atmosphere, tris(dibenzylideneacetone)dipalladium (95 mg) was added to a Tol (10 ml) solution containing benzyl 3-iodophenyl ether (1.1 g), tert-butyl 1-piperazinecarboxylate (640 mg), sodium tert-butoxide (500 mg) and 2-biphenylyl(dicyclohexyl)phosphine (70 mg), followed by heating at 80° C. for 1 hour. The reaction solution was cooled, diluted with EtOAc, and the organic layer was washed with saturated brine and dried over anhydrous magnesium sulfate. The solvent was evaporated under reduced pressure, and the residue was purified by silica gel column chromatography (eluent: hexane:EtOAc=5:1 (v/v)) to obtain a brown solid (950 mg).

The resulting solid (940 mg) was dissolved in EtOAc (5 ml), and a 4 M hydrogen chloride/EtOAc solution (5 ml) was added thereto, followed by stirring overnight at room temperature. The solid precipitated was collected by filtration, washed with EtOAc, and dried under reduced pressure to obtain 1-[3-(benzyloxy)phenyl]piperazine dihydrochloride (840 mg).

Reference Example 61

Diethyl azodicarboxylate (4.8 ml, 40% Tol solution) was dropwise added to a THF (60 ml) solution containing 4-(benzyloxy)-2-chlorophenol (1.7 g, Beilstein Registry No. 6582932), triphenylphosphine (2.8 g) and tert-butyl 4-hydroxypiperidine-1-carboxylate (2.1 g) at 0° C., followed by stirring at room temperature for 24 hours. The reaction solution was diluted with EtOAc. The organic layer was washed with aqueous saturated sodium hydrogencarbonate solution, and dried over anhydrous magnesium sulfate. The solvent was evaporated under reduced pressure, and the residue was purified by silica gel column chromatography (eluent: hexane:EtOAc=5:1 (v/v)) to obtain a white solid (2.3 g).

The resulting compound (1.0 g) was dissolved in EtOAc (10 ml), and a 4 M hydrogen chloride/EtOAc solution (10 ml) was added thereto, followed by stirring overnight at room temperature. The solid precipitated was collected by filtration, washed with EtOAc, and dried under reduced pressure to obtain 4-[4-(benzyloxy)-2-chlorophenoxy]piperidine hydrochloride (690 mg).

Reference Example 62

Thionyl chloride (10 ml) was dropwise added to a DMF (5 ml) solution of sodium 4-hydroxybenzenesulfonate (1.00 g), followed by heating at 65° C. for 3 hours. The reaction solution was cooled and Tol (10 ml) was added thereto. The solvent was evaporated under reduced pressure, water was added, followed by extraction with chloroform. The organic layer was washed with aqueous saturated brine, and dried over anhydrous magnesium sulfate. The solvent was evaporated under reduced pressure to obtain a colorless solid (587 mg).

At 0° C., an acetonitrile (10 ml) solution of the previously-obtained compound (579 mg) was added to an acetonitrile (10 ml) solution containing 1-tert-butoxycarbonylpiperazine (672 mg) and pyridine (0.58 ml), followed by stirring at room temperature for 2 hours. The solvent was evaporated under reduced pressure, Tol (10 ml) was added thereto and azeotroped. Then, water was added, followed by extraction with EtOAc. The organic layer was washed with saturated brine and dried over anhydrous magnesium sulfate. The solvent was evaporated under reduced pressure to obtain a colorless solid (0.41 g).

Potassium carbonate (248 mg) was added to an acetonitrile (20 ml) solution containing the resulting compound (0.41 g) and 1-(bromomethyl)-3-fluorobenzene (340 mg), followed by heating at 80° C. for 3 hours. The solid was removed through filtration, the resulting filtrate was concentrated under reduced pressure, and the residue was purified by silica gel column chromatography (eluent: hexane:EtOAc=5:1 (v/v)) to obtain a colorless solid (469 mg).

The resulting compound (460 mg) was dissolved in a mixed solution of EtOAc (5 ml) and THF (5 ml), and 4 M hydrogen chloride/EtOAc solution (20 ml) was added thereto, followed by stirring at 70° C. for 3 hours. Then, the solvent was evaporated under reduced pressure. The residue was dissolved in water, neutralized with an aqueous 1 M sodium hydroxide solution, and the solid formed was dried to obtain 4-{4-[(3-fluorobenzyl)oxy]benzenesulfonyl}piperazine (304 mg).

Reference Example 63

Diethyl azodicarboxylate (3.3 ml, 40% Tol solution) was dropwise added to a THF (30 ml) solution containing 4-(benzyloxy)-3-chlorophenol (1.2 g, Beilstein Registry No. 5527577), triphenylphosphine (1.9 g) and tert-butyl 4-hydroxypiperidine-1-carboxylate (1.5 g) at 0° C., followed by stirring at room temperature for 24 hours. The reaction solution was diluted with EtOAc, and the organic layer was washed with an aqueous saturated sodium hydrogencarbonate solution and dried over anhydrous magnesium sulfate. The solvent was evaporated under reduced pressure, and the residue was purified by silica gel column chromatography (eluent: hexane:EtOAc=5:1 (v/v)) to obtain a white solid (1.7 g).

The resulting compound (1.6 g) was dissolved in EtOAc (20 ml), and a 4 M hydrogen chloride/EtOAc solution (15 ml) was added thereto, followed by stirring overnight at room temperature. The solid precipitated was collected by filtration, washed with EtOAc, and dried under reduced pressure to obtain 4-[4-(benzyloxy)-3-chlorophenoxy]piperidine hydrochloride (1.3 g).

Reference Example 64

3-Fluorobenzenesulfonyl chloride (3.2 g) was added to a pyridine (30 ml) solution containing tert-butyl 4-(4-aminophenoxy)-1-piperidinecarboxylate (4.0 g, Beilstein Registry No. 9262581) at 0° C., followed by stirring overnight at room temperature. The solvent was evaporated under reduced pressure, and diluted with chloroform. The organic layer was washed with an aqueous 10% citric acid solution, water and saturated brine in that order, and dried over anhydrous sodium sulfate. The solvent was evaporated under reduced pressure, and the residue was purified by silica gel column chromatography (eluent: chloroform:methanol=60:1 (v/v)) to obtain a white solid (5.3 g).

Potassium carbonate (280 mg) and methyl iodide (0.28 ml) were added to an acetonitrile (10 ml) solution containing the resulting compound (700 mg), followed by stirring at 50° C. for 3 hours. The reaction solution was diluted with EtOAc, the organic layer was washed with water and saturated brine, and dried over anhydrous magnesium sulfate. The solvent was evaporated under reduced pressure, and the residue was purified by silica gel column chromatography (eluent: hexane:EtOAc=3:1 (v/v)) to obtain a colorless oil (700 mg).

The resulting oil (700 mg) was dissolved in EtOAc (10 ml), and a 4 M hydrogen chloride/EtOAc solution (5 ml) was added thereto, followed by stirring overnight at room temperature. The solid precipitated was collected by filtration, washed with EtOAc, and dried under reduced pressure to obtain 3-fluoro-N-methyl-N-[4-(4-piperidinyloxy)phenyl]benzenesulfonamide hydrochloride (480 mg).

Reference Example 65

1-Ethyl-3-(dimethylaminopropyl)carbodiimide hydrochloride (630 mg) and 1-hydroxybenzotriazole (440 mg) were added to a DMF (10 ml) solution containing 1-[(benzyloxy)carbonyl]-4-(tert-butoxycarbonyl)-2-piperidinecarboxylic acid (1.0 g), followed by stirring at room temperature for 1 hour. Then, an aqueous concentrated ammonia (2 ml) was added thereto, followed by stirring at room temperature for 3 hours. Water was added to the reaction solution, and the solid precipitated was collected by filtration, washed with water and dried under reduced pressure to obtain a colorless solid (870 mg).

The resulting solid (860 mg) was dissolved in EtOAc (10 ml), and a 4 M hydrogen chloride/EtOAc solution (5 ml) was added thereto, followed by stirring overnight at room temperature. The precipitated solid was collected by filtration, washed with EtOAc and dried under reduced pressure to obtain benzyl 2-(aminocarbonyl)-1-piperazinecarboxylate hydrochloride (700 mg).

Reference Example 66

Pyridine (1.62 ml) and 4-nitrophenyl chlorocarbonate (2.22 g) were added to an acetonitrile (20 ml) solution containing methyl 4-(hydroxymethyl)benzoate at 0° C., followed by stirring at room temperature for 2 hours. An aqueous 5% citric acid solution was added to the reaction solution, followed by extraction with EtOAc. The organic layer was washed with an aqueous saturated hydrogencarbonate solution and saturated brine, and dried over anhydrous sodium sulfate. The solvent was evaporated under reduced pressure, and the residue was purified by silica gel column chromatography (eluent: hexane:EtOAc=4:1 (v/v)) to obtain a pale brown powder (2.39 g).

Tert-butyl piperazine-1-carboxylate (1.47 g) was added to an acetonitrile (30 ml) solution containing the resulting compound (2.37 g), followed by stirring at room temperature for 8 hours. The reaction solution was diluted with EtOAc and washed with an aqueous 0.5 M sodium hydroxide solution. The organic layer was washed with saturated brine, dried over anhydrous sodium sulfate, and the solvent was evaporated under reduced pressure. The resulting residue was purified by silica gel column chromatography (eluent: hexane:EtOAc=2:1 (v/v)) to obtain a colorless solid (3.32 g).

Methanol (0.34 ml) and an aqueous 1 M sodium hydroxide solution (8.52 ml) were added to a THF (30 ml) solution containing the resulting compound (3.30 g), followed by stirring at room temperature for 26 hours. The solvent was evaporated under reduced pressure, an aqueous 1 M hydrochloric acid solution was added to the residue, followed by extraction with chloroform. The organic layer was washed with saturated brine, and dried over anhydrous sodium sulfate, and the solvent was evaporated under reduced pressure. The resulting residue was recrystallized from hexane/EtOAc to obtain a colorless powder (2.37 g).

Ammonium chloride (321 mg), 1-ethyl-3-(dimethylaminopropyl)carbodiimide hydrochloride (767 mg), 1-hydroxybenzotriazole (270 mg) and TEA (0.83 ml) were added to a DMF (10 ml) solution containing the resulting compound (729 mg), followed by stirring at room temperature for 3 hours. Water was added to the reaction solution, and the solid precipitated was collected by filtration, and washed with water to obtain a pale brown powder (722 mg).

The resulting compound (700 mg) was dissolved in EtOAc (6 ml), a 4 M hydrogen chloride/EtOAc solution (4.8 ml) was added thereto, followed by stirring at room temperature for 3 hours. The solid formed was collected by filtration, washed with EtOAc, and dried to obtain 4-(aminocarbonyl)benzyl piperazine-1-carboxylate hydrochloride (541 mg).

Reference Example 67

A THF (5 ml) solution containing methyl 4-hydroxybenzoate (460 mg) and diethyl azodicarboxylate (0.71 ml) was dropwise added to a THF (5 ml) solution containing cyclohexylmethanol (510 mg) and triphenylphosphine (1.18 g) at 0° C., followed by stirring at room temperature for 24 hours. An aqueous 1 M sodium hydroxide solution (40 ml) was added to the reaction solution, followed by extraction with EtOAc The organic layer was washed with saturated brine and dried over anhydrous sodium sulfate. The solvent was evaporated under reduced pressure, and the residue was purified by silica gel column chromatography (eluent: hexane: EtOAc=4:1 (v/v)) to obtain a colorless solid (930 mg).

An aqueous 1 M sodium hydroxide solution (4.4 ml) was added to a methanol (5 ml)/THF (3 ml) solution containing the resulting compound (920 mg), followed by stirring at 50° C. for 6 hours. This was cooled to room temperature, and EtOAc (40 ml) and water (30 ml) were added thereto, followed by stirring. The organic layer was extracted with an aqueous 1 M sodium hydroxide solution. The aqueous layers were combined and made to have a pH of 1 with concentrated hydrochloric acid. Then, the aqueous layer was extracted with chloroform, and then dried over anhydrous sodium sulfate. The solvent was evaporated under reduced pressure, and the residue was recrystallized from hexane/EtOAc to obtain 4-(cyclohexylmethoxy)benzoic acid (600 mg).

1-Ethyl-3-(dimethylaminopropyl)carbodiimide hydrochloride (359 mg) and 1-hydroxybenzotriazole (254 mg) were added to a DMF (10 ml) solution containing the resulting compound (370 mg) and tert-butyl 1-piperazinecarboxylate (350 mg), followed by stirring at room temperature for 12 hours. Water was added to the reaction solution, and the solid precipitated was collected by filtration, washed with water and dried under reduced pressure to obtain a colorless solid (610 mg).

The resulting compound (600 mg) was dissolved in EtOAc (6 ml), and a 4 M hydrogen chloride/EtOAc solution (4 ml) was added thereto, followed by stirring overnight at room temperature. The solid precipitated was collected by filtration, washed with EtOAc and dried under reduced pressure to obtain 1-[4-(cyclohexylmethoxy)benzoyl]piperazine hydrochloride (580 mg).

In the same manner as in Reference Example 67, the compounds of Reference Examples 68 to 72 were obtained.

Reference Example 73

At −70° C., a 1.59 M normal-butyllithium/THF solution (14.6 ml) was added to s 2 M dimethylamine/THF solution (11.6 ml), followed by stirring for 10 minutes. This was warmed to 0° C., and 3-chloro-5-hydroxypyridine (1.00 g) was added thereto, followed by stirring overnight at room temperature. Ethanol (15 ml) was added, and the solvent was evaporated under reduced pressure. Water was added to the residue, followed by extraction with chloroform. The organic layer was washed with saturated brine, and dried over anhydrous magnesium sulfate. The solvent was evaporated under reduced pressure, and the residue was purified by silica gel column chromatography (eluent: chloroform:methanol=10:1 (v/v)) to obtain 3-dimethylamino-5-hydroxypyridine (176 mg).

Reference Example 74

Tris-dibenzylideneacetone palladium (21 mg), 2,2'-bis (diphenylphosphino)-1,1'-binaphthyl (124 mg) and sodium tert-butoxide (160 mg) were added in that order to a Tol (10 ml) solution containing 3-benzyloxy-5-bromopyridine (400 mg) and morpholine (158 mg), followed by heating at 85° C. for 4 hours. The solvent was evaporated under reduced pressure, and the residue was purified through silica gel column chromatography (eluent: chloroform:methanol=20:1 (v/v)) to obtain a colorless oil (372 mg).

10% Palladium-carbon (catalytic amount) was added to an ethanol (20 ml) solution containing the resulting compound (370 mg), and in a hydrogen gas atmosphere, this was stirred at room temperature and under normal pressure for 1.5 hours. The catalyst was removed by filtration, and the resulting filtrate was concentrated under reduced pressure to obtain 5-hydroxy-3-morpholinylpyridine (248 mg).

In the same manner as in Reference Example 74, the compounds of Reference Examples 75 and 76 were obtained.

Reference Example 77

Sodium methoxide (393 mg) was added to a methanol (20 ml) solution containing 5-(benzenesulfonyloxy)-2-(bromomethyl)pyridine (Beilstein Registry No. 7430370, 800 mg), followed by stirring at room temperature for 4 hours. Water was added to the reaction solution, followed by extraction with EtOAc. The organic layer was washed with saturated brine, and dried over anhydrous magnesium sulfate. The solvent was evaporated under reduced pressure, and the residue was purified by silica gel column chromatography (eluent: EtOAc) to obtain 6-(methoxymethyl)pyridin-3-ol (200 mg).

Reference Example 78

TEA (0.21 ml) and di-tert-butyl dicarbonate (463 mg) were added in that order to a THF (10 ml) solution of 3-benzyloxy-5-aminopyridine (250 mg), followed by heating at 60° C. for 3 h ours. The solvent was evaporated under reduced pressure, water was added thereto, followed by extraction with EtOAc. The organic layer was washed with an aqueous saturated sodium hydrogencarbonate solution and saturated brine, and then dried anhydrous magnesium sulfate. The solvent was evaporated under reduced pressure, and the residue was purified by silica gel column chromatography (eluent: hexane:EtOAc=1:1 (v/v)) to obtain a colorless solid (153 mg).
10% Palladium-carbon (catalytic amount) was added to an ethanol (20 ml) solution containing the resulting compound (240 mg), and in a hydrogen gas atmosphere, this was stirred at room temperature under normal pressure for 1.5 hours. The catalyst was removed by filtration, and the resulting filtrate was concentrated under reduced pressure to obtain tert-butyl (5-hydroxypyridin-3-yl)carbamate (167 mg).

Reference Example 79

At 0° C., a THF (10 ml) suspension of sodium hydride (60% oil mixture, 139 mg) was added to a THF (10 ml) solution of methyl diethylphosphonoacetate (732 mg), followed by stirring for 15 minutes. Then, 5-(benzyloxy)nicotinaldehyde (495 mg) was added, followed by stirring at room temperature for 4 hours. Water was added to the reaction solution, followed by extraction with EtOAc. The organic layer was washed with saturated brine, and dried over anhydrous magnesium sulfate. The solvent was evaporated under reduced pressure to obtain a colorless solid (680 mg).
10% Palladium-carbon (catalytic amount) was added to an ethanol (20 ml) solution containing the resulting compound (330 mg), and in a hydrogen gas atmosphere, this was stirred at room temperature under normal pressure for 2 hours. The catalyst was removed by filtration, and the resulting filtrate was concentrated under reduced pressure to obtain methyl 3-(5-hydroxypyridin-3-yl)propanoate (150 mg).

Reference Example 80

At −78° C., a THF (30 ml) solution of methyl 5-(benzyloxy)nicotinate (3.52 g) was added to a THF (100 ml) suspension of lithium aluminium hydride (1.49 g), followed by stirring for 15 minutes and then stirring at room temperature for 2 hours. The reaction solution was cooled to 0° C., and then water (1.49 ml), an aqueous 15% sodium hydroxide solution (1.49 ml) and water (4.47 ml) were added thereto in that order. The solid was removed by filtration, and the resulting filtrate was concentrated under reduced pressure. The residue was purified by silica gel column chromatography (eluent: chloroform:methanol=10:1 (v/v)) to obtain a colorless solid (1.41 g).
Tert-butyl bromoacetate (609 mg), tetrabutylammonium hydrogensulfate (35 mg) and an aqueous 50% sodium hydroxide solution (2 ml) were added in that order to a benzene (20 ml) solution containing the resulting compound (450 mg), followed by stirring overnight at room temperature. This was neutralized with an aqueous 1 M hydrochloric acid, followed by extraction with EtOAc. The organic layer was washed with saturated brine, and dried over anhydrous magnesium sulfate. The solvent was evaporated under reduced pressure, and the residue was purified by silica gel column chromatography (eluent: hexane:EtOAc=6:4 (v/v)) to obtain a colorless oil (576 mg).
10% palladium-carbon (catalytic amount) was added to an ethanol (20 ml) solution containing the resulting compound (570 mg), and in a hydrogen gas atmosphere, this was stirred at room temperature under normal pressure for 1 hour. The catalyst was removed by filtration, and the resulting filtrate was concentrated under reduced pressure. The residue was purified by silica gel column chromatography (eluent: chloroform:methanol=15:1 (v/v)) to obtain tert-butyl[(5-hydroxypyridin-3-yl)methoxy]acetate (400 mg).

Reference Example 81

Pentamethylbenzene (826 mg) was added to a TFA (10 ml) solution containing methyl (2E)-3-[5-(benzyloxy)pyridin-3-yl]acrylate (300 mg), followed by stirring overnight at 60° C. The solvent was evaporated under reduced pressure, and the residue was purified by silica gel column chromatography (eluent: chloroform:methanol=10:1 (v/v)) to obtain tert-butyl (5-hydroxypyridin-3-yl)acetate (180 mg).

Reference Example 82

Diisopropylethylamine (2.05 ml) and methoxymethyl chloride (0.89 ml) were added in that order to a THF (60 ml) solution of methyl 3-hydroxynicotinate (1.50 g), and then stirred overnight at room temperature. The solvent was evaporated under reduced pressure, water was added thereto, followed by extraction with chloroform. The organic layer was washed with saturated brine and dried over anhydrous magnesium sulfate. The solvent was evaporated under reduced pressure to obtain a colorless oil (2.01 g).
At −78° C., a THF (20 ml) solution of the resulting compound (1.98 g) was added to a THF (50 ml) suspension of lithium aluminium hydride (838 mg), followed by stirring for 30 minutes and then stirring at room temperature for 2 hours. The reaction solution was cooled to 0° C., and water (0.84 ml), an aqueous 15% sodium hydroxide solution (0.84 ml) and water (2.52 ml) were added thereto in that order. The solid was removed by filtration, and the resulting filtrate was concentrated under reduced pressure, and the residue was purified by silica gel column chromatography (eluent: EtOAc) to obtain a colorless oil (838 mg).
Acetic anhydride (1.39 ml) was added to a pyridine (10 ml) solution containing the resulting compound (828 mg), followed by stirring at room temperature for 1.5 hours. The solvent was evaporated under reduced pressure, Tol (10 ml) was added thereto and azeotroped to obtain a colorless oil (1.01 g).
4 M hydrogen chloride/dioxane solution (3.58 ml) was added to a dioxane (10 ml) solution of the resulting compound (1.01 g), followed by stirring at room temperature for 1 hour. The solvent was evaporated under reduced pressure to obtain (5-hydroxypyridin-3-yl)methyl acetate hydrochloride (973 mg).

Reference Example 95

Triphenylphosphine (2.8 g) was added to a Tol (50 ml) solution of 3-cyanobenzyl bromide (2.0 g), followed by stirring at 80° C. for 5 hours. This was cooled to room temperature, and the precipitated solid was collected by filtration, and washed with Tol. This was dried under reduced pressure to obtain (3-cyanobenzyl)(triphenyl)phosphonium bromide (3.4 g).
Under ice cooling, sodium hydride (60% oil, 141 mg) was added to a DMF (20 ml) solution of (3-cyanobenzyl)(triphenyl)phosphonium bromide (1.6 g) and tert-butyl 4-formyl-1-piperidinecarboxylate (0.75 g), followed by stirring overnight at room temperature. The reaction liquid was diluted with EtOAc, washed with water, and dried over anhydrous magnesium sulfate. The solvent was evaporated, and the resulting residue was purified by silica gel column chromatography (eluent: hexane:EtOAc=6:1 (v/v)) to obtain an oil.
10% Palladium-carbon (100 mg) was added to an EtOAc (30 ml) solution of the resulting oil, followed by stirring in a hydrogen stream atmosphere for 2 hours. The catalyst was removed with Celite, and the solvent was concentrated to obtain an oil. The resulting oil was dissolved in EtOAc (10 ml), and 4 M hydrogen chloride/EtOAc solution (5 ml) was added thereto, then stirred at room temperature for 6 hours, and then concentrated. The resulting solid was washed with ether and dried under reduced pressure to obtain 3-[2-(4-piperidinyl)ethyl]benzonitrile hydrochloride (506 mg).

In the same manner as in Reference Example 95, the compounds of Reference Examples 96 to 101 were obtained.

Reference Example 102

Triphenylphosphine (85.8 g) was added to a Tol (400 ml) solution of methyl 3-bromomethylbenzoate (50.0 g), followed by stirring at 80° C. for 10 hours. After this was cooled to room temperature, the crystal precipitated was collected by filtration and washed with Tol. This was dried under reduced pressure to obtain (3-methoxycarbonylbenzyl)(triphenyl)phosphonium bromide (107.6 g).

Under ice cooling, potassium tert-butoxide (22.5 g) was added to a DMF (250 ml) solution of (3-methoxycarbonylbenzyl)(triphenyl)phosphonium bromide (84.6 g), followed by stirring at room temperature for 30 minutes. Then, a DMF (50 ml) solution of tert-butyl 4-formyl-1-piperidinecarboxylate (30.6 g) was added to it under ice cooling, and then stirred overnight at room temperature. Acetic acid (11.5 ml) was added to the reaction liquid, followed by stirring at room temperature for 1 hour. Then, this was diluted with EtOAc, washed with water and saturated brine, and dried over anhydrous sodium sulfate. The solvent was evaporated under reduced pressure, and the resulting residue was purified by silica gel column chromatography (eluent: hexane:EtOAc=7:1 (v/v)). The residue was dissolved in EtOAc, activated charcoal was added thereto, followed by stirring at room temperature for 2 hours. Activated charcoal was removed with Celite, and the solvent was evaporated under reduced pressure to obtain a colorless oil.

10% Palladium-carbon (4.58 g) was added to an EtOAc (400 ml) solution of the resulting oil, followed by stirring in a hydrogen stream atmosphere for 2 hours. The catalyst was removed with Celite, and the solvent was concentrated to obtain tert-butyl 4-{2-[3-(methoxycarbonyl)phenyl]ethyl}-1-piperidinecarboxylate (45.4 g).

In the same manner as in Reference Example 102, the compound of Reference Example 103 was obtained.

Reference Example 104

Aqueous 1 M sodium hydroxide solution (196 ml) was added to a THF (200 ml)/methanol (50 ml) mixed solution of tert-butyl 4-{2-[3-(methoxycarbonyl)phenyl]ethyl}-1-piperidinecarboxylate (45.4 g), followed by stirring at 60° C. for 2 hours. The organic solvent was evaporated under reduced pressure, and under ice cooling, 0.5 M hydrochloric acid (400 ml) was added to the residue. The reaction liquid was diluted with EtOAc, washed with water and saturated brine, and dried over anhydrous sodium sulfate. The solvent was evaporated to obtain 3-{2-[1-(tert-butoxycarbonyl)-4-piperidinyl]ethyl}benzoic acid (43.5 g) was obtained.

In the same manner as in Reference Example 104, the compound of Reference Example 105 was obtained.

Reference Example 106

3-{2-[1-(Tert-butoxycarbonyl)-4-piperidinyl]ethyl}benzoic acid (17.8 g) was dissolved in DMF (200 ml), and 1-[3-(dimethylamino)propyl]-3-ethylcarbodiimide hydrochloride (15.4 g) and 1-hydroxybenzotriazole (10.8 g) were added thereto, followed by stirring at room temperature for 2 hours. Ammonium chloride (8.57 g) and TEA (22.3 ml) were added to the reaction liquid, followed by stirring overnight at room temperature. An aqueous saturated sodium hydrogencarbonate solution was added to the reaction liquid, and the precipitated crystal was collected by filtration and dried to obtain tert-butyl 4-{2-[3-(aminocarbonyl)phenyl]ethyl}-1-piperidinecarboxylate (10.8 g).

In the same manner as in Reference Example 106, the compounds of Reference Examples 107 to 118 were obtained.

Reference Example 119

Tert-butyl 4-[2-(4-{[(2-hydroxyethyl)amino]carbonyl}phenyl)ethyl]piperidine-1-carboxylate (280 mg), carbon tetrabromide (247 mg) and 2,6-lutidine (103 µl) were dissolved in dichloromethane (5.6 ml), and under ice cooling, triphenylphosphine (195 mg) was added thereto, followed by stirring at room temperature for 3 hours. The solvent was evaporated, and the residue was purified by silica gel column chromatography (eluent: hexane:EtOAc=3:7 (v/v)) to obtain tert-butyl 4-{2-[4-(1-aziridinylcarbonyl)phenyl]ethyl}-1-piperidinecarboxylate (136 mg) as a colorless oil.

Reference Example 120

Tert-butyl 4-{2-[3-(aminocarbonyl)phenyl]ethyl}-1-piperidinecarboxylate (13.8 g) was dissolved in EtOAc (200 ml), and 4 M hydrogen chloride/EtOAc solution (130 ml) was added thereto, followed by stirring at room temperature for 4 hours, and then concentrated. Acetonitrile was added to the resulting residue, followed by heating, and the precipitated crystal was collected by filtration, washed with EtOAc, and dried under reduced pressure to obtain 3-[2-(4-piperidinyl)ethyl]benzamide hydrochloride (11.2 g).

In the same manner as in Reference Example 120, the compounds of Reference Examples 121 to 139 were obtained.

Reference Example 140

In an argon stream atmosphere, sodium carbonate (0.43 g) and tetrakis(triphenylphosphine)palladium (80 mg) were added to a Tol (6 ml)/water (2 ml) solution of tert-butyl 4-[2-(3-bromophenyl)ethyl]-1-piperidinecarboxylate (0.50 g) and phenylboronic acid (0.20 g), followed by heating with stirring at 100° C. for 7 hours. This was cooled to room temperature, diluted with EtOAc, and washed with aqueous saturated sodium hydrogencarbonate solution. This was dried over anhydrous magnesium sulfate, then the solvent was evaporated, and the resulting residue was purified by silica gel column chromatography (eluent: hexane:EtOAc=10:1 (v/v)) to obtain tert-butyl 4-[2-(3-biphenyl)ethyl]-1-piperidinecarboxylate (0.41 g).

4 M hydrogen chloride/EtOAc (1.5 ml) was added to an EtOAc (4 ml) solution of tert-butyl 4-[2-(3-biphenyl)ethyl]-1-piperidinecarboxylate (0.41 g), followed by stirring overnight at room temperature. The precipitated crystal was collected by filtration, washed with EtOAc/hexane and dried under reduced pressure to obtain 4-[2-(3-biphenyl)ethyl]piperidine hydrochloride (0.31 g).

In the same manner as in Reference Example 140, the compounds of Reference Examples 141 and 142 were obtained.

Reference Example 143

Under ice cooling, di-tert-butyl dicarbonate (2.6 g) was added to a dichloromethane (50 ml) solution of 4,4'-(1,3-propane-diyl)dipiperidine (5.0 g), followed by stirring overnight at room temperature. The reaction liquid was diluted with chloroform, washed with saturated brine, and dried over anhydrous magnesium sulfate. The solvent was evaporated, and the resulting residue was purified by silica gel column chromatography (eluent: chloroform:methanol:aqueous concentrated ammonia=4:1:0.1 (v/v)) to obtain tert-butyl 4-[3-(4-piperidinyl)propyl]-1-piperidinecarboxylate (2.2 g).

In an argon atmosphere, sodium tert-butoxide, (0.52 g), tris(dibenzylideneacetone)dipalladium (100 mg) and 2-(dicyclohexylphosphino)biphenyl (76 mg) were added to a Tol (22 ml) solution of 2-chloro-6-methylpyridine (0.56 g) and tert-butyl 4-[3-(4-piperidinyl)propyl]-1-piperidinecarboxylate (1.1 g), followed by heating with stirring at 100° C. for 1 hour. This was cooled to room temperature, diluted with EtOAc, and washed with aqueous saturated sodium hydrogencarbonate solution. This was dried over anhydrous magnesium sulfate, the solvent was evaporated, and the resulting residue was purified by silica gel column chromatography (eluent: hexane:EtOAc=10:1 (v/v)) to obtain tert-butyl 4-{3-[1-(6-methyl-2-pyridinyl)-4-piperidyl]propyl}-1-piperidinecarboxylate (1.3 g).

4 M hydrogen chloride/EtOAc (10 ml) was added to an EtOAc (25 ml) solution of tert-butyl 4-{3-[1-(6-methyl-2-pyridinyl)-4-piperidyl]propyl}-1-piperidinecarboxylate (1.3 g), followed by stirring overnight at room temperature. The reaction liquid was concentrated, then 2-propanol/diethyl ether was added thereto, followed by stirring. The precipitated solid was collected by filtration, and dried under reduced pressure to obtain 2-methyl-6-{4-[3-(4-piperidinyl)propyl]-1-piperidyl}pyridine dihydrochloride (1.1 g).

In the same manner as in Reference Example 143, the compounds of Reference Examples 144 and 145 were obtained.

Reference Example 146

Methanesulfonyl chloride (2.7 ml) was dropwise added to a methylene chloride (200 ml) solution of tert-butyl 4-(3-hydroxypropyl)piperidine-1-carboxylate (8.00 g) and TEA (4.8 ml) at 0° C., followed by stirring overnight at room temperature. The reaction liquid was washed with aqueous saturated sodium hydrogencarbonate solution and saturated brine, then dried over anhydrous magnesium sulfate, and the solvent was evaporated. The residue was purified by silica gel column chromatography (eluent: EtOAc:hexane=1:3 (v/v)) to obtain tert-butyl 4-{3-[(methylsulfonyl)oxy]propyl}piperidine-1-carboxylate (10.1 g).

A DMI (20 ml) suspension of tert-butyl 4-{3-[(methylsulfonyl)oxy]propyl}piperidine-1-carboxylate (1.00 g), 1-piperazin-1-yl-isoquinoline dihydrochloride (980 mg), cesium carbonate (1.02 g) and sodium iodide (467 mg) was stirred at 140° C. for 1 hour. EtOAc was added to the reaction liquid, washed with water and aqueous saturated sodium hydrogencarbonate solution in that order, then dried over anhydrous magnesium sulfate, and the solvent was evaporated. The residue was purified by silica gel column chromatography (eluent: hexane:EtOAc=1:1 (v/v)) to obtain tert-butyl 4-[3-(4-isoquinolin-1-ylpiperazin-1-yl)propyl]piperidine-1-carboxylate (1.07 g) as a pale yellow oil.

4 M hydrogen chloride/EtOAc solution (5.0 ml) was dropwise added to an EtOAc (15 ml) solution of tert-butyl 4-[3-(4-isoquinolin-1-ylpiperazin-1-yl)propyl]piperidine-1-carboxylate (1.44 g), followed by stirring overnight. The solvent was evaporated, the solid was washed with EtOAc and collected by filtration to obtain 1-[4-(3-piperidin-4-ylpropyl)piperazin-1-yl]isoquinoline dihydrochloride (1.32 g) as a white solid.

In the same manner as in Reference Example 146, the compound of Reference Example 154 was obtained.

Reference Example 147

4-Nitrophenyl chloroformate (7.0 g) was added to a dichloromethane (100 ml) solution of methyl 5-hydroxynicotinate (5.3 g) and diisopropylethylamine (6.1 ml), followed by stirring at room temperature for 1 hour. The reaction liquid was washed with water, and dried over anhydrous magnesium sulfate. The solvent was evaporated, and the resulting solid was washed with EtOAc/hexane and dried under reduced pressure to obtain methyl 5-{[(4-nitrophenoxy)carbonyl]oxy}nicotinate (8.4 g).

In the same manner as in Reference Example 147, the compound of Reference Example 148 was obtained.

Reference Example 151

A DMF (15 ml) solution of 3-{2-[1-(tert-butoxycarbonyl)-4-piperidinyl]ethyl}benzoic acid (1.25 g), 1-[3-(dimethylamino)propyl]-3-ethylcarbodiimide hydrochloride (863 mg) and 1-hydroxybenzotriazole (608 mg) was stirred at room temperature for 1 hour, and then a TEA (1.6 ml) solution of 2-bromoethylamine hydrobromide (2.30 g) was added thereto, followed by stirring overnight. Aqueous saturated sodium hydrogencarbonate solution was added to the reaction liquid, followed by extraction with EtOAc, then washed with saturated brine, and dried over anhydrous magnesium sulfate, and the solvent was evaporated to obtain a crude product of tert-butyl 4-[2-(3-{[(2-bromoethyl)amino]carbonyl}phenyl)ethyl]piperidine-1-carboxylate.

4 M hydrogen chloride/EtOAc solution (5 ml) was added to an EtOAc (15 ml) solution of the crude tert-butyl 4-[2-(3-{[(2-bromoethyl)amino]carbonyl}phenyl)ethyl]piperidine-1-carboxylate at room temperature, followed by stirring overnight. The solvent was evaporated under reduced pressure to obtain N-(2-bromoethyl)-3-(2-piperidin-4-ylethyl)benzamide hydrochloride (1.27 g) as a white solid.

TEA (0.90 ml) was dropwise added to an acetonitrile (30 ml) suspension of N-(2-bromoethyl)-3-(2-piperidin-4-ylethyl)benzamide hydrochloride (1.20 g) and methyl 5-{[(4-nitrophenoxy)carbonyl]oxy}nicotinate (1.02 g), followed by stirring overnight at room temperature. The reaction solvent was evaporated under reduced pressure, then aqueous saturated sodium hydrogencarbonate solution was added thereto, extracted with EtOAc, and dried over anhydrous magnesium sulfate. This was filtered, the solvent was evaporated, and the residue was purified two times through silica gel column chromatography (basic silica with eluent: hexane:EtOAc=1:2 (v/v), next neutral silica with eluent: chloroform:methanol=19:1 (v/v)) to obtain methyl 5-[{(4-[2-(3-{[(2-bromoethyl)amino]carbonyl}phenyl)ethyl]piperidin-1-yl}carbonyl)oxy]nicotinate (762 mg) as a white powder.

A DMF (10 ml) suspension of methyl 5-[{(4-[2-(3-{[(2-bromoethyl)amino]carbonyl}phenyl)ethyl]piperidin-1-yl}carbonyl)oxy]nicotinate (750 mg), potassium carbonate (300 mg) and potassium iodide (361 mg) was stirred at 80° C. for 1 hour. The reaction liquid was left cooled, then EtOAc was added thereto, washed with aqueous saturated sodium hydrogencarbonate solution and saturated brine in that order, dried over anhydrous magnesium sulfate, and the solvent was evaporated under reduced pressure. The residue was purified by silica gel column chromatography (eluent: chloroform:methanol=20:1 (v/v)) to obtain methyl 5-{[(4-{2-[3-(aziridin-1-ylcarbonyl)phenyl]ethyl}piperidin-1-yl)carbonyl]oxy}nicotinate (630 mg) as a colorless oil.

Reference Example 152

Under ice cooling, diphenylphosphorylazide (540 mg) was added to a Tol solution (10 ml) of 3-{2-[1-(tert-butoxycarbonyl)-4-piperidyl]ethyl]benzoic acid (600 mg) and TEA (0.3 ml), followed by stirring at room temperature for 2 hours. EtOAc was added to the reaction solution, washed with aqueous saturated sodium hydrogencarbonate solution and saturated brine, and dried over anhydrous magnesium sulfate. The solvent was evaporated under reduced pressure to obtain a colorless oil (630 mg). A Tol solution (10 ml) of the resulting oil (400 mg) was stirred at 110° C. for 1 hour. This was cooled to room temperature, and aqueous 30% ammonia solution (0.2 ml) was added thereto, followed by stirring at room temperature for 15 hours. EtOAc was added to the reaction solution, then washed with aqueous 1 N hydrochloric acid solution and saturated brine in that order, and dried over anhydrous magnesium sulfate. The solvent was evaporated under reduced pressure, and the resulting residue was purified by silica gel column chromatography (eluent: chloroform:methanol=95:5 (v/v)) to obtain tert-butyl 4-(2-{3-[(aminocarbonyl)amino]phenyl}ethyl)-1-piperidinecarboxylate (227 mg).

4 M hydrogen chloride/EtOAc (4 ml) was added to an EtOAc (9 ml) solution of tert-butyl 4-(2-{3-[(aminocarbonyl)amino]phenyl}ethyl)-1-piperidinecarboxylate (227 mg), followed by stirring at room temperature for 3 hours. The solvent was evaporated under reduced pressure to obtain 1-{3-[2-(4-piperidyl)ethyl]phenyl}urea hydrochloride (185 mg).

Methyl 5-{[(4-nitrophenoxy)carbonyl]oxy}nicotinate (228 mg) was added to an acetonitrile (5 ml) solution of 1-{3-[2-(4-piperidinyl)ethyl]phenyl}urea hydrochloride (185 mg) and TEA (0.2 ml), followed by stirring overnight at room temperature. The reaction liquid was diluted with EtOAc, washed with aqueous saturated sodium hydrogencarbonate solution and saturated brine in that order, and dried over anhydrous magnesium sulfate. The solvent was evaporated, and the resulting residue was purified by silica gel column chromatography (eluent: chloroform:methanol=10:1 (v/v)) to obtain methyl 5-({[4-(2-{3-[(aminocarbonyl)amino]phenyl}ethyl)-1-piperidyl]carbonyl}oxy)nicotinate (183 mg).

In the same manner as in Reference Example 152, the compound of Reference Example 153 was obtained.

Reference Example 155

Tert-butyl 4-ethynylpiperidine-1-carboxylate (12.5 g) and iodobenzene (12.8 g) was dissolved in THF:TEA=1:1 (v/v) mixed solvent (125 ml), then at room temperature, copper iodide (455 mg) and palladium tetrakistriphenylphosphine complex (1.38 g) were added thereto in that order, followed by stirring overnight at room temperature. The solvent was evaporated, EtOAc was added to it, and washed with aqueous 1 M hydrochloric acid solution, water and saturated brine in that order. This was dried over magnesium sulfate, and the solvent was evaporated to obtain a light brown oil. This was purified by silica gel column chromatography (eluent: hexane:EtOAc=19:1 (v/v)) to obtain tert-butyl 4-(phenylethynyl)piperidine-1-carboxylate (15.5 g) as a light brown oil.

4 M hydrogen chloride/EtOAc solution (70 ml) was added to tert-butyl 4-(phenylethynyl)piperidine-1-carboxylate (7.0 g), followed by stirring at room temperature for 30 minutes. The solvent was evaporated to obtain 4-(phenylethynyl)piperidine hydrochloride (5.4 g) as a white powder.

Example 1

3-Hydroxypyridine (400 mg), TEA (1.17 ml) and DMAP (catalytic amount) were added in that order to a THF (10 ml) solution containing piperidine-1-carbonyl chloride (745 mg), and then heated at 60° C. for 5 hours. The reaction solution was cooled, then water (3 ml) was added thereto, and extracted with EtOAc. The extract was washed with water, and then dried over anhydrous magnesium sulfate. The solvent was evaporated under reduced pressure, and the residue was purified by silica gel column chromatography (eluent: hexane:EtOAc=1:1 (v/v)) to obtain a colorless oil. The resulting oil was dissolved in ethanol, and an ethanol solution of oxalic acid (378 mg) added thereto to obtain a colorless powder. This was recrystallized from hexane/ethanol to obtain (pyridin-3-yl)piperidine-1-carboxylate oxalate (761 mg).

Example 2

A methylene chloride (20 ml) solution containing 3-hydroxypyridine (568 mg) and pyridine (724 µl) was dropwise added to a methylene chloride (25 ml) solution containing triphosgene (590 mg), followed by stirring at room temperature for 1 hour. The solvent was evaporated under reduced pressure, the residue was dissolved in pyridine (30 ml), then the compound (1.2 g) obtained in Reference Example 22 was added thereto, followed by heating at 70° C. for 4 hours. The reaction solution was concentrated under reduced pressure, then chloroform and aqueous sodium hydrogencarbonate solution was added thereto, and the organic layer was dried over anhydrous magnesium sulfate. The solvent was evaporated under reduced pressure, and the residue was purified by silica gel column chromatography (eluent: hexane:EtOAc=1:2 (v/v)) to obtain a colorless powder. This was recrystallized from hexane/EtOAc to obtain (pyridin-3-yl) 4-{4-[(3-fluorobenzyl)oxy]phenoxy}piperidine-1-carboxylate (861 mg).

In the same manner as in Example 2, the compounds of Examples 3 to 118, 389 to 391, 416 and 417 and Reference Examples 83 to 93 were obtained.

Example 119

A methylene chloride (20 ml) solution containing 3-hydroxypyridine (1.43 g) and pyridine (1.46 ml) was dropwise added to a methylene chloride (30 ml) solution containing triphosgene (1.48 g), followed by stirring at room temperature for 1 hour. A methylene chloride (5 ml) solution containing tert-butyl 1-piperazinecarboxylate (2.0 g) and pyridine (0.97 ml) was dropwise added to the reaction solution, then pyridine (20 ml) was added thereto, followed by heating at 70° C. for 4 hours. The reaction solution was concentrated under reduced pressure, diluted with EtOAc, and the organic layer was washed with aqueous saturated sodium hydrogencarbonate solution, and then dried over anhydrous magnesium sulfate. The solvent was evaporated under reduced pressure, and the residue was purified through basic silica gel column chromatography (eluent: hexane:EtOAc=4:1 (v/v)) to obtain a colorless solid (3.0 g).

The resulting compound (3.0 g) was dissolved in EtOAc (20 ml)/2-propanol (10 ml), then 4 M hydrogen chloride/EtOAc solution (10 ml) was added thereto, followed by stirring overnight at room temperature. The reaction solution was concentrated under reduced pressure, and the resulting solid was washed with EtOAc and dried under reduced pressure to obtain 3-pyridyl 1-piperazinecarboxylate dihydrochloride (2.66 g).

1-Ethyl-3-(dimethylaminopropyl)carbodiimide hydrochloride (150 mg), 1-hydroxybenzotriazole (110 mg) and diisopropylethylamine (0.23 ml) were added to a DMF (5 ml) solution containing the resulting compound (190 mg) and 4-(cyclooctylmethoxy)benzoic acid (176 mg) prepared from cyclooctylmethanol with reference to Reference Example 70, followed by stirring overnight at room temperature. The reaction solution was diluted with EtOAc, the organic layer was washed with aqueous saturated sodium hydrogencarbonate solution, and dried over anhydrous sodium sulfate. The solvent was evaporated under reduced pressure, and the residue was recrystallized from EtOAc/hexane to obtain 3-pyridyl 4-[4-(cyclooctylmethoxy)benzoyl]-1-piperazinecarboxylate (240 mg).

In the same manner as in Example 119, the compounds of Examples 120 to 136 were obtained.

Example 137

Potassium tert-butoxide (810 mg) was added to a DMF (10 ml) solution containing 6-chloronicotinonitrile (1.0 g) and 3-chlorobenzyl alcohol (1.0 g), followed by stirring overnight at room temperature. Water was added to the reaction solution, and the precipitated solid was collected by filtration, washed with water and hexane in that order, and dried under reduced pressure to obtain a brown solid (1.3 g).

An aqueous 5 M sodium hydroxide solution (10 ml) was added to an ethanol (10 ml) solution containing the resulting compound (1.3 g), followed by stirring at 100° C. for 4 hours. After this was cooled to room temperature, 1 N hydrochloric acid (56 ml) was added thereto, and the precipitated solid was collected by filtration, washed with water and dried under reduced pressure to obtain a colorless solid (0.82 g).

1-Ethyl-3-(dimethylaminopropyl)carbodiimide hydrochloride (150 mg), 1-hydroxybenzotriazole (110 mg) and diisopropylethylamine (0.23 ml) were added to a DMF (5 ml) solution containing the resulting compound (176 mg) and 3-pyridyl 1-piperazinecarboxylate dihydrochloride (166 mg), followed by stirring overnight at room temperature. The reaction solution was diluted with EtOAc, the organic layer was washed with aqueous saturated sodium hydrogencarbonate solution, and dried over anhydrous magnesium sulfate. The solvent was evaporated under reduced pressure, and the residue was purified through basic silica gel column chromatography (eluent: hexane:EtOAc=1:2 (v/v)) to obtain a colorless oil (140 mg).

Oxalic acid (35 mg) was added to a 2-propanol solution containing the resulting compound (140 mg), followed by stirring for 30 minutes. The precipitated solid was collected by filtration, washed with 2-propanol/hexane, and dried under reduced pressure to obtain 3-pyridyl 4-({6-[(3-chlorobenzyl)oxy]-3-pyridyl}carbonyl)-1-piperazinecarboxylate 0.5-oxalate (120 mg).

In the same manner as in Example 137, the compound of Example 138 was obtained.

Example 139

Potassium carbonate (1.04 g) and ethyl bromoacetate (0.610 ml) were added to an acetonitrile (15 ml) solution containing 4-hydroxybenzamide (686 mg), followed by heating at 80° C. for 2 hours. The reaction solution was cooled, water (45 ml) was added thereto, and the precipitated solid was collected by filtration, washed with water and dried to obtain ethyl[4-(aminocarbonyl)phenoxy]acetate (893 mg) as pale brown powder.

The resulting compound (870 mg) was dissolved in THF (10 ml), and ethanol (0.274 ml) and an aqueous 1 M sodium hydroxide solution (4.68 ml) were added thereto, followed by stirring at room temperature for 4 hours. The reaction solution was concentrated under reduced pressure, acidified with an aqueous 1 M hydrochloric acid solution, and the precipitated solid was collected by filtration and dried to obtain a pale brown powder [4-(aminocarbonyl)phenoxy]acetic acid (714 mg).

TEA (0.251 ml), 1-[3-(dimethylamino)propyl]-3-ethylcarbodiimide hydrochloride (259 mg), 1-hydroxybenzotriazole (122 mg) and the above-produced compound [4-(aminocarbonyl)phenoxy]acetic acid (184 mg) were added to a DMF (5 ml) solution containing 3-pyridyl 1-piperidinecarboxylate dihydrochloride (252 mg) obtained in the method of Example 121, followed by stirring at room temperature for 5 hours. An aqueous saturated sodium hydrogencarbonate solution was added to the reaction solution, followed by extraction with chloroform. The organic layer was dried over anhydrous magnesium sulfate. The solvent was evaporated under reduced pressure, the residue was purified by silica gel column chromatography (eluent: chloroform:methanol=95:5 (v/v)), and the resulting solid was recrystallized from EtOAc/acetonitrile to obtain pyridin-3-yl 4-{[4-(aminocarbonyl)phenoxy]acetyl}piperidine-1-carboxylate (274 mg).

In the same manner as in Example 139, the compounds of Examples 140 and 141 were obtained.

Example 142

TEA (0.23 ml) and benzenesulfonyl chloride (0.075 ml) were added to a dichloromethane (5 ml) solution containing 3-pyridyl 1-piperazinecarboxylate dihydrochloride (150 mg), followed by stirring overnight at room temperature. The reaction solution was diluted with chloroform, the organic layer was washed with aqueous saturated sodium hydrogencarbonate solution, and dried over anhydrous magnesium sulfate. The solvent was evaporated under reduced pressure, the residue was purified by silica gel column chromatography (eluent: chloroform), and the resulting solid was recrystallized from 2-propanol to obtain 3-pyridyl 4-(phenylsulfonyl)-1-piperazinecarboxylate (130 mg).

In the same manner as in Example 142, the compound of Example 143 was obtained.

Example 144

Benzyl chloroformate (91 mg) was added to a pyridine (3 ml) solution containing 3-pyridyl 1-piperazinecarboxylate dihydrochloride (150 mg), followed by stirring at room temperature for 12 hours. The reaction solution was concentrated under reduced pressure, diluted with EtOAc, and the organic layer was washed with aqueous saturated sodium hydrogencarbonate solution, and dried over anhydrous magnesium sulfate. The solvent was evaporated under reduced pressure, the residue was diluted with 2-propanol (3 ml), and toluenesulfonic acid hydrate (100 mg) was added thereto, followed by stirring. The crystal precipitated was collected by filtration and recrystallized from 2-propanol to obtain benzyl 3-pyridyl 1,4-piperazinedicarboxylate tosylate (98 mg).

In the same manner as in Example 144, the compounds of Examples 145 and 146 were obtained.

Example 147

10% Palladium-carbon (catalytic amount) was added to a THF (20 ml)/2-propanol (20 ml) solution containing 3-pyridyl 4-[(4-benzyloxy)benzoyl]-1-piperazinecarboxylate (1.3 g), and in a hydrogen gas atmosphere, this was stirred at room temperature under normal pressure for 12 hours. The catalyst was removed by filtration, the filtrate was concentrated under reduced pressure, and the resulting solid was recrystallized from EtOAc/hexane to obtain 3-pyridyl 4-(4-hydroxybenzoyl)-1-piperazinecarboxylate (950 mg).

A THF (5 ml) solution containing 3-pyridyl 4-(4-hydroxybenzoyl)-1-piperazinecarboxylate (300 mg) and diethyl azodicarboxylate (0.62 ml, 40% Tol solution) was dropwise added to a THF (5 ml) solution containing 3-chlorobenzyl alcohol (200 mg) and triphenylphosphine (360 mg), at 0° C., followed by stirring at room temperature for 3 days. The reaction solution was diluted with chloroform, washed with an aqueous saturated sodium hydrogencarbonate solution, and dried over anhydrous magnesium sulfate. The solvent was evaporated under reduced pressure, and the residue was purified by silica gel column chromatography (eluent: chloroform:methanol=95:5 (v/v)), and the resulting solid was recrystallized from 2-propanol to obtain 3-pyridyl 4-{4-[(3-chlorobenzoyl)oxy]benzyl}-1-piperazinecarboxylate (260 mg).

In the same manner as in Example 147, the compounds of Examples 148 to 166 were obtained.

Example 167

Potassium carbonate (270 mg) was added to an acetonitrile (10 ml) solution containing 3-pyridyl 4-(4-hydroxybenzoyl)-1-piperazinecarboxylate (530 mg) and methyl 3-(bromomethyl)benzoate (450 mg), followed by stirring at 80° C. for 1 hour. Water was added to the reaction solution, followed by extraction with EtOAc. The organic layer was washed with water and dried over anhydrous magnesium sulfate. The solvent was evaporated under reduced pressure, and the residue was purified by silica gel column chromatography (eluent: hexane:EtOAc=1:4 (v/v)) to obtain a colorless solid (470 mg).

The resulting solid (100 mg) was recrystallized from EtOAc to obtain 3-pyridyl 4-(4-{[3-(methoxycarbonyl)benzyl]oxy}benzoyl)-1-piperazinecarboxylate (88 mg).

Example 168

4-Ethyl 1-pyridin-3-yl piperidine-1,4-dicarboxylate (0.732 g) was dissolved in THF (15 ml) and ethanol (8.0 ml), and under ice cooling, an aqueous 1 M sodium hydroxide solution (3.9 ml) was dropwise added thereto. This was stirred at room temperature for 2 hours, and neutralized with 1 M hydrochloric acid (0.5 ml). The reaction liquid was concentrated under reduced pressure, methanol was added to the residue, and the precipitated salt was removed through suction filtration. The filtrate was concentrated to obtain 1-[(pyridin-3-yloxy)carbonyl]piperidine-4-carboxylic acid (0.727 g) as a colorless solid.

The resulting compound (0.60 g) was dissolved in dimethylformamide (10 ml), and 1-[3-(dimethylamino)propyl]-3-ethylcarbodiimide hydrochloride (0.93 g), 1-hydroxybenzotriazole (0.51 g) and cyclohexanemethylamine (0.43 g) were added thereto, followed by stirring at room temperature for 15 hours. Water was added to the reaction solution, followed by further stirring for 1 hour. Then, sodium hydrogencarbonate solution was added thereto, followed by Extraction with EtOAc. The organic layer was washed with 0.5 M hydrochloric acid and saturated brine in that order. The organic layer was dried over anhydrous magnesium sulfate, the solvent was evaporated under reduced pressure, and the residue was purified by silica gel column chromatography (eluent: hexane:EtOAc=1:4 (v/v)) to obtain a colorless powder (0.69 g). This was recrystallized from ethanol and hexane to obtain (pyridin-3-yl) 4-{[(cyclohexylmethyl)amino]carbonyl}piperidine-1-carboxylate (261 mg).

In the same manner as in Example 168, the compounds of Examples 169 to 192, 383 to 388 and Reference Example 94 were obtained.

Example 193

3-Pyridinyl chlorocarbonate (330 mg) was added to a pyridine (10 ml) solution containing 1-benzyl 2-methyl-1,2-piperazinedicarboxylate (660 mg, Beilstein Registry No. 4236331), followed by stirring at 80° C. for 7 hours. The reaction solution was concentrated under reduced pressure, diluted with chloroform, and the organic layer was washed with aqueous saturated sodium hydrogencarbonate solution and dried over anhydrous magnesium sulfate. The solvent was evaporated under reduced pressure, and the residue was purified through basic silica gel column chromatography (eluent: hexane:EtOAc=1:1 (v/v)) to obtain a colorless oil (700 mg).

An aqueous 1 M sodium hydroxide solution (1.2 ml) was added to a THF (5 ml) solution containing the resulting compound (430 mg), followed by stirring at 50° C. for 3 hours. Aqueous 1 M sodium hydroxide solution (0.8 ml) was added thereto, and further heated at 50° C. for 1 hours, then cooled to room temperature, and 1 N hydrochloric acid (2 ml) was added thereto. The reaction solution was extracted with EtOAc, the organic layer was washed with saturated brine, and dried over anhydrous magnesium sulfate. The solvent was evaporated under reduced pressure, and the precipitated solid was washed with EtOAc/hexane, and dried under reduced pressure to obtain 1-[(benzyloxy)carbonyl]-4-[(3-pyridyloxy)carbonyl]-2-piperidinecarboxylic acid (140 mg).

In the same manner as in Example 193, the compounds of Examples 194 and 195 were obtained.

Example 196

Pyridin-3-yl 4-({[2-(methylamino)phenyl]amino}carbonyl)piperidine-1-carboxylate (0.41 g) was dissolved in acetic acid (10 ml), followed by heating under reflux for 2 hours. The solvent was evaporated, and the residue was recrystallized from methanol and diethyl ether to obtain (pyridin-3-yl) 4-(1-methyl-1H-benzimidazol-2-yl)piperidine-1-carboxylate (307 mg).

Example 197

Pyridin-3-yl 4-[(tert-butoxycarbonyl)amino]piperidine-1-carboxylate (0.249 g) was dissolved in THF (5.0 ml), and under ice cooling, 4 M hydrogen chloride/EtOAc solution (2.10 ml) was added thereto, followed by stirring at room temperature for 24 hours. The reaction solution was concentrated to dryness to obtain pyridin-3-yl 4-aminopiperidine-1-carboxylate dihydrochloride (0.280 g).

The resulting compound (0.28 g) was dissolved in dimethylformamide (10 ml), and 1-[3-(dimethylamino)propyl]-3-ethylcarbodiimide hydrochloride (0.28 g), 1-hydroxybenzotriazole (0.16 g), TEA (0.54 ml) and 6-phenylhexanoic acid (0.18 g) were added thereto, followed by stirring at room temperature for 15 hours. Water was added to the reaction solution and further stirred for 1 hour. Then, sodium hydrogencarbonate solution was added thereto, followed by extraction with EtOAc. The organic layer was washed with saturated brine. The organic layer was dried over anhydrous magnesium sulfate, the solvent was evaporated under reduced pressure, and the residue was purified by silica gel column chromatography (eluent: EtOAc) to obtain a colorless powder. This was recrystallized from methanol and diethyl ether to obtain (pyridin-3-yl) 4-[(6-phenylhexanoyl)amino]piperidine-1-carboxylate (108 mg).

Example 198

10% Palladium-carbon (catalytic amount) was added to a THF (75 ml)/2-propanol (75 ml) solution containing 3-pyridyl 4-[3-(benzyloxy)phenoxy]-1-piperidinecarboxylate (4.0 g), and in a hydrogen gas atmosphere, this was stirred at room temperature under normal pressure for 24 hours. The catalyst was removed by filtration, and the filtrate was concentrated under reduced pressure, and the resulting solid was washed with EtOAc/hexane, and dried under reduced pressure to obtain 3-pyridyl 4-(3-hydroxyphenoxy)-1-piperidinecarboxylate (2.2 g).

Example 199

10% Palladium-carbon (catalytic amount) was added to a THF (75 ml)/2-propanol (75 ml) solution containing 3-pyridyl 4-[4-(benzyloxy)phenoxy]-1-piperidinecarboxylate (3.7 g), and in a hydrogen gas atmosphere, this was stirred at room temperature under normal pressure for 24 hours. The catalyst was removed by filtration, and the filtrate was concentrated under reduced pressure, and the resulting solid was washed with EtOAc/hexane, and dried under reduced pressure to obtain 3-pyridyl 4-(4-hydroxyphenoxy)-1-piperidinecarboxylate (2.4 g).

Example 200

Diethyl azodicarboxylate (0.35 ml, 40% Tol solution) was dropwise added to a THF (5 ml) solution containing 3-pyridyl 4-(3-hydroxyphenoxy)-1-piperidinecarboxylate (160 mg), cyclohexylmethanol (87 mg) and triphenylphosphine (200 mg), at 0° C., followed by stirring at room temperature for 24 hours. The reaction solution was diluted with chloroform, washed with aqueous saturated sodium hydrogencarbonate solution, and dried over anhydrous magnesium sulfate. The solvent was evaporated under reduced pressure, and the residue was purified by silica gel column chromatography (eluent: hexane:EtOAc=1:1 (v/v)). The resulting oil was dissolved in EtOAc (5 ml), 4 M hydrogen chloride/EtOAc solution (1 ml) was added thereto, followed by stirring at room temperature. The solvent was evaporated under reduced pressure, and the precipitated solid was washed with EtOAc/2-propanol and dried under reduced pressure to obtain 3-pyridyl 4-[3-(cyclohexylmethoxy)phenoxy]-1-piperidinecarboxylate hydrochloride (94 mg).

In the same manner as in Example 200, the compounds of Examples 201 to 205 were obtained.

Example 206

Diethyl azodicarboxylate (0.35 ml, 40% Tol solution) was dropwise added to a THF (5 ml) solution containing 3-pyridyl 4-(4-hydroxyphenoxy)-1-piperidinecarboxylate (160 mg), 3-chlorobenzyl alcohol (110 mg) and triphenylphosphine (200 mg) at 0° C., followed by stirring at room temperature for 24 hours. The reaction solution was diluted with chloroform, washed with aqueous saturated sodium hydrogencarbonate solution, and dried over anhydrous magnesium sulfate. The solvent was evaporated under reduced pressure, and the residue was purified by silica gel column chromatography (eluent: hexane:EtOAc=1:3 (v/v)). The resulting oil was dissolved in EtOAc (5 ml), and 4 M hydrogen chloride/EtOAc solution (1 ml) was added thereto, followed by stirring at room temperature. The solvent was evaporated under reduced pressure, and the precipitated solid was recrystallized from EtOAc/2-propanol to obtain 3-pyridyl 4-{4-[(3-chlorobenzyl)oxy]phenoxy}-1-piperidinecarboxylate hydrochloride (45 mg).

In the same manner as in Example 206, the compounds of Examples 207 to 212 were obtained.

Example 213

10% Palladium-carbon (catalytic amount) was added to an ethanol (100 ml) solution containing methyl 5-[({4-[4-(benzyloxy)phenoxy]piperidin-1-yl}carbonyl)oxy]nicotinate, and in a hydrogen gas atmosphere, this was stirred overnight at room temperature under normal pressure. The catalyst was removed by filtration, the resulting filtrate was concentrated under reduced pressure, and the residue was purified by silica gel column chromatography (eluent: chloroform:methanol=15:1 (v/v)) to obtain a colorless oil (1.08 g).

2.2 M diethyl azodicarboxylate (1.01 ml) and triphenylphosphine (581 mg) were added to a THF (20 ml) solution containing the resulting compound (450 mg) and 3-cyclohexyl-1-propanol (315 mg), followed by heating at 50° C. for 22 hours. Water was added to the reaction solution, followed by extraction with chloroform. The organic layer was washed with saturated brine and dried over anhydrous magnesium sulfate. The solvent was evaporated under reduced pressure, and the residue was purified by silica gel column chromatography (eluent: hexane:EtOAc=2:1 (v/v)) to obtain methyl 5-[({4-[4-[(3-cyclohexylpropoxy)phenoxy]piperidin-1-yl}carbonyl)oxy]nicotinate (242 mg).

In the same manner as in Example 213, the compounds of Examples 214 to 216 were obtained.

Example 217

10% Palladium-carbon (catalytic amount) was added to a THF (10 ml) solution containing 5-[({4-[4-(benzyloxy)phenoxy]piperidin-1-yl}carbonyl)oxy]nicotinic acid (200 mg), and in a hydrogen gas atmosphere, this was stirred at room temperature under normal pressure for 3 hours. The catalyst was removed by filtration, and the resulting filtrate was concentrated under reduced pressure to obtain 5-[({4-[4-(hydroxy)phenoxy]piperidin-1-yl}carbonyl)oxy]nicotinic acid (55 mg).

Example 218

The compound (4.0 g) of Example 29, obtained in the same method as in Example 2, was dissolved in THF (30 ml) and methanol (15 ml), and under ice cooling, an aqueous 1 M sodium hydroxide solution (12 ml) was dropwise added thereto. This was stirred at room temperature for 30 minutes, and then under ice cooling, this was neutralized with 1 M hydrochloric acid (12 ml). The colorless solid precipitated was collected by filtration to obtain 5-{[(4-{4-[(3-fluorobenzyl)oxy]phenoxy}piperidin-1-yl)carbonyl]oxy}nicotinic acid (3.52 g).

In the same manner as in Example 218, the compounds of Examples 219 to 224 and Examples 226 to 243 were obtained.

Example 225

A methylene chloride (30 ml) solution containing methyl 5-hydroxynicotinate (2.20 g) and pyridine (4 ml) was dropwise added to a methylene chloride (50 ml) solution containing triphosgene (1.56 g), followed by stirring at room temperature for 1 hour. The solvent was evaporated under reduced pressure, the residue was dissolved in pyridine (50 ml), and 4-(2-phenylethyl)piperidine hydrochloride (2.70 g) was added thereto, followed by heating overnight at 80° C. The reaction solution was concentrated under reduced pressure, then EtOAc and an aqueous sodium hydrogencarbonate solution were added thereto. The organic layer was dried over anhydrous magnesium sulfate. The solvent was evaporated under reduced pressure, and the residue was purified by silica gel column chromatography (eluent: hexane:EtOAc=1:1 (v/v)) to obtain a colorless powder. This was recrystallized from hexane/EtOAc to obtain methyl 5-({[4-(2-phenylethyl)piperidin-1-yl]carbonyl}oxy)nicotinate (3.95 g).

Methyl 5-({[4-(2-phenylethyl)piperidin-1-yl]carbonyl}oxy)nicotinate (3.95 g) was dissolved in THF (32 ml) and methanol (16 ml), and under ice cooling, aqueous 1 M sodium hydroxide solution (16 ml) was dropwise added thereto. This was stirred at room temperature for 30 minutes, and under ice cooling, this was neutralized with 1 M hydrochloric acid (16 ml). The colorless solid precipitated was collected by filtration, and recrystallized from methanol/water to obtain 5-({[4-(2-phenylethyl)piperidin-1-yl]carbonyl}oxy)nicotinic acid (3.70 g).

Example 244

The compound of Example 219, 5-{[(4-{4-[(3-fluorobenzyl)oxy]phenoxy}piperidin-1-yl)carbonyl]oxy}nicotinic acid (0.50 g) was dissolved in DMF (8.0 ml), and 1-[3-(dimethylamino)propyl]-3-ethylcarbodiimide hydrochloride (0.38 g), 1-hydroxybenzotriazole (0.22 g) and glycine tert-butyl ester (0.21 g) were added thereto, followed by stirring at room temperature for 15 hours. Water was added to the reaction solution, followed by stirring for 1 hours. Then, sodium hydrogencarbonate solution was added thereto, followed by extraction with EtOAc. The organic layer was washed with saturated brine, and dried over anhydrous magnesium sulfate. The solvent was evaporated under reduced pressure, and the residue was purified by silica gel column chromatography (eluent: hexane:EtOAc=1:1 (v/v)) to obtain a colorless oil (0.444 g).

The resulting compound (0.444 g) was dissolved in methylene chloride (5.0 ml), and under ice cooling, TFA (1.15 ml) was added thereto. This was stirred at that temperature for 24 hours, and then the reaction liquid was concentrated to obtain a yellow solid. This was recrystallized from ethanol and diethyl ether to obtain {[(5-{[(4-{4-[(3-fluorobenzyl)oxy]phenoxy}piperidin-1-yl)carbonyl]oxy}pyridin-3-yl)carbonyl]amino}acetic acid (348 mg).

According to the amidation as in Example 244, the compounds of Examples 245 to 257 were obtained.

Example 258

Water (4 ml), sodium carbonate (337 mg) and tetrakistriphenylphosphine palladium (115 mg) were added in that order to a dimethoxyethane (12 ml) solution containing the compound (400 mg) of Example 54 and [3-(aminocarbonyl)phenyl]boronic acid (176 mg), followed by heating at 80° C. for 5 hours. The reaction solution was cooled and diluted with EtOAc. The organic layer was washed with water and dried over anhydrous magnesium sulfate. The solvent was evaporated under reduced pressure, and the residue was purified by silica gel column chromatography (eluent: hexane:EtOAc=1:5 (v/v)) to obtain 5-[3-(aminocarbonyl)phenyl]pyridin-3-yl-4-benzylpiperidine-1-carboxylate (205 mg).

In the same manner as in Example 258, the compounds of Examples 259, 265, 266 and 399 were obtained.

Example 260

A 4 M hydrogen chloride/dioxane solution (1.8 ml) was added to a THF (10 ml) solution containing 5-[(tert-butoxycarbonyl)amino]pyridin-3-yl 4-{4-[(3-fluorobenzyl)oxy]phenoxy}piperidine-1-carboxylate (174 mg), followed by stirring at 60° C. for 4 hours. The solvent was evaporated under reduced pressure to obtain 5-aminopiperidin-3-yl 4-{4-[(3-fluorobenzyl)oxy]phenoxy}pyridine-1-carboxylate hydrochloride (74 mg).

Example 261

An aqueous 1 M sodium hydroxide solution (3.24 ml) was added to a THF (10 ml) solution containing 5-[4-(ethoxycarbonyl)piperidin-1-yl]pyridin-3-yl 4-{4-[(3-fluorobenzyl)oxy]phenoxy}piperidine-1-carboxylate oxalate (240 mg), followed by stirring at 60° C. for 5 hours. 1 M hydrochloric acid (3.24 ml) was added to the reaction solution and the solvent was evaporated under reduced pressure. The residue was purified by silica gel column chromatography (eluent: chloroform:methanol=10:1 (v/v)). The resulting oil was dissolved in ethanol/water, then oxalic acid (24 mg) was added thereto for crystallization to obtain 1-(5-{[(4-{4-[(3-fluorobenzyl)oxy]phenoxy}piperidin-1-yl)carbonyl]oxy}pyridin-3-yl)piperidine-4-carboxylic acid oxalate (93 mg).

Example 262

TFA (1.0 ml) was added to a methylene chloride (10 ml) solution containing 5-[(2-tert-butoxy-2-oxoethoxy)methyl]pyridin-3-yl 4-{4-[(3-(3-fluorobenzyl)oxy]phenoxy}piperidin-1-carboxylate (333 mg), followed by stirring overnight at room temperature. The solvent was evaporated under reduced pressure to obtain [(5-{[(4-{4-[(3-fluorobenzyl)oxy]phenoxy}piperidin-1-yl)carbonyl]oxy}pyridin-3-yl}methoxy]acetic acid (232 mg).

Example 263

An aqueous 1 M sodium hydroxide solution (7.65 ml) was added to a THF (20 ml) solution containing 5-[(acetoxy)methyl]pyridin-3-yl 4-{4-[(3-fluorobenzyl)oxy]phenoxy}piperidine-1-carboxylate oxalate (1.10 g), followed by stirring at 65° C. for 3 hours. The reaction liquid was neutralized with 1 M hydrochloric acid, followed by extraction with chloroform and drying over anhydrous magnesium sulfate. The solvent was evaporated under reduced pressure, and the residue was purified by silica gel column chromatography (eluent: chloroform:methanol=12:1 (v/v)) to obtain 5-(hydroxymethyl)piperidin-3-yl 4-{4-[(3-fluorobenzyl)oxy]phenoxy}piperidine-1-carboxylate (770 mg).

Example 264

An aqueous 1 M sodium hydroxide solution (1.11 ml) was added to a THF (5 ml) solution containing 5-[(1E)-3-methoxy-3-oxoprop-1-en-1-yl]pyridin-3-yl 4-{4-[(3-fluorobenzyl)oxy]phenoxy}piperidine-1-carboxylate (158 mg), followed by stirring at 60° C. for 3 hours. The solvent was evaporated under reduced pressure, and the residue was purified by silica gel column chromatography (eluent: chloroform:methanol=10:1 (v/v)) to obtain (2E)-3-(5-{[(4-{4-[(3-fluorobenzyl)oxy]phenoxy}piperidin-1-yl)carbonyl]oxy}pyridin-3-yl)acrylic acid (88 mg).

Example 267

(a) Methyl 5-{[(4-nitrophenoxy)carbonyl]oxy}nicotinate (723 mg) was added to an acetonitrile (10 ml) solution of 3-[2-(4-piperidyl)ethyl]benzonitrile hydrochloride (475 mg) and TEA (0.58 ml), followed by stirring overnight at room temperature. The reaction liquid was diluted with EtOAc, followed by washing with an aqueous saturated sodium hydrogencarbonate solution and drying over anhydrous magnesium sulfate. The solvent was evaporated, the resulting residue was subjected to basic silica gel column chromatography (eluent: hexane:EtOAc=1:1 (v/v)) and the side-product, nitrophenol was removed. Then, this was purified by silica gel column chromatography (eluent: hexane:EtOAc=3:2 (v/v)) to obtain methyl 5-[({4-[2-(3-cyanophenyl)ethyl]-1-piperidyl}carbonyl)oxy]nicotinate (284 mg).

(b) An aqueous 1 M sodium hydroxide solution (0.69 ml) was added to a THF (5 ml)/water (4 ml) solution of methyl 5-[({4-[2-(3-cyanophenyl)ethyl]-1-piperidyl}carbonyl)oxy]nicotinate (272 mg), followed by stirring overnight at room temperature. 1 M hydrochloric acid (0.69 ml) was added to the reaction liquid, and the crystal precipitated was collected by filtration. The crystal was washed with a hot methanol/water solution, and dried to obtain 5-[({4-[2-(3-cyanophenyl)ethyl]-1-piperidyl}carbonyl)oxy]nicotinic acid (240 mg).

In the same manner as in the step (a) in Example 267, the compounds of Reference Examples 149 to 150, and Examples 268 to 272, 392, 396, 400, 402, 413, 419, 421 and 422 were obtained.

According to the same method containing the step (b) after the step (a) as in Example 267, the compounds of Examples 273 to 317, 393 to 395, 401, 403, 405, 406, 414 and 418 were obtained.

Example 318

1-[3-(dimethylamino)propyl]-3-ethylcarbodiimide hydrochloride (62 mg), 1-hydroxybenzotriazole (43 mg), ammonium chloride (43 mg) and TEA (0.038 ml) were added to a DMF (3.0 ml) solution of 5-[({4-[2-(3-cyanophenyl)ethyl]-1-piperidyl}carbonyl)oxy]nicotinic acid (102 mg), followed by stirring overnight at room temperature. An aqueous saturated sodium hydrogencarbonate solution was added to the reaction liquid, and the crystal precipitated was collected by filtration and dried. The resulting crystal was recrystallized from EtOAc/hexane to give 5-(aminocarbonyl)-3-pyridyl 4-[2-(3-cyanophenyl)ethyl]-1-piperidinecarboxylate (81 mg).

In the same manner, the compounds of Examples 319 to 382, 397, 398, 404, 408 to 412, 415, 420 and 423 were obtained.

Example 407

Under ice cooling, potassium tert-butoxide (2.73 g) was added to a DMF (50 ml) solution of triphenyl(pyridin-4-ylmethyl)phosphonium chloride hydrochloride (4.75 g) and tert-butyl 4-formylpiperidine-1-carboxylate (1.91 g), followed by stirring overnight at room temperature. The reaction liquid was diluted with EtOAc, washed with water and saturated brine in that order, and dried over anhydrous magnesium sulfate. The solvent was evaporated, and the residue was purified by silica gel column chromatography (eluent: hexane:EtOAc=1:2 (v/v)) to obtain a white solid (2.05 g).

The resulting solid (2.04 g) was dissolved in EtOAc (30 ml), and 10% palladium-carbon (200 mg) was added thereto, followed by stirring in the presence of hydrogen at room temperature for 3 hours. The catalyst was removed by filtration, the solvent was concentrated, and the residue was purified by silica gel column chromatography (eluent: hexane:ethyl acetate=1:1 (v/v)) to obtain tert-butyl 4-[(E)-2-pyridin-4-ylvinyl]piperidine-1-carboxylate (1.70 g) as a white solid.

A 4 M hydrogen chloride/EtOAc solution (0.88 ml) and platinum oxide (100 mg) were added to an ethanol (25 ml) solution of tert-butyl 4-[(E)-2-pyridin-4-ylvinyl]piperidine-1-carboxylate (1.02 g), followed by stirring in the presence of hydrogen (3.5 atm) for 24 hours. This was purged with argon, diluted with methanol, filtered through Celite, and concentrated under reduced pressure. The solid precipitated was washed with EtOAc/hexane, and dried under reduced pressure to obtain tert-butyl 4-(2-piperidin-4-ylethyl)piperidine-1-carboxylate hydrochloride (850 mg) as a white solid.

2-(Dicyclohexylphosphino)biphenyl (71 mg) and (1E,4E)-1,5-diphenyl-1,4-pentadien-3-one-palladium (93 mg) were added to a toluene (10 ml) suspension of tert-butyl 4-(2-piperidin-4-ylethyl)piperidine-1-carboxylate hydrochloride (1.13 g), 2-chloro-6-methylpyridine (431 mg) and sodium tert-butoxide (487 mg), followed by stirring at 120° C. for 1 hour. The reaction liquid was left cooled, then an aqueous saturated sodium carbonate solution was added thereto, followed by extraction with EtOAc. The organic layer was washed with saturated brine and dried over anhydrous magnesium sulfate. Then, the solvent was evaporated and the residue was purified by silica gel column chromatography (eluent: hexane:EtOAc=10:1 (v/v)) to obtain tert-butyl 4-{2-[1-(6-methylpyridin-2-yl)piperidin-4-yl]ethyl}piperidine-1-carboxylate (660 mg) as a red oil.

A 4 M hydrogen chloride/EtOAc solution (2 ml) was added to an EtOAc (10 ml) solution of tert-butyl 4-{2-[1-(6-methylpyridin-2-yl)piperidin-4-yl]ethyl}piperidine-1-carboxylate (650 mg), followed by stirring at room temperature for 2 days. The reaction liquid was concentrated to obtain 2-methyl-6-[4-(2-piperidin-4-ylethyl)piperidin-1-yl]pyridine dihydrochloride (644 mg) as a yellow amorphous substance.

Methyl 5-{[(4-nitrophenoxy)carbonyl]oxy}nicotinate (505 mg) was added to an acetonitrile (10 ml) solution of 2-methyl-6-[4-(2-piperidin-4-ylethyl)piperidin-1-yl]pyridine dihydrochloride (520 mg) and TEA (0.50 ml), followed by stirring at room temperature for 3 hours. The reaction liquid was diluted with EtOAc, washed with an aqueous saturated sodium hydrogencarbonate solution, and dried over anhydrous magnesium sulfate. The solvent was evaporated, and the resulting residue was purified by silica gel column chromatography (eluent: chloroform:methanol=98:2 (v/v)) to obtain methyl 5-{[(4-{2-[1-(6-methylpyridin-2-yl)piperidin-4-yl]ethyl}piperidin-1-yl)carbonyl]oxy}nicotinate (424 mg).

An aqueous 1 M sodium hydroxide solution (0.45 ml) was added to a THF (5 ml) solution of methyl 5-{[(4-{2-[1-(6-methylpyridin-2-yl)piperidin-4-yl]ethyl}piperidin-1-yl)carbonyl]oxy}nicotinate (208 mg), followed by stirring overnight at room temperature. The reaction liquid was concentrated to obtain sodium 5-{[(4-{2-[1-(6-methylpyridin-2-yl)piperidin-4-yl]ethyl}piperidin-1-yl)carbonyl]oxy}nicotinate (158 mg).

1-[3-(dimethylamino)propyl]-3-ethylcarbodiimide hydrochloride (103 mg), 1-hydroxybenzotriazole (90 mg) and ammonium chloride (119 mg) were added to a DMF (10 ml) solution of sodium 5-{[(4-{2-[1-(6-methylpyridin-2-yl)piperidin-4-yl]ethyl}piperidin-1-yl)carbonyl]oxy}nicotinate (210 mg), followed by stirring overnight at room temperature.

The reaction liquid was diluted with EtOAc, washed with an aqueous saturated sodium hydrogencarbonate solution and saturated brine in that order, and dried over anhydrous magnesium sulfate. The solvent was evaporated under reduced pressure, and the resulting residue was recrystallized from EtOAc/hexane to obtain 5-(aminocarbonyl)pyridin-3-yl 4-{2-[1-(6-methylpyridin-2-yl)piperidin-4-yl]ethyl}piperidine-1-carboxylate (150 mg).

Example 438

Screening for FAAH Activity-Inhibiting Substance with Rat Brain Homogenate (1) Preparation of Rat Brain Homogenate:

The head of a 10-week age SD-line male rat (Japan SLC) was cut off, and its cerebrum was taken out and weighed. Five times by volume its weight of an ice-cooled buffer (50 mM Tris-HCl (pH 7.4), 0.32 M sucrose) was added, and this was homogenized with a homogenizer in ice to give a uniform suspension. This was centrifuged (1500×g, 4° C., 15 minutes), and the supernatant was again centrifuged (15000×g, 4° C., 20 minutes) to obtain a precipitate. Further, using an ultrasonic wave generator (UR-20P, Tommy Seiko), this was ultrasonicated (power dial 4) for 5 seconds. The protein concentration of the resulting homogenate was measured according to a dye-coupling method (protein assay CBB solution, Nacalai Tesque). Using a buffer (50 mM Tris-HCl (pH 8.0), 1 mM EDTA, 0.1 mg/ml BSA, 100 mM NaCl), the rat brain suspension was diluted so that its protein concentration could be 60 μg/ml, thereby preparing an enzyme solution.

(2) Screening for FAAH Activity-Inhibiting Substance:

A substrate solution was prepared, comprising 2 μCi/ml radiolabeled anandamide (Anandamide [ethanolamine 1-$^3$H] (American Radiolabeled Chemical)), 8 μM anandamide (Funakoshi), 50 mM Tris-HCl (pH 8.0), 1 mM EDTA, 0.1 mg/ml BSA and 100 mM NaCl. Test substance solutions were prepared, dissolved in DMSO to have a concentration of from 1 nM to 100 μM. 50 μl of the substrate solution and 1 μm of the test substance solution were added to 50 μl of the enzyme solution, and left for 1 hour. As a control, DMSO was used in place of the test substance solution. To this, added was 200 μl of a 1:1 (by volume) solution of chloroform/methanol, followed by vortexing. This was centrifuged (15000 rpm, 2 minutes), whereby the decomposed product ethanolamine (ethanolamine 1-$^3$H) was separated in the upper layer (water/methanol layer) and the unreacted radiolabeled anandamide (Anandamide [ethanolamine 1-$^3$H]) was in the lower layer (chloroform layer). 30 μl of the upper layer was transferred into a 96-well organic solvent-resistant white microplate (PicoPlate-96; Perkin Elmer), 150 μl of Microscint-20 (Perkin Elmer) was added thereto, and this was measured with a microplate scintillation counter (TopCount™; Beckman). As compared with the control, the substance that gave a decreased value was selected as an FAAH activity-inhibiting substance.

(3) Measurement of $IC_{50}$ Value of FAAH Activity-Inhibiting Substance:

A test compound was dissolved in DMSO to have a varying concentration of from 1 nM to 100 μM to prepare test substance solutions. According to the method mentioned above, the compound was analyzed for its influence on FAAH activity. As a control, DMSO was used. A measured value of a case where a buffer (50 mM Tris-HCl (pH 8.0), 1 mM EDTA, 0.1 mg/ml BSA, 100 mM NaCl) was reacted in place of the enzyme solution was subtracted from every measured value. Based on the measured value of the control, 100%, $IC_{50}$ value of the test substance was obtained. For example, $IC_{50}$ of the compounds of Examples 2, 151, 225, 228, 273, 324, 325 and 359 was 0.14 nM, 27 nM, 0.37 nM, 0.19 nM, 0.65 nM, 0.54 nM, 2.5 mM and 1.3 nM, respectively.

The above results confirm that, when a test substance is contacted with a homogenate of a tissue that expresses FAAH or functional FAAH and when the test substance-dependent FAAH activity change is measured, then it may be screened for an FAAH activity-inhibiting substance, or that is, a remedy for urinary frequency and urinary incontinence, a remedy for overactive bladder and/or a remedy for pain.

Example 439

Screening for FAAH Activity-Inhibiting Substance with Human Bladder Epithelial Cancer-Derived Cell (1) Screening for FAAH Activity-Inhibiting Substance:

Human bladder epithelial cancer-derived cell line 5678 cells (HTB-9; ATCC) were seeded on a 48-well cell culture plate in an amount of $1\times10^5$ cell/well, using 10% fetal bovine serum (HyClone)-containing RPMI1640 medium (Invitrogen). After incubated at 37° C. for at least 12 hours, the cells were washed with 400 μl/well of a buffer (Hank's Balanced Salt Solution, 20 mM Hepes-NaOH (pH 7.4)). A test substance dissolved in DMSO was added to a substrate solution (the above buffer containing 3 μCi/ml radiolabeled anandamide (Anandamide [ethanolamine 1-3H]) and 10 μM anandamide) so as to have a concentration of from 0.003 nM to 30 nM. As a control, DMSO alone was added. 100 μl/well of the substrate solution was added to the above cells, and incubated in a $CO_2$ incubator at 37° C. for 30 minutes. Next, the cell culture plate was transferred onto ice, and the substrate solution was removed by suction; and 75 μl/well of a cytolytic solution (the above buffer containing 0.5% Triton X-100, and 10 μM of FAAH-inhibitory activity-having compound, 3'-carbamoylbiphenyl-3-yl cyclohexylcarbamate (URB597; Cayman chemical; Kathuria et al., Nature Med., Vol. 9, pp. 76-81, 2003)) was added thereto, followed by stirring. The resulting cell lysate in every well was individually transferred into a 1.5 ml sample tube, to which was added 150 μl of 1:1 (by volume) chloroform/methanol solution, followed by vortexing. This was centrifuged (15000 rpm, 2 minutes), whereby the decomposed product, ethanolamine (ethanolamine 1-$^3$H) was separated in the upper layer (water/methanol layer) and the unreacted radiolabeled anandamide was in the lower layer (chloroform layer). 25 μl of the upper layer was transferred into a 96-well organic solvent-resistant white microplate (PicoPlate-96; Perkin Elmer), 150 μl of Microscint-20 (Perkin Elmer) was added thereto, and this was measured with a microplate scintillation counter (TopCount™; Beckman). As compared with the control, the substance that gave a decreased value was selected as an FAAH activity-inhibiting substance.

(2) Measurement of $IC_{50}$ Value of FAAH Activity-Inhibiting Substance:

A test compound dissolved in DMSO to have a concentration of 10 mM was dissolved in the substrate solution so as to have a varying concentration of from 0.003 nM to 30 μM. According to the method mentioned above, the compound was analyzed for its influence on FAAH activity. As a negative control, DMSO was used. As a positive control, URB597 was added to the substrate solution to have a concentration of 10 μM. Based on the measured value of the positive control, 0%, and on the measured value of the negative control, 100%, $IC_{50}$ value of the test substance was obtained. The test results are shown in Table 64.

The above results confirm the excellent FAAH inhibitory activity of typical compounds of the present invention. In addition, these indicate that, when a test substance is contacted with a cell that expresses FAAH or functional FAAH and when the test substance-dependent FAAH activity change is measured, then it may be screened for an FAAH activity-inhibiting substance, or that is, a remedy for urinary frequency and urinary incontinence, a remedy for overactive bladder and/or a remedy for pain.

Example 440

Screening for FAAH Activity-Inhibiting Substance with Tissue Homogenate of Rat Administered with Test Substance (1) Administration to Rat, and Preparation of Tissue Homogenate:

A test substance suspended in 0.5% methyl cellulose (MC) solution was orally administered to two 9-week age Wistar male rats (Japan SLC) at a dose of from 1 to 3 mg/kg. As a control, 0.5% MC solution was administered to other two rats. After 30 minutes, the blood was collected from each rat under ether anesthesia through its aorta. With that, the head of each rat was cut off, and its cerebrum was taken out.

3 ml of the collected blood was diluted with the same amount of physiological saline water, and gently put on 3 ml of a hemocyte-separating agent (Nycoplep; AXIS-SHIELD) in a centrifugal tube. This was centrifuged (400×g, 20 minutes) to collect the monocytic layer. The resulting monocytes were washed twice with physiological saline, and frozen and stored at −20° C. until their use for measurement.

To the collected rat brain, added was five times by volume its weight of an ice-cooled buffer (50 mM Tris-HCl (pH 8.0), 1 mM EDTA), and this was homogenized with a homogenizer in ice to give a uniform suspension. Further, using an ultrasonic wave generator (UR-20P (power dial 4), Tommy Seiko), this was ultrasonicated for 5 seconds. To the above frozen monocytes, added was 1001 of an ice-cooled buffer (50 mM Tris-HCl (pH 8.0), 1 mM EDTA), and using an ultrasonic wave generator (UR-20P (power dial 4), Tommy Seiko), this was ultrasonicated for 5 seconds. The protein concentration of each of the homogenates of brain and monocytes was measured according to a dye-coupling method (protein assay CBB solution, Nacalai Tesque). Using a buffer (50 mM Tris-HCl (pH 8.0), 1 mM EDTA, 0.1 mg/ml BSA, 100 mM NaCl), the homogenates of brain and monocytes were diluted so that their protein concentration could be 80 μg/ml and 400 μg/ml thereby preparing enzyme solutions.

(2) Measurement of FAAH Activity:

50 μl of the enzyme solution was reacted with 50 μl of a substrate solution (2 μCi/ml radiolabeled anandamide (Anandamide [ethanolamine 1-$^3$H] (American Radiolabeled Chemical)), 8 μM anandamide (Funakoshi), 50 mM Tris-HCl (pH 8.0), 1 mM EDTA) added thereto, at room temperature for 1 hour. 200 μl of a 1:1 (by volume) solution of chloroform and methanol was added to it, followed by vortexing. This was centrifuged (12000×g, 2 minutes), whereby the decomposed product ethanolamine (ethanolamine 1-$^3$H) was separated in the upper layer (water/methanol layer) and the unreacted radiolabeled anandamide (Anandamide [ethanolamine 1-$^3$H]) was in the lower layer (chloroform layer). 25 μl of the upper layer was transferred into a 96-well organic solvent-resistant white microplate (PicoPlate-96; Perkin Elmer), 150 μl of Microscinti-20 (Perkin Elmer) was added thereto, and this was measured with a microplate scintillation counter (TopCount™; Beckman).

Based on the FAAH activity of the control, test substance-free, rat brain or monocyte homogenate, 100%, and on the FAAH activity of the tissue homogenate-free buffer (50 mM Tris-HCl (pH 8.0), 1 mM EDTA, 0.1 mg/ml BSA, 100 mM NaCl), 0%, the relative value (%) of the FAAH activity of the tissue homogenate of the rat administered with the test substance was obtained. The substance that decreased the relative value of FAAH activity was selected as an FAAH activity-inhibiting substance.

The above results confirm that, when a test substance is administered to a test animal and when the test substance-dependent FAAH activity change in the tissue homogenate of the animal is measured, then it may be screened for an FAAH activity-inhibiting substance, or that is, a remedy for urinary frequency and urinary incontinence, a remedy for overactive bladder and/or a remedy for pain.

Example 441

Effect of Compound to Cyclophosphamide (CPA)-Induced Urinary Frequency in Rat

Compounds were tested for their bladder irritation-relieving effect, using pathologic models. It is known that systemic administration of cyclophosphamide (CPA) converts the compound into its metabolite, acrolein, and, as existing in urine, this injures the bladder mucosa. In rats, CPA administration induces bladder pain or urinary frequency accompanied by hemorrhagic cystitis, and therefore using such rats, it is possible to evaluate the potency of drug for these symptoms. In this experiment, used were 9-week age Wistar female rats (Charles River). CPA (100 mg/kg) was intraperitoneally administered to the rats, and after 2 days, the rats were tested. A test compound was orally administered (p.o.) to the rats; and after 15 minutes, distilled water (30 ml/kg) was forcedly orally administered thereto. The rats were put in a metabolic cage, and their urine was continuously measured for 1 hour. The overall urine amount was divided by the overall urination frequency, and the effective bladder capacity was thus calculated. As a result, in the group administered with the solvent, 0.5% methyl cellulose (MC), the effective bladder capacity reduced, and the rats showed urinary frequency. In oral administration, effective dose of compounds of Examples 2, 218 and 261 was 3 mg/kg; that of compounds of Examples 225, 228, 273, 313, 324, 325 and 359 was 1 mg/kg. These compounds increased the reduced effective bladder capacity and relieved the condition of urinary frequency.

Example 442

Anti-Allodynia Effect of Compounds for L5/L6 Spinal Nerve-Ligated Rat (Neuropathic Pain Model)

A 5 to 6-week age male SD rat was subjected to operation of ligating its left-side L5 and L6 spinal nerves with silk threads. For evaluating the analgesic effect of a test substance, employed was a von Frey hair test. Briefly, the hind paw of the animal was picked with hair, whereupon the minimum strength of the hair for limb withdrawal response was referred to as the response threshold (log gram) to the mechanical stimulation. In the preliminary test, it was confirmed that the response threshold of the operated paw of the animal remarkably lowered within 7 to 14 days after the operation (under allodynia), and the anti-allodynia effect of the test compound was evaluated on any day within 7 to 14 days after the operation. On the day before the test date, the response threshold before test compound administration was measured. The test animals were so grouped that the mean value difference and fluctuation in the threshold before test compound administration in the groups could be small. In the evaluation test of test compounds, the response threshold value after test compound administration was measured. The test compound was orally administered 60 minutes before the response threshold value measurement. Based on the response thresholds of operated and non-operated paws in the solvent-administered group, 0% and 100%, respectively, the potency of the test compound for its anti-allodynia effect was calculated. As a result, in 10 mg/kg oral administration of the compound of Example 126, it showed an anti-allodynia potency of 74%.

TABLE 1

| Rex No. | Str | MS m/z (M + H)+ |
|---|---|---|
| 1 | 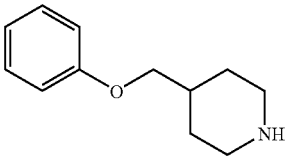 | 192:FAB |
| 2 | 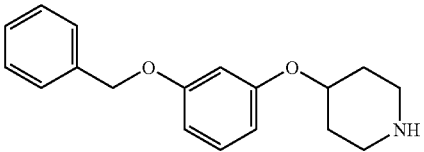 | 284:FAB |
| 3 | 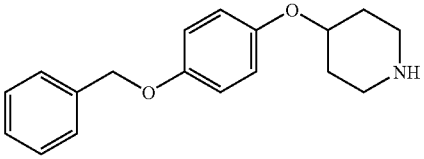 | 284:FAB |
| 4 | 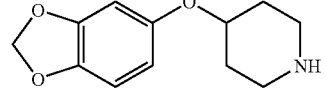 | 222:ESI |
| 5 | 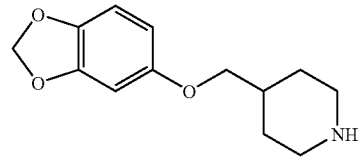 | 236:ESI |
| 6 | 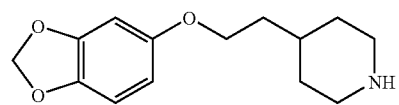 | 250:ESI |
| 7 | 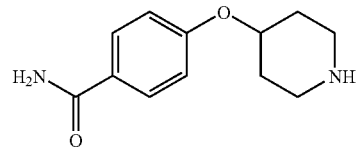 | 221:FAB |
| 8 | 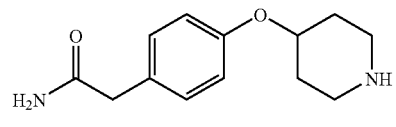 | 235:FAB |
| 9 | 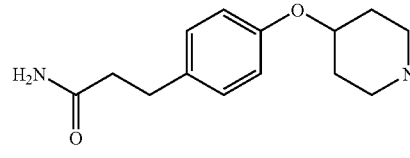 | 249:FAB |
| 10 | 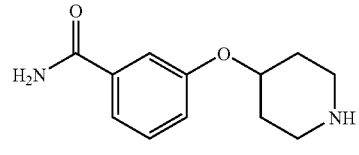 | 221:FAB |
| 11 | 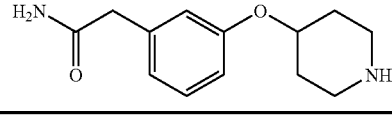 | 235:FAB |

TABLE 2

| Rex No. | Str | MS m/z (M + H)+ |
|---|---|---|
| 12 | 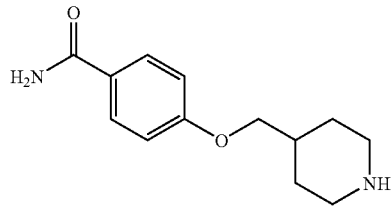 | 235:FAB |

TABLE 2-continued
| Rex No. | Str | MS m/z (M + H)+ |
|---|---|---|
| 13 | 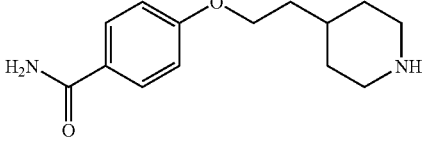 | 249:FAB |
| 14 | 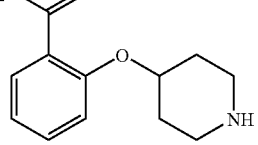 | 221:FAB |
| 15 | 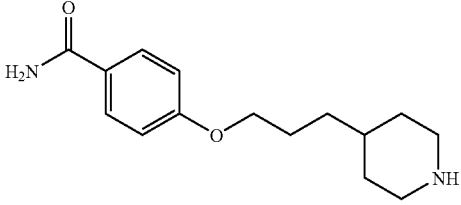 | 263:FAB |
| 16 | 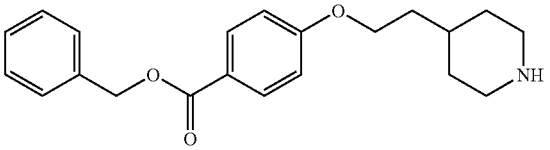 | 340:FAB |
| 17 | 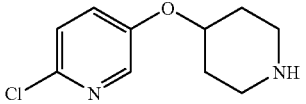 | 213:FAB |
| 18 | 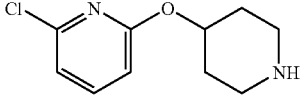 | 213:FAB |
| 19 | 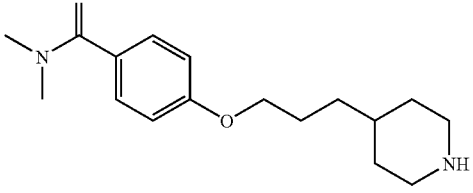 | 291:FAB |
| 20 | 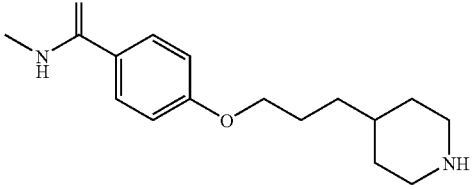 | 277:FAB |

TABLE 2-continued
| Rex No. | Str | MS m/z (M + H)+ |
|---|---|---|
| 21 | 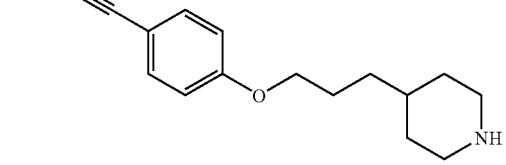 | 245:FAB |
| 22 | 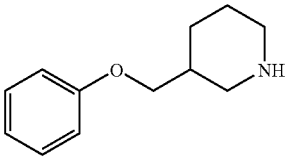 | 192:FAB |
TABLE 3
| Rex No. | Str | MS m/z (M + H)+ |
|---|---|---|
| 23 | 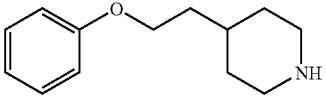 | 206:FAB |
| 24 | 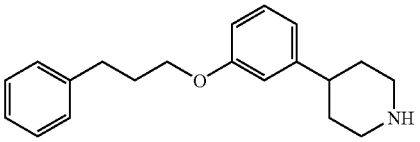 | 296:ESI |
| 25 | 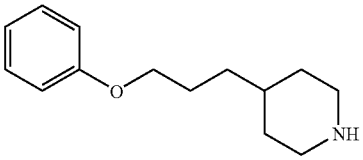 | 220:FAB |
| 26 | 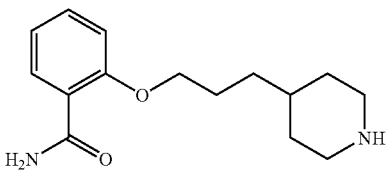 | 263:FAB |
| 27 | 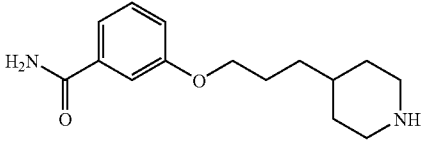 | 263:FAB |
| 28 | 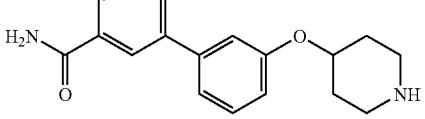 | 297:FAB |
| 29 | 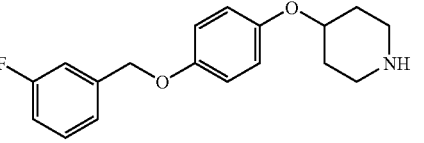 | 302:FAB |
| 30 | 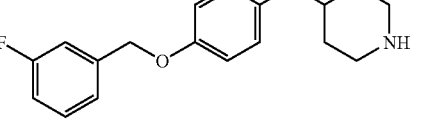 | 314:FAB |
| 31 | 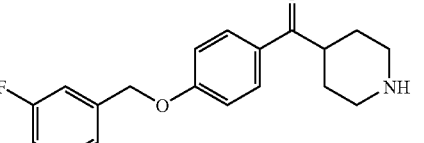 | 290:FAB |
| 32 | 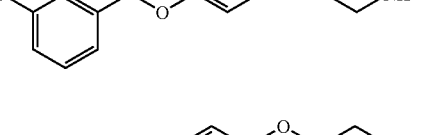 | 264:ESI |
| 33 | 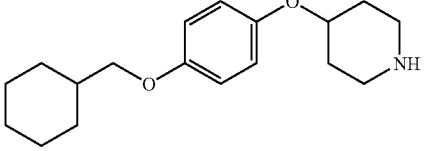 | 268:ESI |

TABLE 4

| Rex No. | Str | MS m/z (M + H)+ |
|---|---|---|
| 34 | 3-fluorobenzyl 3-(piperidin-4-yloxy)phenyl ether | 302:FAB |
| 35 | 3-cyanobenzyl 3-(piperidin-4-yloxy)phenyl ether | 309:FAB |
| 36 | 2-cyclohexylethyl 3-(piperidin-4-yloxy)phenyl ether | 304:FAB |
| 37 | 3-fluorobenzyl 6-(piperidin-4-yloxy)pyridin-2-yl ether | 303:FAB |
| 38 | 2-cyclohexylethyl 6-(piperidin-4-yloxy)pyridin-2-yl ether | 305:FAB |
| 39 | 3-[6-(piperidin-4-yloxy)pyridin-2-yl]benzamide | 298:FAB |
| 40 | 4-[2-(3-phenylpropoxy)ethyl]piperidine | 248:ESI |
| 41 | 3-fluorobenzyl 4-(piperidin-4-ylthio)phenyl ether | 318:FAB |
| 42 | 3-fluorobenzyl 3-(piperidin-4-ylthio)phenyl ether | 318:FAB |

TABLE 4-continued
| Rex No. | Str | MS m/z (M + H)+ |
|---|---|---|
| 43 | 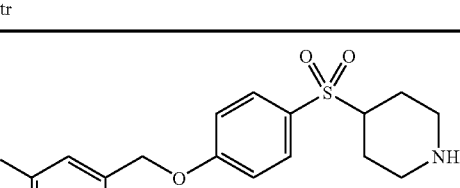 | 350:FAB |
| 44 | | 332:FAB |
TABLE 5
| Rex No. | Str | MS m/z (M + H)+ |
|---|---|---|
| 45 | 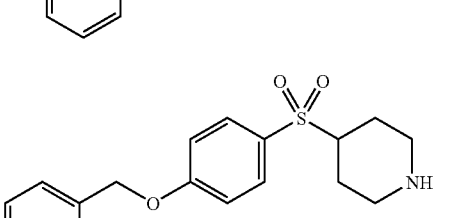 | 357:FAB |
| 46 | | 366:FAB |
| 47 | | 338:FAB |
| 48 | | 352:FAB |
| 49 | | 192:ESI |

TABLE 5-continued

| Rex No. | Str | MS m/z (M + H)+ |
|---|---|---|
| 50 | 4-((piperidin-4-yloxy)methyl)benzamide | 235:FAB |
| 51 | 4-(2-(benzyloxy)ethyl)piperidine | 220:ESI |
| 52 | 4-((benzyloxy)methyl)piperidine | 206:ESI |
| 53 | 4-((cinnamyloxy)methyl)piperidine | 232:ESI |
| 54 | 5-((3-fluorobenzyl)oxy)-2-(piperidin-4-yloxy)pyridine | 303:FAB |

TABLE 6

| Rex No. | Str | MS m/z (M + H)+ |
|---|---|---|
| 55 | N-benzyl-2-(piperidin-4-yl)acetamide | 233:ESI |
| 56 | 1-methyl-2-(3-(piperidin-4-yl)propyl)-1H-benzo[d]imidazole | 258:ESI |
| 57 | (E)-4-(2-(piperidin-4-yl)vinyl)benzamide | 231:FAB |
| 58 | 4-(2-(piperidin-4-yl)ethyl)benzamide | 233:FAB |
| 59 | N-(cyclohexylmethyl)-N-methyl-4-(piperidin-4-yloxy)aniline | 303:FAB |
| 60 | 1-(3-(benzyloxy)phenyl)piperazine | 269:FAB |

TABLE 6-continued

| Rex No. | Str | MS m/z (M + H)+ |
|---|---|---|
| 61 | | 318:FAB |
| 62 | | 351:ESI |
| 63 | | 318:FAB |
| 64 | | 365:FAB |
| 65 | | 264:FAB |

TABLE 7

| Rex No. | Str | MS m/z (M + H)+ |
|---|---|---|
| 66 | | 264:FAB |
| 67 | | 303:FAB |
| 68 | | 315:FAB |
| 69 | | 317:FAB |

TABLE 7-continued

| Rex No. | Str | MS m/z (M + H)+ |
|---|---|---|
| 70 | 4-(cycloheptylmethoxy)phenyl piperazin-1-yl ketone | 317:FAB |
| 71 | 4-(benzyloxy)phenyl piperazin-1-yl ketone | 297:FAB |
| 72 | N-butyl-2-[4-(piperazin-1-ylcarbonyl)phenoxy]acetamide | 320:FAB |
| 73 | 5-(dimethylamino)pyridin-3-ol | 139:ESI |
| 74 | 5-(morpholin-4-yl)pyridin-3-ol | 181:ESI |

TABLE 8

| Rex No. | Str | MS m/z (M + H)+ |
|---|---|---|
| 75 | 5-{[2-(dimethylamino)ethyl](methyl)amino}pyridin-3-ol | 196:ESI |
| 76 | ethyl 1-(5-hydroxypyridin-3-yl)piperidine-4-carboxylate | 251:ESI |
| 77 | 6-(methoxymethyl)pyridin-3-ol | 140:ESI |

TABLE 8-continued

| Rex No. | Str | MS m/z (M + H)+ |
|---|---|---|
| 78 | | 209:ESI |
| 79 | | 182:ESI |
| 80 | | 240:ESI |
| 81 | | 180:ESI |
| 82 | | 168:ESI |
| 83 | | 369:ESI |
| 84 | | 370:FAB |
| 85 | | 383:ESI |

TABLE 9
| Rex No. | Str | MS m/z $(M + H)^+$ |
|---|---|---|
| 86 | 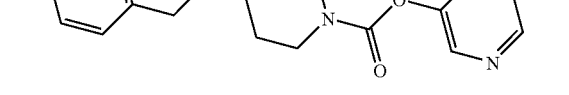 | 412:FAB |
| 87 | 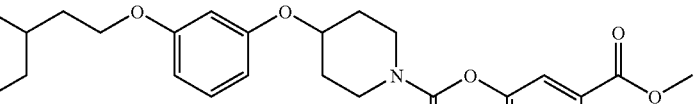 | 483:FAB |
| 88 |  | 384:FAB |
| 89 | 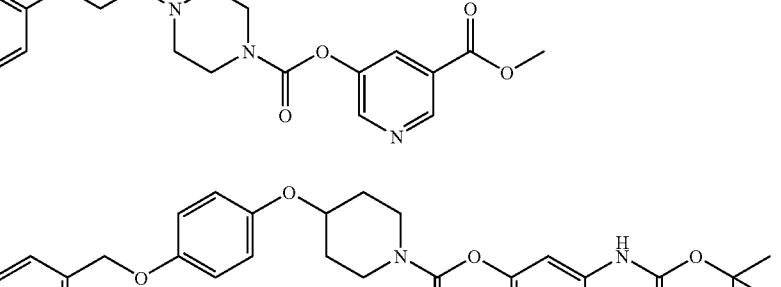 | 538:ESI |
| 90 | 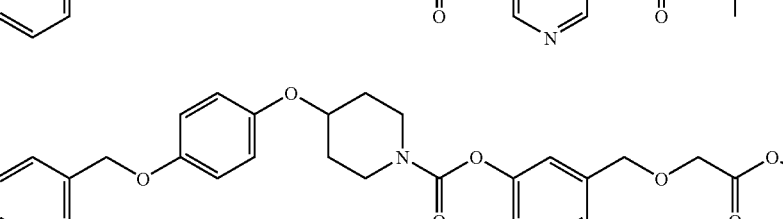 | 567:ESI |
| 91 | 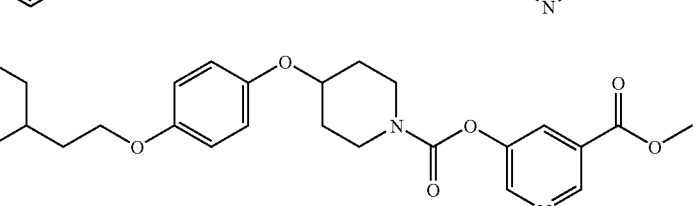 | 483:ESI |
| 92 | 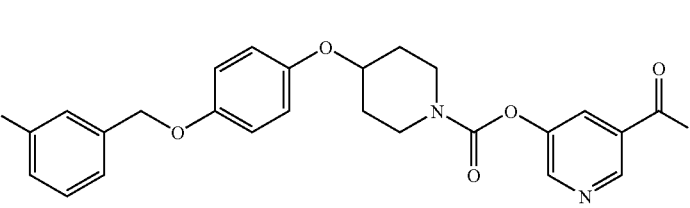 | 493:ESI |
| 93 | 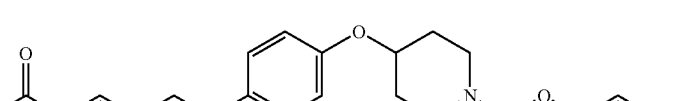 | 522:ESI |

TABLE 9-continued

| Rex No. | Str | MS m/z (M + H)⁺ |
|---|---|---|
| 94 | [structure: piperidine-4-carboxylic acid with N-C(=O)-O-pyridin-3-yl] | 251:ESI |

TABLE 10

| Rex No. | Str | MS m/z (M + H)⁺ or (M − H)⁻ or (M)⁺ FAB or ESI or EI |
|---|---|---|
| 95 | [3-cyanophenyl-ethyl-piperidine] | 215(M + H)⁺ FAB |
| 96 | [3-bromophenyl-ethyl-piperidine] | 268, 270(M + H)⁺ FAB |
| 97 | [3-fluorophenyl-ethyl-piperidine] | 208(M + H)⁺ FAB |
| 98 | [3-methoxyphenyl-ethyl-piperidine] | 220(M + H)⁺ FAB |
| 99 | [3-chlorophenyl-ethyl-piperidine] | 224(M + H)⁺ FAB |
| 100 | [4-cyanophenyl-ethyl-piperidine] | 215(M + H)⁺ FAB |
| 101 | [2-cyanophenyl-ethyl-piperidine] | 215(M + H)⁺ FAB |
| 102 | [methyl 3-[2-(1-Boc-piperidin-4-yl)ethyl]benzoate] | 348(M + H)⁺ FAB |

TABLE 10-continued

| Rex No. | Str | MS m/z (M + H)+ or (M − H)− or (M)+ FAB or ESI or EI |
|---|---|---|
| 103 | (structure) | 348(M + H)+ ESI |
| 104 | (structure) | 332(M − H)− ESI |
| 105 | (structure) | 332(M − H)− ESI |
| 106 | (structure) | 333(M + H)+ ESI |

TABLE 11

| Rex No. | Str | MS m/z (M + H)+ or (M − H)− or (M)+ FAB or ESI or EI |
|---|---|---|
| 107 | (structure) | 375(M + H)+ ESI |
| 108 | (structure) | 389(M + H)+ ESI |
| 109 | (structure) | 377(M − H)− API |

TABLE 11-continued
| Rex No. | Str | MS m/z (M + H)+ or (M − H)− or (M)+ FAB or ESI or EI |
|---|---|---|
| 110 | 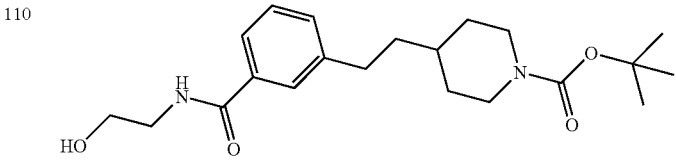 | 375(M − H)− API |
| 111 | 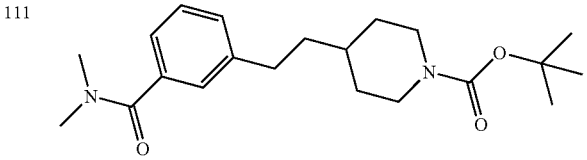 | 361(M + H)+ ESI |
| 112 | 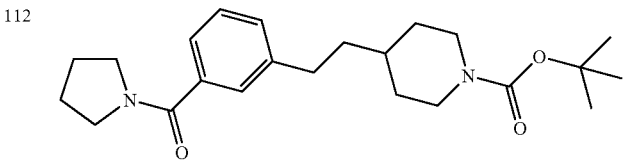 | 387(M + H)+ FAB |
| 113 | 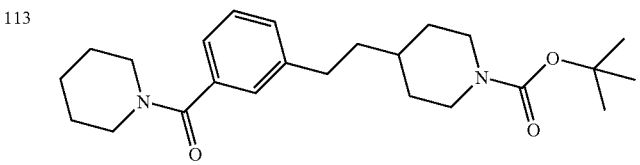 | 401(M + H)+ FAB |
| 114 | 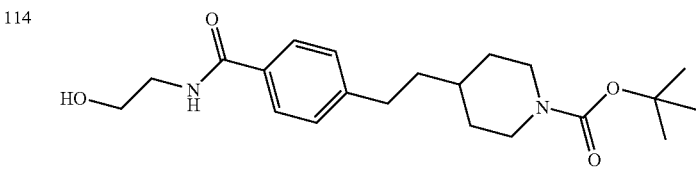 | 377(M + H)+ ESI |
| 115 | 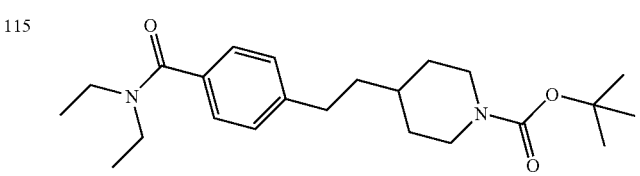 | 389(M + H)+ ESI |
| 116 | 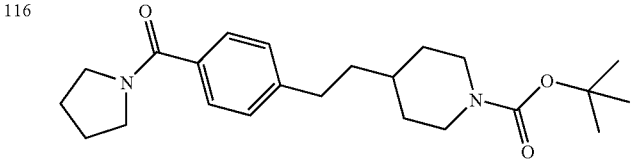 | 387(M + H)+ ESI |
| 117 | 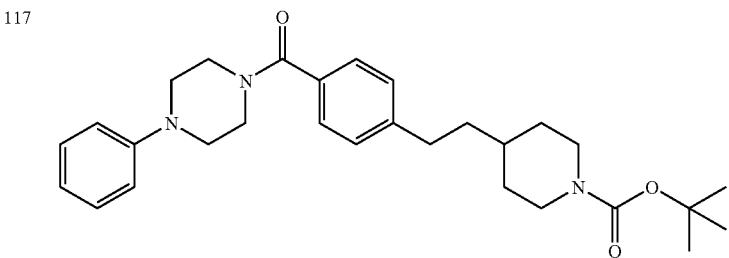 | 478(M + H)+ ESI |

TABLE 11-continued
| Rex No. | Str | MS m/z (M + H)+ or (M − H)− or (M)+ FAB or ESI or EI |
|---|---|---|
| 118 | 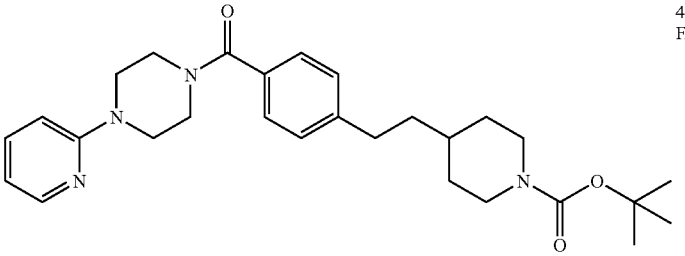 | 479(M + H)+ FAB |
TABLE 12
| Rex No. | Str | MS m/z (M + H)+ or (M − H)− or (M)+ FAB or ESI or EI |
|---|---|---|
| 119 | 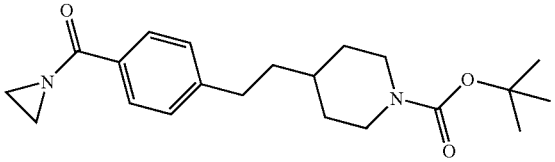 | 359(M + H)+ ESI |
| 120 | 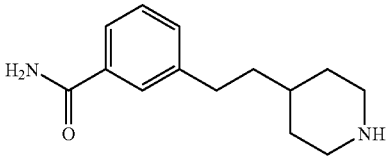 | 233(M + H)+ FAB |
| 121 | 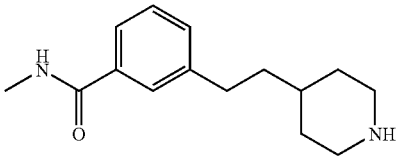 | 247(M + H)+ FAB |
| 122 | 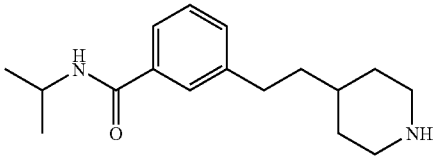 | 275(M + H)+ ESI |
| 123 | 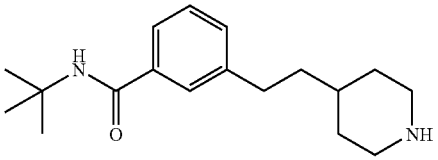 | 289(M + H)+ ESI |
| 124 | 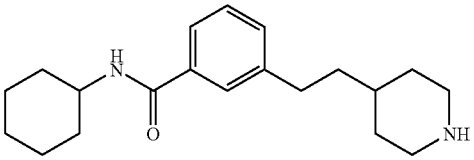 | 315(M + H)+ FAB |

TABLE 12-continued

| Rex No. | Str | MS m/z (M + H)⁺ or (M − H)⁻ or (M)⁺ FAB or ESI or EI |
|---|---|---|
| 125 | | 279(M + H)⁺ ESI |
| 126 | | 277(M + H)⁺ ESI |
| 127 | | 261(M + H)⁺ FAB |
| 128 | | 287(M + H)⁺ ESI |
| 129 | | 301(M + H)⁺ ESI |
| 130 | | 303(M + H)⁺ ESI |

TABLE 13

| Rex No. | Str | MS m/z (M + H)⁺ or (M − H)⁻ or (M)⁺ FAB or ESI or EI |
|---|---|---|
| 131 | | 378(M + H)⁺ ESI |

TABLE 13-continued
| Rex No. | Str | MS m/z (M + H)+ or (M − H)− or (M)+ FAB or ESI or EI |
|---|---|---|
| 132 | 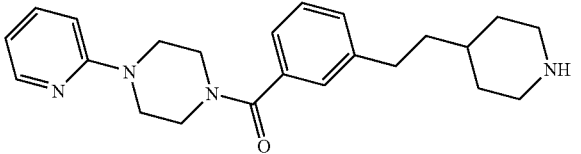 | 379(M + H)+ ESI |
| 133 | 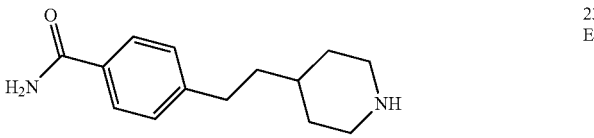 | 233(M + H)+ ESI |
| 134 | 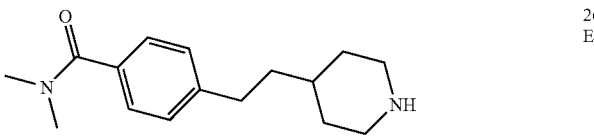 | 260(M)+ ESI |
| 135 | 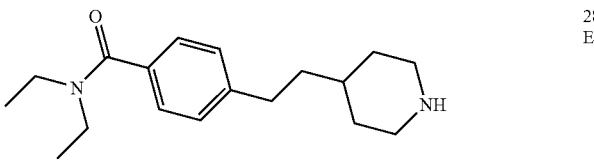 | 288(M + H)+ ESI |
| 136 | 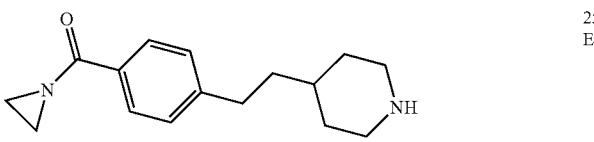 | 259(M + H)+ ESI |
| 137 | 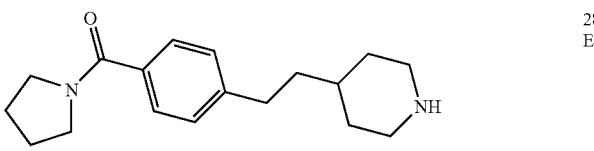 | 286(M + H)+ ESI |
| 138 | 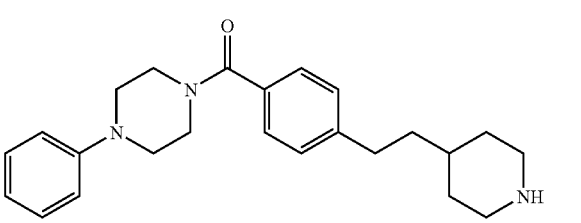 | 378(M + H)+ ESI |
| 139 | 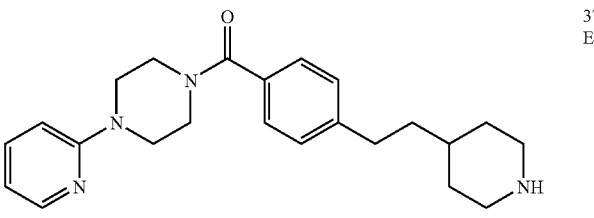 | 379(M + H)+ ESI |

TABLE 13-continued
| Rex No. | Str | MS m/z (M + H)+ or (M − H)− or (M)+ FAB or ESI or EI |
|---|---|---|
| 140 | 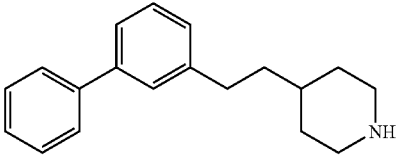 | 266(M + H)+ FAB |
| 141 | 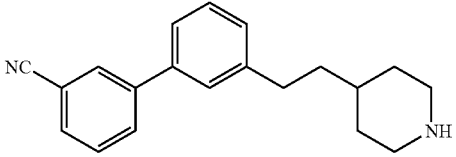 | 291(M + H)+ FAB |
| 142 | 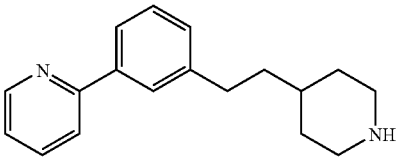 | 267(M + H)+ FAB |
| 143 | 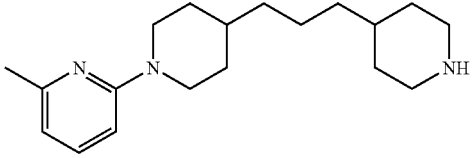 | 302(M + H)+ FAB |
TABLE 14
| Rex No. | Str | MS m/z (M + H)+ or (M − H)− or (M)+ FAB or ESI or EI |
|---|---|---|
| 144 | 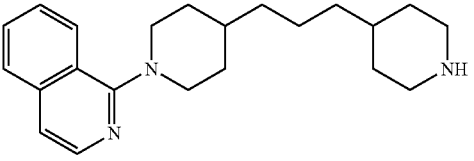 | 338 (M + H)+ ESI |
| 145 | 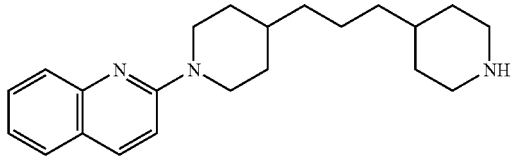 | 338 (M + H)+ FAB |
| 146 | 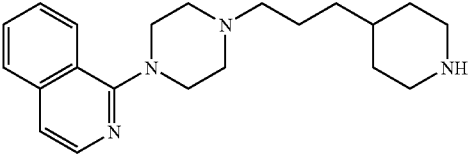 | 339 (M + H)+ ESI |

TABLE 14-continued
| Rex No. | Str | MS m/z $(M + H)^+$ or $(M - H)^-$ or $(M)^+$ FAB or ESI or EI |
|---|---|---|
| 147 | 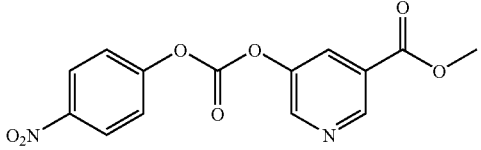 | 341 $(M + Na)^+$ ESI |
| 148 | 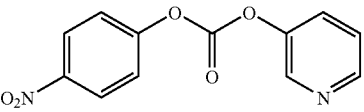 | 261 $(M + H)^+$ ESI |
| 149 | 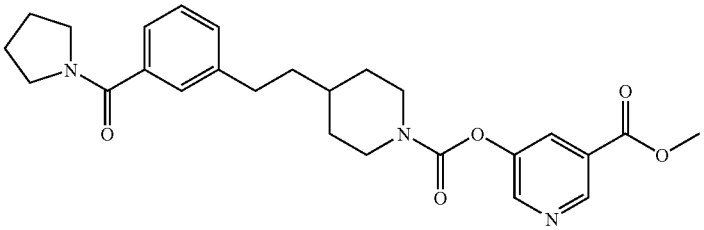 | 466 $(M + H)^+$ FAB |
| 150 | 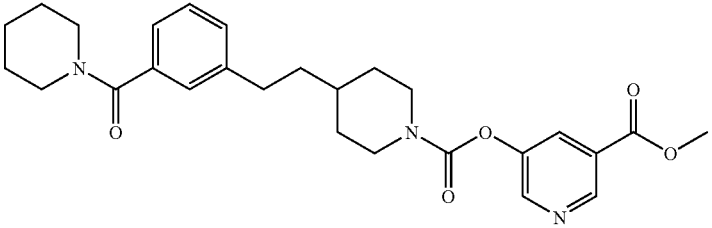 | 480 $(M + H)^+$ ESI |
| 151 | 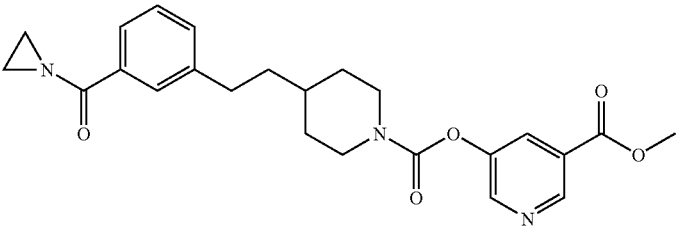 | 438 $(M + H)^+$ ESI |
| 152 | 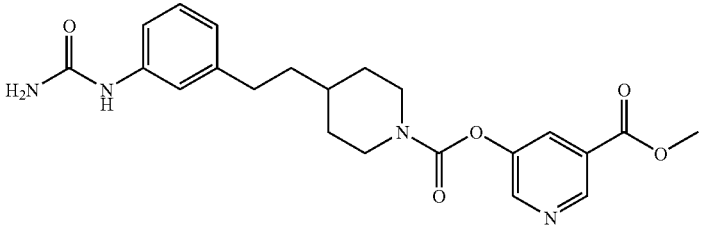 | 427 $(M + H)^+$ ESI |
| 153 | 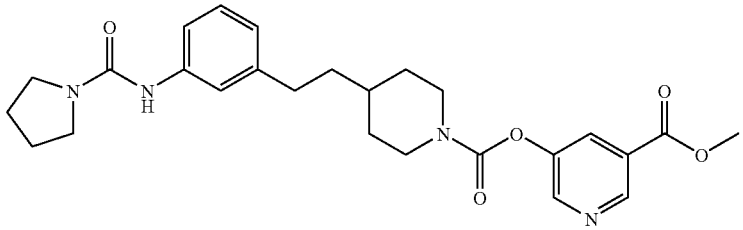 | 481 $(M + H)^+$ FAB |

TABLE 15

| Rex No. | Str | MS m/z (M + H)⁺ or (M − H)⁻ or (M)⁺ FAB or ESI or EI |
|---|---|---|
| 154 | 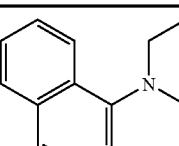 | 338 (M + H)⁺ ESI |
| 155 | 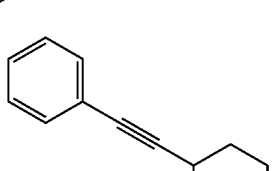 | 186 (M + H)⁺ ESI |

TABLE 16

| Ex No. | T | R¹ | R² | R⁴ | Sal |
|---|---|---|---|---|---|
| 001 | CH | H | H | H | oxal |
| 002 | CH | 4-(3-FPhCH$_2$O)PhO | H | H | free |
| 003 | CH | 4-(3-FPhCH$_2$O)PhCO | H | H | free |
| 004 | N | 4-(3-FPhCH$_2$O)PhCO | H | H | oxal |
| 005 | N | 4-cHexCH$_2$OPhCO | H | H | free |
| 006 | N | 4-cHex(CH$_2$)$_2$OPhCO | H | H | free |
| 007 | N | 4-cHepCH$_2$OPhCO | H | H | free |
| 008 | N | 4-PhCH$_2$OPhCO | H | H | free |
| 009 | CH | 4-cHexCH$_2$OPhO | H | H | free |
| 010 | CH | PhCH$_2$ | H | H | oxal |
| 011 | CH | 3-PhCH$_2$OPhO | H | H | free |
| 012 | CH | 4-PhCH$_2$OPhO | H | H | free |
| 013 | CH | 4-(3-FPhCH$_2$O)PhO | H | 6'-Me | HCl |
| 014 | CH | PhCO | H | H | free |
| 015 | CH | 4-FPh | H | H | free |
| 016 | CH | PhCONH | H | H | free |
| 017 | N | Ph(CH$_2$)$_2$ | H | H | free |
| 018 | CH | (6-methoxy-1,3-benzodioxol-5-yl) | H | H | HCl |
| 019 | CH | (1,3-benzodioxol-5-yl)OCH$_2$— | H | H | free |
| 020 | CH | (1,3-benzodioxol-5-yl)O(CH$_2$)$_2$— | H | H | HCl |
| 021 | CH | PhO | H | H | HCl |

TABLE 16-continued

| Ex No. | T | R¹ | R² | R⁴ | Sal |
|---|---|---|---|---|---|
| 023 | N | Ph | H | H | free |
| 024 | CH | 4-H$_2$NCOPhO | H | H | free |

TABLE 17

| Ex No. | T | R¹ | R² | R⁴ | Sal |
|---|---|---|---|---|---|
| 025 | CH | 4-H$_2$NCOCH$_2$PhO | H | H | free |
| 026 | CH | 4-H$_2$NCO(CH$_2$)$_2$PhO | H | H | free |
| 027 | CH | 3-H$_2$NCOPhO | H | H | oxal |
| 028 | CH | 3-H$_2$NCOCH$_2$PhO | H | H | oxal |
| 029 | CH | 4-(3-FPhCH$_2$O)PhO | H | 5'-COOMe | free |
| 030 | CH | 4-(3-FPhCH$_2$O)PhO | H | 5'-NMe$_2$ | HCl |
| 031 | CH | 4-cHexCH$_2$N(Me)PhO | H | H | 2HCl |
| 033 | N | Ph(CH$_2$)$_5$ | H | H | 2HCl |
| 034 | N | 4-PhCH$_2$OPh | H | H | free |
| 035 | CH | Ph(CH$_2$)$_2$ | H | H | HCl |
| 036 | CH | PhCH$_2$O | H | H | HCl |
| 037 | C | Ph | 4-HO | H | HCl |
| 039 | C | Ph | 4-Ac | H | free |
| 040 | CH | Ph | H | H | HCl |
| 041 | CH | 4-H$_2$NCOPhOCH$_2$ | H | H | free |
| 042 | CH | 4-(3-FPhCH$_2$O)PhO | H | 5'-Cl | free |
| 043 | CH | 4-H$_2$NCOPhO(CH$_2$)$_2$ | H | H | free |
| 044 | CH | 4-(3-FPhCH$_2$O)PhO | H | 5'-Br | free |

TABLE 17-continued

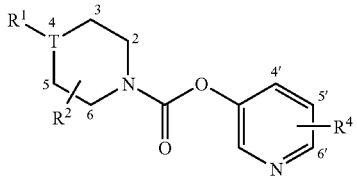

| Ex No. | T | R¹ | R² | R⁴ | Sal |
|---|---|---|---|---|---|
| 045 | CH | 4-(3-FPhCH₂O)PhO | H | 5'-Mo4 | HCl |
| 046 | CH | 4-H₂NCOPhCH₂O | H | H | free |
| 047 | CH | PhCH₂NHCO | H | H | free |
| 048 | N | 3-PhCH₂OPh | H | H | 2HCl |
| 049 | N | Ph(CH₂)₄ | H | H | free |
| 050 | N | tBuOCO | H | H | free |
| 051 | CH | 2-Cl-4-PhCH₂OPhO | H | H | HCl |
| 052 | CH | PhCH₂ | H | 6'-Me | HCl |
| 053 | CH | PhCH₂O(CH₂)₂ | H | H | HCl |
| 054 | CH | PhCH₂ | H | 5'-Br | free |
| 055 | CH | PhCH₂ | H | 6'-CH₂OMe | free |
| 056 | CH | 4-(3-FPhCH₂O)PhO | H | 5'-N(Me)(CH₂)₂NMe₂ | 2HCl |
| 057 | CH | 2-H₂NCOPhO | H | H | oxal |
| 058 | N | 4-(3-FPhCH₂O)PhSO₂ | H | H | free |
| 059 | CH | Ph₂(HO)C | H | H | HCl |
| 060 | CH | 3-HOPh | H | H | free |
| 061 | CH | 4-(3-FPhCH₂O)PhO | H | 5'-(CH₂)₂COOMe | free |
| 062 | N | Ph(CH₂)₂OCO | H | H | free |
| 063 | CH | 4-H₂NCOPh(CH₂)₂ | H | H | free |
| 064 | CH | PhCH₂NHCOCH₂ | H | H | HCl |

TABLE 18

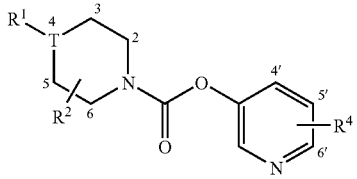

| Ex No. | T | R¹ | R² | R⁴ | Sal |
|---|---|---|---|---|---|
| 066 | CH | 1-MeBenzIM2(CH₂)₃ | H | H | free |
| 067 | C | Ph | 4-NC | H | HCl |
| 068 | CH | 2-oxoBenzIM 1 | H | H | free |
| 069 | CH | 4-H₂NCOPhO(CH₂)₃ | H | H | free |
| 070 | CH | 3-Cl-4-PhCH₂OPhO | H | H | oxal |
| 071 | CH | 4-[3-FPhSO₂N(Me)]PhO | H | H | HCl |
| 072 | N | PhCH₂OCO | 3-H₂NCO | H | HCl |
| 073 | CH | 4-(3-FPhCH₂O)PhO | H | 5'-(4-EtOCOPIPE1)- | oxal |
| 074 | C | PhCH₂ | 4-HO | H | HCl |
| 075 | N | 4-BuNHCOCH₂OPhCO | H | H | p-tol |
| 076 | CH | 4-(3-FPhCH₂O)PhS | H | H | p-tol |
| 077 | CH | 3-EtOCOCH₂OPh | H | H | oxal |
| 078 | CH | 3-PhCH₂OPh | H | H | oxal |
| 079 | CH | 4-PhCH₂OCOPhO(CH₂)₂ | H | H | free |
| 080 | CH | 4-(3-FPhCH₂O)PhSO₂ | H | H | free |
| 081 | CH | PhCH₂OCH₂ | H | H | oxal |
| 082 | CH | 4-PhCH₂OPh | H | 5'-COOMe | free |
| 083 | CH | 3-(3-H₂NCOPh)PhO | H | H | HCl |
| 084 | N | Ph(CH₂)₂ | 3-oxo | H | free |
| 085 | N | Ph(CH₂)₂ | H | 5'-Cl | free |
| 086 | N | Ph(CH₂)₂ | H | 5'-COOMe | free |
| 087 | CH | 6-ClPy3O | H | H | free |
| 088 | CH | 4-PhCH₂OPhSO₂ | H | H | free |
| 089 | CH | 4-(3-NCPhCH₂O)PhSO₂ | H | H | free |
| 090 | CH | 4-cHexCH₂OPhSO₂ | H | H | free |
| 091 | CH | 4-cHex(CH₂)₂OPhSO₂ | H | H | free |

TABLE 18-continued

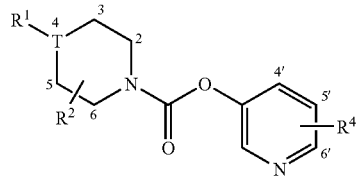

| Ex No. | T | R¹ | R² | R⁴ | Sal |
|---|---|---|---|---|---|
| 092 | CH | 6-ClPy2O | H | H | HCl |
| 093 | CH | 6-(3-FPhCH₂O)Py2O | H | H | oxal |
| 094 | CH | 6-(3-H₂NCOPh)Py2O | H | H | free |
| 095 | CH | 4-(3-ClPhCH₂O)PhSO₂ | H | H | free |
| 096 | N | 4-H₂NCOPhCH₂OCO | H | H | free |
| 097 | CH | 4-(3-FPhCH₂O)PhO | H | 5'-Me | free |
| 098 | CH | 4-Me₂NCOPhO(CH₂)₃ | H | H | p-tol |
| 099 | CH | 4-MeNHCOPhO(CH₂)₃ | H | H | free |
| 100 | CH | 4-(3-FPhCH₂O)PhO | H | 5'-CH₂OAc | oxal |
| 101 | CH | 3-(3-FPhCH₂O)PhS | H | H | p-tol |

TABLE 19

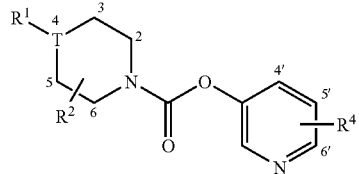

| Ex No. | T | R¹ | R² | R⁴ | Sal |
|---|---|---|---|---|---|
| 102 | CH | 6-[cHex(CH₂)₂O]Py2O | H | H | oxal |
| 103 | CH | 5-(3-FPhCH₂O)Py2O | H | H | oxal |
| 105 | CH | 3-(3-FPhCH₂O)PhSO₂ | H | H | free |
| 106 | CH | 4-NCPhO(CH₂)₃ | H | 5'-COOMe | free |
| 107 | CH | H | 3-PhOCH₂ | H | p-tol |
| 108 | CH | 4-NCPhO(CH₂)₃ | H | H | free |
| 109 | CH | HO | H | H | free |
| 110 | CH | PhOCH₂ | H | H | free |
| 111 | CH | PhO(CH₂)₂ | H | H | p-tol |
| 112 | CH | Ph(CH₂)₃O(CH₂)₂ | H | H | oxal |
| 113 | CH | 3-Ph(CH₂)₃OPh | H | H | oxal |
| 114 | CH | PhO(CH₂)₃ | H | H | free |
| 115 | CH | 2-H₂NCOPhO(CH₂)₃ | H | H | free |
| 116 | CH | 3-H₂NCOPhO(CH₂)₃ | H | H | p-tol |
| 118 | CH | 4-(3-FPhCH₂O)PhO | H | 5'-F | HCl |
| 119 | N | 4-cOctCH₂OPhCO | H | H | free |
| 120 | N | 4-[3-FPhCH₂N(Me)]PhCO | H | H | free |
| 121 | N | 4-cHexCH₂N(Me)PhCO | H | H | free |
| 122 | N | 3-cHexCH₂OPhCO | H | H | HCl |
| 123 | N | 3-cHexCH₂N(Me)PhCO | H | H | HBr |
| 124 | N | Ph(CH₂)₂CO | H | H | p-tol |
| 125 | N | PhCO | H | H | free |
| 127 | N | PhOCH₂CO | H | H | p-tol |
| 128 | N | PhCH₂CO | H | H | p-tol |
| 129 | N | PhNHCH₂CO | H | H | free |
| 130 | N | Ph(CH₂)₃CO | H | H | p-tol |
| 132 | N | PhCONHCH₂CO | H | H | oxal |
| 133 | N | PhN(Me)CH₂CO | H | H | 2oxal |
| 134 | N | 4-HepOPhCO | H | H | p-tol |
| 135 | N | 4-(3-NCPhCH₂O)PhCO | 2-Me | H | HCl |
| 136 | N | 4-(3-NCPhCH₂O)PhCO | 3-Me | H | free |
| 137 | N | 6-(3-ClPhCH₂O)Py3CO | H | H | oxal |
| 138 | N | 3-ClPhCH₂O)PhCO | H | H | HCl |
| 139 | N | 4-H₂NCOPhOCH₂CO | H | H | free |
| 140 | N | 2-H₂NCOPhOCH₂CO | H | H | free |
| 141 | N | 3-H₂NCOPhOCH₂CO | H | H | free |
| 142 | N | PhSO₂ | H | H | free |

TABLE 20

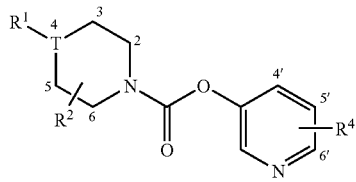

| Ex No. | T | R¹ | R² | R⁴ | Sal |
|---|---|---|---|---|---|
| 143 | N | PhCH₂SO₂ | H | H | free |
| 144 | N | PhCH₂O—CO | H | H | p-tol |
| 145 | N | Py3O—CO | H | H | free |
| 146 | N | PhCH₂NHCO | H | H | free |
| 147 | N | 4-(3-ClPhCH₂O)PhCO | H | H | free |
| 148 | N | 4-(3-MePhCH₂O)PhCO | H | H | oxal |
| 149 | N | 4-(3-F₃CPhCH₂O)PhCO | H | H | free |
| 150 | N | 4-(3-MeOPhCH₂O)PhCO | H | H | oxal |
| 151 | N | 4-(3-NCPhCH₂O)PhCO | H | H | free |
| 152 | N | 4-(3,5-diFPhCH₂O)PhCO | H | H | free |
| 153 | N | 4-(3-F₃COPhCH₂O)PhCO | H | H | free |
| 154 | N | 4-(3-O₂NPhCH₂O)PhCO | H | H | free |
| 155 | N | 4-(4-FPhCH₂O)PhCO | H | H | free |
| 156 | N | 4-(2-FPhCH₂O)PhCO | H | H | free |
| 157 | N | 4-Py2CH₂OPhCO | H | H | free |
| 158 | N | 4-(1-MeAzep3O)PhCO | H | H | free |
| 159 | N | 4-(3-BrPhCH₂O)PhCO | H | H | free |
| 160 | N | 4-[3-ClPh(CH₂)₂O]PhCO | H | H | free |
| 161 | N | 4-(4-NCPhCH₂O)PhCO | H | H | free |
| 162 | N | 4-(3-IPhCH₂O)PhCO | H | H | free |
| 163 | N | 4-(3-Me₂NPhCH₂O)PhCO | H | H | free |
| 164 | N | 2-Cl-4-(3-NCPhCH₂O)PhCO | H | H | free |
| 165 | N | 3-Cl-4-(3-NCPhCH₂O)PhCO | H | H | free |
| 166 | N | 4-(3-NCPhCH₂O)-3-MeO-PhCO | H | H | HCl |
| 167 | N | 4-(3-MeOCOPhCH₂O)PhCO | H | H | free |
| 168 | CH | cHexCH₂NHCO | H | H | free |
| 169 | CH | MeOCO(CH₂)₃ | H | H | oxal |
| 170 | CH | H₂NCO(CH₂)₃ | H | H | oxal |
| 171 | CH | PhCH₂N(Me)CO | H | H | free |
| 172 | CH | Py3CH₂NHCO | H | H | free |
| 173 | CH | PhNHCO | H | H | free |
| 174 | CH | Ph(CH₂)₂NHCO | H | H | free |
| 175 | CH | Ph(CH₂)₄NHCO | H | H | free |
| 176 | CH | 4-OctPhNHCO | H | H | free |
| 177 | CH | 4-H₂NCOPhNHCO(CH₂)₃ | H | H | free |
| 178 | CH | 3-H₂NCOPhNHCO(CH₂)₃ | H | H | free |
| 179 | CH | 3-H₂NCOCH₂OPh | H | H | HCl |

TABLE 21

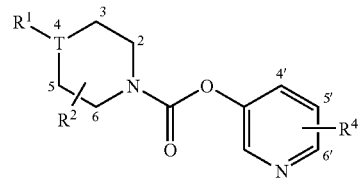

| Ex No. | T | R¹ | R² | R⁴ | Sal |
|---|---|---|---|---|---|
| 180 | CH | 3-(4-H₂NCOPIPE1COCH₂O)Ph | H | H | HCl |
| 181 | CH | 2-H₂NCOPhNHCO(CH₂)₃ | H | H | fum |
| 182 | CH | 4-BuPhNHCO | H | H | free |
| 183 | CH | 4-BuOPhNHCO | H | H | free |
| 184 | CH | 4-HexOPh(CH₂)₂NHCO | H | H | free |
| 185 | CH | 4-Ph(CH₂)₄OPh(CH₂)₂NHCO | H | H | free |
| 186 | CH | 4-cPen(CH₂)₃OPh(CH₂)₂NHCO | H | H | free |
| 187 | CH | 4-HexPhNHCO | H | H | free |
| 188 | CH | 4-[4-MeOCOPh(CH₂)₂]PhNHCO | H | H | free |
| 189 | CH | 4-HO(CH₂)₂PhNHCO | H | H | free |
| 190 | CH | 4-PhCH₂OPhNHCO | H | H | free |
| 191 | CH | 2-H₂NCO(CH₂)₂PhNHCO | H | H | free |
| 192 | CH | 4-Ph-1,3-Thiaz2NHCO | H | H | free |
| 193 | N | PhCH₂OCO | 3-COOH | H | free |
| 194 | CH | 4-HOOCPhO(CH₂)₂ | H | H | free |
| 195 | CH | 3-HOOCCH₂OPh | H | H | free |
| 196 | CH | 1-MeBenzIM2 | H | H | free |
| 197 | CH | Ph(CH₂)₅CONH | H | H | free |
| 198 | CH | 3-HOPhO | H | H | free |
| 199 | CH | 4-HOPhO | H | H | free |
| 200 | CH | 3-cHexCH₂OPhO | H | H | HCl |
| 201 | CH | 3-cHex(CH₂)₂OPhO | H | H | HCl |
| 202 | CH | 3-(3-FPhCH₂O)PhO | H | H | HCl |
| 203 | CH | 3-(2-FPhCH₂O)PhO | H | H | HCl |
| 204 | CH | 3-(4-FPhCH₂O)PhO | H | H | HCl |
| 205 | CH | 3-(3-NCPhCH₂O)PhO | H | H | oxal |
| 206 | CH | 4-(3-ClPhCH₂O)PhO | H | H | HCl |
| 207 | CH | 4-cHex(CH₂)₂OPhO | H | H | HCl |
| 208 | CH | 4-(2-FPhCH₂O)PhO | H | H | HCl |
| 209 | CH | 4-(4-FPhCH₂O)PhO | H | H | HCl |
| 210 | CH | 4-(3-NCPhCH₂O)PhO | H | H | oxal |
| 211 | CH | 4-(3-MeOCOPhCH₂O)PhO | H | H | free |
| 212 | CH | 4-(3-H₂NCOPhCH₂O)PhO | H | H | free |
| 213 | CH | 4-cHex(CH₂)₃OPhO | H | 5'-COOMe | free |

TABLE 22

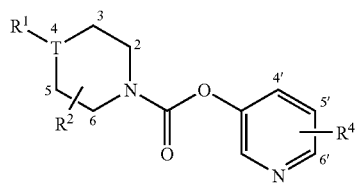

| Ex No. | T | R¹ | R² | R⁴ | Sal |
|---|---|---|---|---|---|
| 214 | CH | 4-PIPE1(CH₂)₂OPhO | H | 5'-COOMe | HCl |
| 215 | CH | 4-(3-NCPhCH₂O)PhO | H | 5'-COOMe | oxal |
| 216 | CH | 4-cHexCH₂OPhO | H | 5'-COOMe | free |
| 217 | CH | 4-HOPhO | H | 5'-COOH | free |
| 218 | CH | 4-(3-FPhCH₂O)PhO | H | 5'-COOH | free |
| 219 | CH | PhCH₂ | H | 5'-COOH | free |
| 220 | CH | Ph | H | 5'-COOH | free |
| 221 | CH | 4-PhCH₂OPhO | H | 5'-COOH | free |
| 223 | CH | PhCO | H | 5'-COOH | free |
| 224 | CH | PhCH₂O | H | 5'-COOH | free |
| 225 | CH | Ph(CH₂)₂ | H | 5'-COOH | free |

TABLE 22-continued

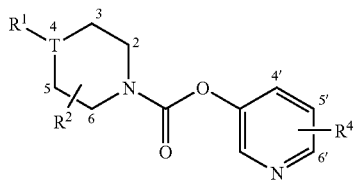

| Ex No. | T | R¹ | R² | R⁴ | Sal |
|---|---|---|---|---|---|
| 226 | CH | 4-PIPERI1(CH₂)₂OPhO | H | 5'-COOH | free |
| 227 | CH | 4-NCPhO(CH₂)₃ | H | 5'-COOH | free |
| 228 | CH | 4-cHex(CH₂)₂OPhO | H | 5'-COOH | free |
| 229 | CH | 4-cHex(CH₂)₃OPhO | H | 5'-COOH | free |
| 230 | CH | 4-(3-NCPhCH₂O)PhO | H | 5'-COOH | free |
| 231 | N | Ph(CH₂)₂ | H | 5'-COOH | 2HCl |
| 232 | CH | PhCH₂OCH₂ | H | 5'-COOH | free |
| 233 | CH | 4-(3-MeOPhCH₂O)PhO | H | 5'-COOH | free |
| 234 | CH | 3-(3-FPhCH₂O)PhO | H | 5'-COOH | free |
| 235 | CH | 3-(3-NCPhCH₂O)PhO | H | 5'-COOH | free |
| 236 | CH | 4-(3-MeOCOPhCH₂O)PhO | H | 5'-COOH | free |
| 237 | CH | 4-cHexCH₂OPhO | H | 5'-COOH | free |
| 238 | CH | Ph(CH₂)₃ | H | 5'-COOH | free |
| 239 | CH | PhO(CH₂)₃ | H | 5'-COOH | free |
| 240 | CH | PhO(CH₂)₂ | H | 5'-COOH | free |
| 241 | CH | 4-H₂NCOPh(CH₂)₂ | H | 5'-COOH | free |
| 242 | CH | 3-cHex(CH₂)₂OPhO | H | 5'-COOH | free |
| 243 | N | Ph(CH₂)₃ | H | 5'-COONa | free |
| 244 | CH | 4-(3-FPhCH₂O)PhO | H | 5'-CONHCH₂COOH | free |
| 245 | CH | 4-(3-FPhCH₂O)PhO | H | 5-CONH₂ | free |
| 246 | CH | 4-PhCH₂OPhO | H | 5-CONH₂ | free |
| 247 | CH | PhCH₂ | H | 5'-CONHCH₂CONH₂ | HCl |
| 248 | CH | PhCH₂ | H | 5'-(4-H₂NCOPIPERI1CO)— | HCl |

TABLE 23

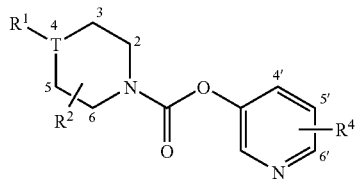

| Ex No. | T | R¹ | R² | R⁴ | Sal |
|---|---|---|---|---|---|
| 249 | CH | 4-(3-FPhCH₂O)PhO | H | 5'-CONHCH₂CONH₂ | HCl |
| 250 | CH | 4-(3-FPhCH₂O)PhO | H | 5'-Mo4(CH₂)₂NHCO— | oxal |
| 251 | CH | 4-(3-FPhCH₂O)PhO | H | 5'-CONH(CH₂)₂OMe | oxal |
| 252 | CH | 4-(3-FPhCH₂O)PhO | H | 5-(4-H₂NCOPIPE1CO)— | free |
| 253 | CH | 4-(3-FPhCH₂O)PhO | H | 5'-CONH(CH₂)₂CONH₂ | HCl |
| 254 | CH | 4-(3-FPhCH₂O)PhO | H | 5'-PIPE1(CH₂)₂NHCO— | 2HCl |
| 255 | CH | 4-(3-FPhCH₂O)PhO | H | 5'-CONH(CH₂)₂OH | HCl |
| 256 | CH | 4-(3-FPhCH₂O)PhO | H | 5'-(4-HOPh(CH₂)₂NHCO)— | free |

TABLE 23-continued

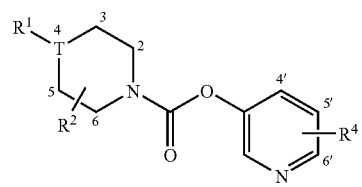

| Ex No. | T | R¹ | R² | R⁴ | Sal |
|---|---|---|---|---|---|
| 257 | CH | 4-(3-FPhCH₂O)PhO | H | 5'-(4-MePIPERA1CO)— | oxal |
| 258 | CH | PhCH₂ | H | 5'-(3-H₂NCOPh)- | free |
| 259 | CH | PhCH₂ | H | 5'-Py3 | free |
| 260 | CH | 4-(3-FPhCH₂O)PhO | H | 5'-NH₂ | HCl |
| 261 | CH | 4-(3-FPhCH₂O)PhO | H | 5'-(4-HOOCPIPE1)- | oxal |
| 262 | CH | 4-(3-FPhCH₂O)PhO | H | 5'-CH₂OCH₂COOH | free |
| 263 | CH | 4-(3-FPhCH₂O)PhO | H | 5-CH₂OH | free |

TABLE 24

| Ex No. | Str | Sal |
|---|---|---|
| 022 | (structure shown) | free |

TABLE 24-continued

| Ex No. | Str | Sal |
|---|---|---|
| 032 | | 2HCl |
| 038 | | free |
| 065 | | free |
| 104 | | fum |
| 117 | | free |
| 126 | | p-tol |
| 131 | | p-tol |
| 222 | | free |

TABLE 24-continued

| Ex No. | Str | Sal |
|---|---|---|
| 264 | [structure: 3-fluorobenzyl-O-phenyl-O-piperidine-N-C(=O)-O-pyridine-CH=CH-COOH] | free |

TABLE 25

[Structure: R¹-T(4,3,5,2,6)-N-C(=O)-O-pyridine(4',5',6') with R⁴]

| Ex No. | T | R¹ | R⁴ | Sal |
|---|---|---|---|---|
| 265 | CH | Ph(CH₂)₂ | 5'-(4-MeOCOPh)- | free |
| 266 | CH | Ph(CH₂)₂ | 5'-(3-H₂NCOPh)- | free |
| 267 | CH | 3-NCPh(CH₂)₂ | 5'-COOH | free |
| 268 | CH | [trans-cinnamyl/propenylphenyl] | H | free |
| 269 | CH | [cis-propenylphenyl] | H | free |
| 270 | CH | Ph(CH₂)₂ | 5'-Br | free |
| 271 | CH | cHex(CH₂)₂ | H | free |
| 272 | CH | cHex(CH₂)₂ | 5'-COOMe | free |
| 273 | CH | [propenylphenyl] | 5'-COOH | free |
| 274 | CH | 3-ClPh(CH₂)₂ | 5'-COOH | free |
| 275 | CH | 4-NCPh(CH₂)₂ | 5'-COOH | free |
| 276 | CH | 3-MeOPh(CH₂)₂ | 5'-COOH | free |
| 277 | CH | 3-FPh(CH₂)₂ | 5'-COOH | free |
| 278 | CH | 2-NCPh(CH₂)₂ | 5'-COOH | free |
| 279 | CH | 3-H₂NCOPh(CH₂)₂ | 5'-COOH | free |
| 280 | CH | 3-Me₂NCOPh(CH₂)₂ | 5'-COOH | free |
| 281 | CH | BIP4(CH₂)₂ | 5'-COOH | Na |
| 282 | CH | 4-FPh(CH₂)₂ | 5'-COOH | free |
| 283 | CH | 2-ClPh(CH₂)₂ | 5'-COOH | free |
| 284 | CH | 4-ClPh(CH₂)₂ | 5'-COOH | free |
| 285 | CH | 4-BrPh(CH₂)₂ | 5'-COOH | free |

TABLE 26

[Structure: R¹-T(4,3,5,2,6)-N-C(=O)-O-pyridine(4',5',6') with R⁴]

| Ex No. | T | R¹ | R⁴ | Sal |
|---|---|---|---|---|
| 286 | CH | 4-MeOPh(CH₂)₂ | 5'-COOH | free |
| 287 | CH | Ph(CH₂)₄ | 5'-COOH | free |
| 288 | CH | 2-FPh(CH₂)₂ | 5'-COOH | free |
| 289 | CH | cHex(CH₂)₂ | 5'-COOH | free |
| 290 | CH | 4-Py2Ph(CH₂)₂ | 5'-COOH | free |
| 291 | CH | Ph(CH₂)₂ | 5'-CH=CH-COOH | free |
| 292 | CH | 3-BrPh(CH₂)₂ | 5'-COOH | free |
| 293 | CH | BIP3(CH₂)₂ | 5'-COOH | free |
| 294 | CH | 3'-NCBIP3(CH₂)₂ | 5'-COOH | free |
| 295 | CH | Py4Ph(CH₂)₂ | 5'-COOH | free |
| 296 | CH | Py3Ph(CH₂)₂ | 5'-COOH | free |
| 297 | CH | Py2(CH₂)₂ | 5'-COOH | free |
| 298 | CH | 3-Py2Ph(CH₂)₂ | 5'-COOH | Na |
| 299 | CH | 4'-FBIP4(CH₂)₂ | 5'-COOH | free |
| 300 | CH | 4'-MeOBIP4(CH₂)₂ | 5'-COOH | free |
| 301 | CH | 4'-NCBIP4(CH₂)₂ | 5'-COOH | free |
| 302 | CH | 3'-FBIP4(CH₂)₂ | 5'-COOH | free |
| 303 | CH | 3'-MeOBIP4(CH₂)₂ | 5'-COOH | free |
| 304 | CH | 2'-FBIP4(CH₂)₂ | 5'-COOH | free |
| 305 | CH | 3-cHexNHCOPh(CH₂)₂ | 5'-COOH | Na |
| 306 | CH | 3-PIPE1COPh(CH₂)₂ | 5'-COOH | Na |
| 307 | CH | 3-Mo4COPh(CH₂)₂ | 5'-COOH | Na |
| 308 | CH | 4-PIPE1COPh(CH₂)₂ | 5'-COOH | Na |
| 309 | CH | 4-Mo4COPh(CH₂)₂ | 5'-COOH | Na |
| 310 | CH | 3-PYRR1COPh(CH₂)₂ | 5'-COOH | Na |
| 311 | CH | 3-(4-Py2PIPERA1CO)Ph(CH₂)₂ | 5'-COOH | free |

TABLE 27

[Structure: R¹-T(4,3,5,2,6)-N-C(=O)-O-pyridine(4',5',6') with R⁴]

| Ex No. | T | R¹ | R⁴ | Sal |
|---|---|---|---|---|
| 312 | CH | 4-Et₂NCOPh(CH₂)₂ | 5'-COOH | free |
| 313 | CH | 1-(6-MePy2)PIPE4(CH₂)₃ | 5'-COOH | Na |

TABLE 27-continued

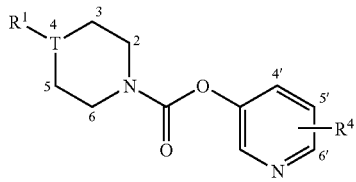

| Ex No. | T | R¹ | R⁴ | Sal |
|---|---|---|---|---|
| 314 | CH | 1-ISOQUI1PIPE4(CH₂)₃ | 5'-COOH | Na |
| 315 | CH | 1-QUI2PIPE4(CH₂)₃ | 5'-COOH | Na |
| 316 | CH | 4-ISOQUI1PIPERA1(CH₂)₃ | 5'-COOH | Na |
| 317 | CH | 1-NAPH1PIPE4(CH₂)₃ | 5'-COOH | Na |
| 318 | CH | 3-NCPh(CH₂)₂ | 5-CONH₂ | free |
| 319 | CH | Ph(CH₂)₂ | 5'-CONH(CH₂)₂OH | oxal |
| 320 | CH | Ph(CH₂)₂ | 5'-CONH₂ | free |
| 321 | CH | 3-MeOPh(CH₂)₂ | 5'-CONH₂ | free |
| 322 | CH | 3-FPh(CH₂)₂ | 5'-CONH₂ | free |
| 323 | CH | 2-NCPh(CH₂)₂ | 5'-CONH₂ | free |
| 324 | CH | 3-H₂NCOPh(CH₂)₂ | 5'-CONH₂ | free |
| 325 | CH | 3-Me₂NCOPh(CH₂)₂ | 5'-CONH₂ | free |
| 326 | CH | cHex(CH₂)₂ | 5'-CONH₂ | free |

TABLE 27-continued

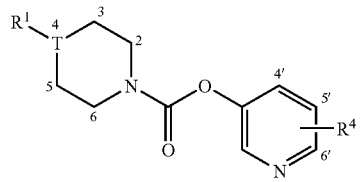

| Ex No. | T | R¹ | R⁴ | Sal |
|---|---|---|---|---|
| 327 | CH | 3-ClPh(CH₂)₂ | 5'-CONH(CH₂)₂OH | oxal |
| 328 | CH | 3-MeOPh(CH₂)₂ | 5'-CONH(CH₂)₂OH | oxal |
| 329 | CH | 3-FPh(CH₂)₂ | 5'-CONH(CH₂)₂OH | oxal |
| 330 | CH | 3-NCPh(CH₂)₂ | 5'-CONH(CH₂)₂OH | oxal |
| 331 | CH | 2-NCPh(CH₂)₂ | 5'-CONH(CH₂)₂OH | oxal |
| 332 | CH | Ph(CH₂)₂ | 5'-CONH(CH₂)₂SO₃H | HCl |
| 333 | CH | Ph(CH₂)₂ | 5'-CONH(CH₂)₂CONH₂ | free |
| 334 | CH | 2-FPh(CH₂)₂ | 5'-CONH₂ | free |
| 335 | CH | Ph(CH₂)₂ | 5'-∼∼CONH₂ | free |
| 336 | CH | Py4(CH₂)₂ | 5'-CONH₂ | free |

TABLE 28

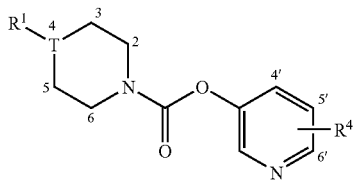

| Ex No. | T | R¹ | R⁴ | Sal |
|---|---|---|---|---|
| 337 | CH | Py3(CH₂)₂ | 5'-CONH₂ | free |
| 338 | CH | 4'-FBIP4(CH₂)₂ | 5'-CONH₂ | free |
| 339 | CH | 4'-MeOBIP4(CH₂)₂ | 5'-CONH₂ | free |
| 340 | CH | BIP3(CH₂)₂ | 5'-CONH₂ | free |
| 341 | CH | 3'-NCBIP3(CH₂)₂ | 5'-CONH₂ | free |
| 342 | CH | Ph(CH₂)₂ | 5'-CONH(CH₂)₃OH | oxal |
| 343 | CH | Ph(CH₂)₂ | 5'-CONH(CH₂)₃NMe₂ | oxal |
| 344 | CH | 4'-NCBIP4(CH₂)₂ | 5'-CONH₂ | free |
| 345 | CH | 3'-FBIP4(CH₂)₂ | 5'-CONH₂ | free |
| 346 | CH | 2'-FBIP4(CH₂)₂ | 5'-CONH₂ | free |
| 347 | CH | Ph(CH₂)₂ | 5'-CONH(CH₂)₂Py4 | oxal |
| 348 | CH | Ph(CH₂)₂ | 5'-CONH(CH₂)₂Py3 | oxal |
| 349 | CH | 3-Py2Ph(CH₂)₂ | 5'-CONH₂ | free |
| 350 | CH | 2-Me₂NCOPh(CH₂)₂ | 5'-CONH₂ | free |
| 351 | CH | 3-cHexNHCOPh(CH₂)₂ | 5'-CONH₂ | free |
| 352 | CH | 3-MeNHCOPh(CH₂)₂ | 5'-CONH₂ | free |
| 353 | CH | 4-H₂NCOPh(CH₂)₂ | 5'-CONH₂ | free |
| 354 | CH | 4-Me₂NCOPh(CH₂)₂ | 5'-CONH₂ | free |
| 355 | CH | 3-PIPE1COPh(CH₂)₂ | 5'-CONH₂ | free |
| 356 | CH | 3-Mo4COPh(CH₂)₂ | 5'-CONH₂ | free |
| 357 | CH | 4-PIPE1COPh(CH₂)₂ | 5'-CONH₂ | free |
| 358 | CH | 4-Mo4COPh(CH₂)₂ | 5'-CONH₂ | free |
| 359 | CH | 3-PYRR1COPh(CH₂)₂ | 5'-CONH₂ | free |
| 360 | CH | 3-Et₂NCOPh(CH₂)₂ | 5'-CONH₂ | free |
| 361 | CH | [aziridine-C(O)-3-propylphenyl] | 5'-CONH₂ | free |

TABLE 29

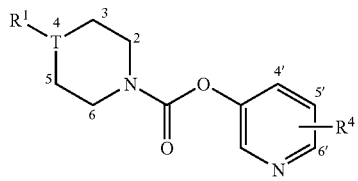

| Ex No. | T | R¹ | R⁴ | Sal |
|---|---|---|---|---|
| 362 | CH | 4-Et₂NCOPh(CH₂)₂ | 5'-CONH₂ | free |
| 363 | CH | 4-PYRR1COPh(CH₂)₂ | 5'-CONH₂ | free |
| 364 | CH | 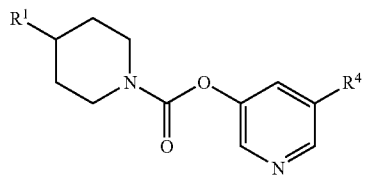 | 5'-CONH₂ | free |
| 365 | CH | 3-(4-Py2PIPERA1CO)Ph(CH₂)₂ | 5'-CONH₂ | free |
| 366 | CH | 3-(4-PhPIPERA1CO)Ph(CH₂)₂ | 5'-CONH₂ | free |
| 367 | CH | 4-(4-Py2PIPERA1CO)Ph(CH₂)₂ | 5'-CONH₂ | free |
| 368 | CH | 4-(4-PhPIPERA1CO)Ph(CH₂)₂ | 5'-CONH₂ | free |
| 369 | CH | 3-FCH₂CH₂NHCOPh(CH₂)₂ | 5'-CONH₂ | HCl |
| 370 | CH | 3-HO(CH₂)₂NHCOPh(CH₂)₂ | 5'-CONH₂ | free |
| 371 | CH | 3-tBuNHCOPh(CH₂)₂ | 5'-CONH₂ | free |
| 372 | CH | 3-iPrNHCOPh(CH₂)₂ | 5'-CONH₂ | free |
| 373 | CH | 4-(2,2-DIFPYRR1CO)Ph(CH₂)₂ | 5'-CONH₂ | free |
| 374 | CH | 3-H₂NCONHPh(CH₂)₂ | 5'-CONH₂ | free |
| 375 | CH | 3-PYRR1CONHPh(CH₂)₂ | 5'-CONH₂ | free |
| 376 | CH | 3-(2,2-DIFPYRR1CO)Ph(CH₂)₂ | 5'-CONH₂ | free |
| 377 | CH | 3-(4-NAPH1PIPERA1CO)Ph(CH₂)₂ | 5'-CONH₂ | free |
| 378 | CH | 1-(6-MePy2)PIPE4(CH₂)₃ | 5'-CONH₂ | free |
| 379 | CH | 1-ISOQUI1PIPE4(CH₂)₃ | 5'-CONH₂ | free |
| 380 | CH | 1-QUI2PIPE4(CH₂)₃ | 5'-CONH₂ | free |
| 381 | CH | 4-ISOQUI1PIPERA1(CH₂)₃ | 5'-CONH₂ | free |
| 382 | CH | 1-NAPH1PIPE4(CH₂)₃ | 5'-CONH₂ | free |

TABLE 30

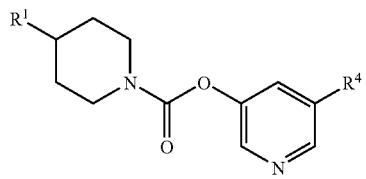

| Ex No. | R¹ | R⁴ | Sal |
|---|---|---|---|
| 383 | 3-HepOPhNHCO | H | free |
| 384 | 4-HepOPhNHCO | H | free |
| 385 | Py2NHCO(CH₂)₃ | H | 2HCl |
| 386 | 4-OctPhNHCO(CH₂)₃ | H | oxal |
| 387 | Ph(CH₂)₄NHCO(CH₂)₃ | H | oxal |
| 388 | 4-HexPhNHCO | CONH₂ | free |
| 389 | 4-(3-FPhCH₂O)PhO | OAc | oxal |
| 390 | 4-(3-FPhCH₂O)PhO | OH | free |
| 391 | 4-(3-FPhCH₂O)PhO | CN | free |
| 392 | 4-cHex(CH₂)₄OPhO | H | free |
| 393 | benzo[1,3]dioxol-5-yloxypropyl | CO₂H | free |
| 394 | 6-methoxy-benzo[1,3]dioxol-5-yl | CO₂H | free |
| 395 | 4-cPen(CH₂)₂OPhO | CO₂H | free |
| 396 | 4-(3-FPhCH₂O)PhOCH₂ | H | free |

TABLE 31

| Ex No. | R¹ | R⁴ | Sal |
|---|---|---|---|
| 397 | benzo[1,3]dioxol-5-yloxypropyl | CONH₂ | free |
| 398 | 6-methoxy-benzo[1,3]dioxol-5-yl | CONH₂ | free |
| 399 | Ph(CH₂)₂ | 3-methylbenzoic acid | free |

TABLE 31-continued (structure: R¹-piperidine-N-C(=O)-O-pyridine-R⁴)

| Ex No. | R¹ | R⁴ | Sal |
|---|---|---|---|
| 400 | 4-(3-FPhCH₂O)PhCH₂ | H | HCl |
| 401 | 4-(3-FPhCH₂O)PhCH₂ | CO₂H | free |
| 402 | Ph(CH₂)₂ | OH | free |
| 403 | (phenyl-C≡C-CH₃ structure) | CO₂H | free |
| 404 | (4-H₂NC(O)-C₆H₄-CH=CH-CH₃ structure) | CONH₂ | free |
| 405 | 4-NAPH1PIPERA1(CH₂)₃ | CO₂H | Na |
| 406 | 1-(6-MePy2)PIPE4(CH₂)₂ | CO₂H | Na |
| 407 | 1-(6-MePy2)PIPE4(CH₂)₂ | CONH₂ | free |
| 408 | 4-NAPH1PIPERA1(CH₂)₃ | CONH₂ | free |

TABLE 32

(structure: R¹-piperazine-N-C(=O)-O-pyridine-R⁴)

| Ex No. | R¹ | R⁴ | Sal |
|---|---|---|---|
| 409 | Ph(CH₂)₃ | CONH₂ | free |
| 410 | Ph | CONH₂ | free |

TABLE 32-continued (structure: R¹-piperazine-N-C(=O)-O-pyridine-R⁴)

| Ex No. | R¹ | R⁴ | Sal |
|---|---|---|---|
| 411 | Ph(CH₂)₅ | CONH(CH₂)₂OH | 2HCl |
| 412 | Ph(CH₂)₅ | CONH₂ | free |
| 413 | 4-(3-FPhCH₂O)PhCH₂ | H | 2HCl |
| 414 | BIP4(CH₂)₂ | CO₂H | Na |
| 415 | BIP4(CH₂)₂ | CONH₂ | free |

TABLE 33

| Ex No. | Str | Sal |
|---|---|---|
| 416 | 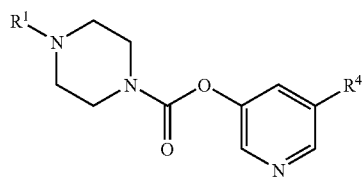 | p-tol |

TABLE 33-continued

| Ex No. | Str | Sal |
|---|---|---|
| 417 | | free |
| 418 | | free |
| 419 | | p-tol |
| 420 | | oxal |
| 421 | | free |
| 422 | | HCl |
| 423 | | free |

TABLE 34

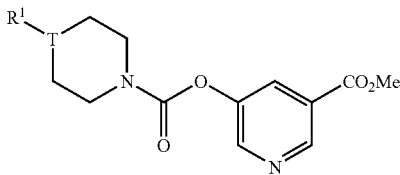

| Ex No. | T | R¹ | Sal |
|---|---|---|---|
| 424 | CH | Ph(CH$_2$)$_2$ | free |
| 425 | N | Ph(CH$_2$)$_2$ | free |
| 426 | CH | Ph(CH$_2$)$_3$ | free |
| 427 | CH | 4-H$_2$NCOPh(CH$_2$)$_2$ | free |
| 428 | CH | 3-cHex(CH$_2$)$_2$OPhO | free |
| 429 | N | Ph(CH$_2$)$_3$ | free |
| 430 | CH | 4-cHex(CH$_2$)$_2$OPhO | free |
| 431 | CH | 4-(3-MeOPhCH$_2$O)PhO | free |
| 432 | CH | 4-(3-MeOCOPhO)PhO | free |
| 433 | CH | 3-PYRR1COPh(CH$_2$)$_2$ | free |
| 434 | CH | 3-PIPE1COPh(CH$_2$)$_2$ | free |

TABLE 34-continued

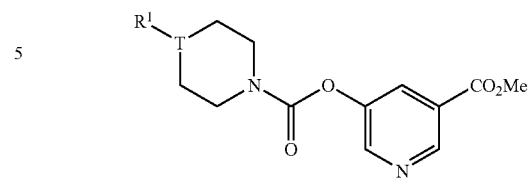

| Ex No. | T | R¹ | Sal |
|---|---|---|---|
| 435 | CH | ![aziridine-propyl-benzoyl] | free |
| 436 | CH | 3-H$_2$NCONHPh(CH$_2$)$_2$ | free |
| 437 | CH | 3-PIPE1CONHPh(CH$_2$)$_2$ | free |

TABLE 35

| Ex No. | DAT $^1$H-NMR δ (ppm), solvent: MS m/z |
|---|---|
| 001 | 207 (M + H)$^+$FAB |
| 002 | 1.59-1.74 (2H, br), 1.90-2.05 (2H, br), 3.33-3.45 (1H, br), 3.45-3.55 (1H, br), 3.65-3.79 (1H, br), 3.84-3.94 (1H, br), 4.45-4.55 (1H, m), 5.07 (2H, s), 6.97 (4H, s), 7.15 (1H, dt, J = 2.4, 8.1 Hz), 7.24-7.30 (2H, m), 7.40-7.47 (2H, m), 7.64-7.66 (1H, m), 8.41-8.45 (2H, m), DMSO: 423 (M + H)$^+$FAB |
| 003 | 1.40-1.70 (2H, m), 1.85 (2H, d, J = 12.7 Hz), 3.10 (1H, t, J = 12.7 Hz) 3.25 (1H, t, J = 12.2 Hz), 3.65-3.75 (1H, m), 4.06 (1H, d, J = 12.2 Hz), 4.23 (1H, d, J = 12.7 Hz), 5.26 (2H, s), 7.14-7.22 (3H, m), 7.29-7.34 (2H, m), 7.42-7.50 (2H, m), 7.64-7.67 (1H, m), 8.03 (2H, d, J = 9.3 Hz), 8.44-8.45 (2H, m), DMSO: 435 (M + H)$^+$FAB |
| 004 | 436 (M + H)$^+$FAB |
| 005 | 424 (M + H)$^+$FAB |
| 006 | 438 (M + H)$^+$FAB |
| 007 | 438 (M + H)$^+$FAB |
| 008 | 418 (M + H)$^+$FAB |
| 009 | 411 (M + H)$^+$FAB |
| 010 | 1.10-1.30 (2H, br), 1.64 (2H, d, J = 12.7 Hz), 1.71-1.82 (1H, m), 2.56 (2H, d, J = 7.4 Hz), 2.83 (1H, t, J = 11.8 Hz), 2.99 (1H, t, J = 11.8 Hz), 4.00 (1H, d, J = 11.8 Hz), 4.15 (1H, d, J = 11.8 Hz), 7.16-7.23 (3H, m), 7.26-7.32 (2H, m), 7.44 (1H, dd, J = 4.4, 8.3 Hz), 7.59-7.64 (1H, m), 8.40 (1H, d, J = 2.0 Hz), 8.43 (1H, d, J = 4.4 Hz), DMSO: 297 (M + H)$^+$FAB |
| 011 | 1.59-1.75 (2H, br), 1.90-2.06 (2H, br), 3.33-3.43 (1H, br), 3.45-3.55 (1H, br), 3.65-3.79 (1H, br), 3.83-3.94 (1H, br), 4.60-4.69 (1H, m), 5.09 (2H, s), 6.57-6.66 (3H, m), 7.19 (1H, t, J = 8.3 Hz), 7.30-7.47 (6H, m), 7.62-7.66 (1H, m), 8.41-8.45 (2H, m), DMSO: 405 (M + H)$^+$FAB |
| 012 | 1.59-1.74 (2H, br), 1.90-2.05 (2H, br), 3.33-3.43 (1H, br), 3.45-3.55 (1H, br), 3.65-3.79 (1H, br), 3.84-3.94 (1H, br), 4.47-4.55 (1H, m), 5.04 (2H, s), 6.95 (4H, s), 7.30-7.46 (6H, m), 7.61-7.66 (1H, m), 8.41-8.45 (2H, m), DMSO: 405 (M + H)$^+$FAB |
| 013 | 1.59-1.76 (1H, br), 1.90-2.05 (2H, br), 2.69 (3H, s), 3.33-3.45 (1H, br), 3.45-3.60 (1H, br), 3.65-3.79 (1H, br), 3.84-3.94 (1H, br), 4.48-4.57 (1H, m), 5.07 (2H, s), 6.97 (4H, s), 7.15 (1H, dt, J = 2.4, 8.3 Hz), 7.24-7.30 (2H, m), 7.40-7.47 (2H, m), 7.81 (1H, d, J = 8.7 Hz), 8.19 (1H, dd, J = 2.5, 8.3 Hz), 8.74 (1H, d, J = 2.4 Hz), DMSO: 437 (M + H)$^+$FAB |
| 014 | 1.50-1.70 (2H, br), 1.89 (2H, d, J = 12.7 Hz), 3.11 (1H, t, J = 11.7 Hz), 3.27 (1H, t, J = 11.7 Hz), 3.75 (1H, tt, J = 3.2, 11.3 Hz), 4.07 (1H, d, J = 11.7 Hz), 4.23 (1H, d, J = 11.7 Hz), 7.45 (1H, dd, J = 5.4, 8.3 Hz), 7.57 (2H, t, J = 7.8 Hz), 7.63-7.69 (2H, m), 8.03 (2H, dd, J = 1.4, 8.3 Hz), 8.44 (2H, dd, J = 1.4, 4.9 Hz), DMSO: 311 (M + H)$^+$FAB |

TABLE 36

| Ex No. | DAT $^1$H-NMR δ (ppm), solvent: MS m/z |
|---|---|
| 015 | 1.55-1.75 (2H, br), 1.83 (2H, d, J = 12.2 Hz), 2.81 (1H, tt, J = 3.4, 12.2 Hz), 4.15 (1H, d, J = 12.2 Hz), 4.31 (1H, d, J = 12.2 Hz), 7.10-7.17 (2H, m), 7.31-7.37 (2H, m), 7.44-7.48 (1H, m), 7.63-7.67 (1H, m), 8.43-8.46 (2H, m), DMSO: 301 (M + H)$^+$FAB |
| 016 | 326 (M + H)$^+$FAB |

TABLE 36-continued

| Ex. No. | DAT $^1$H-NMR δ (ppm), solvent: MS m/z |
|---|---|
| 017 | 2.46-2.62 (6H, m), 2.72-2.80 (2H, m), 3.40-3.50 (2H, br), 3.57-3.65 (2H, br), 7.16-7.32 (5H, m), 7.45 (1H, dd, J = 4.6, 8.3), 7.61-7.65 (1H, m), 8.42-8.45 (2H, m), DMSO: 312 (M + H)$^+$FAB |
| 018 | 1.60-1.75 (2H, br), 1.95-2.10 (2H, br), 3.33-3.41 (1H, br), 3.47-3.56 (1H, br), 3.69-3.78 (1H, br), 3.84-4.03 (1H, br), 5.96 (2H, s), 6.46 (1H, dd, J = 2.4, 8.7 Hz), 6.73 (1H, d, J = 2.4 Hz), 6.82 (1H, d, J = 8.7 Hz), 7.74-7.78 (1H, m), 8.04 (1H, d, J = 8.3 Hz), 8.62 (1H, d, J = 4.9 Hz), 8.72 (1H, s), DMSO: 343 (M + H)$^+$FAB |
| 019 | 1.20-1.40 (2H, br), 1.79-1.89 (2H, br), 1.94-2.04 (1H, m), 2.94 (1H, t, J = 11.8 Hz), 3.07 (1H, t, J = 11.8 Hz), 3.80 (2H, d, J = 6.3 Hz), 4.05 (1H, d, J = 11.8 Hz), 4.22 (1H, d, J = 11.8 Hz), 5.95 (2H, s), 6.37 (1H, dd, J = 2.5, 8.3 Hz), 6.64 (1H, d, J = 2.5 Hz), 6.80 (1H, d, J = 8.3 Hz), 7.45 (1H, dd, J = 4.9, 8.3 Hz), 7.630 (1H, d, J = 8.3 Hz), 8.40-8.45 (2H, m), DMSO: 357 (M + H)$^+$FAB |
| 020 | 1.16-1.32 (2H, br), 1.64-1.82 (3H, m), 2.92 (1H, t, J = 11.7 Hz), 3.06 (1H, t, J = 11.7 Hz), 3.96 (2H, t, J = 6.4 Hz), 4.01 (1H, d, J = 11.7 Hz), 4.17 (1H, d, J = 11.7 Hz), 5.95 (2H, s), 6.37 (1H, dd, J = 2.5, 8.3 Hz), 6.63 (1H, d, J = 2.5 Hz), 6.80 (1H, d, J = 8.3 Hz), 7.74-7.80 (1H, m), 8.02-8.07 (1H, m), 8.61 (1H, d, J = 5.4 Hz), 8.71 (1H, brs), DMSO: 371 (M + H)$^+$FAB |
| 021 | 1.63-1.80 (2H, br), 1.97-1.99 (2H, br), 3.35-3.45 (1H, br), 3.50-3.60 (1H, br), 3.71-3.79 (1H, br), 3.86-3.95 (1H, br), 4.63-4.70 (1H, m), 6.94 (1H, t, J = 7.3 Hz), 7.01 (2H, d, J = 8.3 Hz), 7.30 (2H, t, J = 7.3 Hz), 7.76 (1H, dd, J = 4.8, 8.3 Hz), 8.05 (1H, d, J = 8.3 Hz), 8.62 (1H, d, J = 4.8 Hz), 8.73 (1H, s), DMSO: 299 (M + H)$^+$FAB |
| 022 | 2.85-2.98 (2H, m), 3.68 (1H, t, J = 4.9 Hz), 3.84 (1H, t, J = 5.8 Hz), 4.62 (1H, s), 4.82 (1H, s), 7.20-7.28 (4H, m), 7.46 (1H, dd, J = 4.4, 8.3 Hz), 7.65-7.69 (1H, m), 8.44-8.47 (2H, m), DMSO: 255 (M + H)$^+$FAB |
| 023 | 3.20-3.24 (4H, br), 3.55-3.65 (2H, br), 3.72-3.80 (2H, br), 6.83 (1H, t, J = 7.1), 7.00 (2H, d, J = 8.3), 7.25 (2H, t, J = 7.3), 7.46 (1H, dd, J = 4.4, 8.3), 7.63-7.69 (1H, m), 8.43-8.46 (2H, m), DMSO: 284 (M + H)$^+$FAB |
| 024 | 1.61-1.80 (2H, m), 1.97-2.12 (2H, m), 3.28-3.62 (2H, m), 3.68-3.99 (2H, m), 4.71-4.80 (1H, m), 7.05 (2H, d, J = 8.8 Hz), 7.12-7.22 (1H, m), 7.45 (1H, dd, J = 4.9, 8.3 Hz), 7.61-7.68 (1H, m), 7.78-7.88 (3H, m), 8.41-8.46 (2H, m), DMSO: 342 (M + H)$^+$FAB |
| 025 | 356 (M + H)$^+$FAB |
| 026 | 370 (M + H)$^+$FAB |
| 027 | 342 (M + H)$^+$FAB |

TABLE 37

| Ex. No. | DAT $^1$H-NMR δ (ppm), solvent: MS m/z |
|---|---|
| 028 | 356 (M + H)$^+$FAB |
| 029 | 481 (M + H)$^+$FAB |
| 030 | 1.60-1.78 (2H, m), 1.93-2.06 (2H, m), 3.04 (6H, s), 3.30-3.93 (4H, m), 4.49-4.56 (1H, m), 5.07 (2H, s), 6.96 (4H, s), 7.12-7.18 (1H, m), 7.24-7.30 (2H, m), 7.40-7.52 (2H, m), 8.05-8.08 (2H, m), DMSO: 466 (M + H)$^+$FAB |
| 031 | 424 (M + H)$^+$FAB |
| 032 | 2.04-2.20 (1H, m), 2.40-2.60 (1H, m), 3.10-4.10 (8H, m), 4.32-4.44 (2H, m), 7.41-7.50 (3H, m), 7.66-7.82 (2H, m), 8.05-8.16 (1H, m), 8.62 (1H, br), 8.80 (1H, d, J = 12.7 Hz), 11.58 (1H, br), DMSO: 312 (M + H)$^+$FAB |
| 033 | 1.25-1.35 (2H, m), 1.55-1.66 (2H, m), 1.70-1.83 (2H, m), 2.60 (2H, t, J = 7.3 Hz), 3.00-3.22 (4H, m), 3.40-3.70 (4H, m), 4.00-4.35 (2H, m), 7.15-7.33 (5H, m), 7.62 (1H, br), 7.85 (1H, br), 8.50-8.65 (2H, m), 10.90-11.40 (1H, br), DMSO: 354 (M + H)$^+$FAB |
| 034 | 3.09 (4H, br), 3.50-3.80 (4H, m), 5.04 (2H, s), 6.94 (4H, d, J = 1.7 Hz), 7.30-7.49 (6H, m), 7.63-7.68 (1H, m), 8.43-8.46 (2H, m), DMSO: 390 (M + H)$^+$FAB |
| 035 | 1.10-1.32 (2H, m), 1.46-1.60 (3H, m), 1.80 (2H, d, J = 11.7 Hz), 2.62 (2H, t, J = 7.8 Hz), 2.88 (1H, t, J = 12.2 Hz), 3.03 (1H, t, J = 12.2 Hz), 4.17 (1H, t, J = 12.2 Hz), 7.16-7.23 (3H, m), 7.27-7.31 (2H, m), 7.89 (1H, dd, J = 5.3, 8.8 Hz), 8.18-8.22 (1H, m), 8.69 (1H, dd, J = 1.0, 5.3 Hz), 8.82 (1H, d, J = 2.5 Hz), DMSO: 311 (M + H)$^+$FAB |
| 036 | 1.52-1.68 (2H, br), 1.88-2.01 (2H, br), 3.22-3.33 (1H, br), 3.37-3.48 (1H, br), 3.65-3.75 (2H, m), 3.82-3.91 (1H, br), 4.56 (2H, s), 7.26-7.32 (1H, m), 7.36 (4H, d, J = 4.4 Hz), 7.70 (1H, dd, J = 1.0, 8.3 Hz), 7.95 (1H, dd, J = 1.0, 8.3 Hz), 8.58 (1H, d, J = 4.9 Hz), 8.66 (1H, s), DMSO: 313 (M + H)$^+$FAB |
| 037 | 1.69 (2H, d, J = 12.7 Hz), 1.91-2.11 (2H, m), 3.33 (1H, t, J = 12.7 Hz), 3.47 (1H, t, J = 12.7 Hz), 3.93-4.07 (2H, m), 4.13 (1H, d, J = 12.7 Hz), 7.23 (1H, t, J = 7.4 Hz), 7.35 (2H, t, J = 7.4 Hz), 7.52-7.55 (2H, m), 7.81 (1H, dd, J = 5.4, 8.3 Hz), 8.10-8.14 (1H, m), 8.63 (1H, d, J = 4.9 Hz), 8.77 (1H, d, J = 2.4 Hz), DMSO: 299 (M + H)$^+$FAB |
| 038 | 2.58 (1H, br), 2.64 (1H, br), 3.67 (1H, br), 3.83 (1H, br), 4.13 (1H, s), 4.32 (1H, s), 6.21 (1H, s), 7.29 (1H, t, J = 7.3 Hz), 7.37 (2H, t, J = 7.3 Hz), 7.44-7.50 (3H, m), 7.67 (1H, d, J = 8.3 Hz), 8.44-8.47 (2H, m), DMSO: 281 (M + H)$^+$FAB |
| 039 | 1.95 (3H, s), 2.00-2.16 (2H, br), 2.39-2.47 (2H, br), 3.20-3.30 (1H, br), 3.35-3.45 (1H, br), 3.63-3.73 (1H, br), 3.79-3.89 (1H, br), 7.29-7.34 (1H, m), 7.37-7.46 (5H, m), 7.60-7.64 (1H, m), 8.40-8.43 (2H, m), DMSO: 325 (M + H)$^+$FAB |

TABLE 38

| Ex. No. | DAT $^1$H-NMR δ (ppm), solvent: MS m/z |
|---|---|
| 040 | 1.61-1.81 (2H, m), 1.83 (2H, d, J = 12.2 Hz), 2.77-2.87 (1H, m), 3.05 (1H, t, J = 12.2 Hz), 3.19 (1H, t, J = 12.2 Hz), 4.16 (1H, d, J = 12.2 Hz), 4.33 (1H, d, J = 12.2 Hz), 7.19-7.24 (1H, m), 7.27-7.36 (5H, m), 7.91 (1H, dd, J = 5.3, 8.3 Hz), 7.36 (1H, d, J = 8.3 Hz), 8.70 (1H, d, J = 4.9 Hz), 8.85 (1H, s), DMSO: 283 (M + H)$^+$FAB |
| 041 | 35 (M + H)$^+$FAB |
| 042 | 1.60-1.76 (2H, m), 1.92-2.05 (2H, m), 3.30-3.92 (4H, m), 4.48-4.55 (1H, m), 5.07 (2H, s), 6.95 (4H, s), 7.12-7.18 (1H, m), 7.23-7.30 (2H, m), 7.39-7.48 (1H, m), 7.93-7.96 (1H, m), 8.44 (1H, d, J = 2.0 Hz), 8.52 (1H, d, J = 2.0 Hz), DMSO: 457 (M + H)$^+$FAB |
| 043 | 1.14-1.35 (2H, m), 1.68-1.84 (5H, m), 2.89 (1H, t, J = 11.7 Hz), 3.05 (1H, t, J = 11.7 Hz), 3.96-4.21 (4H, m), 6.98 (2H, d, J = 8.8 Hz), 7.16 (1H, brs), 7.44 (1H, dd, J = 4.9, 8.3 Hz), 7.60-7.65 (1H, m), 7.76-7.87 (3H, m), 8.40-8.44 (2H, m), DMSO: 370 (M + H)$^+$FAB |
| 044 | 1.60-1.75 (2H, m), 1.92-2.05 (2H, m), 3.30-3.92 (4H, m), 4.46-4.55 (1H, m), 5.07 (2H, s), 6.95 (4H, s), 7.12-7.18 (1H, m), 7.24-7.29 (2H, m), 7.40-7.47 (1H, m), 8.06-8.086 (1H, m), 8.47 (1H, d, J = 2.0 Hz), 8.59 (1H, d, J = 2.0 Hz), DMSO: 501 (M$^+$)FAB |
| 045 | 1.60-1.78 (2H, m), 1.93-2.06 (2H, m), 3.31-3.57 (6H, m), 3.70-3.93 (6H, m), 4.49-4.56 (1H, m), 5.07 (2H, s), 6.96 (4H, s), 7.12-7.17 (1H, m), 7.24-7.30 (2H, m), 7.41-7.47 (1H, m), 7.78 (1H, s), 8.19-8.22 (1H, m), 8.30-8.33 (1H, m), DMSO: 508 (M + H)$^+$FAB |
| 046 | 1.51-1.70 (2H, m), 1.87-2.02 (2H, m), 3.20-3.31 (1H, m), 3.36-3.47 (1H, m), 3.62-3.72 (1H, m), 3.66-3.77 (1H, m), 3.80-3.93 (1H, m), 4.61 (2H, s), 7.33 (1H, br s), 7.42 (2H, d, J = 8.3 Hz), 7.44 (1H, dd, J = 8.3, 4.4 Hz), 7.63 (1H, ddd, J = 8.3, 2.4, 1.5 Hz), 7.86 (2H, d, J = 8.3 Hz), 7.94 (1H, br s), 8.42 (1H, s), 8.43 (1H, dd, J = 6.3, 1.5 Hz), DMSO: 356 (M + H)$^+$FAB |
| 047 | 340 (M + H)$^+$FAB |
| 048 | 390 (M + H)$^+$FAB |
| 049 | 1.40-1.52 (2H, m), 1.55-1.65 (2H, m), 2.30-2.45 (4H, m), 2.60 (2H, t, J = 7.6 Hz), 3.38-3.64 (4H, m), 7.12-7.22 (3H, m), 7.25-7.31 (2H, m), 7.44 (1H, dd, J = 4.8, 7.5 Hz), 7.60-7.65 (1H, m), 8.40-8.45 (2H, m), DMSO: 340 (M + H)$^+$FAB |
| 050 | 308 (M + H)$^+$FAB |
| 051 | 1.60-1.84 (2H, br), 1.92-2.06 (2H, br), 3.40-3.52 (1H, br), 3.55-3.75 (2H, br), 3.79-3.91 (1H, br), 4.59-4.65 (1H, m), 5.08 (2H, s), 6.97 (1H, dd, J = 2.9, 9.3 Hz), 7.15 (1H, d, J = 2.9 Hz), 7.22 (1H, d, J = 8.8 Hz), 7.31-7.47 (5H, m), 7.88 (1H, dd, J = 5.4, 8.8 Hz), 8.20 (1H, d, J = 8.3 Hz), 8.68 (1H, d, J = 5.4 Hz), 8.83 (1H, d, J = 1.9 Hz), DMSO: 439 (M + H)$^+$FAB |

TABLE 39

| Ex No. | DAT $^1$H-NMR δ (ppm), solvent: MS m/z |
|---|---|
| 052 | 311 (M + H)$^+$FAB |
| 053 | 1.07-1.27 (2H, m), 1.53 (2H, q, J = 6.4 Hz), 1.62-1.76 (3H, m), 2.90 (1H, t, J = 13.2 Hz), 3.04 (1H, t, J = 13.2 Hz), 3.50 (2H, t, J = 6.4 Hz), 3.99 (1H, d, J = 13.2 Hz), 4.15 (1H, d, J = 13.2 Hz), 4.46 (2H, s), 7.26-7.39 (5H, m), 7.73-7.78 (1H, m), 8.03 (1H, d, J = 8.3 Hz), 8.62 (1H, d, J = 4.4 Hz), 8.70 (1H, s), DMSO: 341 (M + H)$^+$FAB |
| 054 | 374, 376 (M + H)$^+$FAB |
| 055 | 1.10-1.30 (2H, m), 1.64 (2H, d, J = 13.2 Hz), 1.71-1.83 (1H, m), 2.56 (2H, d, J = 7.4 Hz), 2.83 (1H, t, J = 12.2 Hz), 2.98 (1H, t, J = 12.2 Hz), 3.36 (3H, s), 3.99 (1H, d, J = 12.2 Hz), 4.15 (1H, d, J = 12.2 Hz), 4.65 (2H, s), 7.17-7.22 (3H, m), 7.27-7.32 (2H, m), 7.43 (1H, d, J = 8.8 Hz), 7.60 (1H, dd, J = 2.5, 8.8 Hz), 8.33 (1H, d, J = 2.5 Hz), DMSO: 341 (M + H)$^+$FAB |
| 056 | 523 (M + H)$^+$FAB |
| 057 | 342 (M + H)$^+$FAB |
| 058 | 471 (M + H)$^+$FAB |
| 059 | 389 (M + H)$^+$FAB |
| 060 | 299 (M + H)$^+$FAB |
| 061 | 1.58-1.75 (2H, m), 1.90-2.04 (2H, m), 2.69 (2H, t, J = 7.8 Hz), 2.89 (2H, t, J = 7.8 Hz), 3.30-3.91 (7H, m), 4.47-4.55 (1H, m), 5.07 (2H, s), 6.95 (4H, s), 7.12-7.18 (1H, m), 7.23-7.30 (2H, m), 7.39-7.47 (1H, m), 7.51-7.55 (1H, m), 8.24-8.27 (1H, m), 8.30-8.34 (1H, m), DMSO: 509 (M + H)$^+$FAB |
| 062 | 356 (M + H)+FAB |
| 063 | 1.07-1.31 (2H, m), 1.42-1.55 (1H, m), 1.52-1.64 (2H, m), 1.72-1.86 (2H, m), 2.68 (2H, t, J = 7.5 Hz), 2.78-2.91 (1H, m), 2.94-3.07 (1H, m), 3.93-4.07 (1H, m), 4.09-4.23 (1H, m), 7.26 (1H, br s), 7.29 (2H, d, J = 8.6 Hz), 7.44 (1H, dd, J = 8.6, 4.8 Hz), 7.61 (1H, ddd, J = 8.6, 2.7, 1.5 Hz), 7.80 (2H, d, J = 8.0 Hz), 7.89 (1H, br s), 8.41 (1H, d, J = 2.7 Hz), 8.42 (1H, dd, J = 4.8, 1.1 Hz), DMSO: 354 (M + H)$^+$FAB |
| 064 | 354 (M + H)$^+$FAB |
| 065 | 1.34-1.57 (2H, m), 1.78-1.90 (2H, m), 2.40-2.48 (1H, m), 2.92-3.08 (1H, m), 3.07-3.23 (1H, m), 3.98-4.13 (1H, m), 4.14-4.28 (1H, m), 6.44 (1H, dd, J = 16.1, 5.9 Hz), 6.50 (1H, d, J = 16.1 Hz), 7.30 (1H, br s), 7.45 (1H, dd, J = 8.3, 4.4 Hz), 7.48 (2H, d, J = 8.3 Hz), 7.63 (1H, ddd, J = 8.3, 2.5, 1.5 Hz), 7.83 (2H, d, J = 8.3 Hz), 7.92 (1H, br s), 8.43 (1H, d, J = 1.9 Hz), 8.43 (1H, dd, J = 4.4, 1.9 Hz), DMSO: 352 (M + H)$^+$FAB |
| 066 | 1.03-1.23 (2H, m), 1.35-1.43 (2H, m), 1.46-1.62 (1H, m), 1.72-1.87 (4H, m), 2.82-2.92 (3H, m), 3.03 (1H, t, J = 11.8 Hz), 3.74 (3H, s), 4.01 (1H, d, J = 11.8 Hz), 4.17 (1H, d, J = 11.8 Hz), 7.11-7.21 (2H, m), 7.42-7.49 (2H, m), 7.52-7.56 (1H, m), 7.59-7.63 (1H, m), 8.40-8.44 (2H, m), DMSO: 379 (M + H)$^+$ESI |

TABLE 40

| Ex No. | DAT $^1$H-NMR δ (ppm), solvent: MS m/z |
|---|---|
| 067 | 308 (M + H)$^+$FAB |
| 068 | 339 (M + H)$^+$FAB |
| 069 | 1.04-1.26 (2H, m), 1.35-1.45 (2H, m), 1.48-1.61 (1H, m), 1.70-1.83 (4H, m), 2.80-2.94 (1H, m), 2.94-3.10 (1H, m), 3.96-4.06 (1H, m), 4.03 (2H, t, J = 6.4 Hz), 4.12-4.22 (1H, m), 6.96 (2H, d, J = 8.8 Hz), 7.15 (1H, br s), 7.44 (1H, dd, J = 8.3, 4.9 Hz), 7.61 (1H, ddd, J = 8.3, 2.9, 1.5 Hz), 7.81 (1H, br s), 7.83 (2H, d, J = 8.8 Hz), 8.41 (1H, d, J = 2.4 Hz), 8.42 (1H, dd, J = 4.9, 1.4 Hz), DMSO: 384 (M + H)$^+$FAB |
| 070 | 1.57-1.75 (2H, br), 1.90-2.06 (2H, br), 3.30-3.42 (1H, br), 3.45-3.56 (1H, br), 3.65-3.78 (1H, br), 3.80-3.95 (1H, br), 4.55-4.61 (1H, m), 5.14 (2H, s), 6.95 (1H, dd, J = 2.9, 9.3 Hz), 7.14-7.18 (2H, m), 7.31-7.48 (6H, m), 7.62-7.67 (1H, m), 8.42-8.45 (2H, m), DMSO: 439 (M + H)$^+$FAB |
| 071 | 486 (M + H)$^+$FAB |
| 072 | 385 (M + H)$^+$FAB |
| 073 | 578 (M + H)$^+$FAB |
| 074 | 313 (M + H)$^+$FAB |
| 075 | 441 (M + H)$^+$FAB |
| 076 | 439 (M + H)$^+$FAB |
| 077 | 1.21 (3H, t, J = 7.4 Hz), 1.58-1.78 (2H, m), 1.83 (2H, d, J = 12.7 Hz), 2.77 (1H, tt, J = 3.8, 12.2 Hz), 2.98 (1H, t, J = 12.2 Hz), 3.14 (1H, t, J = 12.2 Hz), 4.10-4.21 (3H, m), 4.31 (1H, d, J = 12.2 Hz), 4.76 (2H, s), 6.76 (1H, dd, J = 2.0, 7.4 Hz), 6.87 (1H, t, J = 2.0 Hz), 6.90 (1H, d, J = 7.4 Hz), 7.23 (1H, t, J = 7.8 Hz), 7.46 (1H, dd, J = 4.9, 8.3 Hz), 7.64-7.67 (1H, m), 8.42-8.47 (2H, br), DMSO: 385 (M + H)$^+$FAB |
| 078 | 1.58-1.78 (2H, m), 1.83 (2H, d, J = 12.2 Hz), 2.77 (1H, tt, J = 3.4, 12.2 Hz), 2.98 (1H, t, J = 12.2 Hz), 3.14 (1H, t, J = 12.2 Hz), 4.15 (1H, d, J = 12.2 Hz), 4.31 (1H, d, J = 12.2 Hz), 5.10 (2H, s), 6.84-6.90 (2H, m), 6.95 (1H, t, J = 2.0 Hz), 7.23 (1H, t, J = 7.8 Hz), 7.31-7.48 (6H, m), 7.64-7.67 (1H, m), 8.42-8.47 (2H, m), DMSO: 389 (M + H)$^+$FAB |
| 079 | 461 (M + H)$^+$FAB |
| 080 | 1.40-1.66 (2H, m), 1.88-2.00 (2H, m), 2.82-2.97 (1H, m), 2.97-3.14 (1H, m), 3.47-3.57 (1H, m), 4.01-4.17 (1H, m), 4.18-4.33 (1H, m), 5.26 (2H, s), 7.16-7.23 (1H, m), 7.30 (2H, d, J = 9.0 Hz), 7.30-7.36 (2H, m), 7.41-7.46 (1H, m), 7.45-7.51 (1H, m), 7.62 (1H, ddd, J = 8.3, 2.7, 1.5 Hz), 7.81 (2H, d, J = 8.8 Hz), 8.40 (1H, d, J = 2.4 Hz), 8.42 (1H, dd, J = 4.7, 1.5 Hz), DMSO: 471 (M + H)$^+$FAB |
| 081 | 1.10-1.34 (2H, m) 1.70-1.80 (2H, m), 1.80-1.92 (1H, m), 2.80-2.95 (1H, m), 2.95-3.10 (1H, m), 2.70-3.95 (1H, br s), 3.34 (2H, d, J = 6.4 Hz), 3.95-4.07 (1H, m), 4.11-4.23 (1H, m), 4.48 (2H, s), 7.25-7.38 (7H, m), 7.44 (1H, dd, J = 8.3, 4.6 Hz), 7.62 (1H, ddd, J = 8.3, 2.6 1.2 Hz), DMSO: 327 (M + H)$^+$AFB |
| 082 | 462 (M$^+$)FAB |
| 083 | 418 (M + H)$^+$FAB |

TABLE 41

| Ex No. | DAT $^1$H-NMR δ (ppm), solvent: MS m/z |
|---|---|
| 084 | 326 (M + H)$^+$FAB |
| 085 | 2.49-2.62 (6H, m), 2.73-2.81 (2H, m), 3.40-3.66 (4H, m), 7.15-7.32 (5H, m), 7.93 (1H, t, J = 1.9 Hz), 8.44 (1H, d, J = 2.4 Hz), 8.52 (1H, d, J = 2.0 Hz), DMSO: 346 (M + H)$^+$FAB |
| 086 | 2.49-2.62 (6H, m), 2.73-2.81 (2H, m), 3.46 (2H, br), 3.62 (2H, br), 3.90 (3H, s), 7.15-7.32 (5H, m), 8.11 (1H, dd, J = 2.0, 2.7 Hz), 8.70 (1H, d, J = 2.8 Hz), 8.94 (1H, d, J = 1.7 Hz), DMSO: 370 (M + H)$^+$FAB |
| 087 | 1.63-1.80 (2H, br), 1.97-2.11 (2H, br), 3.33-3.41 (1H, br), 3.43-3.58 (1H, br), 3.68-3.82 (1H, br), 3.83-3.96 (1H, br), 4.72-4.80 (1H, m), 7.43-7.48 (2H, m), 7.59 (1H, dd, J = 3.2, 8.8 Hz), 7.62-7.67 (1H, m), 8.19 (1H, d, J = 2.2 Hz), 8.43-8.45 (2H, m), DMSO: 334 (M + H)$^+$FAB |
| 088 | 1.39-1.65 (2H, m), 1.88-1.98 (2H, m), 2.83-3.13 (2H, m), 3.46-3.55 (1H, m), 4.03-4.33 (2H, m), 5.23 (2H, s), 7.29 (2H, d, J = 8.8 Hz), 7.33-7.51 (6H, m), 7.62 (1H, ddd, J = 1.5, 2.9, 8.3 Hz), 7.80 (2H, d, J = 8.8 Hz), 8.40 (1H, d, J = 2.4 Hz), 8.42 (1H, dd, J = 1.5, 4.9 Hz), DMSO: 453 (M + H)$^+$FAB |
| 089 | 1.40-1.65 (2H, m), 1.88-1.99 (2H, m), 2.83-3.14 (2H, m), 3.47-3.57 (1H, m), 4.03-4.34 (2H, m), 5.30 (2H, s), 7.31 (2H, d, J = 8.8 Hz), 7.44 (1H, dd, J = 4.9, 8.3 Hz), 7.59-7.68 (2H, m), 7.79-7.87 (4H, m), 7.96-7.98 (1H, m), 8.40 (1H, d, J = 2.4 Hz), 8.42 (1H, dd, J = 1.5, 4.9 Hz), DMSO: 478 (M + H)$^+$FAB |
| 090 | 469 (M + H)$^+$FAB |
| 091 | 473 (M + H)$^+$FAB |
| 092 | 334 (M + H)$^+$FAB |
| 093 | 424 (M + H)$^+$FAB |
| 094 | 419 (M + H)$^+$FAB |
| 095 | 487 (M + H)$^+$FAB |
| 096 | 385 (M + H)$^+$FAB |
| 097 | 437 (M + H)$^+$FAB |
| 098 | 1.06-1.26 (2H, m), 1.37-1.44 (2H, m), 1.50-1.60 (1H, m), 1.73-1.82 (4H, m), 2.86 (1H, t, J = 12.2 Hz), 2.94 (6H, s), 3.05 (1H, t, J = 12.2 Hz), 3.97-4.04 (3H, m), 4.18 (1H, d, J = 11.7 Hz), 6.96 (2H, d, J = 8.8 Hz), 7.36 (2H, d, J = 8.8 Hz), 7.73 (1H, dd, J = 4.8, 8.3 Hz), 7.96-8.01 (1H, m), 8.59 (1H, dd, J = 1.5, 4.8 Hz), 8.67 (1H, d, J = 2.4 Hz), DMSO: 412 (M + H)$^+$FAB |

TABLE 41-continued

| Ex No. | DAT $^1$H-NMR δ (ppm), solvent: MS m/z |
|---|---|
| 099 | 1.02-1.22 (2H, m), 1.36-1.44 (2H, m), 1.49-1.61 (1H, m), 1.72-1.82 (4H, m), 2.75 (3H, d, J = 4.4 Hz), 2.87 (1H, t, J = 12.2 Hz), 3.02 (1H, t, J = 12.2 Hz), 3.98-4.05 (3H, m), 4.17 (1H, d, J = 12.2 Hz), 6.97 (2H, d, J = 8.8 Hz), 7.43 (1H, dd, J = 4.4, 8.3 Hz), 7.59-7.64 (1H, m), 7.78 (2H, d, J = 8.3 Hz), 8.22-8.27 (1H, m), 8.38-8.43 (2H, m), DMSO: 398 (M + H)$^+$FAB |

TABLE 42

| Ex No. | DAT $^1$H-NMR δ (ppm), solvent: MS m/z |
|---|---|
| 100 | 1.58-1.74 (2H, m), 1.90-2.06 (2H, m), 2.50 (3H, s), 3.30-3.95 (4H, m), 4.48-4.58 (3H, m), 5.07 (2H, s), 6.95 (4H, s), 7.12-7.18 (1H, m), 7.24-7.30 (2H, m), 7.40-7.47 (1H, m), 7.54-7.57 (1H, m), 8.27-8.34 (1H, m), 8.34-8.42 (1H, m), DMSO: 495 (M + H)$^+$FAB |
| 101 | 1.40-1.64 (2H, m), 1.90-2.03 (2H, m), 3.05-3.18 (1H, m), 3.20-3.34 (1H, m), 3.51-3.62 (1H, m), 3.88-4.01 (1H, m), 4.02-4.14 (1H, m), 5.16 (2H, s), 6.90-6.95 (1H, m), 6.98-7.03 (1H, m), 7.03-7.06 (1H, m), 7.13-7.19 (1H, m), 7.25-7.32 (3H, m), 7.41-7.47 (1H, m), 7.72 (1H, dd, J = 8.8, 5.4 Hz), 7.99 (1H, ddd, J = 8.3, 2.4, 1.0 Hz), 8.56-8.61 (1H, m), 8.67 (1H, d, J = 2.4 Hz), DMSO: 439 (M + H)$^+$FAB |
| 102 | 426 (M + H)$^+$FAB |
| 103 | 1.58-1.78 (2H, br), 1.97-2.11 (2H, br), 3.30-3.60 (2H, br), 3.70-3.79 (1H, br), 3.85-3.96 (1H, br), 5.11-5.16 (3H, m), 6.79 (1H, d, J = 8.8 Hz), 7.12-7.20 (1H, m), 7.25-7.30 (2H, m), 7.40-7.50 (3H, m), 7.61-7.67 (1H, m), 7.93 (1H, d, J = 3.5 Hz), 8.40-8.46 (2H, br), DMSO: 424 (M + H)$^+$FAB |
| 104 | 1.16-1.32 (2H, m) 1.70-1.82 (2H, m), 1.79-1.91 (1H, m), 2.82-2.99 (1H, m), 2.95-3.12 (1H, m), 3.34 (2H, d, J = 6.3 Hz), 3.98-4.07 (1H, m), 4.11 (2H, dd, J = 5.8, 1.4 Hz), 4.14-4.23 (1H, m), 6.36 (1H, ddd, J = 16.1, 5.8, 5.8 Hz), 6.61 (1H, d, J = 16.1 Hz), 6.63 (1H, s), 7.21-7.29 (1H, m), 7.30-7.38 (2H, m), 7.40-7.49 (2H, m), 7.61 (1H, ddd, J = 8.3, 2.4, 1.4 Hz), 8.37-8.64 (2H, m), 13.12 (1H, br s), DMSO: 353 (M + H)$^+$FAB |
| 105 | 471 (M + H)$^+$FAB |
| 106 | 424 (M + H)$^+$FAB |
| 107 | 313 (M + H)$^+$FAB |
| 108 | 1.04-1.24 (2H, br), 1.36-1.43 (2H, m), 1.48-1.61 (1H, m), 1.72-1.82 (4H, m), 2.87 (1H, t, J = 11.7 Hz), 3.03 (1H, t, J = 11.7 Hz), 4.01 (1H, d, J = 11.7 Hz), 4.07 (2H, t, J = 6.4 Hz), 4.17 (1H, d, J = 11.7 Hz), 7.10 (2H, d, J = 8.8 Hz), 7.44 (1H, dd, J = 5.4, 8.3 Hz), 7.59-7.63 (1H, m), 7.76 (2H, d, J = 8.8 Hz), 8.40-8.44 (2H, m), DMSO: 366 (M + H)$^+$FAB |
| 109 | 223 (M + H)$^+$FAB |
| 110 | 1.23-1.43 (2H, m), 1.86 (2H, d, J = 12.7 Hz), 1.97-2.09 (1H, m), 2.93 (1H, t, J = 12.2 Hz), 3.09 (1H, t, J = 12.2 Hz), 3.88 (2H, d, J = 12.7 Hz), 4.07 (1H, d, J = 12.2 Hz), 4.23 (1H, d, J = 12.2 Hz), 6.90-6.96 (3H, m), 7.26-7.31 (3H, m), 7.44 (1H, dd, J = 4.4, 8.3 Hz), 7.61-7.65 (1H, m), 8.41-8.44 (2H, m), DMSO: 313 (M + H)$^+$FAB |
| 111 | 1.16-1.36 (2H, m), 1.67-1.85 (5H, m), 2.93 (1H, t, J = 12.2 Hz), 3.08 (1H, t, J = 12.2 Hz), 4.00 (1H, d, J = 12.2 Hz), 4.03 (2H, t, J = 6.3 Hz), 4.17 (1H, d, J = 12.2 Hz), 6.90-6.96 (3H, m), 7.26-7.31 (2H, m), 7.78 (1H, dd, J = 4.9, 8.3 Hz), 8.03-8.08 (1H, m), 8.62 (1H, dd, J = 1.0, 4.9 Hz), 8.72 (1H, d, J = 2.5 Hz), DMSO: 327 (M + H)$^+$FAB |

TABLE 43

| Ex No. | DAT $^1$H-NMR δ (ppm), solvent: MS m/z |
|---|---|
| 112 | 1.05-1.25 (2H, m), 1.47-1.52 (2H, m), 1.58-1.68 (1H, m), 1.70-1.84 (4H, m), 2.62 (2H, t, J = 7.4 Hz), 2.87 (2H, t, J = 12.2 Hz), 3.03 (1H, t, J = 12.2 Hz), 4.00 (1H, d, J = 12.2 Hz), 4.15 (1H, d, J = 12.2 Hz), 7.15-7.22 (3H, m), 7.25-7.30 (2H, m), 7.45 (1H, dd, J = 4.9, 8.3 Hz), 7.59-7.64 (1H, m), 8.38-8.44 (2H, m), DMSO: 369 (M + H)$^+$FAB |
| 113 | 1.65-1.75 (2H, m), 1.83 (2H, d, J = 12.2 Hz), 1.98-2.05 (2H, m), 2.72-2.80 (3H, m), 2.98 (1H, t, J = 12.2 Hz), 3.14 (1H, t, J = 12.2 Hz), 3.97 (2H, t, J = 6.3 Hz), 4.15 (1H, d, J = 11.7 Hz), 4.31 (1H, d, J = 11.7 Hz), 6.75-6.79 (1H, m), 6.83-6.87 (2H, m), 7.16-7.32 (6H, m), 7.46 (1H, dd, J = 4.9, 8.8 Hz), 7.64-7.68 (1H, m), 8.42-8.47 (2H, br), DMSO: 417 (M + H)$^+$FAB |
| 114 | 1.10-1.26 (2H, m), 1.35-1.45 (2H, m), 1.48-1.62 (1H, m), 1.70-1.82 (4H, m), 2.80-2.95 (1H, m), 2.96-3.11 (1H, m), 3.96 (2H, t, J = 6.4 Hz), 3.97-4.07 (1H, m), 4.10-4.24 (1H, m), 6.89-6.95 (3H, m), 7.24-7.32 (2H, m), 7.44 (1H, dd, J = 8.3, 3.9 Hz), 7.61 (1H, ddd, J = 8.3, 2.9, 1.5 Hz), 8.40 (1H, d, J = 2.9 Hz), 8.42 (1H, dd, J = 4.4, 1.5 Hz), DMSO: 341 (M + H)$^+$FAB |
| 115 | 1.06-1.26 (2H, br), 1.37-1.45 (2H, m), 1.50-1.62 (1H, m), 1.72-1.88 (4H, m), 2.88 (1H, t, J = 13.2 Hz), 3.03 (1H, t, J = 13.2 Hz), 4.01 (1H, d, J = 11.7 Hz), 4.13 (2H, t, J = 6.3 Hz), 4.18 (1H, d, J = 11.7 Hz), 7.02 (1H, t, J = 7.8 Hz), 7.14 (1H, d, J = 7.8 Hz), 7.42-7.49 (2H, m), 7.53-7.64 (3H, m), 7.81 (1H, dd, J = 1.9, 7.8 Hz), 8.40-8.44 (2H, m), DMSO: 384 (M + H)$^+$FAB |
| 116 | 1.05-1.25 (2H, br), 1.36-1.45 (2H, m), 1.52-1.64 (1H, m), 1.73-1.83 (4H, m), 2.88 (1H, t, J = 12.7 Hz), 3.05 (1H, t, J = 12.7 Hz), 3.99-4.05 (3H, m), 4.18 (1H, d, J = 12.7 Hz), 7.05-7.09 (1H, m), 7.34 (2H, t, J = 8.3 Hz), 7.41-7.46 (2H, m), 7.73 (1H, dd, J = 4.9, 8.3 Hz), 7.92-8.02 (2H, m), 8.57-8.60 (1H, m), 8.67 (1H, d, J = 2.4 Hz), DMSO: 384 (M + H)$^+$FAB |

TABLE 43-continued

| Ex No. | DAT <sup>1</sup>H-NMR δ (ppm), solvent: MS m/z |
|---|---|
| 117 | 1.59-1.74 (2H, m), 1.96-2.03 (2H, m), 3.27-3.56 (2H, m), 3.70-3.95 (5H, m), 4.48-4.58 (3H, m), 5.08 (2H, s), 6.85 (1H, d, J = 16.1 Hz), 6.96 (4H, s), 7.12-7.18 (1H, m), 7.24-7.30 (2H, m), 7.40-7.47 (1H, m), 7.72 (1H, d, J = 16.1 Hz), 8.10 (1H, dd, J = 1.5 Hz, 2.4 Hz), 8.46 (1H, d, J = 2.4 Hz), 8.75 (1H, d, J = 1.5 Hz), DMSO: 507 (M + H)$^+$FAB |
| 118 | 1.60-1.76 (2H, m), 1.92-2.05 (2H, m), 3.30-3.55 (2H, m), 3.66-3.93 (2H, m), 4.48-4.56 (1H, m), 5.07 (2H, s), 6.95 (4H, s), 7.12-7.18 (1H, m), 7.23-7.30 (2H, m), 7.39-7.47 (1H, m), 7.75-7.82 (1H, m), 8.35-8.40 (1H, m), 8.50 (1H, d, J = 2.5 Hz), DMSO: 441 (M + H)$^+$FAB |
| 119 | 452 (M + H)$^+$FAB |
| 120 | 449 (M + H)$^+$FAB |
| 121 | 437 (M + H)$^+$FAB |
| 122 | 0.96-1.27 (5H, m), 1.60-1.86 (6H, m), 3.26-3.82 (8H, m), 3.82 (2H, d, J = 6.3 Hz), 6.92-7.04 (3H, m), 7.36 (1H, t, J = 8.3 Hz), 7.62-7.69 (1H, m), 7.90 (1H, br), 8.50-8.66 (2H, m), DMSO: 424 (M + H)$^+$FAB |
| 123 | 437 (M + H)$^+$FAB |

TABLE 44

| Ex No. | DAT <sup>1</sup>H-NMR δ (ppm), solvent: MS m/z |
|---|---|
| 124 | 2.29 (3H, s), 2.68 (2H, t, J = 7.3 Hz), 2.84 (2H, t, J = 7.3 Hz), 3.37-3.62 (8H, m), 7.12 (2H, d, J = 7.9 Hz), 7.15-7.22 (1H, m), 7.24-7.32 (4H, m), 7.49 (2H, d, J = 7.8 Hz), 7.80 (1H, dd, J = 4.9, 8.3 Hz), 8.05-8.10 (1H, m), 8.63 (1H, dd, J = 1.0, 4.9 Hz), 8.73 (1H, d, J = 2.4 Hz), DMSO: 340 (M + H)$^+$FAB |
| 125 | 312 (M + H)$^+$FAB |
| 126 | 3.46-3.59 (2H, m), 3.61-3.77 (4H, m), 3.78-3.92 (2H, m), 7.30 (1H, d, J = 15.5 Hz), 7.36-7.45 (2H, m), 7.48 (1H, d, J = 8.0 Hz), 7.54 (1H, d, J = 15.5 Hz), 7.71-7.76 (1H, m), 7.80 (1H, dd, J = 8.6, 4.8 Hz), 8.07-8.12 (1H, m), 8.64 (1H, dd, J = 5.3, 1.1 Hz), 8.75 (1H, d, J = 2.2 Hz), DMSO: 338 (M + H)ES |
| 127 | 342 (M + H)$^+$ESI |
| 128 | 326 (M + H)$^+$FAB |
| 129 | 341 (M + H)$^+$ESI |
| 130 | 354 (M + H)$^+$FAB |
| 131 | 352 (M + H)$^+$FAB |
| 132 | 369 (M + H)$^+$FAB |
| 133 | 355 (M + H)$^+$FAB |
| 134 | 426 (M + H)$^+$FAB |
| 135 | 457 (M + H)$^+$FAB |
| 136 | 457 (M + H)$^+$FAB |
| 137 | 453 (M + H)$^+$FAB |
| 138 | 3.30-3.82 (8H, br), 5.08 (2H, s), 7.02 (1H, d, J = 7.8), 7.06-7.08 (1H, m), 7.11-7.14 (1H, m), 7.38-7.47 (4H, m), 7.53 (1H, s), 7.70-7.80 (1H, br), 7.95-8.08 (1H, br), 8.58 (2H, m), DMSO: 452 (M + H)$^+$FAB |
| 139 | 385 (M + H)$^+$ESI |
| 140 | 385 (M + H)$^+$ESI |
| 141 | 385 (M + H)$^+$ESI |
| 142 | 348 (M + H)$^+$FAB |
| 143 | 362 (M + H)$^+$FAB |
| 144 | 2.29 (3H, s), 3.40-3.71 (8H, m), 5.12 (2H, s), 7.12 (2H, d, J = 7.8 Hz), 7.30-7.41 (5H, m), 7.49 (2H, d, J = 8.3 Hz), 7.80 (1H, dd, J = 5.4, 8.3 Hz), 8.02-8.11 (1H, m), 8.63 (1H, d, J = 5.4 Hz), 8.73 (1H, d, J = 1.9 Hz), DMSO: 342 (M + H)$^+$FAB |
| 145 | 329 (M + H)$^+$FAB |
| 146 | 341 (M + H)$^+$FAB |
| 147 | 3.44-3.71 (8H, m), 5.18 (2H, s), 7.10 (2H, d, J = 8.8 Hz), 7.38-7.50 (6H, m), 7.54 (1H, s), 7.61-7.67 (1H, m), 8.40-8.44 (2H, m), DMSO: 452 (M + H)$^+$FAB |
| 148 | 432 (M + H)$^+$FAB |
| 149 | 3.40-3.71 (8H, m), 5.28 (2H, s), 7.12 (2H, d, J = 8.8 Hz), 7.40-7.48 (3H, m), 7.62-7.68 (2H, m), 7.72 (1H, d, J = 7.8 Hz), 7.79 (1H, d, J = 7.3 Hz), 7.84 (1H, s), 8.42-8.46 (2H, m), DMSO: 486 (M + H)$^+$FAB |

TABLE 45

| Ex No. | DAT <sup>1</sup>H-NMR δ (ppm), solvent: MS m/z |
|---|---|
| 150 | 448 (M + H)$^+$FAB |
| 151 | 3.43-3.74 (8H, m), 5.23 (2H, s), 7.10 (2H, d, J = 8.8 Hz), 7.40-7.48 (3H, m), 7.60-7.67 (2H, m), 7.79-7.85 (2H, m), 7.95 (1H, br), 8.42-8.46 (2H, m), DMSO: 443 (M + H)$^+$FAB |
| 152 | 3.43-3.74 (8H, m), 5.20 (2H, s), 7.09 (2H, d, J = 8.8 Hz), 7.14-7.26 (3H, m), 7.40-7.49 (3H, m), 7.60-7.68 (1H, m), 8.42-8.46 (2H, m), DMSO: 454 (M + H)$^+$FAB |
| 153 | 502 (M + H)$^+$FAB |

TABLE 45-continued

| Ex No. | DAT $^1$H-NMR δ (ppm), solvent: MS m/z |
|---|---|
| 154 | 3.42-3.74 (8H, m), 5.33 (2H, s), 7.13 (2H, d, J = 8.8 Hz), 7.42-7.49 (3H, m), 7.63-7.67 (1H, m), 7.72 (1H, t, J = 7.8 Hz), 7.94 (1H, d, J = 8.1 Hz), 8.19-8.23 (1H, m), 8.34 (1H, br), 8.42-8.46 (2H, m), DMSO: 463 (M + H)$^+$ESI |
| 155 | 3.43-3.74 (8H, m), 5.14 (2H, s), 7.07 (2H, d, J = 8.8 Hz), 7.23 (2H, t, J = 8.8 Hz), 7.40-7.56 (5H, m), 7.60-7.67 (1H, m), 8.40-8.46 (2H, m), DMSO: 436 (M + H)$^+$FAB |
| 156 | 436 (M + H)$^+$FAB |
| 157 | 419 (M + H)$^+$FAB |
| 158 | 439 (M + H)$^+$ESI |
| 159 | 3.43-3.74 (8H, m), 5.17 (2H, s), 7.10 (2H, d, J = 8.8 Hz), 7.38 (1H, t, J = 7.8 Hz), 7.40-7.50 (4H, m), 7.55 (1H, d, J = 7.8 Hz), 7.63-7.70 (2H, m), 8.42-8.47 (2H, m), DMSO: 496, (M + H)$^+$FAB |
| 160 | 3.07 (2H, t, J = 7.0 Hz), 3.43-3.74 (8H, m), 4.26 (2H, t, J = 6.6 Hz), 7.01 (2H, d, J = 8.6 Hz), 7.24-7.48 (7H, m), 7.62-7.67 (1H, m), 8.42-8.46 (2H, m), DMSO: 466 (M + H)$^+$FAB |
| 161 | 443 (M + H)$^+$FAB |
| 162 | 544 (M + H)$^+$FAB |
| 163 | 461 (M + H)$^+$FAB |
| 164 | 477 (M + H)$^+$FAB |
| 165 | 477 (M + H)$^+$FAB |
| 166 | 473 (M + H)$^+$FAB |
| 167 | 476 (M + H)$^+$FAB |
| 168 | 346 (M + H)$^+$FAB |
| 169 | 307 (M + H)$^+$FAB |
| 170 | 1.00-1.20 (2H, m), 1.18-1.25 (2H, m), 1.35-1.50 (1H, m), 1.45-1.58 (2H, m), 1.68-1.78 (2H, m), 2.14 (2H, t, J = 7.4 Hz), 2.77-2.91 (1H, m), 2.92-3.09 (1H, m), 3.90-4.07 (1H, m), 4.10-4.22 (1H, m), 6.68 (1H, br s), 7.22 (1H, br s), 7.45 (1H, dd, J = 8.3, 4.9 Hz), 7.56-7.66 (1H, m), 8.25-8.50 (2H, m), DMSO: 292 (M + H)$^+$FAB |
| 171 | 354 (M + H)$^+$FAB |
| 172 | 341 (M + H)$^+$FAB |

TABLE 46

| Ex No. | DAT $^1$H-NMR δ (ppm), solvent: MS m/z |
|---|---|
| 173 | 1.54-1.79 (2H, m), 1.82-1.96 (2H, m), 2.62 (1H, dddd, J = 11.2, 11.2, 3.4, 3.4 Hz), 2.88-3.07 (1H, m), 3.04-3.23 (1H, m), 4.00-4.16 (1H, m), 4.16-4.32 (1H, m), 6.99-7.07 (1H, m), 7.25-7.34 (2H, m), 7.45 (1H, dd, J = 8.3, 4.9 Hz), 7.58-7.65 (2H, m), 7.65 (1H, ddd, J = 8.3, 2.4, 1.4 Hz), 8.41-8.46 (2H, m), 9.94 (1H, s), DMSO: 326 (M + H)$^+$FAB |
| 174 | 1.42-1.65 (2H, m), 1.65-1.79 (2H, m), 2.35 (1H, dddd, J = 11.3, 11.3, 3.4, 3.4 Hz), 2.72 (2H, t, J = 7.3 Hz), 2.83-2.99 (1H, m), 3.00-3.16 (1H, m), 3.28 (2H, t, J = 7.3 Hz), 3.91-4.06 (1H, m), 4.08-4.23 (1H, m), 7.16-7.23 (3H, m), 7.25-7.33 (2H, m), 7.44 (1H, dd, J = 8.3, 4.9 Hz), 7.62 (1H, ddd, J = 8.3, 2.5, 1.0 Hz), 7.90 (1H, br t, J = 5.4 Hz), 8.41 (1H, d, J = 2.5 Hz), 8.43 (1H, dd, J = 4.9, 1.5 Hz), DMSO: 354 (M + H)$^+$FAB |
| 175 | 1.40 (2H, tt, J = 7.3, 7.3 Hz), 1.56 (2H, tt, J = 7.3, 7.3 Hz), 1.47-1.66 (2H, m), 1.68-1.79 (2H, m), 2.30-2.40 (1H, m), 2.57 (2H, t, J = 7.8 Hz), 2.86-2.94 (1H, m), 3.00-3.08 (1H, m), 3.07 (2H, dt, J = 6.9, 6.9 Hz), 3.93-4.07 (1H, m), 4.10-4.24 (1H, m), 7.12-7.21 (3H, m), 7.23-7.31 (2H, m), 7.44 (1H, dd, J = 8.3, 4.9 Hz), 7.62 (1H, ddd, J = 8.3, 3.0, 1.5 Hz), 7.81 (1H, br t, J = 5.4 Hz), 8.41 (1H, d, J = 2.4 Hz), 8.43 (1H, dd, J = 4.4, 3.0 Hz), DMSO: 382 (M + H)$^+$FAB |
| 176 | 0.85 (3H, t, J = 6.4 Hz), 1.17-1.32 (10H, m), 1.45-1.58 (2H, m), 1.54-1.76 (2H, m), 1.80-1.93 (2H, m), 2.51 (2H, t, J = 6.4 Hz), 2.55-2.64 (1H, m), 2.88-3.04 (1H, m), 2.99-3.20 (1H, m), 4.00-4.14 (1H, m), 4.15-4.30 (1H, m), 7.10 (2H, d, J = 8.3 Hz), 7.45 (1H, dd, J = 8.3, 4.4 Hz), 7.50 (2H, d, J = 8.3 Hz), 7.64 (1H, ddd, J = 8.3, 2.5, 1.5 Hz), 8.40-8.46 (2H, m), 9.85 (1H, s), DMSO: 438 (M + H)$^+$FAB |
| 177 | 411 (M + H)$^+$FAB |
| 178 | 411 (M + H)$^+$FAB |
| 179 | 1.58-1.78 (2H, m), 1.85 (2H, d, J = 12.2 Hz), 2.75-2.83 (1H, m), 3.03 (1H, t, J = 12.2 Hz), 3.18 (1H, t, J = 12.2 Hz), 4.15 (1H, d, J = 12.7 Hz), 4.32 (1H, d, J = 12.7 Hz), 4.42 (2H, s), 6.80 (1H, dd, J = 2.0, 8.3 Hz), 6.88-6.92 (2H, m), 7.24 (1H, t, J = 8.3 Hz), 7.38 (1H, br), 7.52 (1H, br), 7.77 (1H, dd, J = 5.3, 8.3 Hz), 8.02-8.09 (1H, m), 8.62 (1H, d, J = 5.3 Hz), 8.74 (1H, d, J = 2.0 Hz), DMSO: 356 (M + H)$^+$FAB |
| 180 | 467 (M + H)$^+$ESI |
| 181 | 411 (M + H)$^+$FAB |
| 182 | 382 (M + H)$^+$FAB |
| 183 | 398 (M + H)$^+$FAB |
| 184 | 454 (M + H)$^+$FAB |
| 185 | 502 (M + H)$^+$FAB |
| 186 | 480 (M + H)$^+$FAB |
| 187 | 410 (M + H)$^+$FAB |
| 188 | 488 (M + H)$^+$FAB |
| 189 | 370 (M + H)$^+$FAB |
| 190 | 432 (M + H)$^+$FAB |

TABLE 47

| Ex No. | DAT ¹H-NMR δ (ppm), solvent: MS m/z |
|---|---|
| 191 | 397 (M + H)⁺FAB |
| 192 | 409 (M + H)⁺ESI |
| 193 | 386 (M + H)⁺FAB |
| 194 | 371 (M + H)⁺FAB |
| 195 | 357 (M + H)⁺ESI |
| 196 | 337 (M + H)⁺FAB |
| 197 | 1.20-1.32 (2H, m), 1.28-1.48 (2H, m), 1.47-1.62 (4H, m), 1.70-1.86 (2H, m), 2.06 (2H, t, J = 7.3 Hz), 2.56 (2H, t, J = 7.3 Hz), 2.98-3.10 (1H, m), 3.12-3.25 (1H, m), 3.73-3.86 (1H, m), 3.83-3.97 (1H, m), 3.98-4.13 (1H, m), 7.12-7.21 (3H, m), 7.22-7.30 (2H, m), 7.45 (1H, dd, J = 8.3, 4.4 Hz), 7.62 (1H, ddd, J = 8.3, 2.5, 1.5 Hz), 7.78 (1H, br d, J = 7.3 Hz), 8.41 (1H, d J = 2.5 Hz), 8.43 (1H, dd, J = 4.9, 1.5 Hz), DMSO: 396 (M + H)⁺FAB |
| 198 | 315 (M + H)⁺FAB |
| 199 | 1.57-1.75 (2H, br), 1.90-2.03 (2H, br), 3.28-3.40 (1H, br), 3.43-3.57 (1H, br), 3.64-3.79 (1H, br), 3.82-3.93 (1H, br), 4.38-4.46 (1H, m), 6.69 (2H, brd, J = 8.8 Hz), 6.83 (2H, brd, J = 8.8 Hz), 7.44 (1H, dd, J = 4.9, 8.3 Hz), 7.61-7.66 (1H, m), 8.43 (2H, d, J = 3.0 Hz), 8.96 (1H, s), DMSO: 315 (M + H)⁺FAB |
| 200 | 0.96-1.30 (5H, m), 1.60-1.83 (8H, m), 1.94-2.09 (2H, m), 3.33-3.44 (1H, br), 3.48-3.60 (1H, br), 3.70-3.80 (1H, br), 3.75 (2H, d, J = 6.3 Hz), 3.85-3.95 (1H, br), 4.64-4.70 (1H, m), 6.50-6.60 (3H, m), 7.17 (1H, t, J = 13.7 Hz), 7.87 (1H, dd, J = 5.4, 8.3 Hz), 8.18 (1H, d, J = 8.8 Hz), 8.68 (1H, d, J = 5.4 Hz), 8.82 (1H, d, J = 1.9 Hz), DMSO: 411 (M + H)⁺FAB |
| 201 | 425 (M + H)⁺FAB |
| 202 | 1.60-1.76 (2H, br), 1.95-2.07 (2H, br), 3.33-3.45 (1H, br), 3.47-3.58 (1H, br), 3.70-3.80 (1H, br), 3.85-3.96 (1H, br), 4.63-4.70 (1H, m), 5.13 (2H, s), 6.59-6.64 (3H, m), 7.13-7.23 (2H, m), 7.26-7.31 (1H, m), 7.41-7.48 (1H, m), 7.78 (1H, dd, J = 5.4, 8.8 Hz), 8.06 (1H, brd, J = 7.3 Hz), 8.62 (1H, d, J = 4.8 Hz), 8.73 (1H, d, J = 2.4 Hz), DMSO: 423 (M + H)⁺FAB |
| 203 | 1.60-1.80 (2H, br), 1.90-2.07 (2H, br), 3.33-3.45 (1H, br), 3.47-3.60 (1H, br), 3.70-3.81 (1H, br), 3.85-3.96 (1H, br), 4.63-4.71 (1H, m), 5.12 (2H, s), 6.60-6.69 (3H, m), 7.18-7.28 (3H, m), 7.39-7.47 (1H, m), 7.56 (1H, dt, J = 1.4, 7.8 Hz), 7.83-7.89 (1H, m), 8.15-8.20 (1H, m), 8.68 (1H, brd, J = 5.4 Hz), 8.81 (1H, br), DMSO: 423 (M + H)⁺FAB |
| 204 | 423 (M + H)⁺FAB |
| 205 | 1.60-1.84 (2H, br), 1.94-2.06 (2H, br), 3.30-3.42 (1H, br), 3.45-3.56 (1H, br), 3.70-3.80 (1H, br), 3.84-3.96 (1H, br), 4.61-4.69 (1H, m), 5.16 (2H, m), 6.61 (1H, d, J = 2.5 Hz), 6.63 (1H, d, J = 2.5 Hz), 6.66 (1H, t, J = 1.9 Hz), 7.20 (1H, t, J = 7.8 Hz), 7.46 (1H, dd, J = 4.9, 8.3 Hz), 7.60-7.67 (2H, m), 7.78-7.83 (2H, m), 7.92 (1H, br), 8.45 (2H, m), DMSO: 430 (M + H)⁺FAB |

TABLE 48

| Ex No. | DAT ¹H-NMR δ (ppm), solvent: MS m/z |
|---|---|
| 206 | 1.59-1.76 (2H, br), 1.91-2.07 (2H, br), 3.33-3.42 (1H, br), 3.45-3.56 (1H, br), 3.69-3.80 (1H, br), 3.82-3.94 (1H, br), 4.45-4.55 (1H, m), 5.06 (2H, s), 6.96 (4H, s), 7.36-7.46 (3H, m), 7.50 (1H, br), 7.75 (1H, dd, J = 4.9, 8.3 Hz), 8.02 (1H, d, J = 8.3 Hz), 8.60 (1H, d, J = 4.9 Hz), 8.70 (1H, d, J = 2.5 Hz), DMSO: 439 (M + H)⁺FAB |
| 207 | 0.88-1.01 (2H, m), 1.09-1.30 (3H, m), 1.40-1.51 (1H, m), 1.55-1.76 (9H, m), 1.93-2.05 (2H, m), 3.30-3.42 (1H, br), 3.46-3.60 (1H, br), 3.70-3.80 (1H, br), 3.85-3.95 (3H, m), 4.45-4.55 (1H, m), 6.84-6.94 (4H, m), 7.66 (1H, dd, J = 4.9, 8.3 Hz), 7.98 (1H, d, J = 8.3 Hz), 8.58 (1H, d, J = 4.8 Hz), 8.66 (1H, d, J = 1.9 Hz), DMSO: 425 (M + H)⁺FAB |
| 208 | 1.60-1.80 (2H, br), 1.94-2.07 (2H, br), 3.31-3.44 (1H, br), 3.46-3.60 (1H, br), 3.69-3.82 (1H, br), 3.84-3.96 (1H, br), 4.50-4.58 (1H, m), 5.08 (2H, s), 6.97 (4H, s), 7.20-7.28 (2H, m), 7.39-7.45 (1H, m), 7.54 (1H, dt, J = 1.5, 7.3 Hz), 7.81 (1H, dd, J = 5.4, 8.3 Hz), 8.10 (1H, brd, J = 8.3 Hz), 8.64 (1H, d, J = 5.3 Hz), 8.77 (1H, s), DMSO: 423 (M + H)⁺FAB |
| 209 | 1.60-1.80 (2H, br), 1.94-2.07 (2H, br), 3.31-3.44 (1H, br), 3.46-3.60 (1H, br), 3.69-3.80 (1H, br), 3.82-3.96 (1H, br), 4.48-4.58 (1H, m), 5.03 (2H, s), 6.96 (4H, s), 7.18-7.26 (2H, m), 7.45-7.51 (2H, m), 7.78-7.89 (1H, m), 8.07-8.19 (1H, m), 8.67 (1H, brd, J = 4.9 Hz), 8.80 (1H, br), DMSO: 423 (M + H)⁺FAB |
| 210 | 1.60-1.75 (2H, br), 1.91-2.06 (2H, br), 3.30-3.42 (1H, br), 3.45-3.56 (1H, br), 3.70-3.80 (1H, br), 3.84-3.96 (1H, br), 4.49-4.56 (1H, m), 5.11 (2H, m), 6.96 (4H, s), 7.46 (1H, dd, J = 4.8, 8.6 Hz), 7.61 (1H, t, J = 7.5 Hz), 7.64-7.68 (1H, m), 7.76-7.83 (2H, m), 7.90 (1H, br), 8.43-8.47 (2H, m), DMSO: 430 (M + H)⁺FAB |
| 211 | 463 (M + H)⁺FAB |
| 212 | 1.58-1.74 (2H, br), 1.91-2.05 (2H, br), 3.30-3.42 (1H, br), 3.45-3.55 (1H, br), 3.65-3.79 (1H, br), 3.83-3.94 (1H, br), 4.48-4.55 (1H, m), 5.09 (2H, s), 6.96 (4H, s), 7.36-7.50 (3H, m), 7.59 (1H, d, J = 7.9 Hz), 7.62-7.66 (1H, m), 7.84 (1H, d, J = 7.8 Hz), 7.96 (1H, s), 8.00 (1H, br), 8.41-8.45 (2H, m), DMSO: 448 (M + H)⁺FAB |
| 213 | 497 (M + H)⁺FAB |
| 214 | 484 (M + H)⁺FAB |
| 215 | 488 (M + H)⁺FAB |
| 216 | 0.96-1.08 (2H, m), 1.10-1.31 (3H, m), 1.60-1.83 (8H, m), 1.91-2.05 (2H, m), 3.25-3.57 (2H, m), 3.65-3.95 (7H, m), 4.46-4.54 (1H, m), 6.81-6.87 (2H, m), 6.89-6.95 (2H, m), 8.13 (1H, dd, J = 2.0 Hz, 2.4 Hz), 8.70 (1H, d, J = 2.4 Hz), 8.94 (1H, d, J = 2.0 Hz), DMSO: 469 (M + H)⁺FAB |

TABLE 48-continued

| Ex No. | DAT $^1$H-NMR δ (ppm), solvent: MS m/z |
|---|---|
| 217 | 1.58-1.76 (2H, m), 1.90-2.04 (2H, m), 2.80-4.00 (4H, m), 4.38-4.47 (1H, m), 6.70 (2H, d, J = 8.8 Hz), 6.83 (2H, d, J = 8.8 Hz), 8.05-8.10 (1H, m), 8.66 (1H, d, J = 2.4 Hz), 8.90-8.94 (1H, m), DMSO: 359 (M + H)$^+$FAB |

TABLE 49

| Ex No. | DAT $^1$H-NMR δ (ppm), solvent: MS m/z |
|---|---|
| 218 | 1.60-1.78 (2H, m), 1.93-2.05 (2H, m), 3.35-3.95 (4H, m), 4.48-4.56 (1H, m), 5.07 (2H, s), 6.96 (4H, s), 7.12-7.18 (1H, m), 7.24-7.30 (2H, m), 7.40-7.47 (1H, m), 8.07-8.10 (1H, m), 8.67 (1H, d, J = 2.4 Hz), 8.91-8.94 (1H, m), 13.30-13.75 (1H, br), DMSO: 467 (M + H)$^+$FAB |
| 219 | 341 (M + H)$^+$FAB |
| 220 | 327 (M + H)$^+$ESI |
| 221 | 449 (M + H)$^+$FAB |
| 222 | 325 (M + H)$^+$ESI |
| 223 | 353 (M − H)$^−$FAB |
| 224 | 355 (M − H)$^−$FAB |
| 225 | 1.12-1.32 (2H, m), 1.45-1.60 (3H, m), 1.79 (2H, d, J = 11.7 Hz), 2.63 (2H, t, J = 7.5 Hz), 2.87 (1H, t, J = 12.2 Hz), 3.02 (1H, t, J = 12.2 Hz), 4.01 (1H, d, J = 12.7 Hz), 4.18 (1H, t, J = 12.7 Hz), 7.15-7.31 (5H, m), 8.05 (1H, dd, J = 2.0, 2.4 Hz), 8.65 (1H, d, J = 2.4 Hz), 8.92 (1H, t, J = 2.0 Hz), 13.59 (1H, br s), DMSO: 355 (M + H)$^+$FAB |
| 226 | 470 (M + H)$^+$FAB |
| 227 | 410 (M + H)$^+$FAB |
| 228 | 0.88-1.00 (2H, m), 1.08-1.28 (4H, m), 1.39-1.51 (1H, m), 1.54-1.77 (10H, m), 1.91-2.05 (2H, m), 3.20-3.96 (6H, m), 4.46-4.54 (1H, m), 6.83-6.88 (2H, m), 6.90-6.95 (2H, m), 8.08 (1H, dd, J = 2.0 Hz, 2.4 Hz), 8.66 (1H, d, J = 2.4 Hz), 8.92 (1H, d, J = 1.5 Hz), DMSO: 469 (M + H)$^+$FAB |
| 229 | 483 (M + H)$^+$FAB |
| 230 | 474 (M + H)$^+$FAB |
| 231 | 356 (M + H)$^+$FAB |
| 232 | 371 (M + H)$^+$FAB |
| 233 | 1.58-1.78 (2H, m), 1.91-2.06 (2H, m), 3.25-3.95 (7H, m), 4.49-4.56 (1H, m), 5.02 (2H, s), 6.86-7.03 (7H, m), 7.30 (1H, dd, J = 7.8 Hz, 8.3 Hz), 8.07 (1H, s), 8.64 (1H, s), 8.92 (1H, s), DMSO: 479 (M + H)$^+$FAB |
| 234 | 1.60-1.80 (2H, br), 1.92-2.10 (2H, br), 3.30-3.60 (2H, br), 3.70-3.80 (1H, br), 3.85-3.96 (1H, br), 4.60-4.70 (1H, br), 5.12 (2H, s), 6.58-6.68 (3H, m), 7.24-7.32 (4H, m), 7.42-7.50 (1H, m), 8.09 (1H, t, J = 2.4 Hz), 8.67 (1H, d, J = 2.4 Hz), 8.92 (1H, d, J = 1.9 Hz), 13.50 (1H, br), DMSO: 467 (M + H)$^+$FAB |
| 235 | 1.60-1.80 (2H, br), 1.92-2.10 (2H, br), 3.30-3.60 (2H, br), 3.70-3.80 (1H, br), 3.85-3.96 (1H, br), 4.60-4.72 (1H, br), 5.16 (2H, s), 6.60-6.68 (3H, m), 7.21 (1H, t, J = 8.3 Hz), 7.62 (1H, t, J = 8.3 Hz), 7.78-7.84 (2H, m), 7.92 (1H, s), 8.09 (1H, dd, J = 1.4, 2.4 Hz), 8.67 (1H, d, J = 3.0 Hz), 8.93 (1H, d, J = 1.4 Hz), 13.50 (1H, br), DMSO: 474 (M + H)$^+$FAB |

TABLE 50

| Ex No. | DAT $^1$H-NMR δ (ppm), solvent: MS m/z |
|---|---|
| 236 | 1.60-1.74 (2H, m), 1.91-2.06 (2H, m), 3.30-3.95 (7H, m), 4.47-4.57 (1H, m), 5.14 (2H, s), 6.96 (4H, s), 7.55 (1H, dd, J = 7.4 Hz, 7.8 Hz), 7.72 (1H, d, J = 7.4 Hz), 7.92 (1H, d, J = 7.8 Hz), 8.04 (1H, s), 8.08 (1H, dd, J = 2.0 Hz, 2.4 Hz), 8.67 (1H, d, J = 2.4 Hz), 8.92 (1H, d, J = 2.0 Hz), DMSO: 507 (M + H)$^+$FAB |
| 237 | 455 (M + H)$^+$FAB |
| 238 | 369 (M + H)$^+$ESI |
| 239 | 385 (M + H)$^+$ESI |
| 240 | 371 (M + H)$^+$ESI |
| 241 | 398 (M + H)$^+$FAB |
| 242 | 0.73-2.10 (17H, m), 3.20-4.02 (6H, br), 4.60-4.70 (1H, m), 6.49-6.60 (3H, m), 7.17 (1H, t, J = 8.3 Hz), 8.09 (1H, br), 8.67 (1H, d, J = 2.0 Hz), 8.92 (1H, br), 13.40-13.80 (1H, br), DMSO: 469 (M + H)$^+$FAB |
| 243 | 370 (M + H)$^+$FAB |
| 244 | 524 (M + H)$^+$FAB |
| 245 | 1.60-1.77 (2H, m), 1.92-2.06 (2H, m), 3.35-3.96 (4H, m), 4.48-4.56 (1H, m), 5.07 (2H, s), 6.95 (4H, s), 7.12-7.18 (1H, m), 7.24-7.30 (2H, m), 7.40-7.47 (1H, m), 7.63-7.71 (1H, m), 8.07-8.10 (1H, m), 8.14-8.23 (1H, m), 8.58 (1H, d, J = 2.4 Hz), 8.90 (1H, d, J = 1.9 Hz), DMSO: 466 (M + H)$^+$FAB |

TABLE 50-continued

| Ex No. | DAT<br>¹H-NMR δ (ppm), solvent: MS m/z |
|---|---|
| 246 | 1.59-1.78 (2H, m), 1.91-2.05 (2H, m), 3.25-3.57 (2H, m), 3.68-3.96 (2H, m), 4.47-4.56 (1H, m), 5.04 (2H, s), 6.95 (4H, s), 7.29-7.46 (5H, m), 7.64-7.70 (1H, m), 8.04 (1H, dd, J = 1.9 Hz, 2.4 Hz), 8.15-8.21 (1H, m), 8.58 (1H, d, J = 2.4 Hz), 8.89 (1H, d, J = 1.9 Hz), DMSO: 448 (M + H)⁺FAB |
| 247 | 397 (M + H)⁺FAB |
| 248 | 451 (M + H)⁺FAB |
| 249 | 523 (M + H)⁺FAB |
| 250 | 579 (M + H)⁺ESI |
| 251 | 524 (M + H)⁺FAB |
| 252 | 577 (M + H)⁺FAB |
| 253 | 537 (M + H)⁺FAB |
| 254 | 577 (M + H)⁺FAB |
| 255 | 1.58-1.78 (2H, br), 1.93-2.06 (2H, br), 3.32-3.42 (3H, m), 3.48-3.58 (3H, m), 3.70-3.80 (1H, br), 3.85-3.95 (1H, br), 4.48-4.58 (1H, m), 4.92 (1H, br), 5.07 (2H, s), 6.95 (4H, s), 7.15 (1H, dt, J = 2.4, 8.8 Hz), 7.24-7.30 (2H, m), 7.41-7.47 (1H, m), 8.14 (1H, t, J = 2.0 Hz), 8.63 (1H, d, J = 2.4 Hz), 8.75 (1H, t J = 5.3 Hz), 8.93 (1H, d, J = 1.4 Hz), DMSO: 510 (M + H)⁺FAB |

TABLE 51

| Ex No. | DAT<br>¹H-NMR δ (ppm), solvent: MS m/z |
|---|---|
| 256 | 586 (M + H)⁺FAB |
| 257 | 549 (M + H)⁺FAB |
| 258 | 1.13-1.33 (2H, br), 1.66 (2H, d, J = 12.7 Hz), 1.73-1.85 (1H, m), 2.57 (2H, d, J = 6.8 Hz), 2.86 (1H, t, J = 12.2 Hz), 3.02 (1H, t, J = 12.2 Hz), 4.03 (1H, d, J = 12.2 Hz), 4.20 (1H, d, J = 12.2 Hz), 7.18-7.23 (3H, m), 7.27-7.32 (2H, m), 7.48 (1H, s), 7.60 (1H, t, J = 7.8 Hz), 7.93 (2H, d, J = 7.3 Hz), 8.01 (1H, t, J = 2.4 Hz), 8.13 (1H, s), 8.23 (1H, s), 8.44 (1H, d, J = 2.4 Hz), 8.84 (1H, d, J = 2.0 Hz), DMSO: 416 (M + H)⁺FAB |
| 259 | 374 (M + H)⁺FAB |
| 260 | 1.60-1.75 (2H, m), 1.92-2.04 (2H, m), 3.30-3.91 (4H, m), 4.49-4.56 (1H, m), 5.07 (2H, s), 6.96 (4H, s), 7.12-7.18 (1H, m), 7.24-7.30 (2H, m), 7.39-7.47 (2H, m), 7.92 (1H, d, J = 2.0 Hz), 8.02 (1H, d, J = 2.0 Hz), DMSO: 438 (M + H)⁺FAB |
| 261 | 550 (M + H)⁺FAB |
| 262 | 1.58-1.75 (2H, m), 1.90-2.05 (2H, m), 3.30-3.57 (2H, m), 3.67-3.95 (2H, m), 4.13 (2H, s), 4.48-4.55 (1H, m), 5.07 (2H, s), 6.95 (4H, s), 7.12-7.18 (1H, m), 7.24-7.30 (2H, m), 7.40-7.47 (1H, m), 7.61-7.64 (1H, m), 8.35-8.39 (1H, m), 8.40-8.44 (1H, m), DMSO: 510 (M⁺)FAB |
| 263 | 1.58-1.74 (2H, m), 1.91-2.04 (2H, m), 2.50 (3H, s), 3.30-3.95 (4H, m), 4.48-4.58 (3H, m), 5.07 (2H, s), 5.40 (1H, t, J = 5.9 Hz), 6.95 (4H, s), 7.12-7.18 (1H, m), 7.24-7.30 (2H, m), 7.40-7.47 (1H, m), 7.53-7.56 (1H, m), 8.28-8.31 (1H, m), 8.36-8.39 (1H, m), DMSO: 453 (M + H)⁺FAB |
| 264 | 1.59-1.74 (2H, m), 1.96-2.03 (2H, m), 3.27-3.57 (2H, m), 3.70-3.65 (2H, m), 4.48-4.58 (3H, m), 5.08 (2H, s), 6.72 (1H, d, J = 16.1 Hz), 6.96 (4H, s), 7.12-7.18 (1H, m), 7.24-7.30 (2H, m), 7.40-7.47 (1H, m), 7.64 (1H, d, J = 16.1 Hz), 8.07 (1H, dd, J = 2.0 Hz, 2.0 Hz), 8.45 (1H, d, J = 2.5 Hz), 8.71 (1H, d, J = 1.4 Hz), 12.40-12.74 (1H, br), DMSO: 493 (M + H)⁺FAB |
| 265 | 445 (M + H)⁺FAB |
| 266 | 1.10-1.33 (2H, m), 1.45-1.61 (3H, m), 1.75-1.87 (2H, br), 2.64 (2H, t, J = 7.6 Hz), 2.81-3.10 (2H, br), 3.92-4.27 (2H, br), 7.14-7.32 (5H, m), 7.43-7.52 (1H, m), 7.60 (1H, d, J = 8.0 Hz), 7.90-7.98 (2H, m), 8.05-8.17 (2H, m), 8.21-8.27 (1H, m), 8.48 (1H, d, J = 2.4 Hz), 8.87 (1H, d, J = 2.4 Hz), DMSO 380 (M + H)⁺FAB |
| 267 | 380 (M + H)⁺FAB |
| 268 | 1.33-1.56 (2H, m), 1.77-1.88 (2H, m), 2.37-2.48 (1H, m), 2.93-3.04 (1H, m), 3.09-3.21 (1H, m), 3.98-4.12 (1H, m), 4.14-4.28 (1H, m), 6.31 (1H, dd, J = 16.1, 6.8 Hz), 6.45 (1H, d, J = 16.1 Hz), 7.18-7.24 (1H, m), 7.28-7.35 (2H, m), 7.38-7.48 (3H, m), 7.63 (1H, ddd, J = 8.3, 2.5, 1.5 Hz), 8.41-8.45 (2H, m), DMSO-d6: 309 (M + H)⁺FAB |
| 269 | 1.33-1.56 (2H, m), 1.67-1.79 (2H, m), 2.73-2.88 (1H, m), 2.88-3.02 (1H, m), 2.88-3.02 (1H, m), 3.04-3.18 (1H, m), 3.95-4.07 (1H, m), 4.10-4.23 (1H, m), 5.54 (1H, dd, J = 11.8, 9.7 Hz), 6.42 (1H, d, J = 11.8 Hz), 7.23-7.34 (3H, m), 7.35-7.42 (2H, m), 7.44 (1H, dd, J = 8.3, 4.8 Hz), 7.63 (1H, ddd, J = 8.3, 2.4, 1.5 Hz), 8.40-8.45 (2H, m), DMSO: 309 (M + H)⁺FAB |
| 270 | 1.08-1.30 (2H, m), 1.43-1.60 (3H, m), 1.73-1.82 (2H, br), 2.63 (2H, t, J = 7.8 Hz), 2.77-3.08 (2H, br), 3.92-4.20 (2H, br), 7.13-7.32 (5H, m), 8.04 (1H, dd, J = 2.0, 2.4 Hz), 8.45 (1H, d, J = 2.4 Hz), 8.58 (1H, d, J = 2.0 Hz), DMSO: 389 (M⁺)FAB |

TABLE 52

| Ex No. | DAT $^1$H-NMR δ (ppm), solvent: MS m/z |
|---|---|
| 271 | 0.78-0.94 (2H, m), 1.00-1.24 (10H, m), 1.37-1.50 (1H, m), 1.57-1.76 (7H, m), 2.80-2.92 (1H, br), 2.96-3.08 (1H, br), 3.93-4.05 (1H, br), 4.08-4.21 (1H, br), 7.68 (1H, dd, J = 4.8, 7.6 Hz), 7.93-8.00 (1H, m), 8.58 (1H, d, J = 7.6 Hz), 8.62-8.69 (1H, m), DMSO: 317 (M + H)$^+$FAB |
| 272 | 0.79-0.92 (2H, m), 1.04-1.29 (10H, m), 1.36-1.49 (1H, m), 1.57-1.76 (7H, m), 2.80-2.92 (1H, br), 2.95-3.08 (1H, br), 3.90 (3H, s), 3.92-4.05 (1H, br), 4.08-4.21 (1H, br), 8.09 (1H, dd, J = 2.0, 2.4 Hz), 8.68 (1H, d, J = 2.4 Hz), 8.93 (1H, d, J = 2.0 Hz), DMSO: 375 (M + H)$^+$FAB |
| 273 | 1.44-1.59 (2H, m), 1.77-1.88 (2H, m), 2.37-2.48 (1H, m), 2.93-3.07 (1H, m), 3.07-3.23 (1H, m), 3.98-4.14 (1H, m), 4.14-4.29 (1H, m), 6.31 (1H, dd, J = 16.1, 6.9 Hz), 6.45 (1H, d, J = 16.1 Hz), 7.17-7.25 (1H, m), 7.27-7.36 (2H, m), 7.38-7.44 (2H, m), 8.05-8.09 (1H, m), 8.67 (1H, d, J = 2.4 Hz), 8.92 (1H, d, J = 1.5 Hz), 13.60 (1H, br s), DMSO: 353 (M + H)$^+$FAB |
| 274 | 1.10-1.30 (2H, m), 1.45-1.60 (3H, m), 1.75-1.85 (2H, m), 2.63 (2H, t, J = 8.3 Hz), 2.80-3.10 (2H, m), 3.95-4.24 (2H, m), 7.16-7.34 (4H, m), 8.04 (1H, dd, J = 1.5, 2.0 Hz), 8.64 (1H, d, J = 2.4 Hz), 8.91 (1H, d, J = 1.9 Hz), 13.60 (1H, s), DMSO: 389 (M + H)$^+$FAB |
| 275 | 380 (M + H)$^+$FAB |
| 276 | 1.10-1.30 (2H, m), 1.44-1.60 (3H, m), 1.73-1.82 (2H, m), 2.60 (2H, t, J = 7.3 Hz), 2.80-3.10 (2H, m), 3.74 (3H, s), 3.95-4.24 (2H, m), 6.72-6.81 (3H, m), 7.19 (1H, t, J = 8.3 Hz), 8.04 (1H, t, J = 1.9 Hz), 8.64 (1H, d, J = 2.4 Hz), 8.92 (1H, d, J = 1.5 Hz), 13.60 (1H, s)DMSO: 385 (M + H)$^+$FAB |
| 277 | 1.10-1.30 (2H, m), 1.44-1.60 (3H, m), 1.73-1.82 (2H, m), 2.60 (2H, t, J = 7.4 Hz), 2.80-3.10 (2H, m), 3.95-4.24 (2H, m), 6.95-7.10 (3H, m), 7.29-7.36 (1H, m), 8.04 (1H, t, J = 2.0 Hz), 8.65 (1H, d, J = 2.4 Hz), 8.92 (1H, d, J = 1.9 Hz), 13.60 (1H, s), DMSO: 373 (M + H)$^+$FAB |
| 278 | 380 (M + H)$^+$FAB |
| 279 | 396 (M − H)$^-$FAB |
| 280 | 426 (M + H)$^+$FAB |
| 281 | 1.10-1.33 (2H, m), 1.46-1.59 (1H, m), 1.54-1.66 (2H, m), 1.75-1.87 (2H, m), 2.68 (2H, dd, J = 7.6, 7.6 Hz), 2.79-2.94 (1H, m), 2.95-3.10 (1H, m), 3.95-4.09 (1H, m), 4.11-4.25 (1H, m), 7.29-7.38 (3H, m), 7.41-7.49 (2H, m), 7.58 (1H, d, J = 8.3 Hz), 7.62-7.68 (2H, m), 7.78-7.81 (1H, m), 8.28 (1H, d, J = 2.5 Hz), 8.78 (1H, d, J = 1.4 Hz), DMSO: 431 (M + H)$^+$FAB |
| 282 | 1.07-1.33 (2H, m), 1.42-1.54 (1H, m), 1.47-1.59 (1H, m), 1.72-1.83 (2H, m), 2.62 (2H, dd, J = 7.6, 7.6 Hz), 2.78-2.93 (1H, m), 2.93-3.10 (1H, m), 3.92-4.08 (1H, m), 4.08-4.24 (1H, m), 7.05-7.13 (2H, m), 7.20-7.28 (2H, m), 8.04 (1H, dd, J = 2.5, 2.1 Hz), 8.64 (1H, d, J = 2.5 Hz), 8.92 (1H, d, J = 2.1 Hz), 13.62 (1H, br s), DMSO: 373 (M + H)$^+$FAB |
| 283 | 1.10-1.35 (2H, m), 1.46-1.62 (3H, m), 1.74-1.88 (2H, m), 2.74 (2H, dd, J = 7.8, 7.8 Hz), 2.80-2.96 (1H, m), 2.96-3.12 (1H, m), 3.94-4.08 (1H, m), 4.11-4.26 (1H, m), 7.18-7.32 (2H, m), 7.32-7.43 (2H, m), 8.05 (1H, dd, J = 2.1, 1.6 Hz), 8.65 (1H, d, J = 2.1 Hz), 8.91 (1H, d, J = 1.6 Hz), 13.62 (1H, br s), DMSO: 387 (M − H)$^-$FAB |
| 284 | 1.08-1.32 (2H, m), 1.41-1.55 (1H, m), 1.48-1.60 (2H, m), 1.71-1.83 (2H, m), 2.62 (2H, dd, J = 7.8, 7.8 Hz), 2.78-2.93 (1H, m), 2.93-3.09 (1H, m), 3.94-4.08 (1H, m), 4.10-4.23 (1H, m), 7.25 (2H, d, J = 8.6 Hz), 7.33 (2H, d, J = 8.0 Hz), 8.04 (1H, dd, J = 2.2, 1.6 Hz), 8.64 (1H, d, J = 2.2 Hz), 8.91 (1H, d, J = 1.6 Hz), 13.61 (1H, br s), DMSO: 389 (M + H)$^+$FAB |
| 285 | 1.06-1.32 (2H, m), 1.40-1.54 (1H, m), 1.47-1.60 (1H, m), 1.70-1.84 (2H, m), 2.61 (2H, dd, J = 7.6, 7.6 Hz), 2.79-2.94 (1H, m), 2.94-3.09 (1H, m), 3.92-4.08 (1H, m), 4.08-4.25 (1H, m), 7.19 (2H, d, J = 8.4 Hz), 7.46 (2H, d, J = 8.4 Hz), 8.04 (1H, dd, J = 2.4, 1.2 Hz), 8.64 (1H, d, J = 2.4 Hz), 8.91 (1H, d, J = 1.2 Hz), 13.60 (1H, br s), DMSO: 431 (M − H)$^-$FAB |
| 286 | 1.08-1.32 (2H, m), 1.42-1.58 (3H, m), 1.70-1.84 (2H, m), 2.56 (2H, dd, J = 7.4, 7.4 Hz), 2.78-2.93 (1H, m), 2.93-3.07 (1H, m), 3.72 (3H, s), 3.94-4.08 (1H, m), 4.08-4.23 (1H, m), 6.84 (2H, d, J = 8.0 Hz), 7.12 (2H, d, J = 8.0 Hz), 8.04 (1H, dd, J = 2.8, 1.6 Hz), 8.64 (1H, d, J = 2.8 Hz), 8.91 (1H, d, J = 1.6 Hz), 13.60 (1H, br s), DMSO: 385 (M + H)$^+$FAB |

TABLE 53

| Ex No. | DAT $^1$H-NMR δ (ppm), solvent: MS m/z |
|---|---|
| 287 | 1.01-1.74 (11H, m), 2.58 (2H, t, J = 7.2 Hz), 2.80-3.10 (2H, m), 3.95-4.24 (2H, m), 7.14-7.31 (5H, m), 8.04 (1H, t, J = 2.4 Hz), 8.64 (1H, d, J = 2.4 Hz), 8.91 (1H, d, J = 1.6 Hz), 13.60 (1H, s), DMSO: 383 (M + H)$^+$FAB |
| 288 | 1.08-1.34 (2H, m), 1.44-1.60 (3H, m), 1.73-1.86 (2H, m), 2.66 (2H, dd, J = 7.4, 7.4 Hz), 2.78-2.95 (1H, m), 2.95-3.12 (1H, m), 3.93-4.09 (1H, m), 4.10-4.26 (1H, m), 7.08-7.18 (2H, m), 7.20-7.27 (1H, m), 7.27-7.36 (1H, m), 8.05 (1H, dd, J = 2.4, 1.6 Hz), 8.65 (1H, d, J = 2.4 Hz), 8.91 (1H, d, J = 1.6 Hz), 13.60 (1H, br s), DMSO: 373 (M + H)$^+$FAB |
| 289 | 0.79-0.93 (2H, m), 1.00-1.28 (10H, m), 1.35-1.48 (1H, m), 1.57-1.76 (7H, m), 2.80-3.08 (2H, br), 3.96-4.22 (2H, br), 8.02-8.05 (1H, m), 8.62-8.66 (1H, m), 8.89-8.93 (1H, m), 13.53-13.64 (1H, br), DMSO: 361 (M + H)$^+$FAB |
| 290 | 1.13-1.32 (2H, m), 1.46-1.59 (1H, m), 1.54-1.62 (2H, m), 1.75-1.87 (2H, m), 2.69 (2H, dd, J = 7.8, 7.8 Hz), 2.81-2.94 (1H, m), 2.94-3.10 (1H, m), 3.94-4.10 (1H, m), 4.10-4.27 (1H, m), 7.29-7.38 (3H, m), 7.86 (1H, ddd, J = 7.4, 7.4, 1.6 Hz), 7.93 (1H, d, J = 8.0 Hz), 8.01 (2H, d, J = 8.0 Hz), 8.05 (1H, dd, J = 2.8, 1.6 Hz), 8.62-8.68 (2H, m), 8.92 (1H, d, J = 1.6 Hz), 13.60 (1H, br s), DMSO: 432 (M + H)$^+$ESI |

TABLE 53-continued

| Ex No. | DAT ¹H-NMR δ (ppm), solvent: MS m/z |
|---|---|
| 291 | 1.08-1.32 (2H, m), 1.44-1.61 (3H, m), 1.77-1.83 (2H, br), 2.63 (2H, t, J = 7.6 Hz), 2.79-3.08 (2H, br), 3.95-4.23 (2H, br), 6.73 (1H, d, J = 16.0 Hz), 7.14-7.22 (3H, m), 7.25-7.32 (2H, m), 7.64 (1H, d, J = 16.0 Hz), 8.02-8.06 (1H, m), 8.40-8.44 (1H, m), 8.68-8.73 (1H, m), 12.55-12.63 (1H, br), DMSO: 381 (M + H)⁺FAB |
| 292 | 1.10-1.32 (2H, m), 1.45-1.60 (3H, m), 1.75-1.85 (2H, m), 2.63 (2H, t, J = 8.4 Hz), 2.80-3.10 (2H, m), 3.95-4.24 (2H, m), 7.20-7.28 (2H, m), 7.36-7.40 (1H, br), 7.44 (1H, br), 8.04 (1H, t, J = 2.0 Hz), 8.64 (1H, d, J = 2.4 Hz), 8.91 (1H, d, J = 1.6 Hz), 13.60 (1H, s), DMSO: 435, 433 (M + H)⁺ESI |
| 293 | 1.10-1.32 (2H, m), 1.45-1.67 (3H, m), 1.75-1.87 (2H, m), 2.71 (2H, t, J = 7.6 Hz), 2.80-3.10 (2H, m), 3.95-4.24 (2H, m), 7.22 (1H, d, J = 7.2 Hz), 7.33-7.52 (6H, m), 7.64-7.68 (1H, m), 8.04 (1H, dd, J = 1.2, 2.4 Hz), 8.64 (1H, d, J = 2.4 Hz), 8.91 (1H, d, J = 2.0 Hz), 13.60 (1H, s), DMSO: 431 (M + H)⁺ESI |
| 294 | 1.10-1.32 (2H, m), 1.45-1.67 (3H, m), 1.75-1.87 (2H, m), 2.71 (2H, t, J = 7.6 Hz), 2.80-3.10 (2H, m), 3.95-4.24 (2H, m), 7.29 (1H, d, J = 7.6 Hz), 7.41 (1H, t, J = 8.0 Hz), 7.55 (1H, d, J = 7.6 Hz), 7.62 (1H, s), 7.67 (1H, t, J = 8.0 Hz), 7.82 (1H, d, J = 8.0 Hz), 8.00-8.08 (2H, m), 8.16 (1H, s), 8.65 (1H, br), 8.91 (1H, br), 13.60 (1H, s), DMSO: 456 (M + H)⁺FAB |
| 295 | 1.07-1.34 (2H, m), 1.41-1.58 (1H, m), 1.50-1.63 (2H, m), 1.70-1.85 (2H, m), 2.65 (2H, dd, J = 7.6, 7.6 Hz), 2.78-2.94 (1H, m), 2.93-3.21 (1H, m), 3.92-4.09 (1H, m), 4.06-4.26 (1H, m), 7.26 (2H, d, J = 6.0 Hz), 8.04 (1H, dd, J = 2.8, 2.0 Hz), 8.45 (2H, br d, J = 4.4 Hz), 8.64 (1H, d, J = 2.8 Hz), 8.91 (1H, d, J = 2.0 Hz), DMSO: 356 (M + H)⁺FAB |
| 296 | 1.08-1.35 (2H, m), 1.43-1.58 (1H, m), 1.50-1.63 (2H, m), 1.71-1.86 (2H, m), 2.65 (2H, dd, J = 7.2, 7.2 Hz), 2.77-2.96 (1H, m), 2.90-3.11 (1H, m), 3.90-4.08 (1H, m), 4.10-4.26 (1H, m), 7.31 (1H, dd, J = 8.0, 4.8 Hz), 7.65 (1H, d, J = 8.0 Hz), 8.04 (1H, dd, J = 2.4, 2.0 Hz), 8.40 (1H, br d, J = 3.2 Hz), 8.46 (1H, br s), 8.65 (1H, d, J = 2.4 Hz), 8.91 (1H, d, J = 2.0 Hz), DMSO: 354 (M − H)⁻FAB |
| 297 | 1.08-1.35 (2H, m), 1.43-1.60 (1H, m), 1.60-1.72 (2H, m), 1.74-1.85 (2H, m), 2.78 (2H, dd, J = 7.2, 7.2 Hz), 2.81-2.93 (1H, m), 2.94-3.08 (1H, m), 3.95-4.07 (1H, m), 4.11-4.24 (1H, m), 7.16-7.22 (1H, m), 7.27 (1H, d, J = 8.0 Hz), 7.69 (1H, ddd, J = 8.0, 8.0, 2.0 Hz), 8.04 (1H, dd, J = 2.4, 2.0 Hz), 8.48 (1H, d, J = 4.4 Hz), 8.64 (1H, d, J = 2.4 Hz), 8.91 (1H, d, J = 2.0 Hz), DMSO: 354 (M − H)⁻FAB |
| 298 | 1.10-1.32 (2H, m), 1.45-1.67 (3H, m), 1.75-1.87 (2H, m), 2.69-2.75 (2H, m), 2.80-3.10 (2H, m), 3.95-4.24 (2H, m), 7.27-7.46 (3H, m), 7.80-7.99 (5H, m), 8.30 (1H, d, J = 2.8 Hz), 8.66 (1H, d, J = 4.4 Hz), 8.80 (1H, d, J = 1.6 Hz), DMSO: 432 (M + H)⁺FAB |

TABLE 54

| Ex No. | DAT ¹H-NMR δ (ppm), solvent: MS m/z |
|---|---|
| 299 | 1.10-1.36 (2H, m), 1.45-1.60 (1H, m), 1.54-1.66 (2H, m), 1.74-1.87 (2H, m), 2.67 (2H, dd, J = 7.2, 7.2 Hz), 2.80-2.95 (1H, m), 2.95-3.10 (1H, m), 3.92-4.10 (1H, m), 4.10-4.25 (1H, m), 7.26 (2H, d, J = 8.8 Hz), 7.30 (2H, d, J = 8.8 Hz), 7.56 (2H, d, J = 8.8 Hz), 7.68 (2H, dd, J = 8.8, 5.2 Hz), 8.05 (1H, dd, J = 3.2, 1.6 Hz), 8.65 (1H, d, J = 3.2 Hz), 8.92 (1H, d, J = 1.6 Hz), 13.60 (1H, br s), DMSO: 449 (M + H)⁺FAB |
| 300 | 1.11-1.36 (2H, m), 1.46-1.59 (1H, m), 1.54-1.64 (2H, m), 1.74-1.86 (2H, m), 2.66 (2H, dd, J = 7.6, 7.6 Hz), 2.81-2.95 (1H, m), 2.95-3.10 (1H, m), 3.79 (3H, s), 3.95-4.07 (1H, m), 4.12-4.25 (1H, m), 7.01 (2H, d, J = 8.8 Hz), 7.27 (2H, d, J = 8.0 Hz), 7.53 (2H, d, J = 8.0 Hz), 7.58 (2H, d, J = 8.8 Hz), 8.05 (1H, dd, J = 2.8, 2.0 Hz), 8.65 (1H, d, J = 2.8 Hz), 8.92 (1H, d, J = 2.0 Hz), 13.60 (1H, br s), DMSO: 461 (M + H)⁺FAB |
| 301 | 1.10-1.36 (2H, m), 1.45-1.59 (1H, m), 1.55-1.66 (2H, m), 1.75-1.87 (2H, m), 2.69 (2H, dd, J = 7.2, 7.2 Hz), 2.80-2.94 (1H, m), 2.96-3.12 (1H, m), 3.93-4.10 (1H, m), 4.10-4.27 (1H, m), 7.36 (2H, d, J = 8.4 Hz), 7.68 (2H, d, J = 8.4 Hz), 7.87 (2H, d, J = 8.8 Hz), 7.91 (2H, d, J = 8.8 Hz), 8.05 (1H, dd, J = 2.4, 1.6 Hz), 8.65 (1H, d, J = 2.4 Hz), 8.92 (1H, d, J = 1.6 Hz), 13.61 (1H, br s), DMSO: 456 (M + H)⁺FAB |
| 302 | 1.10-1.36 (2H, m), 1.45-1.58 (1H, m), 1.55-1.65 (2H, m), 1.71-1.88 (2H, m), 2.68 (2H, dd, J = 7.6, 7.6 Hz), 2.78-2.95 (1H, m), 2.95-3.12 (1H, m), 3.92-4.10 (1H, m), 4.10-4.26 (1H, m), 7.10-7.22 (1H, m), 7.32 (2H, d, J = 8.0 Hz), 7.42-7.54 (3H, m), 7.63 (2H, d, J = 8.0 Hz), 8.05 (1H, dd, J = 2.4, 2.0 Hz), 8.65 (1H, d, J = 2.4 Hz), 8.92 (1H, d, J = 2.0 Hz), 13.61 (1H, br s), DMSO: 449 (M + H)⁺FAB |
| 303 | 1.11-1.35 (2H, m), 1.46-1.58 (1H, m), 1.54-1.64 (2H, m), 1.75-1.86 (2H, m), 2.67 (2H, dd, J = 7.6, 7.6 Hz), 2.80-2.95 (1H, m), 2.95-3.12 (1H, m), 3.82 (3H, s), 3.94-4.10 (1H, m), 4.10-4.25 (1H, m), 6.91 (1H, ddd, J = 8.4, 2.4, 0.8 Hz), 7.14-7.18 (1H, m), 7.18-7.23 (1H, m), 7.30 (2H, d, J = 8.4 Hz), 7.36 (1H, dd, J = 8.0, 8.0 Hz), 7.59 (2H, d, J = 8.4 Hz), 8.05 (1H, dd, J = 2.4, 2.0 Hz), 8.65 (1H, d, J = 2.4 Hz), 8.92 (1H, d, J = 2.0 Hz), 13.60 (1H, br s), DMSO: 459 (M − H)⁻ESI |
| 304 | 1.10-1.36 (2H, m), 1.47-1.58 (1H, m), 1.55-1.66 (2H, m), 1.74-1.88 (2H, m), 2.87 (2H, dd, J = 7.6, 7.6 Hz), 2.82-2.96 (1H, m), 2.96-3.13 (1H, m), 3.95-4.10 (1H, m), 4.10-4.26 (1H, m), 7.24-7.32 (2H, m), 7.33 (2H, d, J = 8.4 Hz), 7.36-7.44 (1H, m), 7.44-7.50 (2H, m), 7.48-7.55 (1H, m), 8.05 (1H, dd, J = 2.4, 1.6 Hz), 8.65 (1H, d, J = 2.4 Hz), 8.92 (1H, d, J = 1.6 Hz), 13.61 (1H, br s), DMSO: 449 (M + H)⁺FAB |
| 305 | 480 (M + H)⁺FAB |
| 306 | 488 (M + Na)⁺ESI |
| 307 | 490 (M + Na)⁺ESI |

TABLE 54-continued

| Ex No. | DAT $^1$H-NMR δ (ppm), solvent: MS m/z |
|---|---|
| 308 | 1.12-1.29 (2H, m), 1.50-1.63 (9H, m), 1.78-1.81 (2H, br), 2.64-2.69 (2H, m), 2.86 (1H, br), 3.02 (1H, br), 3.23-3.38 (2H, m), 3.51-3.64 (2H, m), 4.01 (1H, m), 4.17 (1H, m), 7.25-7.31 (4H, m), 7.80 (1H, m), 8.28 (1H, m), 8.80 (1H, m), DMSO: 464 (M − H)$^-$FAB |
| 309 | 1.15-1.28 (2H, m), 1.47-1.60 (3H, m), 1.78-1.81 (2H, br), 2.65-2.69 (2H, br), 2.86 (1H, m), 3.02 (1H, m), 3.40-3.63 (8H, br), 4.01 (1H, m), 4.18 (1H, m), 7.28-7.34 (4H, m), 7.80 (1H, m), 8.28 (1H, m), 8.80 (1H, m), DMSO: 468 (M + H)$^+$FAB |
| 310 | 452 (M + H)$^+$FAB |
| 311 | 544 (M + H)$^+$ESI |
| 312 | 454 (M + H)$^+$ESI |
| 313 | 1.10-1.80 (16H, m), 2.27 (3H, s), 2.65-2.74 (2H, m), 2.80-3.10 (2H, m), 3.95-4.32 (4H, m), 6.42 (1H, d, J = 7.6 Hz), 6.56 (1H, d, J = 8.8 Hz), 7.36 (1H, t, J = 8.0 Hz), 7.80 (1H, br), 8.27 (1H, d, J = 3.2 Hz), 8.79 (1H, br), DMSO: 467 (M + H)$^+$FAB |
| 314 | 1.07-1.21 (2H, m), 1.27-1.51 (10H, m), 1.73-1.77 (2H, br), 1.81-1.84 (2H, br) 2.83-2.89 (3H, br), 3.04 (1H, br), 3.72-3.76 (2H, br), 4.02 (1H, br), 4.18 (1H, br), 7.33 (1H, m), 7.58 (1H, m), 7.68 (1H, m), 7.80 (1H, m), 7.86 (1H, m), 8.04 (1H, m), 8.08 (1H, m), 8.28 (1H, m), 8.79 (1H, m), DMSO: 503 (M + H)$^+$FAB |

TABLE 55

| Ex No. | DAT $^1$H-NMR δ (ppm), solvent: MS m/z |
|---|---|
| 315 | 1.00-1.82 (16H, m), 2.77-3.08 (4H, m), 3.95-4.23 (2H, m), 4.53 (2H, d, J = 12.0 Hz), 7.10-7.23 (2H, m), 7.42-7.58 (2H, m), 7.66 (1H, d, J = 7.5 Hz), 7.81 (1H, s), 7.99 (1H, d, J = 8.5 Hz), 8.29 (1H, d, J = 2.2 Hz), 8.80 (1H, s), DMSO: 503 (M + H)$^+$FAB |
| 316 | 1.08-1.23 (2H, m), 1.26-1.32 (2H, m), 1.47-1.57 (3H, m), 1.73-1.77 (2H, m), 2.37-2.41 (2H, m) 2.61-2.67 (4H, br), 2.87 (1H, m), 2.03 (1H, m), 3.27-3.33 (4H, br), 4.02 (1H, br), 4.18 (1H, br), 7.37 (1H, m), 7.59 (1H, m), 7.70 (1H, m), 7.81 (1H, m), 7.87 (1H, m), 8.06-8.11 (2H, m), 8.29 (1H, m), 8.80 (1H, m), DMSO: 526 (M + Na)$^+$ESI |
| 317 | 1.07-1.21 (2H, m), 1.27-1.51 (10H, m), 1.73-1.77 (2H, br), 1.82-1.85 (2H, br) 2.67-2.73 (2H, br), 2.87 (1H, m), 3.02 (1H, br), 3.28-3.39 (2H, br), 4.02 (1H, br), 4.18 (1H, br), 7.09 (1H, m), 7.41 (1H, m), 7.46-7.52 (2H, m), 7.55 (1H, m), 7.82 (1H, m), 7.86 (1H, m), 8.08 (1H, m), 8.29 (1H, m), 8.80 (1H, m), DMSO: 524 (M + Na)$^+$FAB |
| 318 | 1.10-1.30 (2H, m), 1.44-1.62 (3H, m), 1.75-1.83 (2H, m), 2.70 (2H, t, J = 7.3 Hz), 2.80-3.10 (2H, m), 3.95-4.24 (2H, m), 7.47-7.74 (5H, m), 8.02 (1H, t, J = 2.5 Hz), 8.17 (1H, s), 8.55 (1H, d, J = 2.4 Hz), 8.89 (1H, d, J = 2.0 Hz), DMSO: 379 (M + H)$^+$FAB |
| 319 | 1.10-1.30 (2H, m), 1.45-1.59 (3H, m), 1.80 (2H, d, J = 12.2 Hz), 2.63 (2H, t, J = 7.4 Hz), 2.88 (1H, t, J = 12.2 Hz), 3.03 (1H, t, J = 12.2 Hz), 3.31-3.38 (2H, m), 3.50-3.55 (2H, m), 4.02 (1H, d, J = 12.2 Hz), 4.18 (1H, d, J = 12.2 Hz), 7.15-7.31 (5H, m), 8.01 (1H, t, J = 2.4 Hz), 8.55 (1H, s), 8.69 (1H, t, J = 5.6 Hz), 8.88 (1H, s), DMSO: 398 (M + H)$^+$FAB |
| 320 | 1.10-1.30 (2H, m), 1.45-1.60 (3H, m), 1.75-1.85 (2H, m), 2.63 (2H, t, J = 7.4 Hz), 2.80-3.10 (2H, m), 3.95-4.24 (2H, m), 7.15-7.31 (5H, m), 7.67 (1H, s), 8.01 (1H, t, J = 1.9 Hz), 8.17 (1H, s), 8.55 (1H, d, J = 2.4 Hz), 8.89 (1H, d, J = 2.0 Hz), DMSO: 354 (M + H)$^+$FAB |
| 321 | 1.10-1.30 (2H, m), 1.45-1.60 (3H, m), 1.75-1.85 (2H, m), 2.60 (2H, t, J = 7.3 Hz), 2.80-3.10 (2H, m), 3.74 (3H, s), 3.95-4.24 (2H, m), 6.70-6.84 (3H, m), 7.13-7.24 (1H, m), 7.66 (1H, s), 8.01 (1H, br), 8.18 (1H, s), 8.55 (1H, d, J = 2.4 Hz), 8.89 (1H, br), DMSO: 384 (M + H)$^+$FAB |
| 322 | 1.10-1.30 (2H, m), 1.44-1.60 (3H, m), 1.75-1.83 (2H, m), 2.65 (2H, t, J = 7.3 Hz), 2.80-3.10 (2H, m), 3.95-4.24 (2H, m), 6.96-7.10 (3H, m), 7.29-7.36 (1H, m), 7.66 (1H, s), 8.01 (1H, t, J = 2.5 Hz), 8.17 (1H, s), 8.55 (1H, d, J = 2.4 Hz), 8.89 (1H, d, J = 1.9 Hz), DMSO: 372 (M + H)$^+$FAB |
| 323 | 1.10-1.34 (2H, m), 1.50-1.64 (3H, m), 1.75-1.88 (2H, m), 2.80-3.10 (4H, m), 3.95-4.24 (2H, m), 7.41 (1H, dt, J = 1.0, 7.4 Hz), 7.51 (1H, d, J = 7.8 Hz), 7.62-7.70 (2H, m), 7.79 (1H, dd, J = 1.5, 7.8 Hz), 8.02 (1H, t, J = 2.0 Hz), 8.17 (1H, s), 8.56 (1H, d, J = 2.4 Hz), 8.89 (1H, d, J = 2.0 Hz), DMSO: 379 (M + H)$^+$FAB |
| 324 | 1.10-1.34 (2H, m), 1.45-1.64 (3H, m), 1.75-1.88 (2H, m), 2.66 (2H, t, J = 7.8 Hz), 2.80-3.10 (2H, m), 3.95-4.24 (2H, m), 7.26-7.40 (3H, m), 7.64-7.75 (3H, m), 7.92 (1H, s), 8.01 (1H, br), 8.17 (1H, s), 8.55 (1H, d, J = 2.4 Hz), 8.89 (1H, d, J = 2.4 Hz), DMSO: 397 (M + H)$^+$FAB |
| 325 | 1.10-1.34 (2H, m), 1.45-1.64 (3H, m), 1.75-1.85 (2H, m), 2.66 (2H, t, J = 7.3 Hz), 2.80-3.10 (8H, m), 3.95-4.24 (2H, m), 7.16-7.37 (4H, m), 7.66 (1H, s), 8.01 (1H, br), 8.17 (1H, s), 8.55 (1H, d, J = 2.4 Hz), 8.89 (1H, d, J = 1.4 Hz), DMSO: 425 (M + H)$^+$FAB |
| 326 | 0.79-0.93 (2H, m), 1.02-1.30 (10H, m), 1.37-1.49 (1H, m) 1.57-1.77 (7H, m), 2.81-2.92 (1H, br), 2.96-3.08 (1H, br), 3.94-4.05 (1H, br), 4.10-4.21 (1H, br), 7.63-7.70 (1H, br), 8.00 (1H, dd, J = 3.0 Hz, 2.4 Hz), 8.13-8.21 (1H, m), 8.55 (1H, d, J = 3.0 Hz),, 8.88 (1H, d, J = 2.4 Hz), DMSO: 360 (M + H)$^+$FAB |
| 327 | 1.10-1.30 (2H, m), 1.45-1.60 (3H, m), 1.75-1.85 (2H, m), 2.63 (2H, t, J = 7.2 Hz), 2.80-3.10 (2H, m), 3.30-3.38 (2H, m), 3.49-3.55 (2H, m), 3.95-4.24 (2H, m), 7.16-7.34 (4H, m), 8.02 (1H, t, J = 2.4 Hz), 8.55 (1H, br), 8.69 (1H, t, J = 5.6 Hz), 8.87 (1H, s), DMSO: 432 (M + H)$^+$FAB |

TABLE 56

| Ex No. | DAT ¹H-NMR δ (ppm), solvent: MS m/z |
|---|---|
| 328 | 1.10-1.30 (2H, m), 1.45-1.60 (3H, m), 1.75-1.85 (2H, m), 2.60 (2H, t, J = 7.6 Hz), 2.80-3.10 (2H, m), 3.30-3.38 (2H, m), 3.49-3.55 (2H, m), 3.74 (3H, s), 3.95-4.24 (2H, m), 6.71-6.82 (3H, m), 7.19 (1H, t, J = 7.2 Hz), 8.01 (1H, br), 8.55 (1H, br), 8.68 (1H, t, J = 6.0 Hz), 8.87 (1H, br), DMSO: 428 (M + H)⁺FAB |
| 329 | 1.10-1.30 (2H, m), 1.45-1.60 (3H, m), 1.75-1.85 (2H, m), 2.65 (2H, t, J = 8.4 Hz), 2.80-3.10 (2H, m), 3.30-3.38 (2H, m), 3.49-3.55 (2H, m), 3.95-4.24 (2H, m), 7.05-7.10 (3H, m), 7.30-7.35 (1H, m), 8.00 (1H, t, J = 2.4 Hz), 8.55 (1H, br), 8.68 (1H, t, J = 5.6 Hz), 8.87 (1H, br), DMSO: 416 (M + H)⁺FAB |
| 330 | 1.10-1.30 (2H, m), 1.45-1.62 (3H, m), 1.75-1.85 (2H, m), 2.70 (2H, t, J = 7.2 Hz), 2.80-3.10 (2H, m), 3.30-3.38 (2H, m), 3.49-3.55 (2H, m), 3.95-4.24 (2H, m), 7.50 (1H, t, J = 8.0 Hz), 7.56-7.74 (3H, m), 8.02 (1H, t, J = 2.0 Hz), 8.55 (1H, d, J = 2.0 Hz), 8.69 (1H, t, J = 6.0 Hz), 8.87 (1H, br), DMSO: 423 (M + H)⁺FAB |
| 331 | 1.10-1.34 (2H, m), 1.50-1.64 (3H, m), 1.75-1.89 (2H, m), 2.84 (2H, t, J = 8.0 Hz), 2.84-3.11 (2H, m), 3.31-3.38 (2H, m), 3.49-3.55 (2H, m), 3.95-4.25 (2H, m), 7.40 (1H, dt, J = 0.8, 7.6 Hz), 7.52 (1H, d, J = 7.2 Hz), 7.65 (1H, dt, J = 1.6, 7.6 Hz), 7.79 (1H, dd, J = 1.2, 8.0 Hz), 8.04 (1H, t, J = 2.0 Hz), 8.55 (1H, d, J = 2.4 Hz), 8.69 (1H, t, J = 5.6 Hz), 8.87 (1H, d, J = 1.6 Hz), DMSO: 423 (M + H)⁺FAB |
| 332 | 462 (M + H)⁺FAB |
| 333 | 1.10-1.30 (2H, m), 1.45-1.60 (3H, m), 1.80 (2H, d, J = 12.0 Hz), 2.37 (2H, t, J = 7.2 Hz), 2.63 (2H, t, J = 7.2 Hz), 2.87 (1H, t, J = 12.2 Hz), 3.03 (1H, t, J = 12.2 Hz), 3.41-3.49 (2H, m), 4.01 (1H, d, J = 12.2 Hz), 4.18 (1H, d, J = 12.2 Hz), 6.83 (1H, s), 7.15-7.31 (5H, m), 7.36 (1H, s), 7.99 (1H, t, J = 2.4 Hz), 8.55 (1H, d, J = 3.2 Hz), 8.76 (1H, t, J = 5.6 Hz), 8.85 (1H, t, J = 2.0 Hz), DMSO: 425 (M + H)⁺FAB |
| 334 | 1.08-1.32 (2H, m), 1.45-1.60 (3H, m), 1.74-1.86 (2H, m), 2.66 (2H, dd, J = 7.2, 7.2 Hz), 2.80-2.95 (1H, m), 2.95-3.11 (1H, m), 3.95-4.08 (1H, m), 4.11-4.25 (1H, m), 7.09-7.17 (2H, m), 7.20-7.28 (1H, m), 7.28-7.36 (1H, m), 7.67 (1H, br s), 8.02 (1H, dd, J = 2.4, 2.0 Hz), 8.18 (1H, br s), 8.55 (1H, d, J = 2.4 Hz), 8.89 (1H, d, J = 2.0 Hz), DMSO: 372 (M + H)⁺FAB |
| 335 | 1.08-1.32 (2H, m), 1.44-1.61 (3H, m), 1.77-1.83 (2H, br), 2.63 (2H, t, J = 7.6 Hz), 2.79-3.08 (2H, br), 3.95-4.23 (2H, br), 6.73 (1H, d, J = 16.0 Hz), 7.14-7.22 (3H, m), 7.25-7.32 (2H, m), 7.64 (1H, d, J = 16.0 Hz), 8.02-8.06 (1H, m), 8.40-8.44 (1H, m), 8.68-8.73 (1H, m), 12.55-12.63 (1H, br), DMSO: 380 (M + H)⁺FAB |
| 336 | 1.09-1.31 (2H, m), 1.43-1.56 (1H, m), 1.53-1.64 (2H, m), 1.71-1.86 (2H, m), 2.67 (2H, dd, J = 8.0, 8.0 Hz), 2.79-2.96 (1H, m), 2.92-3.11 (1H, m), 3.93-4.10 (1H, m), 4.08-4.24 (1H, m), 7.31 (2H, d, J = 5.2 Hz), 7.67 (1H, s), 8.01 (1H, dd, J = 2.4, 1.6 Hz), 8.19 (1H, s), 8.49 (2H, br s), 8.56 (1H, d, J = 2.4 Hz), 8.89 (1H, d, J = 1.6 Hz), DMSO: 355 (M + H)⁺ESI |
| 337 | 1.08-1.32 (2H, m), 1.43-1.57 (1H, m), 1.52-1.63 (2H, m), 1.72-1.86 (2H, m), 2.66 (2H, dd, J = 7.2, 7.2 Hz), 2.80-2.95 (1H, m), 2.95-3.11 (1H, m), 3.93-4.08 (1H, m), 4.10-4.25 (1H, m), 7.33 (1H, dd, J = 7.6, 4.8 Hz), 7.62-7.72 (2H, m), 8.01 (1H, dd, J = 2.4, 1.6 Hz), 8.19 (1H, br s), 8.41 (1H, br s), 8.47 (1H, br s), 8.56 (1H, d, J = 2.4 Hz), 8.89 (1H, d, J = 1.6 Hz), DMSO: 355 (M + H)⁺ESI |
| 338 | 1.10-1.33 (2H, m), 1.45-1.59 (1H, m), 1.54-1.65 (2H, m), 1.75-1.87 (2H, m), 2.67 (2H, dd, J = 7.6, 7.6 Hz), 2.81-2.95 (1H, m), 2.96-3.10 (1H, m), 3.92-4.08 (1H, m), 4.11-4.25 (1H, m), 7.27 (2H, t, J = 8.8 Hz), 7.31 (2H, d, J = 8.4 Hz), 7.56 (2H, d, J = 8.4 Hz), 7.63-7.72 (3H, m), 8.02 (1H, dd, J = 2.4, 2.0 Hz), 8.19 (1H, br s), 8.56 (1H, d, J = 2.4 Hz), 8.89 (1H, d, J = 2.0 Hz), DMSO: 448 (M + H)⁺FAB |
| 339 | 1.10-1.33 (2H, m), 1.47-1.63 (1H, m), 1.53-1.65 (2H, m), 1.76-1.88 (2H, m), 2.66 (2H, dd, J = 7.2, 7.2 Hz), 2.80-2.96 (1H, m), 2.96-3.11 (1H, m), 3.79 (3H, s), 3.96-4.07 (1H, m), 4.12-4.25 (1H, m), 7.01 (2H, d, J = 8.4 Hz), 7.28 (2H, d, J = 8.4 Hz), 7.53 (2H, d, J = 8.4 Hz), 7.58 (2H, d, J = 8.4 Hz), 7.67 (1H, br s), 8.02 (1H, dd, J = 2.4, 2.0 Hz), 8.19 (1H, br s), 8.56 (1H, d, J = 2.4 Hz), 8.89 (1H, d, J = 2.0 Hz), DMSO: 458 (M + H)⁺FAB |

TABLE 57

| Ex No. | DAT ¹H-NMR δ (ppm), solvent: MS m/z |
|---|---|
| 340 | 1.10-1.32 (2H, m), 1.45-1.67 (3H, m), 1.75-1.87 (2H, m), 2.71 (2H, t, J = 8.0 Hz), 2.80-3.10 (2H, m), 3.95-4.24 (2H, m), 7.23 (1H, d, J = 7.2 Hz), 7.33-7.52 (6H, m), 7.64-7.71 (2H, m), 8.02 (1H, t, J = 2.0 Hz), 8.19 (1H, s), 8.55 (1H, d, J = 2.4 Hz), 8.89 (1H, d, J = 1.6 Hz), DMSO: 430 (M + H)⁺FAB |
| 341 | 1.10-1.32 (2H, m), 1.45-1.67 (3H, m), 1.75-1.87 (2H, m), 2.71 (2H, t, J = 7.6 Hz), 2.80-3.10 (2H, m), 3.95-4.24 (2H, m), 7.29 (1H, d, J = 7.6 Hz), 7.41 (1H, t, J = 7.6 Hz), 7.55 (1H, d, J = 7.2 Hz), 7.60-7.73 (3H, m), 7.82 (1H, d, J = 7.2 Hz), 8.00-8.08 (2H, m), 8.16 (1H, s), 8.20 (1H, s), 8.65 (1H, br), 8.91 (1H, br), DMSO: 455 (M + H)⁺FAB |
| 342 | 1.06-1.30 (2H, m), 1.43-1.56 (3H, m), 1.51-1.61 (2H, m), 1.69 (2H, q, J = 6.4 Hz), 1.74-1.85 (2H, m), 2.63 (2H, dd, J = 7.6, 7.6 Hz), 2.80-2.94 (1H, m), 2.94-3.10 (2H, m), 3.33 (2H, td, J = 6.4, 6.4 Hz), 3.47 (2H, t, J = 6.4 Hz), 3.93-4.09 (1H, m), 4.09-4.24 (1H, m), 7.13-7.24 (3H, m), 7.24-7.31 (2H, m), 7.99 (1H, dd, J = 2.4, 1.6 Hz), 8.54 (1H, d, J = 2.4 Hz), 8.67 (1H, br t, J = 5.2 Hz), 8.85 (1H, d, J = 1.6 Hz), DMSO: 412 (M + H)⁺FAB |

TABLE 57-continued

| Ex No. | DAT $^1$H-NMR δ (ppm), solvent: MS m/z |
|---|---|
| 343 | 1.08-1.31 (2H, m), 1.44-1.56 (1H, m), 1.52-1.61 (2H, m), 1.74-1.86 (2H, m), 1.82-1.93 (2H, m), 2.63 (2H, dd, J = 7.2, 7.2 Hz), 2.72 (6H, s), 2.80-2.93 (1H, m), 2.98-3.09 (3H, m), 3.34 (2H, td, J = 6.4, 6.4 Hz), 3.94-4.07 (1H, m), 4.10-4.24 (1H, m), 7.13-7.24 (3H, m), 7.24-7.32 (2H, m), 8.00 (1H, dd, J = 2.4, 1.6 Hz), 8.57 (1H, d, J = 2.4 Hz), 8.85 (1H, br t, J = 5.6 Hz), 8.88 (1H, d, J = 1.6 Hz), DMSO: 439 (M + H)$^+$FAB |
| 344 | 1.09-1.34 (2H, m), 1.45-1.60 (1H, m), 1.55-1.66 (2H, m), 1.75-1.87 (2H, m), 2.70 (2H, dd, J = 7.6, 7.6 Hz), 2.80-2.96 (1H, m), 2.96-3.11 (1H, m), 3.94-4.09 (1H, m), 4.10-4.26 (1H, m), 7.37 (2H, d, J = 8.4 Hz), 7.68 (1H, br s), 7.69 (2H, d, J = 8.4 Hz), 7.87 (2H, d, J = 8.4 Hz), 7.91 (2H, d, J = 8.4 Hz), 8.02 (1H, dd, J = 2.4, 2.0 Hz), 8.19 (1H, br s), 8.56 (1H, d, J = 2.4 Hz), 8.89 (1H, d, J = 2.0 Hz), DMSO: 455 (M + H)$^+$FAB |
| 345 | 1.10-1.34 (2H, m), 1.46-1.60 (1H, m), 1.54-1.66 (2H, m), 1.75-1.89 (2H, m), 2.68 (2H, dd, J = 7.6, 7.6 Hz), 2.80-2.96 (1H, m), 2.96-3.12 (1H, m), 3.95-4.09 (1H, m), 4.11-4.26 (1H, m), 7.13-7.21 (1H, m), 7.33 (2H, d, J = 8.0 Hz), 7.45-7.52 (3H, m), 7.63 (2H, d, J = 8.0 Hz), 7.67 (1H, br s), 8.02 (1H, dd, J = 2.4, 2.0 Hz), 8.19 (1H, br s), 8.56 (1H, d, J = 2.4 Hz), 8.89 (1H, d, J = 2.0 Hz), DMSO: 448 (M + H)$^+$FAB |
| 346 | 1.10-1.35 (2H, m), 1.48-1.61 (1H, m), 1.56-1.66 (2H, m), 1.76-1.90 (2H, m), 2.69 (2H, dd, J = 8.0, 8.0 Hz), 2.81-2.97 (1H, m), 2.97-3.13 (1H, m), 3.95-4.10 (1H, m), 4.10-4.26 (1H, m), 7.25-7.32 (2H, m), 7.33 (2H, d, J = 8.0 Hz), 7.36-7.44 (1H, m), 7.44-7.50 (2H, m), 7.48-7.56 (1H, m), 7.67 (1H, br s), 8.02 (1H, dd, J = 2.8, 2.0 Hz), 8.19 (1H, br s), 8.56 (1H, d, J = 2.8 Hz), 8.89 (1H, d, J = 2.0 Hz), DMSO: 448 (M + H)$^+$FAB |
| 347 | 1.08-1.31 (2H, m), 1.43-1.55 (1H, m), 1.50-1.61 (2H, m), 1.72-1.85 (2H, m), 2.63 (2H, dd, J = 7.8, 7.8 Hz), 2.80-2.93 (1H, m), 2.90 (2H, t, J = 6.8 Hz), 2.96-3.09 (1H, m), 3.56 (2H, td, J = 6.8, 6.8 Hz), 3.93-4.08 (1H, m), 4.08-4.23 (1H, m), 7.14-7.24 (3H, m), 7.24-7.31 (2H, m), 7.33 (2H, d, J = 5.6 Hz), 7.95 (1H, dd, J = 2.8, 1.6 Hz), 8.50 (2H, br s), 8.55 (1H, d, J = 2.8 Hz), 8.81 (1H, d, J = 1.6 Hz), 8.81 (1H, t, J = 6.0 Hz), DMSO: 459 (M + H)$^+$FAB |
| 348 | 1.08-1.31 (2H, m), 1.43-1.57 (1H, m), 1.50-1.62 (2H, m), 1.73-1.86 (2H, m), 2.63 (2H, dd, J = 7.8, 7.8 Hz), 2.80-2.93 (1H, m), 2.89 (2H, t, J = 6.8 Hz), 2.96-3.09 (1H, m), 3.54 (2H, td, J = 6.8, 6.8 Hz), 3.94-4.09 (1H, m), 4.09-4.25 (1H, m), 7.13-7.25 (3H, m), 7.25-7.32 (2H, m), 7.35 (1H, dd, J = 7.6, 4.8 Hz), 7.71 (1H, d, J = 7.6 Hz), 7.92-7.97 (1H, m), 8.44 (1H, br s), 8.49 (1H, br s), 8.52-8.59 (1H, m), 8.77-8.85 (2H, m), DMSO: 459 (M + H)$^+$FAB |
| 349 | 1.10-1.32 (2H, m), 1.45-1.67 (3H, m), 1.75-1.87 (2H, m), 2.69-2.78 (2H, m), 2.80-3.10 (2H, m), 3.95-4.24 (2H, m), 7.27-7.46 (3H, m), 7.66 (1H, s), 7.83-8.03 (5H, m), 8.18 (1H, s), 8.55 (1H, d, J = 2.4 Hz), 8.66 (1H, br), 8.89 (1H, d, J = 1.2 Hz), DMSO: 431 (M + H)$^+$FAB |
| 350 | 425 (M + H)$^+$FAB |
| 351 | 1.05-1.85 (17H, m), 2.67 (2H, t, J = 7.6 Hz), 2.80-3.10 (2H, m), 3.70-3.80 (1H, m), 3.95-4.24 (2H, m), 7.33-7.37 (2H, m), 7.62-7.70 (3H, m), 8.01 (1H, t, J = 2.0 Hz), 8.13 (1H, d, J = 7.6 Hz), 8.17 (1H, s), 8.55 (1H, d, J = 2.8 Hz), 8.89 (1H, d, J = 2.0 Hz), DMSO: 479 (M + H)$^+$FAB |

TABLE 58

| Ex No. | DAT $^1$H-NMR δ (ppm), solvent: MS m/z |
|---|---|
| 352 | 411 (M + H)$^+$FAB |
| 353 | 1.08-1.32 (2H, m), 1.43-1.58 (1H, m), 1.52-1.64 (2H, m), 1.72-1.87 (2H, m), 2.68 (2H, dd, J = 7.8, 7.8 Hz), 2.78-2.95 (1H, m), 2.97-3.12 (1H, m), 3.93-4.09 (1H, m), 4.10-4.25 (1H, m), 7.26 (1H, br s), 7.29 (2H, d, J = 8.0 Hz), 7.67 (1H, br s), 7.79 (2H, d, J = 8.0 Hz), 7.89 (1H, br s), 8.01 (1H, dd, J = 2.4, 1.2 Hz), 8.18 (1H, br s), 8.55 (1H, d, J = 2.4 Hz), 8.89 (1H, d, J = 1.2 Hz), DMSO: 397 (M + H)$^+$FAB |
| 354 | 1.08-1.33 (2H, m), 1.44-1.58 (1H, m), 1.52-1.64 (2H, m), 1.73-1.88 (2H, m), 2.67 (2H, dd, J = 7.8, 7.8 Hz), 2.80-2.96 (1H, m), 2.92 (3H, s), 2.95 (3H, s), 2.96-3.12 (1H, m), 3.92-4.08 (1H, m), 4.09-4.25 (1H, m), 7.27 (2H, d, J = 7.6 Hz), 7.32 (2H, d, J = 7.6 Hz), 7.67 (1H, br s), 8.01 (1H, dd, J = 2.4, 1.6 Hz), 8.18 (1H, br s), 8.56 (1H, d, J = 2.4 Hz), 8.89 (1H, d, J = 1.6 Hz), DMSO: 425 (M + H)$^+$FAB |
| 355 | 1.11-1.31 (2H, m), 1.40-1.66 (9H, m), 1.74-1.86 (2H, br), 2.64-2.69 (2H, m), 2.86 (1H, br), 3.02 (1H, br), 3.23-3.38 (2H, m), 3.51-3.64 (2H, m), 4.01 (1H, m), 4.17 (1H, m), 7.15-7.20 (2H, m), 7.30-7.37 (2H, m), 7.67 (1H, s), 8.01 (1H, m), 8.18 (1H, s), 8.55 (1H, m), 8.89 (1H, m), DMSO: 465 (M + H)$^+$ESI |
| 356 | 1.21-1.36 (2H, m), 1.54-1.59 (3H, m), 1.78-1.82 (2H, br), 2.64-2.69 (2H, br), 2.87 (1H, m), 3.03 (1H, m), 3.37-3.69 (8H, br), 3.99 (1H, m), 4.16 (1H, m), 7.15-7.20 (2H, m), 7.30-7.37 (2H, m), 7.67 (1H, s), 8.01 (1H, m), 8.18 (1H, s), 8.55 (1H, m), 8.89 (1H, m), DMSO: 467 (M + H)$^+$ESI |
| 357 | 1.15-1.28 (2H, m), 1.44-1.62 (9H, m), 1.79-1.83 (2H, br), 2.65-2.68 (2H, m), 2.88 (1H, br), 3.03 (1H, br), 3.24-3.37 (2H, br), 3.47-3.62 (2H, m), 4.01 (1H, m), 4.18 (1H, m), 7.26-7.30 (4H, m), 7.67 (1H, s), 8.02 (1H, m), 8.18 (1H, s), 8.55 (1H, m), 8.89 (1H, m), DMSO: 465 (M + H)$^+$FAB |
| 358 | 1.13-1.28 (2H, m), 1.48-1.61 (3H, m), 1.79-1.82 (2H, br), 2.65-2.69 (2H, br), 2.88 (1H, m), 3.04 (1H, m), 3.34-3.65 (8H, br), 4.01 (1H, m), 4.18 (1H, m), 7.15-7.20 (2H, m), 7.28-7.34 (4H, m), 7.66 (1H, s), 8.01 (1H, m), 8.17 (1H, s), 8.55 (1H, m), 8.89 (1H, m), DMSO: 467 (M + H)$^+$FAB |

TABLE 58-continued

| Ex No. | DAT ¹H-NMR δ (ppm), solvent: MS m/z |
|---|---|
| 359 | 1.16-1.25 (2H, m), 1.51-1.61 (3H, m), 1.79-1.88 (6H, br), 2.65-2.69 (2H, m), 2.87 (1H, br), 3.03 (1H, br), 3.31-3.38 (2H, br), 3.44-3.47 (2H, m), 4.01 (1H, m), 4.18 (1H, m), 7.29-7.36 (4H, m), 7.68 (1H, s), 8.01 (1H, m), 8.19 (1H, s), 8.55 (1H, m), 8.89 (1H, m), DMSO: 451 (M + H)⁺ESI |
| 360 | 1.03-1.31 (8H, m), 1.46-1.66 (3H, m), 1.78-1.83 (2H, br), 2.64-2.69 (2H, m), 2.87 (1H, br), 3.03 (1H, br), 3.14-3.24 (2H, br), 3.35-3.49 (2H, m), 4.03 (1H, m), 4.18 (1H, m), 7.12-7.18 (2H, m), 7.27-7.37 (2H, m), 7.68 (1H, s), 8.02 (1H, m), 8.19 (1H, s), 8.56 (1H, m), 8.89 (1H, m), DMSO: 453 (M + H)⁺ESI |
| 361 | 1.13-1.30 (2H, m), 1.48-1.61 (3H, m), 1.78-1.83 (2H, br), 2.65-2.71 (2H, m), 2.87 (1H, br), 3.03 (1H, br), 3.92-3.98 (2H, m), 4.00 (1H, m), 4.18 (1H, m), 4.37-4.43 (2H, m), 7.38-7.41 (2H, m), 7.66-7.70 (2H, m), 7.73 (1H, s), 8.01 (1H, m), 8.19 (1H, s), 8.56 (1H, m), 8.89 (1H, m), DMSO: 423 (M + H)⁺API |
| 362 | 1.04-1.37 (8H, m), 1.45-1.68 (3H, m), 1.83 (2H, d, J = 12.8 Hz), 2.69 (2H, t, J = 7.3 Hz), 2.86 (1H, t, J = 12.1 Hz), 2.99 (1H, t, J = 12.1 Hz), 3.28 (2H, br), 3.53 (2H, br), 4.15-4.34 (2H, m), 7.20 (2H, d, J = 8.1 Hz), 7.31 (2H, d, J = 8.1 Hz), 8.01 (1H, s), 8.59 (1H, s), 8.89 (1H, s)CDCl3: 453 (M + H)⁺ESI |
| 363 | 1.18-1.36 (2H, m), 1.44-1.68 (3H, m), 1.76-2.12 (6H, m), 2.69 (2H, t, J = 7.5 Hz), 2.84 (2H, t, J = 11.9 Hz), 2.98 (2H, t, J = 11.9 Hz), 4.25 (4H, br), 6.02 (1H, br), 6.73 (1H, br), 7.20 (2H, d, J = 7.9 Hz), 7.45 (2H, d, J = 7.9 Hz), 7.98 (1H, s), 8.57 (1H, s), 8.85 (1H, s)CDCl3: 451 (M + H)⁺ESI |

TABLE 59

| Ex No. | DAT ¹H-NMR δ (ppm), solvent: MS m/z |
|---|---|
| 364 | 1.18-1.36 (2H, m), 1.44-1.70 (3H, m), 1.77-1.92 (2H, m), 2.72 (2H, t, J = 7.5 Hz), 2.85 (2H, t, J = 11.4 Hz), 2.99 (2H, t, J = 11.4 Hz), 4.08 (2H, t, J = 9.6 Hz), 4.26 (2H, br), 4.47 (2H, t, J = 9.6 Hz), 7.25 (2H, d, J = 7.8 Hz), 7.91 (2H, d, J = 7.8 Hz), 7.94-7.99 (1H, m), 8.58 (1H, d, J = 2.4 Hz), 8.83 (1H, d, J = 2.4 Hz)CDCl3: 423 (M + H)⁺ESI |
| 365 | 1.03 (2H, d, J = 6.2 Hz), 1.12-1.30 (2H, m), 1.48-1.62 (3H, m), 1.80 (2H, d, J = 12.8 Hz), 2.68 (2H, t, J = 7.4 Hz), 2.87 (1H, t, J = 12.8 Hz), 3.03 (1H, t, J = 12.8 Hz), 3.38-3.80 (6H, m), 4.01 (1H, d, J = 12.8 Hz), 4.17 (1H, d, J = 12.8 Hz), 6.65-6.68 (1H, m), 6.84 (1H, d, J = 8.4 Hz), 7.23-7.39 (4H, m), 7.53-7.57 (1H, m), 7.66 (1H, s), 8.00-8.02 (1H, m), 8.11-8.13 (1H, m), 8.18 (1H, s), 8.55 (1H, d, J = 2.4 Hz), 8.88 (1H, d, J = 2.0 Hz), DMSO: 543 (M + H)⁺FAB |
| 366 | 1.03 (2H, d, J = 6.2 Hz), 1.12-1.30 (2H, m), 1.48-1.62 (3H, m), 1.80 (2H, d, J = 12.4 Hz), 2.68 (2H, t, J = 7.4 Hz), 2.87 (1H, t, J = 12.4 Hz), 3.03 (1H, t, J = 12.4 Hz), 3.10-3.28 (3H, m), 3.40-3.83 (3H, m), 4.02 (1H, d, J = 12.4 Hz), 4.18 (1H, d, J = 12.4 Hz), 6.80 (1H, t, J = 7.6 Hz), 6.95 (2H, d, J = 7.6 Hz), 7.20-740 (6H, m), 7.66 (1H, s), 8.00 (1H, t, J = 2.4 Hz), 8.18 (1H, s), 8.55 (1H, d, J = 2.4 Hz), 8.88 (1H, d, J = 2.0 Hz), DMSO: 542 (M + H)⁺FAB |
| 367 | 1.12-1.32 (2H, m), 1.48-1.63 (3H, m), 1.82 (2H, d, J = 12.4 Hz), 2.68 (2H, t, J = 7.2 Hz), 2.88 (1H, t, J = 12.4 Hz), 3.04 (1H, t, J = 12.4 Hz), 3.40-3.75 (8H, m), 4.02 (1H, d, J = 12.4 Hz), 4.18 (1H, d, J = 12.4 Hz), 6.65-6.68 (1H, m), 6.84 (1H, d, J = 8.8 Hz), 7.31 (2H, d, J = 8.0 Hz), 7.36 (2H, d, J = 8.0 Hz), 7.53-7.57 (1H, m), 7.66 (1H, s), 8.01 (1H, d, J = 2.4 Hz), 8.11-8.13 (1H, m), 8.18 (1H, s), 8.55 (1H, d, J = 2.8 Hz), 8.89 (1H, d, J = 2.0 Hz), DMSO: 543 (M + H)⁺FAB |
| 368 | 1.11-1.31 (2H, m), 1.48-1.63 (3H, m), 1.81 (2H, d, J = 12.2 Hz), 2.68 (2H, t, J = 7.2 Hz), 2.88 (1H, t, J = 12.8 Hz), 3.04 (1H, t, J = 12.8 Hz), 3.10-3.25 (4H, m), 3.42-3.81 (4H, m), 4.02 (1H, d, J = 12.8 Hz), 4.18 (1H, d, J = 12.8 Hz), 6.81 (1H, t, J = 7.2 Hz), 6.95 (2H, d, J = 8.4 Hz), 7.21-7.37 (6H, m), 7.66 (1H, s), 8.01 (1H, s), 8.18 (1H, s), 8.55 (1H, d, J = 2.4 Hz), 8.88 (1H, s), DMSO: 542 (M + H)⁺FAB |
| 369 | 1.19-1.23 (2H, m), 1.52-1.62 (3H, m), 1.78-1.85 (2H, m), 2.70 (2H, d, J = 7.8 Hz), 2.88 (1H, t, J = 11.9 Hz), 3.03 (1H, t, J = 10.7 Hz), 3.52 (2H, dd, J = 5.4, 5.2 Hz), 3.59 (1H, dd, J = 5.3, 5.3 Hz), 4.02 (1H, m), 4.18 (1H, m), 4.48 (1H, t, J = 5.2 Hz), 4.60 (1H, t, J = 5.2 Hz), 7.35-7.38 (2H, m), 7.68-7.69 (2H, m), 7.72-7.75 (1H, m), 8.02-8.07 (1H, m), 8.18-8.23 (1H, m), 8.56-8.59 (1H, m), 8.63-8.68 (1H, m), 8.89-8.91 (1H, m), DMSO: 443 (M + H)⁺FAB |
| 370 | 1.13-1.33 (2H, m), 1.52-1.63 (3H, m), 1.75-1.85 (2H, m), 2.68 (2H, d, J = 7.8 Hz), 2.88 (1H, t, J = 10.0 Hz), 3.03 (1H, t, J = 10.0 Hz), 3.30-3.35 (2H, m), 3.46-3.54 (2H, m), 4.15 (1H, d, J = 17.2 Hz), 4.18 (1H, d, J = 16.0 Hz), 7.33-7.39 (2H, m), 7.62-7.72 (3H, m), 8.00-8.01 (1H, m), 8.16-8.18 (1H, m), 8.35-8.29 (1H, m), 8.55 (1H, d, J = 3.4 Hz), 8.89 (1H, d, J = 2.2 Hz), DMSO: 441 (M + H)⁺ESI |
| 371 | 1.21-1.35 (2H, m), 1.48 (9H, s), 1.48-1.60 (1H, m), 1.61-1.69 (2H, m), 1.79-1.87 (2H, m), 2.71 (2H, dd, J = 6.0, 6.0 Hz), 2.86 (1H, t, J = 9.6 Hz), 3.00 (1H, t, J = 9.6 Hz), 4.18-4.33 (2H, m), 5.76 (1H, br), 5.93 (1H, s), 6.28 (1H, br), 7.27-7.35 (2H, m), 7.45-7.50 (1H, m), 7.61 (1H, s), 7.96 (1H, s), 8.58 (1H, s), 8.84 (1H, s)CDCl3: 454 (M + H)⁺ESI |
| 372 | 1.27 (6H, d, J = 4.8 Hz), 1.61-1.69 (2H, m), 1.72-1.88 (5H, m), 2.71 (2H, t, J = 6.0, 6.0 Hz), 2.86 (1H, t, J = 9.0 Hz), 3.00 (1H, t, J = 9.0 Hz), 4.17-4.36 (3H, m), 5.81 (1H, br), 5.95 (1H, br), 6.54 (1H, br), 7.21-7.39 (2H, m), 7.52 (1H, d, J = 6.0 Hz), 7.63 (1H, s), 7.97 (1H, s), 8.61 (1H, s), 8.89 (1H, s)CDCl3: 439 (M + H)⁺ESI |

TABLE 59-continued

| Ex No. | DAT $^1$H-NMR δ (ppm), solvent: MS m/z |
|---|---|
| 373 | 1.10-1.31 (2H, m), 1.47-1.62 (3H, m), 1.78-1.83 (2H, m), 2.39-2.51 (2H, m), 2.66-2.69 (2H, m), 2.82-2.92 (1H, br), 2.98-3.10 (1H, br), 3.65-3.73 (2H, br), 3.89 (2H, t, J = 13.1 Hz), 3.98-4.22 (2H, m), 7.31 (2H, d, J = 8.2 Hz), 7.48 (2H, d, J = 8.2 Hz), 7.63-7.69 (1H, br), 8.00-8.02 (1H, m), 8.15-8.21 (1H, br), 8.55-8.56 (1H, m), 8.88-8.89 (1H, m), DMSO: 487 (M + H)$^+$FAB |

TABLE 60

| Ex No. | DAT $^1$H-NMR δ (ppm), solvent: MS m/z |
|---|---|
| 374 | 1.10-1.31 (2H, m), 1.47-1.59 (3H, m), 1.77-1.83 (2H, m), 2.56 (2H, t, J = 7.5 Hz), 2.82-3.08 (2H, m), 3.99-4.21 (2H, m), 5.77-5.82 (2H, br), 6.75 (1H, d, J = 7.5 Hz), 7.11 (1H, t, J = 7.5 Hz), 7.17-7.20 (1H, m), 7.25-7.27 (1H, br), 7.65-7.70 (1H, br), 8.00-8.03 (1H, m), 8.15-8.21 (1H, br), 8.40-8.45 (1H, br), 8.54-8.56 (1H, m), 8.88-8.90 (1H, m), DMSO: 412 (M + H)$^+$FAB |
| 375 | 1.10-1.30 (2H, m), 1.46-1.60 (3H, m), 1.76-1.90 (6H, m), 2.57 (2H, t, J = 7.4 Hz), 2.82-3.10 (2H, m), 3.32-3.39 (4H, m), 3.97-4.23 (2H, m), 6.77 (1H, d, J = 7.8), 7.12 (1H, t, J = 7.8 Hz), 7.30-7.38 (2H, m), 7.64-7.68 (1H, br), 7.99-8.02 (2H, m), 8.16-8.21 (1H, br), 8.54-8.56 (1H, m), 8.88-8.90 (1H, m), DMSO: 466 (M + H)$^+$FAB |
| 376 | 1.12-1.30 (2H, m), 1.47-1.63 (3H, m), 1.77-1.85 (2H, m), 2.39-2.52 (2H, m), 2.69 (2H, t, J = 7.8 Hz), 2.83-3.08 (2H, m), 3.63-3.75 (2H, m), 3.83-3.94 (2H, m), 3.97-4.24 (2H, m), 7.33-7.41 (4H, m), 7.66-7.70 (1H, br), 8.03-8.05 (1H, m), 8.18-8.22 (1H, br), 8.57 (1H, d, J = 2.4 Hz), 8.90 (1H, d, J = 1.7 Hz), DMSO: 487 (M + H)$^+$FAB |
| 377 | 1.18-1.38 (2H, m), 1.48-1.71 (3H, m), 1.78-1.89 (2H, m), 2.14-2.32 (2H, m), 2.71 (2H, t, J = 7.5 Hz), 2.80-3.24 (6H, m), 3.57-3.83 (2H, m), 4.26 (2H, dd, J = 7.0 Hz), 5.80 (1H, br), 6.51 (1H, br), 7.09 (1H, d, J = 7.5 Hz), 7.22-7.53 (7H, m), 7.60 (1H, d, J = 8.2 Hz), 7.80-7.87 (1H, m), 8.05 (1H, dd, J = 2.0, 2.0 Hz), 8.16-8.25 (1H, m), 8.60 (1H, s), 8.96 (1H, s), DMSO: 593 (M + H)$^+$ESI |
| 378 | 1.00-1.80 (16H, m), 2.27 (3H, s), 2.65-2.74 (2H, m), 2.80-3.10 (2H, m), 3.95-4.32 (4H, m), 6.42 (1H, d, J = 7.6 Hz), 6.56 (1H, d, J = 8.8 Hz), 7.36 (1H, t, J = 7.6 Hz), 7.67 (1H, s), 8.00 (1H, t, J = 2.4 Hz), 8.19 (1H, s), 8.55 (1H, d, J = 2.4 Hz), 8.89 (1H, d, J = 2.0 Hz), DMSO: 466 (M + H)$^+$FAB |
| 379 | 1.11-1.21 (2H, m), 1.27-1.49 (10H, m), 1.74-1.84 (4H, br), 2.83-2.92 (3H, br), 3.05 (1H, br), 3.71-3.75 (2H, br), 4.02 (1H, br), 4.18 (1H, br), 7.34 (1H, m), 7.58 (1H, m), 7.66-7.71 (2H, m), 7.86 (1H, m), 8.00-8.03 (2H, m), 8.07 (1H, m), 8.19 (1H, s), 8.55 (1H, m), 8.89 (1H, m), DMSO: 502 (M + H)$^+$FAB |
| 380 | 1.00-1.82 (16H, m), 2.77-3.10 (4H, m), 3.95-4.23 (2H, m), 4.53 (2H, d, J = 12.0 Hz), 7.15-7.26 (2H, m), 7.45-7.55 (2H, m), 7.62-7.70 (2H, m), 7.95-8.05 (2H, m), 8.20 (1H, s), 8.46 (1H, d, J = 2.8 Hz), 8.89 (1H, d, J = 1.7 Hz), DMSO: 502 (M + H)$^+$FAB |
| 381 | 1.11-1.20 (2H, m), 1.27-1.32 (2H, m), 1.47-1.61 (3H, m), 1.75-1.78 (2H, m), 2.34-2.44 (2H, m), 2.56-2.74 (4H, m), 2.88 (1H, t, J = 12.1 Hz), 3.04 (1H, t, J = 12.5 Hz), 3.23-3.41 (4H, m), 4.01 (1H, d, J = 13.0 Hz), 4.18 (1H, d, J = 12.4 Hz), 7.37 (1H, d, J = 5.6 Hz), 7.57-7.61 (1H, m), 7.68-7.71 (2H, m), 7.87 (1H, d, J = 8.1 Hz), 8.01 (1H, t, J = 2.2 Hz), 8.06-8.10 (2H, m), 8.18 (1H, br), 8.55 (1H, d, J = 2.4 Hz), 8.88 (1H, d, J = 1.8 Hz), DMSO: 503 (M + H)$^+$FAB |
| 382 | 1.15-1.19 (2H, m), 1.27-1.49 (10H, m), 1.74-1.85 (4H, m), 2.70 (2H, m), 2.89 (1H, t, J = 12.4 Hz), 3.04 (1H, t, J = 12.1 Hz), 3.26-3.31 (2H, m), 4.02 (1H, m), 4.18 (1H, d, J = 12.4 Hz), 7.09 (1H, d, J = 14.8 Hz), 7.40 (1H, t, J = 7.8 Hz), 7.46-7.51 (2H, m), 7.55 (1H, d, J = 8.3 Hz), 7.64-7.70 (1H, br), 7.85-7.87 (1H, m), 8.17 (1H, t, J = 2.2 Hz), 8.07-8.09 (1H, m), 8.15-8.21 (1H, br), 8.55 (1H, d, J = 2.8 Hz), 8.89 (1H, d, J = 1.7 Hz), DMSO: 501 (M + H)$^+$FAB |

TABLE 61

| Ex No. | DAT $^1$H-NMR δ (ppm), solvent: MS m/z |
|---|---|
| 383 | 0.87 (3H, t, J = 6.4 Hz), 1.20-1.46 (8H, m), 1.54-1.72 (2H, m), 1.70 (2H, q, J = 6.4 Hz), 1.81-1.94 (2H, m), 2.54-2.64 (1H, m), 2.85-3.05 (1H, m), 3.05-3.25 (1H, m), 3.91 (2H, t, J = 6.4 Hz), 4.00-4.16 (1H, m), 4.15-4.31 (1H, m), 6.56-6.63 (1H, m), 7.07-7.13 (1H, m), 7.17 (1H, dd, J = 8.0, 8.0 Hz), 7.29-7.36 (1H, m), 7.45 (1H, dd, J = 7.8, 5.2 Hz), 7.59-7.67 (1H, m), 8.40-8.46 (2H, m), 9.90 (1H, s), DMSO: 440 (M + H)$^+$FAB |
| 384 | 0.87 (3H, t, J = 6.4 Hz), 1.20-1.45 (8H, m), 1.55-1.77 (4H, m), 1.80-1.93 (2H, m), 2.52-2.62 (1H, m), 2.88-3.04 (1H, m), 3.04-3.19 (1H, m), 3.90 (2H, t, J = 6.4 Hz), 4.00-4.14 (1H, m), 4.16-4.30 (1H, m), 6.85 (2H, d, J = 8.8 Hz), 7.45 (1H, dd, J = 8.3, 4.9 Hz), 7.49 (2H, d, J = 9.2 Hz), 7.61-7.66 (1H, m), 8.40-8.45 (2H, m), 9.78 (1H, s), DMSO: 440 (M + H)$^+$FAB |
| 385 | 369 (M + H)$^+$FAB |
| 386 | 480 (M + H)$^+$FAB |
| 387 | 424 (M + H)$^+$FAB |

TABLE 61-continued

| Ex No. | DAT $^1$H-NMR δ (ppm), solvent: MS m/z |
|---|---|
| 388 | 0.85 (3H, t, J = 7.2 Hz), 1.20-1.32 (6H, m), 1.45-1.58 (2H, m), 1.56-1.78 (2H, m), 1.81-1.94 (2H, m), 2.48-2.54 (2H, m), 2.55-2.66 (1H, m), 2.90-3.05 (1H, m), 3.07-3.21 (1H, m), 4.00-4.15 (1H, m), 4.17-4.32 (1H, m), 7.10 (1H, d, J = 8.0 Hz), 7.50 (2H, d, J = 8.0 Hz), 7.68 (1H, br s), 8.04 (1H, dd, J = 2.8, 2.0 Hz), 8.19 (1H, br), 8.58 (1H, d, J = 2.8 Hz), 8.90 (1H, d, J = 2.0 Hz), 9.86 (1H, br), DMSO: 453 (M + H)$^+$FAB |
| 389 | 1.56-1.74 (2H, br), 1.88-2.04 (2H, br), 2.48-2.53 (3H, m), 3.25-3.55 (2H, br), 3.65-3.92 (2H, br), 4.46-4.55 (1H, m), 5.07 (2H, s), 6.95 (4H, s), 7.01 (1H, s), 7.15 (1H, dt, J = 2.9, 8.8 Hz), 7.23-7.30 (2H, m), 7.40-7.47 (1H, m), 7.70-8.30 (2H, br), DMSO |
| 390 | 1.55-1.74 (2H, br), 1.88-2.04 (2H, br), 3.25-3.55 (2H, br), 3.65-3.92 (2H, br), 4.46-4.54 (1H, m), 5.07 (2H, s), 6.95 (4H, s), 7.01 (1H, s), 7.15 (1H, dt, J = 2.9, 8.8 Hz), 7.23-7.30 (2H, m), 7.40-7.47 (1H, m), 7.86-7.94 (1H, br), 7.97-8.05 (1H, br), 10.19 (1H, s), DMSO: 439 (M + H)$^+$FAB |
| 391 | 1.58-1.77 (2H, br), 1.91-2.06 (2H, br), 3.28-3.41 (1H, br), 3.45-3.57 (1H, br), 3.65-3.78 (1H, br), 3.82-3.94 (1H, br), 4.48-4.57 (1H, m), 5.07 (2H, s), 6.95 (4H, s), 7.11-7.18 (1H, m), 7.23-7.30 (2H, m), 7.40-7.47 (1H, m), 8.29-8.32 (1H, m), 8.78 (1H, d, J = 2.5 Hz), 8.91 (1H, d, J = 2.0 Hz), DMSO: 448 (M + H)$^+$FAB |
| 392 | 0.78-0.93 (2H, m), 1.04-1.26 (6H, m), 1.35-1.45 (2H, m), 1.54-1.74 (9H, m), 1.90-2.04 (2H, br), 3.28-3.55 (2H, m), 3.66-3.95 (4H, m), 4.46-4.54 (1H, m), 6.84 (2H, d, J = 8.8 Hz), 6.93 (2H, d, J = 8.8 Hz), 7.45 (1H, dd, J = 4.8, 8.4 Hz), 7.60-7.66 (1H, m), 8.41-8.45 (2H, m), DMSO: 453 (M + H)$^+$FAB |
| 393 | 415 (M + H)$^+$FAB |
| 394 | 387 (M + H)$^+$FAB |
| 395 | 1.06-1.20 (2H, m), 1.43-1.82 (10H, m), 1.86-2.05 (3H, m), 3.24-3.57 (2H, br), 3.68-3.94 (4H, m) 4.51-4.55 (1H, m), 6.85 (2H, d, J = 9.2 Hz), 6.93 (2H, d, J = 9.2 Hz), 8.08 (1H, dd, J = 1.6, 2.4 Hz), 8.66 (1H, d, J = 2.4 Hz), 8.92 (1H, d, J = 1.6 Hz), 13.38-13.84 (1H, br), DMSO: 455 (M + H)$^+$FAB |
| 396 | 1.21-1.42 (2H, m), 1.78-1.90 (2H, br), 1.93-2.06 (1H, m), 2.85-2.99 (1H, br), 3.01-3.15 (1H, br), 3.81 (2H, d, J = 8.0 Hz), 3.99-4.12 (1H, br), 4.15-4.27 (1H, br), 5.07 (2H, s), 6.88 (2H, d, J = 9.2 Hz), 6.94 (2H, d, J = 9.2 Hz), 7.11-7.18 (1H, m), 7.23-7.29 (2H, m), 7.39-7.47 (2H, m), 7.62 (1H, ddd, J = 1.2, 2.4, 8.0 Hz), 8.40-8.45 (1H, m), DMSO: 437 (M + H)$^+$FAB |
| 397 | 414 (M + H)$^+$FAB |
| 398 | 386 (M + H)$^+$FAB |
| 399 | 1.10-1.33 (2H, m), 1.45-1.61 (3H, m), 1.75-1.87 (2H, br), 2.64 (2H, t, J = 7.6 Hz), 2.80-3.10 (2H, br), 3.95-4.24 (2H, br), 7.12-7.32 (5H, m), 7.90 (2H, d, J = 8.4 Hz), 7.98-8.08 (3H, m), 8.43-8.49 (1H, m), 8.80-8.86 (1H, m), 12.80-13.30 (1H, m),, DMSO: 431 (M + H)$^+$FAB |

TABLE 62

| Ex No. | DAT $^1$H-NMR δ (ppm), solvent: MS m/z |
|---|---|
| 400 | 1.06-1.30 (2H, m), 1.56-1.80 (3H, m), 2.47-2.52 (2H, m), 2.76-2.91 (1H, br), 2.93-3.07 (1H, br), 3.92-4.05 (1H, br), 4.08-4.21 (1H, br), 5.10 (2H, s), 6.94 (2H, d, J = 8.0 Hz), 7.08-7.18 (3H, m), 7.24-7.31 (2H, m), 7.40-7.48 (1H, m), 7.71 (1H, dd, J = 4.8, 8.4 Hz), 7.93-7.99 (1H, m), 8.58 (1H, d, J = 4.4 Hz), 8.62-8.78 (1H, m), DMSO: 421 (M + H)$^+$FAB |
| 401 | 1.08-1.31 (2H, m), 1.58-1.79 (3H, m), 2.47-2.52 (2H, m), 2.76-3.05 (2H, br), 3.92-4.22 (2H, br), 5.10 (2H, s), 6.94 (2H, d, J = 8.4 Hz), 7.08-7.19 (3H, m), 7.24-7.31 (2H, m), 7.40-7.48 (1H, m), 7.98-8.03 (1H, m), 8.56-8.62 (1H, m), 8.87-8.93 (1H, br), DMSO: 465 (M + H)$^+$FAB |
| 402 | 1.07-1.28 (2H, br), 1.43-1.60 (3H, m), 1.73-1.82 (2H, br), 2.62 (2H, t, J = 7.8 Hz), 2.77-3.05 (2H, br), 3.92-4.20 (2H, br), 7.00 (1H, dd, J = 2.0, 2.4 Hz), 7.14-7.31 (5H, m), 8.04 (1H, dd, J = 2.0, 2.4 Hz), 7.86-7.94 (1H, br), 7.97-8.03 (1H, br), 10.06-10.26 (1H, br), DMSO: 327 (M + H)$^+$FAB |
| 403 | 351 (M + H)$^+$FAB |
| 404 | 395 (M + H)$^+$FAB |
| 405 | 503 (M + H)$^+$FAB |
| 406 | 453 (M + H)$^+$FAB |
| 407 | 1.02-1.51 (6H, m), 1.68-1.80 (4H, m), 2.28 (3H, s), 2.66-2.74 (2H, m), 2.82-3.09 (2H, m), 3.95-4.31 (4H, m), 6.43 (1H, d, J = 7.1 Hz), 6.56 (1H, d, J = 8.5 Hz), 7.34-7.39 (1H, m), 7.65-7.69 (1H, br), 7.99-8.01 (1H, m), 8.16-8.19 (1H, br), 8.55 (1H, d, J = 2.5 Hz), 8.88 (1H, d, J = 1.9 Hz), DMSO: 452 (M + H)$^+$FAB |
| 408 | 502 (M + H)$^+$FAB |
| 409 | 369 (M + H)$^+$FAB |
| 410 | 327 (M + H)$^+$FAB |
| 411 | 441 (M + H)$^+$ESI |
| 412 | 1.25-1.65 (6H, m), 2.25-2.48 (6H, m), 2.57 (2H, t, J = 7.8 Hz), 3.36-3.64 (4H, m), 7.12-7.30 (5H, m), 7.68 (1H, s), 8.03 (1H, t, J = 2.4 Hz), 8.19 (1H, s), 8.56 (1H, d, J = 2.4 Hz), 8.90 (1H, d, J = 1.5 Hz), DMSO: 397 (M + H)$^+$FAB |

TABLE 62-continued

| Ex No. | DAT $^1$H-NMR δ (ppm), solvent: MS m/z |
|---|---|
| 413 | 3.00-3.75 (6H, m), 4.01-4.38 (4H, m), 5.17 (2H, s), 7.10 (2H, d, J = 8.8 Hz), 7.13-7.21 (1H, m), 7.27-7.33 (2H, m), 7.42-7.49 (1H, m), 7.59 (2H, d, J = 8.8 Hz), 7.75 (1H, dd, J = 5.2, 7.6 Hz), 7.97-8.02 (1H, m), 8.62 (1H, d, J = 4.4 Hz), 8.70 (1H, d, J = 2.4 Hz), DMSO: 422 (M + H)$^+$FAB |
| 414 | 432 (M + H)$^+$FAB |
| 415 | 431 (M + H)$^+$FAB |
| 416 | 299 (M + H)$^+$FAB |
| 417 | 1.33 (3H, t, J = 6.8 Hz), 1.60-1.76 (2H, br), 1.91-2.07 (2H, br), 3.30-3.43 (1H, br), 3.46-3.60 (1H, br), 3.67-3.75 (1H, br), 3.83-3.96 (1H, br), 4.35 (2H, q, J = 6.8 Hz), 4.47-4.57 (1H, m), 5.07 (2H, s), 6.96 (4H, s), 7.11-7.19 (1H, m), 7.23-7.30 (2H, m), 7.40-7.47 (1H, m), 7.84 (1H, dd, J = 2.4, 8.8 Hz), 8.12 (1H, d, J = 8.8 Hz), 8.58 (1H, d, J = 2.4 Hz), DMSO: 495 (M + H)$^+$FAB |
| 418 | 1.58-1.77 (2H, br), 1.90-2.08 (2H, br), 3.28-3.60 (2H, br), 3.66-3.98 (2H, br), 4.47-4.54 (1H, m), 5.07 (2H, s), 6.96 (4H, s), 7.10-7.19 (1H, m), 7.21-7.32 (2H, m), 7.38-7.49 (1H, m), 7.69-7.77 (1H, m), 8.04 (1H, d, J = 8.6 Hz), 8.60-8.70 (1H, m), DMSO: 467 (M + H)$^+$FAB |
| 419 | 327 (M + H)$^+$FAB |
| 420 | 354 (M + H)$^+$FAB |
| 421 | 437 (M + H)$^+$FAB |
| 422 | 437 (M + H)$^+$FAB |
| 423 | 368 (M + H)$^+$FAB |

TABLE 63

| Ex No. | DAT $^1$H-NMR δ (ppm), solvent: MS m/z |
|---|---|
| 424 | 369 (M + H)$^+$ESI |
| 425 | 370 (M + H)$^+$FAB |
| 426 | 383 (M + H)$^+$ESI |
| 427 | 412 (M + H)$^+$FAB |
| 428 | 483 (M + H)$^+$FAB |
| 429 | 384 (M + H)$^+$FAB |
| 430 | 483 (M + H)$^+$ESI |
| 431 | 493 (M + H)$^+$ESI |
| 432 | 522 (M + H)$^+$ESI |
| 433 | 466 (M + H)$^+$FAB |
| 434 | 480 (M + H)$^+$ESI |
| 435 | 438 (M + H)$^+$ESI |
| 436 | 427 (M + H)$^+$ESI |
| 437 | 481 (M + H)$^+$FAB |

TABLE 64

| Ex No. | cell FAAH IC$_{50}$ (nM) |
|---|---|
| 002 | 0.11 |
| 003 | 0.073 |
| 009 | 0.67 |
| 010 | 0.10 |
| 013 | 0.27 |
| 014 | 0.20 |
| 015 | 0.033 |
| 017 | 0.18 |
| 018 | 0.35 |
| 019 | 0.072 |
| 021 | 0.23 |
| 023 | 0.040 |
| 030 | 0.19 |
| 033 | 0.077 |
| 034 | 0.046 |
| 036 | 0.044 |
| 037 | 0.69 |
| 038 | 0.028 |
| 039 | 0.30 |
| 042 | 0.43 |
| 043 | 0.21 |
| 044 | 0.095 |
| 046 | 0.41 |
| 047 | 0.13 |
| 049 | 0.10 |
| 051 | 0.26 |
| 053 | 0.063 |
| 055 | 0.44 |
| 061 | 0.35 |
| 063 | 0.12 |
| 065 | 0.41 |
| 066 | 0.057 |
| 069 | 0.095 |
| 070 | 0.099 |
| 077 | 0.071 |
| 078 | 0.081 |
| 080 | 0.044 |
| 081 | 0.012 |
| 088 | 0.37 |
| 085 | 0.44 |
| 098 | 0.26 |
| 099 | 0.099 |
| 100 | 0.035 |
| 101 | 0.078 |
| 103 | 0.092 |
| 104 | 0.066 |
| 108 | 0.052 |
| 113 | 0.056 |
| 115 | 0.052 |
| 116 | 0.078 |
| 122 | 0.15 |
| 124 | 0.35 |
| 126 | 0.58 |
| 138 | 0.078 |
| 144 | 0.093 |
| 147 | 0.28 |
| 149 | 0.45 |
| 151 | 0.17 |
| 152 | 0.18 |
| 154 | 0.17 |
| 155 | 0.061 |
| 159 | 0.23 |
| 160 | 0.51 |
| 173 | 0.69 |
| 174 | 0.60 |
| 175 | 0.37 |
| 176 | 0.84 |
| 179 | 0.060 |
| 197 | 0.11 |
| 199 | 0.58 |
| 200 | 0.30 |
| 206 | 0.17 |
| 207 | 0.31 |

TABLE 64-continued

| Ex No. | cell FAAH IC$_{50}$ (nM) |
|---|---|
| 208 | 0.13 |
| 218 | 0.44 |
| 225 | 0.89 |
| 228 | 0.22 |
| 261 | 0.54 |
| 263 | 0.036 |
| 266 | 0.31 |
| 268 | 0.15 |
| 269 | 0.081 |
| 270 | 0.17 |
| 272 | 0.48 |
| 274 | 0.37 |
| 281 | 0.082 |
| 283 | 0.43 |
| 284 | 0.36 |
| 285 | 0.47 |
| 287 | 0.031 |
| 289 | 0.16 |
| 292 | 0.65 |
| 293 | 0.24 |
| 294 | 0.60 |
| 300 | 0.43 |
| 301 | 0.40 |
| 302 | 0.17 |
| 303 | 0.12 |
| 304 | 0.24 |
| 313 | 0.89 |
| 315 | 0.51 |
| 318 | 0.062 |
| 319 | 0.24 |
| 320 | 0.081 |
| 321 | 0.040 |
| 322 | 0.058 |
| 323 | 0.085 |
| 324 | 0.50 |
| 325 | 0.54 |
| 326 | 0.13 |
| 327 | 0.12 |
| 328 | 0.42 |
| 329 | 0.39 |
| 330 | 0.53 |
| 333 | 0.43 |
| 334 | 0.048 |
| 335 | 0.075 |
| 338 | 0.034 |
| 339 | 0.12 |
| 340 | 0.052 |
| 341 | 0.078 |
| 342 | 0.33 |
| 344 | 0.13 |
| 345 | 0.18 |
| 346 | 0.27 |
| 349 | 0.054 |
| 351 | 0.13 |
| 359 | 0.52 |
| 362 | 0.42 |
| 364 | 0.14 |
| 371 | 0.21 |
| 372 | 0.49 |
| 373 | 0.49 |
| 376 | 0.21 |
| 378 | 0.20 |
| 380 | 0.35 |

TABLE 65

| Com No | R$^1$ | R$^4$ |
|---|---|---|
| 1 | HO$_2$C(CH$_2$)$_3$ | H |
| 2 | Mo4(CH$_2$)$_2$NHCO(CH$_2$)$_3$ | H |
| 3 | 4-HexOPh(CH$_2$)$_2$NHCO | CO$_2$H |
| 4 | 4-OctPhNHCO | CO$_2$H |
| 5 | Ph(CH$_2$)$_2$CONH | CO$_2$Me |
| 6 | Ph(CH$_2$)$_2$CONH | H |
| 7 | Ph(CH$_2$)$_2$CONH | CO$_2$H |
| 8 | Ph(CH$_2$)$_4$NHCO | CO$_2$H |
| 9 | 4-BuPhNHCO | CO$_2$H |
| 10 | 4-HexPhNHCO | CO$_2$H |
| 11 | Py2(CH$_2$)$_2$NHCO | H |
| 12 | Py3(CH$_2$)$_2$NHCO | H |
| 13 | Ph(CH$_2$)$_4$NHCO | CONH$_2$ |
| 14 | 4-BuPhNHCO | CONH$_2$ |
| 15 | Ph(CH$_2$)$_3$O(CH$_2$)$_2$ | CO$_2$H |
| 16 | 2-H$_2$NCOPhO(CH$_2$)$_3$ | CO$_2$H |
| 17 | 4-(3-FPhCH$_2$O)PhO | tetrazolyl-methyl |
| 18 | Ph(CH$_2$)$_2$ | 4-carboxyphenyl |
| 19 | 1-MeBenzIM 2 (CH$_2$)$_3$ | CO$_2$H |
| 20 | Ph(CH$_2$)$_2$ | CO$_2$Me |
| 21 | 3-PIPE1Ph(CH$_2$)$_2$ | CO$_2$H |
| 22 | azetidinyl-CO-Ph-propyl | CO$_2$H |
| 23 | Mo4CH$_2$ | H |
| 24 | Mo4(CH$_2$)$_2$ | CO$_2$Me |
| 25 | 4-(3-FPhCH$_2$)PIPERA1(CH$_2$)$_2$ | CO$_2$Me |
| 26 | Mo4(CH$_2$)$_3$ | CO$_2$Me |
| 27 | 4-(3-FPhCH$_2$PIPERA1(CH$_2$)$_2$ | H |
| 28 | Mo(CH$_2$)$_3$ | H |
| 29 | cPen(CH$_2$)$_2$ | H |
| 30 | cPen(CH$_2$)$_2$ | CO$_2$Me |
| 31 | cPen(CH$_2$)$_2$ | CO$_2$H |
| 32 | cPen(CH$_2$)$_2$ | CONH$_2$ |
| 33 | cHexCH$_2$ | H |
| 34 | cHexCH$_2$ | CO$_2$Me |
| 35 | cHexCH$_2$ | CO$_2$H |
| 36 | cHexCH$_2$ | CONH$_2$ |
| 37 | cHex(CH$_2$)$_3$ | H |
| 38 | cHex(CH$_2$)$_3$ | CO$_2$Me |
| 39 | cHex(CH$_2$)$_3$ | CO$_2$H |
| 40 | cHex(CH$_2$)$_3$ | CONH$_2$ |
| 41 | Ph(CH$_2$)$_3$ | H |
| 42 | Ph(CH$_2$)$_3$ | CONH$_2$ |
| 43 | 3-FPh(CH$_2$)$_3$ | H |
| 44 | 3-FPh(CH$_2$)$_3$ | CO$_2$Me |
| 45 | 3-FPh(CH$_2$)$_3$ | CO$_2$H |
| 46 | 3-FPh(CH$_2$)$_3$ | CONH$_2$ |
| 47 | 3-ClPh(CH$_2$)$_3$ | H |
| 48 | 3-ClPh(CH$_2$)$_3$ | CO$_2$Me |
| 49 | 3-ClPh(CH$_2$)$_3$ | CO$_2$H |

TABLE 65-continued

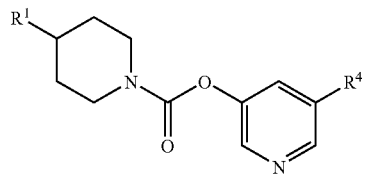

| Com No | R¹ | R⁴ |
|---|---|---|
| 50 | 3-ClPh(CH₂)₃ | CONH₂ |
| 51 | 3-NCPh(CH₂)₃ | H |
| 52 | 3-NCPh(CH₂)₃ | CO₂Me |
| 53 | 3-NCPh(CH₂)₃ | CO₂H |
| 54 | 3-NCPh(CH₂)₃ | CONH₂ |
| 55 | 3-MeOPh(CH₂)₃ | H |
| 56 | 3-MeOPh(CH₂)₃ | CO₂Me |
| 57 | 3-MeOPh(CH₂)₃ | CO₂H |
| 58 | 3-MeOPh(CH₂)₃ | CONH₂ |
| 59 | 4-FPh(CH₂)₃ | H |
| 60 | 4-FPh(CH₂)₃ | CO₂Me |
| 61 | 4-FPh(CH₂)₃ | CO₂H |
| 62 | 4-FPh(CH₂)₃ | CONH₂ |

TABLE 66

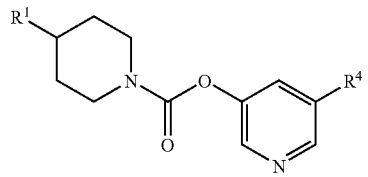

| Com No | R¹ | R⁴ |
|---|---|---|
| 63 | 4-ClPh(CH₂)₃ | H |
| 64 | 4-ClPh(CH₂)₃ | CO₂Me |
| 65 | 4-ClPh(CH₂)₃ | CO₂H |
| 66 | 4-ClPh(CH₂)₃ | CONH₂ |
| 67 | 4-NCPh(CH₂)₃ | H |
| 68 | 4-NCPh(CH₂)₃ | CO₂Me |
| 69 | 4-NCPh(CH₂)₃ | CO₂H |
| 70 | 4-NCPh(CH₂)₃ | CONH₂ |
| 71 | 4-MeOPh(CH₂)₃ | H |
| 72 | 4-MeOPh(CH₂)₃ | CO₂Me |
| 73 | 4-MeOPh(CH₂)₃ | CO₂H |
| 74 | 4-MeOPh(CH₂)₃ | CONH₂ |
| 75 | 2-FPh(CH₂)₃ | H |
| 76 | 2-FPh(CH₂)₃ | CO₂Me |
| 77 | 2-FPh(CH₂)₃ | CO₂H |
| 78 | 2-FPh(CH₂)₃ | CONH₂ |
| 79 | 2-ClPh(CH₂)₃ | H |
| 80 | 2-ClPh(CH₂)₃ | CO₂Me |
| 81 | 2-ClPh(CH₂)₃ | CO₂H |
| 82 | 2-ClPh(CH₂)₃ | CONH₂ |
| 83 | 2-NCPh(CH₂)₃ | H |
| 84 | 2-NCPh(CH₂)₃ | CO₂Me |
| 85 | 2-NCPh(CH₂)₃ | CO₂H |
| 86 | 2-NCPh(CH₂)₃ | CONH₂ |
| 87 | 2-MeOPh(CH₂)₃ | H |
| 88 | 2-MeOPh(CH₂)₃ | CO₂Me |
| 89 | 2-MeOPh(CH₂)₃ | CO₂H |
| 90 | 2-MeOPh(CH₂)₃ | CONH₂ |
| 91 | 3,4-diFPh(CH₂)₃ | H |
| 92 | 3,4-diFPh(CH₂)₃ | CO₂Me |
| 93 | 3,4-diFPh(CH₂)₃ | CO₂H |
| 94 | 3,4-diFPh(CH₂)₃ | CONH₂ |
| 95 | 3,5-diFPh(CH₂)₃ | H |
| 96 | 3,5-diFPh(CH₂)₃ | CO₂Me |
| 97 | 3,5-diFPh(CH₂)₃ | CO₂H |

TABLE 66-continued

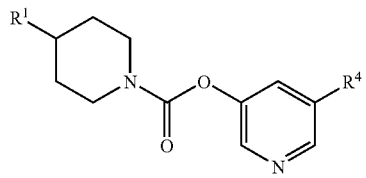

| Com No | R¹ | R⁴ |
|---|---|---|
| 98 | 3,5-diFPh(CH₂)₃ | CONH₂ |
| 99 | 2,5-diFPh(CH₂)₃ | H |
| 100 | 2,5-diFPh(CH₂)₃ | CO₂Me |
| 101 | 2,5-diFPh(CH₂)₃ | CO₂H |
| 102 | 2,5-diFPh(CH₂)₃ | CONH₂ |
| 103 | 3-NC-5-FPh(CH₂)₃ | H |
| 104 | 3-NC-5-FPh(CH₂)₃ | CO₂Me |
| 105 | 3-NC-5-FPh(CH₂)₃ | CO₂H |
| 106 | 3-NC-5-FPh(CH₂)₃ | CONH₂ |
| 107 | 3-FPh(CH₂)₂ | H |
| 108 | 3-ClPh(CH₂)₂ | H |
| 109 | 3-NCPh(CH₂)₂ | H |
| 110 | 3-MeOPh(CH₂)₂ | H |
| 111 | 3-H₂NCOPh(CH₂)₂ | H |
| 112 | 3-Me₂NCOPh(CH₂)₂ | H |
| 113 | 3-PIPE1COPh(CH₂)₂ | H |
| 114 | 3-PYRR1COPh(CH₂)₂ | H |
| 115 | 3-EtNHCOPh(CH₂)₂ | H |
| 116 | 3-Et₂NCOPh(CH₂)₂ | H |
| 117 | 3-cHexNHCOPh(CH₂)₂ | H |
| 118 | 4-FPh(CH₂)₂ | H |
| 119 | 4-ClPh(CH₂)₂ | H |
| 120 | 4-NCPh(CH₂)₂ | H |
| 121 | 4-MeOPh(CH₂)₂ | H |
| 122 | 4-Me₂NCOPh(CH₂)₂ | H |
| 123 | 4-PIPE1COPh(CH₂)₂ | H |
| 124 | 4-PYRR1COPh(CH₂)₂ | H |
| 125 | 4-EtNHCOPh(CH₂)₂ | H |
| 126 | 4-Et₂NCOPh(CH₂)₂ | H |

TABLE 67

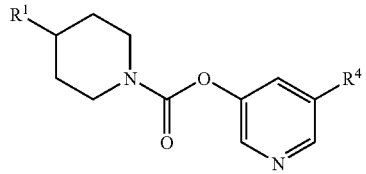

| Com No | R¹ | R⁴ |
|---|---|---|
| 127 | 4-cHexNHCOPh(CH₂)₂ | H |
| 128 | 2-FPh(CH₂)₂ | H |
| 129 | 2-ClPh(CH₂)₂ | H |
| 130 | 2-NCPh(CH₂)₂ | H |
| 131 | 2-MeOPh(CH₂)₂ | H |
| 132 | 3,4-diFPh(CH₂)₂ | H |
| 133 | 3,4-diFPh(CH₂)₂ | CO₂Me |
| 134 | 3,4-diFPh(CH₂)₂ | CO₂H |
| 135 | 3,4-diFPh(CH₂)₂ | CONH₂ |
| 136 | 3,5-diFPh(CH₂)₂ | H |
| 137 | 3,5-diFPh(CH₂)₂ | CO₂Me |
| 138 | 3,5-diFPh(CH₂)₂ | CO₂H |
| 139 | 3,5-diFPh(CH₂)₂ | CONH₂ |
| 140 | 2,5-diFPh(CH₂)₂ | H |

TABLE 67-continued

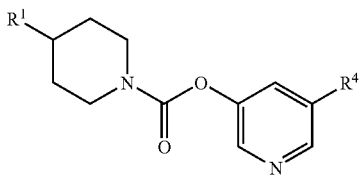

| Com No | R¹ | R⁴ |
|---|---|---|
| 141 | 2,5-diFPh(CH₂)₂ | CO₂Me |
| 142 | 2,5-diFPh(CH₂)₂ | CO₂H |
| 143 | 2,5-diFPh(CH₂)₂ | CONH₂ |
| 144 | 3-Cl-4-FPh(CH₂)₂ | H |
| 145 | 3-Cl-4-FPh(CH₂)₂ | CO₂Me |
| 146 | 3-Cl-4-FPh(CH₂)₂ | CO₂H |
| 147 | 3-Cl-4-FPh(CH₂)₂ | CONH₂ |
| 148 | 3-Cl-5-FPh(CH₂)₂ | H |
| 149 | 3-Cl-5-FPh(CH₂)₂ | CO₂Me |
| 150 | 3-Cl-5-FPh(CH₂)₂ | CO₂H |
| 151 | 3-Cl-5-FPh(CH₂)₂ | CONH₂ |
| 152 | 2-F-5-ClPh(CH₂)₂ | H |
| 153 | 2-F-5-ClPh(CH₂)₂ | CO₂Me |
| 154 | 2-F-5-ClPh(CH₂)₂ | CO₂H |
| 155 | 2-F-5-ClPh(CH₂)₂ | CONH₂ |
| 156 | 3-MeO-4-FPh(CH₂)₂ | H |
| 157 | 3-MeO-4-FPh(CH₂)₂ | CO₂Me |
| 158 | 3-MeO-4-FPh(CH₂)₂ | CO₂H |
| 159 | 3-MeO-4-FPh(CH₂)₂ | CONH₂ |
| 160 | 3-F-5-MeOPh(CH₂)₂ | H |
| 161 | 3-F-5-MeOPh(CH₂)₂ | CO₂Me |
| 162 | 3-F-5-MeOPh(CH₂)₂ | CO₂H |
| 163 | 3-F-5-MeOPh(CH₂)₂ | CONH₂ |
| 164 | 2-F-5-MeOPh(CH₂)₂ | H |
| 165 | 2-F-5-MeOPh(CH₂)₂ | CO₂Me |
| 166 | 2-F-5-MeOPh(CH₂)₂ | CO₂H |
| 167 | 2-F-5-MeOPh(CH₂)₂ | CONH₂ |
| 168 | 2,4-diFPh(CH₂)₂ | H |
| 169 | 2,4-diFPh(CH₂)₂ | CO₂Me |
| 170 | 2,4-diFPh(CH₂)₂ | CO₂H |
| 171 | 2,4-diFPh(CH₂)₂ | CONH₂ |
| 172 | 2-F-4-ClPh(CH₂)₂ | H |
| 173 | 2-F-4-ClPh(CH₂)₂ | CO₂Me |
| 174 | 2-F-4-ClPh(CH₂)₂ | CO₂H |
| 175 | 2-F-4-ClPh(CH₂)₂ | CONH₂ |
| 176 | 2-F-4-NCPh(CH₂)₂ | H |
| 177 | 2-F-4-NCPh(CH₂)₂ | CO₂Me |
| 178 | 2-F-4-NCPh(CH₂)₂ | CO₂H |
| 179 | 2-F-4-NCPh(CH₂)₂ | CONH₂ |
| 180 | 2-F-4-MeOPh(CH₂)₂ | H |
| 181 | 2-F-4-MeOPh(CH₂)₂ | CO₂Me |
| 182 | 2-F-4-MeOPh(CH₂)₂ | CO₂H |
| 183 | 2-F-4-MeOPh(CH₂)₂ | CONH₂ |
| 184 | BIP3(CH₂)₂ | H |
| 185 | 3'-FBIP3(CH₂)₂ | H |
| 186 | 3'-NCBIP3(CH₂)₂ | H |
| 187 | 3'-MeOBIP3(CH₂)₂ | H |
| 188 | 3',4'-diFBIP3(CH₂)₂ | H |
| 189 | 3'-MeO-4'-FBIP3(CH₂)₂ | H |
| 190 | BIP4(CH₂)₂ | H |
| 191 | 3'-FBIP4(CH₂)₂ | H |
| 192 | 3'-NCBIP4(CH₂)₂ | H |

TABLE 68

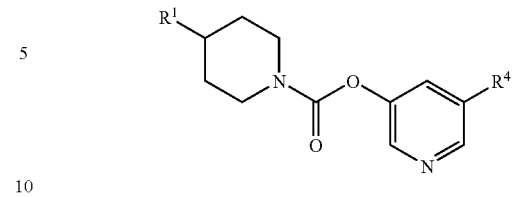

| Com No | R¹ | R⁴ |
|---|---|---|
| 193 | 3'-MeOBIP4(CH₂)₂ | H |
| 194 | 3',4'-diFBIP4(CH₂)₂ | H |
| 195 | 3'-MeO-4'-FBIP4(CH₂)₂ | H |
| 196 | 3-Py2Ph(CH₂)₂ | H |
| 197 | 3-MeOPhNHCO | H |
| 198 | 4-MeOPhNHCO | H |
| 199 | 3-MeO-4-FPhNHCO | H |
| 200 | 3-F-5-MeOPhNHCO | H |
| 201 | 2-F-5-MeOPhNHCO | H |
| 202 | 3-F-4-MeOPhNHCO | H |
| 203 | 2-F-4-MeOPhNHCO | H |
| 204 | 1-(6-MePy2)PIPE4(CH₂)₃ | H |
| 205 | 1-(6-MePy2)PIPE4CH₂ | H |
| 206 | 1-PhCOPIPE4(CH₂)₃ | H |
| 207 | 1-(6-MePy2)PIPE4(CH₂)₂ | H |
| 208 | 1-(6-MePy2)PIPERA4(CH₂)₃ | H |
| 209 | 1-QUI2PIPE4(CH₂)₃ | H |
| 210 | 1-ISOQUI1PIPE4(CH₂)₃ | H |
| 211 | 1-ISOQUI1PIPERA4(CH₂)₃ | H |
| 212 | 1-NAPH1PIPE4(CH₂)₃ | H |
| 213 | PhC≡C– | H |
| 214 | PhC≡C– | CONH₂ |

TABLE 69

| Com No | R¹ | R⁴ |
|---|---|---|
| 215 | Ph(CH₂)₄ | CO₂H |
| 216 | Ph | CO₂H |
| 217 | Ph(CH₂)₃ | CONH(CH₂)₂OH |
| 218 | Ph(CH₂)₅ | CO₂H |
| 219 | cHex(CH₂)₂ | H |
| 220 | Ph(CH₂)₄ | H |
| 221 | Ph(CH₂)₃ | H |
| 222 | 3-MePh(CH₂)₂ | H |
| 223 | 3-MeOPh(CH₂)₂ | H |
| 224 | 3-FPh(CH₂)₂ | H |
| 225 | 3-NCPh(CH₂)₂ | H |
| 226 | 4-MePh(CH₂)₂ | H |
| 227 | 4-MeOPh(CH₂)₂ | H |
| 228 | 4-FPh(CH₂)₂ | H |
| 229 | 4-NCPh(CH₂)₂ | H |
| 230 | 2-MePh(CH₂)₂ | H |
| 231 | 2-MeOPh(CH₂)₂ | H |
| 232 | 2-FPh(CH₂)₂ | H |

TABLE 69-continued

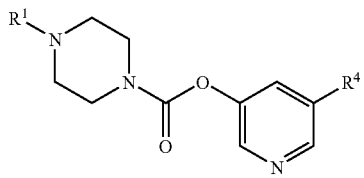

| Com No | R¹ | R⁴ |
|---|---|---|
| 233 | 2-NCPh(CH₂)₂ | H |
| 234 | 3-Me-4-FPh(CH₂)₂ | H |
| 235 | 3-F-5-MePh(CH₂)₂ | H |
| 236 | 2-F-5-MePh(CH₂)₂ | H |
| 237 | 3-MeO-4-FPh(CH₂)₂ | H |
| 238 | 3-F-5-MeOPh(CH₂)₂ | H |
| 239 | 2-F-5-MeOPh(CH₂)₂ | H |
| 240 | 3,4-diFPh(CH₂)₂ | H |
| 241 | 3,5-diFPh(CH₂)₂ | H |
| 242 | 2,5-diFPh(CH₂)₂ | H |
| 243 | 3-iPrOPh(CH₂)₂ | H |
| 244 | 3-NC-4-FPh(CH₂)₂ | H |
| 245 | 4-tBucHex(CH₂)₂ | H |
| 246 | 3-H₂NCOPh(CH₂)₂ | H |
| 247 | 1-(6-MePy2)PIPE4(CH₂)₃ | H |
| 248 | 3-cHexCH₂OPhCO | CONH₂ |
| 249 | 3-cHex(CH₂)₂OPhCO | CONH₂ |
| 250 | 3-cHepCH₂OPhCO | CONH₂ |
| 251 | 3-PhCH₂OPhCO | CONH₂ |
| 252 | 4-PhCH₂OPhCO | CONH₂ |
| 253 | 3-cOctCH₂OPhCO | CONH₂ |
| 254 | 4-cHexCH₂N(Me)PhCO | CONH₂ |
| 255 | 4-(3-ClPhCH₂O)PhCO | CONH₂ |
| 256 | 4-(3-F₃CPhCH₂O)PhCO | CONH₂ |
| 257 | 4-(3-MeOPhCH₂O)PhCO | CONH₂ |
| 258 | 4-(3-NCPhCH₂O)PhCO | CONH₂ |
| 259 | 4-(3,5-diFPhCH₂O)PhCO | CONH₂ |
| 260 | 4-cHexCH₂OPhCO | CONH₂ |
| 261 | PhCH₂OCO | CONH₂ |
| 262 | 4-tBuOPhCO | CONH₂ |
| 263 | 4-PhCH₂OPhCH₂ | CONH₂ |
| 264 | 4-H₂NCOPhOCH₂CO | CONH₂ |
| 265 | Ph(CH₂)₂OCO | CONH₂ |
| 266 | 3-MePh(CH₂)₂ | CONH₂ |
| 267 | 3-MeOPh(CH₂)₂ | CONH₂ |
| 268 | 3-FPh(CH₂)₂ | CONH₂ |
| 269 | 3-NCPh(CH₂)₂ | CONH₂ |
| 270 | 4-MePh(CH₂)₂ | CONH₂ |
| 271 | 4-MeOPh(CH₂)₂ | CONH₂ |
| 272 | 4-FPh(CH₂)₂ | CONH₂ |
| 273 | 4-NCPh(CH₂)₂ | CONH₂ |
| 274 | 2-MePh(CH₂)₂ | CONH₂ |
| 275 | 2-MeOPh(CH₂)₂ | CONH₂ |
| 276 | 2-FPh(CH₂)₂ | CONH₂ |
| 277 | 2-NCPh(CH₂)₂ | CONH₂ |
| 278 | 3-MeO-4-FPh(CH₂)₂ | CONH₂ |
| 279 | 2-F-3-MeOPh(CH₂)₂ | CONH₂ |
| 280 | 2-F-5-MeOPh(CH₂)₂ | CONH₂ |
| 281 | 3-Me-4-FPh(CH₂)₂ | CONH₂ |
| 282 | 3-F-5-MePh(CH₂)₂ | CONH₂ |

TABLE 70

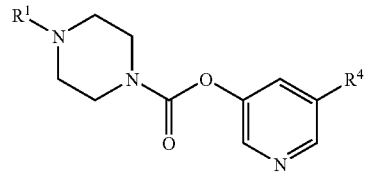

| Com No | R¹ | R⁴ |
|---|---|---|
| 283 | 2-F-5-MePh(CH₂)₂ | CONH₂ |
| 284 | 3,4-diFPh(CH₂)₂ | CONH₂ |
| 285 | 3,5-diFPh(CH₂)₂ | CONH₂ |
| 286 | 2,5-diFPh(CH₂)₂ | CONH₂ |
| 287 | 4-tBucHex(CH₂)₂ | CONH₂ |
| 288 | 3-cHexCH₂OPhCO | CO₂Me |
| 289 | 3-cHex(CH₂)₂OPhCO | CO₂Me |
| 290 | 3-cHepCH₂OPhCO | CO₂Me |
| 291 | 3-PhCH₂OPhCO | CO₂Me |
| 292 | 4-PhCH₂OPhCO | CO₂Me |
| 293 | 3-cOctCH₂OPhCO | CO₂Me |
| 294 | 4-[3-FPhCH₂N(Me)]PhCO | CO₂Me |
| 295 | 4-[3,4-diFPhCH₂N(Me)]PhCO | CO₂Me |
| 296 | 4-[3,5-diFPhCH₂N(Me)]PhCO | CO₂Me |
| 297 | 4-[2,5-diFPhCH₂N(Me)]PhCO | CO₂Me |
| 298 | 4-cHexCH₂N(Me)PhCO | CO₂Me |
| 299 | 4-(3-ClPhCH₂O)PhCO | CO₂Me |
| 300 | 4-(3-F₃CPhCH₂O)PhCO | CO₂Me |
| 301 | 4-(3-MeOPhCH₂O)PhCO | CO₂Me |
| 302 | 4-(3-MeO-4-FPhCH₂O)PhCO | CO₂Me |
| 303 | 4-(3-F-5-MeOPhCH₂O)PhCO | CO₂Me |
| 304 | 4-(3-NCPhCH₂O)PhCO | CO₂Me |
| 305 | 4-(3,5-diFPhCH₂O)PhCO | CO₂Me |
| 306 | 4-cHexCH₂OPhCO | CO₂Me |
| 307 | PhCH₂OCO | CO₂Me |
| 308 | 4-tBuOPhCO | CO₂Me |
| 309 | 4-PhCH₂OPhCH₂ | CO₂Me |
| 310 | 4-H₂NCOPhOCH₂CO | CO₂Me |
| 311 | Ph(CH₂)₂OCO | CO₂Me |
| 312 | 3-Cl-4-(3-NCPhCH₂O)PhCO | CO₂Me |
| 313 | 2-Cl-4-(3-NCPhCH₂O)PhCO | CO₂Me |
| 314 | 4-[3-FPhCH₂N(Me)]PhCO | CO₂H |
| 315 | 4-cHexCH₂N(Me)PhCO | CO₂H |
| 316 | 4-(3-ClPhCH₂O)PhCO | CO₂H |
| 317 | 3-MePh(CH₂)₂ | CO₂Me |
| 318 | 3-MeOPh(CH₂)₂ | CO₂Me |
| 319 | 3-FPh(CH₂)₂ | CO₂Me |
| 320 | 3-NCPh(CH₂)₂ | CO₂Me |
| 321 | 4-MePh(CH₂)₂ | CO₂Me |
| 322 | 4-MeOPh(CH₂)₂ | CO₂Me |
| 323 | 4-FPh(CH₂)₂ | CO₂Me |
| 324 | 4-NCPh(CH₂)₂ | CO₂Me |
| 325 | 2-MePh(CH₂)₂ | CO₂Me |
| 326 | 2-MeOPh(CH₂)₂ | CO₂Me |
| 327 | 2-FPh(CH₂)₂ | CO₂Me |
| 328 | 2-NCPh(CH₂)₂ | CO₂Me |
| 329 | 3-Me-4-FPh(CH₂)₂ | CO₂Me |
| 330 | 2-F-5-MePh(CH₂)₂ | CO₂Me |
| 331 | 3-F-5-MePh(CH₂)₂ | CO₂Me |
| 332 | 3-MeO-4-FPh(CH₂)₂ | CO₂Me |
| 333 | 2-F-5-MeOPh(CH₂)₂ | CO₂Me |
| 334 | 3-F-5-MeOPh(CH₂)₂ | CO₂Me |
| 335 | 3,4-diFPh(CH₂)₂ | CO₂Me |
| 336 | 2,5-diFPh(CH₂)₂ | CO₂Me |
| 337 | 3,5-diFPh(CH₂)₂ | CO₂Me |
| 338 | 4-tBucHex(CH₂)₂ | CO₂Me |
| 339 | 3-cHexCH₂OPhCO | CO₂H |
| 340 | 3-cHex(CH₂)₂OPhCO | CO₂H |
| 341 | 3-cHepCH₂OPhCO | CO₂H |
| 342 | 3-PhCH₂OPhCO | CO₂H |
| 343 | 4-PhCH₂OPhCO | CO₂H |
| 344 | 3-cOctCH₂OPhCO | CO₂H |
| 345 | 4-(3-F₃CPhCH₂O)PhCO | CO₂H |
| 346 | 4-(3-MeOPhCH₂O)PhCO | CO₂H |
| 347 | 4-(3-NCPhCH₂O)PhCO | CO₂H |
| 348 | 4-(3,5-diFPhCH₂O)PhCO | CO₂H |

TABLE 70-continued

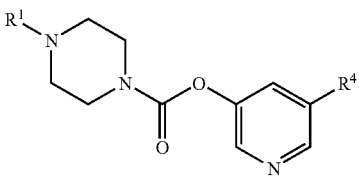

| Com No | R¹ | R⁴ |
|---|---|---|
| 349 | 4-cHexCH₂OPhCO | CO₂H |
| 350 | PhCH₂OCO | CO₂H |

TABLE 71

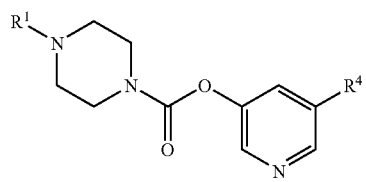

| Com No | R¹ | R⁴ |
|---|---|---|
| 351 | 4-tBuOPhCO | CO₂H |
| 352 | 4-PhCH₂OPhCH₂ | CO₂H |
| 353 | 4-H₂NCOPhOCH₂CO | CO₂H |
| 354 | Ph(CH₂)₂OCO | CO₂H |

TABLE 71-continued

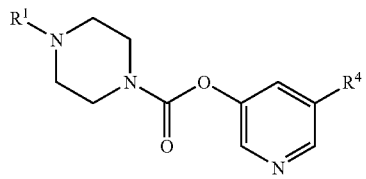

| Com No | R¹ | R⁴ |
|---|---|---|
| 355 | 3-Cl-4-(3-NCPhCH₂O)PhCO | CO₂H |
| 356 | 2-Cl-4-(3-NCPhCH₂O)PhCO | CO₂H |
| 357 | 3-MePh(CH₂)₂ | CO₂H |
| 358 | 3-MeOPh(CH₂)₂ | CO₂H |
| 359 | 3-FPh(CH₂)₂ | CO₂H |
| 360 | 3-NCPh(CH₂)₂ | CO₂H |
| 361 | 4-tBucHex(CH₂)₂ | CO₂H |
| 362 | 4-(4-FPhCH₂O)PhCO | CONH₂ |
| 363 | 4-(4-FPhCH₂O)PhCO | CO₂Me |
| 364 | 4-(4-FPhCH₂O)PhCO | CO₂H |
| 365 | 4-(3,4-diFPhCH₂O)PhCO | CONH₂ |
| 366 | 4-(3,4-diFPhCH₂O)PhCO | CO₂Me |
| 367 | 4-(2,4-diFPhCH₂O)PhCO | CONH₂ |
| 368 | 4-(2,4-diFPhCH₂O)PhCO | CO₂Me |
| 369 | Ph(CH₂)₂ | CONH₂ |
| 370 | Ph(CH₂)₄ | CONH₂ |
| 371 | 4-[3-FPhCH₂N(Me)]PhCO | CONH₂ |
| 372 | 4-[3,4-diFPhCH₂N(Me)]PhCO | CONH₂ |
| 373 | 4-[3,5-diFPhCH₂N(Me)]PhCO | CONH₂ |
| 374 | 4-[3-MeO-4-FPhCH₂N(Me)]PhCO | CONH₂ |
| 375 | 4-[3-F-5-MeOPhCH₂N(Me)]PhCO | CONH₂ |
| 376 | 3-Cl-4-(3-NCPhCH₂O)PhCO | CONH₂ |
| 377 | 2-Cl-4-(3-NCPhCH₂O)PhCO | CONH₂ |

TABLE 72

| Com No | Str |
|---|---|
| 378 | ![structure] |
| 379 | ![structure] |
| 380 | ![structure] |

TABLE 72-continued
| Com No | Str |
|---|---|
| 381 | 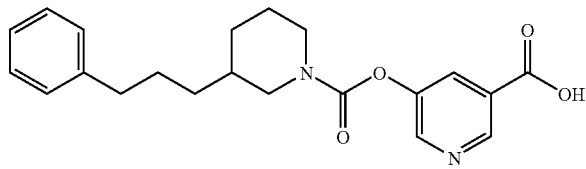 |
| 382 | 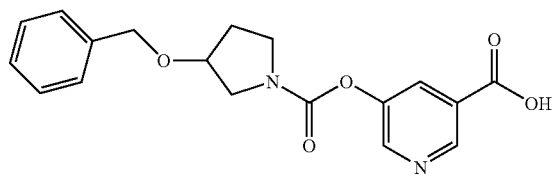 |
| 383 | 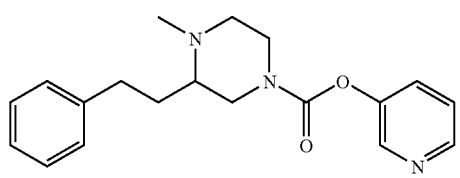 |
| 384 | 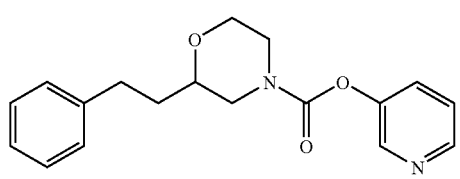 |
| 385 | 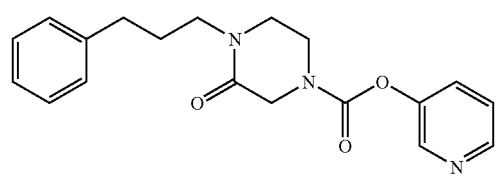 |
| 386 | 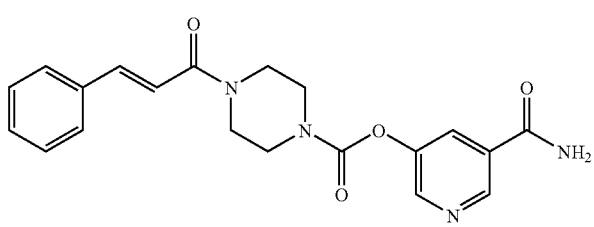 |
| 387 | 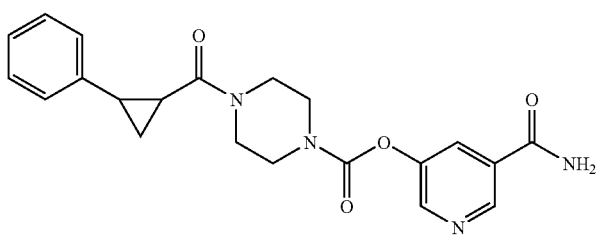 |
| 388 | 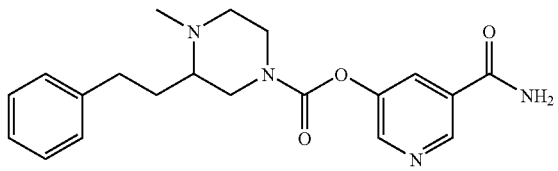 |

US 7,919,495 B2
173                                                                 174
TABLE 72-continued
| Com No | Str |
|---|---|
| 389 | 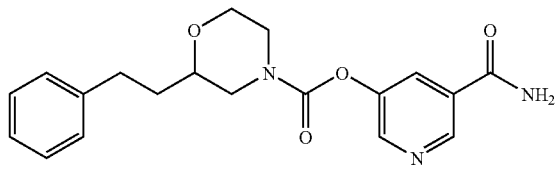 |
| 390 | 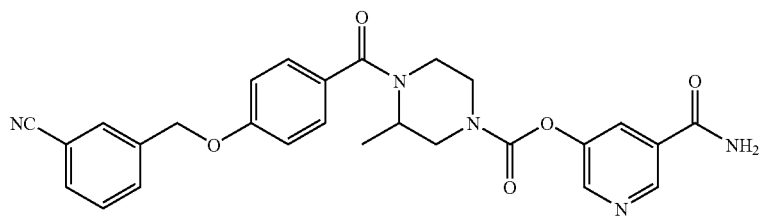 |
| 391 | 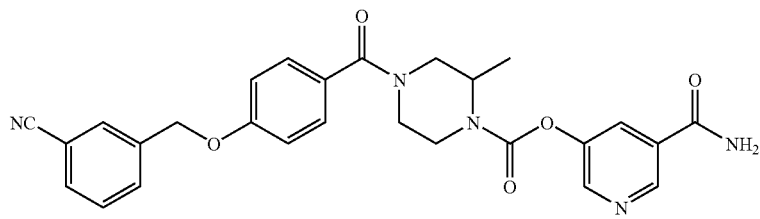 |
| 392 | 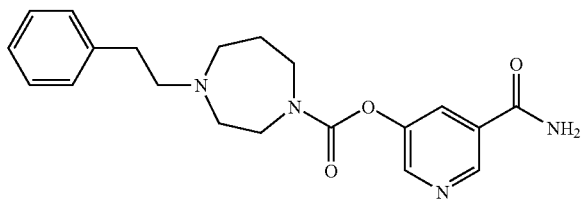 |
| 393 | 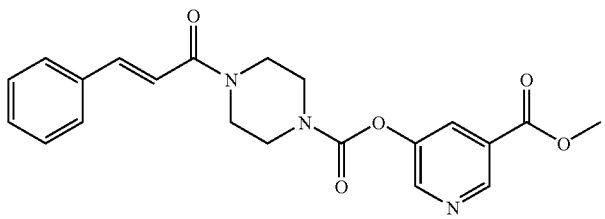 |
| 394 | 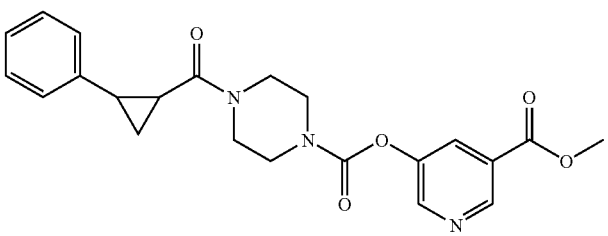 |
| 395 | 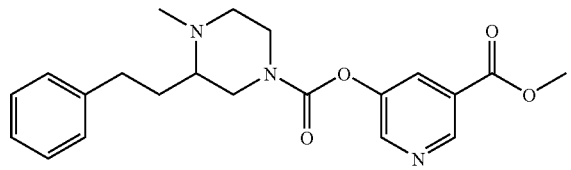 |

TABLE 72-continued

| Com No | Str |
|---|---|
| 396 | |
| 397 | |
| 398 | |
| 399 | |

TABLE 73

| Com No | Str |
|---|---|
| 400 | |
| 401 | |

TABLE 73-continued

| Com No | Str |
|---|---|
| 402 | 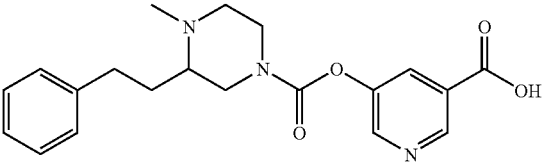 |
| 403 | 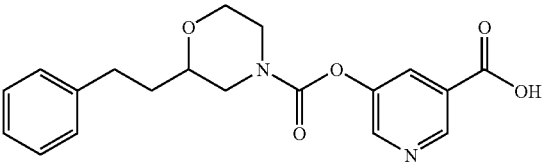 |
| 404 | 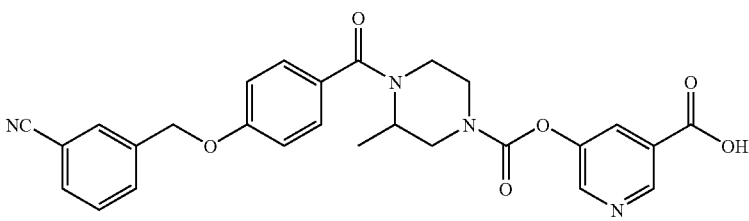 |
| 405 | 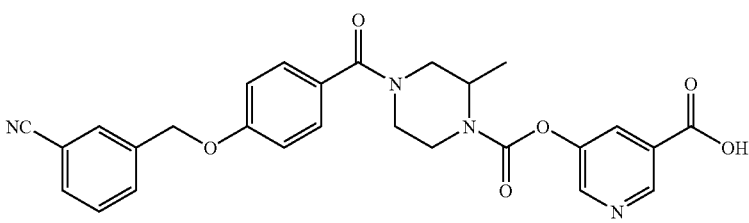 |
| 406 | 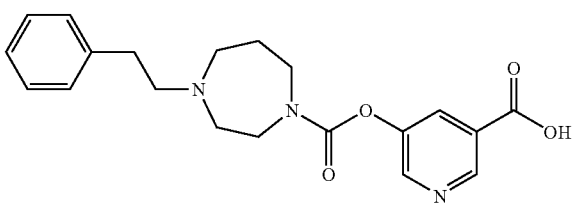 |

INDUSTRIAL APPLICABILITY

The compounds of the present invention have an excellent FAAH-inhibitory activity, and are useful for treatment of FAAH-associated disorders, especially urinary frequency and urinary incontinence, overactive bladder and/or pain.

SEQUENCE LISTING FREE TEXT

The inventor is shown in the numeral entry <223> of SEQ ID NO:1 in the following sequence listing.

The invention claimed is:

1. A pyridyl non-aromatic nitrogen-containing heterocyclic-1-carboxylate compound of a general formula (III) or its pharmaceutically acceptable salt:

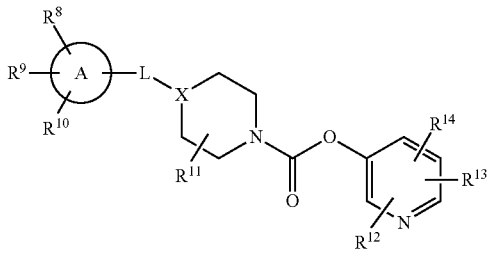

wherein the symbols in formula (III) have the following meanings:

ring A represents benzene ring, cyclopentane ring, cyclohexane ring, cycloheptane ring, or 5- to 7-membered nitrogen-containing hetero ring;

L represents single bond, lower alkylene, lower alkenylene, —N($R^{15}$)—C(=O)—, —C(=O)—N($R^{15}$)—, -(lower alkenylene)-C(=O)—, —O—, or —C(=O)—;

$R^{15}$ represents H, or lower alkyl;

X represents CH, or N;

$R^8$, $R^9$, and $R^{10}$ are the same or different, each representing
  (i) a group selected from the group consisting of H, halo, —CN, —$CF_3$, lower alkyl, and —O-lower alkyl;
  (ii) aryl optionally substituted with the same or different 1 to 5 groups selected from the group consisting of H, halo, —CN, —$CF_3$, lower alkyl, and —O-lower alkyl;
  (iii) nitrogen-containing heteroaryl optionally substituted with the same or different 1 to 5 groups selected from the group consisting of H, halo, —CN, —$CF_3$, lower alkyl, and —O-lower alkyl;
  (iv) $R^{16}$—(lower alkylene)-O—;
  (v) $R^{16}$—(lower alkylene)-N($R^{15}$)—; or
  (vi) $R^{17}R^{18}$N—C(=O)—,
  wherein $R^{16}$ represents
    (i) aryl optionally substituted with the same or different 1 to 5 groups selected from the group consisting of H, halo, —CN, —$CF_3$, lower alkyl, and —O-lower alkyl;
    (ii) nitrogen-containing heteroaryl optionally substituted with the same or different 1 to 5 groups selected from the group consisting of H, halo, —CN, —$CF_3$, lower alkyl, and —O-lower alkyl; or
    (iii) 3- to 8-membered cycloalkyl,
  wherein $R^{17}$ and $R^{18}$ are the same or different, each representing H, lower alkyl, or 3- to 8-membered cycloalkyl, or $R^{17}$ and $R^{18}$ may form, together with the N atom bonding thereto, 3- to 8-membered nitrogen-containing hetero ring, $R^{11}$ represents H, lower alkyl, or oxo (=O), and one of $R^{12}$, $R^{13}$ and $R^{14}$ is —C(=O)—O-(lower alkyl) or —$CO_2H$, and the others are H.

2. The pyridyl non-aromatic nitrogen-containing heterocyclic-1-carboxylate compound or its pharmaceutically acceptable salt according to claim 1, wherein the ring A is benzene ring, cyclohexane ring, piperidine ring, or piperazine ring.

3. The pyridyl non-aromatic nitrogen-containing heterocyclic-1-carboxylate compound or its pharmaceutically acceptable salt according to claim 2, wherein $R^9$, $R^{10}$, $R^{11}$, $R^{12}$ and $R^{13}$ are H.

4. A pyridyl non-aromatic nitrogen-containing heterocyclic-1-carboxylate compound of a general formula (IV) or its pharmaceutically acceptable salt:

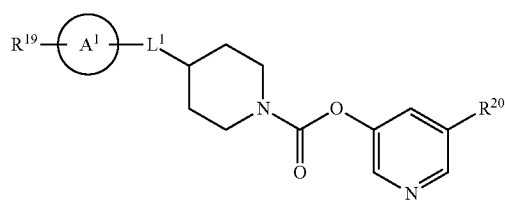

wherein the symbols in formula (IV) have the following meanings:

ring $A^1$ represents benzene ring, piperidine ring or piperazine ring;

$L^1$ represents lower alkylene, lower alkenylene, —N($R^{15}$)—C(=O)—, or —O—, wherein $R^{15}$ represents H, or lower alkyl;

R¹⁹ represents
(i) a group selected from the group consisting of H, halo, —CN, —CF₃, lower alkyl, and —O-lower alkyl;
(ii) nitrogen-containing heteroaryl optionally substituted with the same or different 1 to 5 groups selected from the group consisting of H, halo, —CN, —CF₃, lower alkyl, and —O-lower alkyl;
(iii) R¹⁶—(lower alkylene)-O—; or
(iv) R¹⁷R¹⁸N—C(=O)—;
wherein R¹⁶ represents
(i) aryl optionally substituted with one the same or different 1 to 5 groups selected from the group consisting of H, halo, —CN, —CF₃, lower alkyl, and —O-lower alkyl;
(ii) nitrogen-containing heteroaryl optionally substituted with the same or different 1 to 5 groups selected from the group consisting of H, halo, —CN, —CF₃, lower alkyl, and —O-lower alkyl; or
(iii) 3- to 8-membered cycloalkyl,
wherein R¹⁷ and R¹⁸ are the same or different, each representing H or lower alkyl, or R¹⁷ and R¹⁸ may form, together with the N atom bonding thereto, 5- or 6-membered nitrogen-containing hetero ring, and R²⁰ represents —C(=O)—O-(lower alkyl) or —CO₂H.

5. A pyridyl non-aromatic nitrogen-containing heterocyclic-1-carboxylate compound of a general formula (V) or its pharmaceutically acceptable salt:

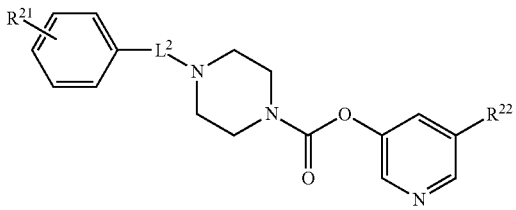

(V)

wherein the symbols in formula (V) have the following meanings:
L² represents lower alkylene, lower alkenylene, or -(lower alkenylene)-C(=O)—,
R²¹ represents H, halo, —CN, —CF₃, lower alkyl, or —O-lower alkyl, and
R²² represents —C(=O)—O-(lower alkyl) or —CO₂H.

6. The pyridyl non-aromatic nitrogen-containing heterocyclic-1-carboxylate compound or its pharmaceutically acceptable salt according to claim 1, the compound being one among the following group:
5-{[(4-{4-[(3-fluorobenzyl)oxy]phenoxy}piperidin-1-yl)carbonyl]oxy}nicotinic acid,
5-({[4-(2-phenylethyl)piperidin-1-yl]carbonyl}oxy)nicotinic acid,
5-[({4-[4-(2-cyclohexylethoxy)phenoxy]piperidin-1-yl}carbonyl)oxy]nicotinic acid,
5-[({4-[(E)-2-phenylvinyl]piperidin-1-yl}carbonyl)oxy]nicotinic acid,
5-{[(4-[3-[1-(6-methylpyridin-2-yl)piperidin-4-yl]propyl}piperidin-1-yl)carbonyl]oxy}nicotinic acid, and
5-(methoxycarbonyl)pyridin-3-yl 4-(2-phenylethyl)piperazine-1-carboxylate.

7. A pharmaceutical composition comprising the pyridyl non-aromatic nitrogen-containing heterocyclic-1-carboxylate compound or its pharmaceutically acceptable salt of claim 1 as an active ingredient thereof.

8. A method for treating urinary frequency, urinary incontinence and/or overactive bladder, comprising administering a therapeutically effective amount of the pyridyl non-aromatic nitrogen-containing heterocyclic-1-carboxylate compound of claim 1 or its pharmaceutically acceptable salt to a patient.

9. A method for treating pain, comprising administering a therapeutically effective amount of the pyridyl non-aromatic nitrogen-containing heterocyclic-1-carboxylate compound of claim 1 or its pharmaceutically acceptable salt to a patient.

10. The pyridyl non-aromatic nitrogen-containing heterocyclic-1-carboxylate compound or its pharmaceutically acceptable salt according to claim 1, wherein the compound is 5-{[(4-{4-[(3-fluorobenzyl)oxy]phenoxy}piperidin-1-yl)carbonyl]oxy}nicotinic acid.

11. The pyridyl non-aromatic nitrogen-containing heterocyclic-1-carboxylate compound or its pharmaceutically acceptable salt according to claim 1, wherein the compound is 5-({[4-(2-phenylethyl)piperidin-1-yl]carbonyl}oxy)nicotinic acid.

12. The pyridyl non-aromatic nitrogen-containing heterocyclic-1-carboxylate compound or its pharmaceutically acceptable salt according to claim 1, wherein the compound is 5-[({4-[4-(2-cyclohexylethoxy)phenoxy]piperidin-1-yl}carbonyl)oxy]nicotinic acid.

13. The pyridyl non-aromatic nitrogen-containing heterocyclic-1-carboxylate compound or its pharmaceutically acceptable salt according to claim 1, wherein the compound is 54({4-[(E)-2-phenylvinyl]piperidin-1-yl}carbonyl)oxy]nicotinic acid.

14. The pyridyl non-aromatic nitrogen-containing heterocyclic-1-carboxylate compound or its pharmaceutically acceptable salt according to claim 1, wherein the compound is 5-{[(4-[3-[1-(6-methylpyridin-2-yl)piperidin-4-yl]propyl}piperidin-1-yl)carbonyl]oxy}nicotinic acid.

15. The pyridyl non-aromatic nitrogen-containing heterocyclic-1-carboxylate compound or its pharmaceutically acceptable salt according to claim 1, wherein the compound is 5-(methoxycarbonyl)pyridin-3-yl 4-(2-phenylethyl)piperazine-1-carboxylate.

* * * * *

UNITED STATES PATENT AND TRADEMARK OFFICE
CERTIFICATE OF CORRECTION

PATENT NO. : 7,919,495 B2
APPLICATION NO. : 11/816508
DATED : April 5, 2011
INVENTOR(S) : Takahiro Ishii et al.

It is certified that error appears in the above-identified patent and that said Letters Patent is hereby corrected as shown below:

Claim 4, column 211, line 9: "$R^{17}R^{18}N$—C(=O)—;" should read
--$R^{17}R^{18}N$—C(=O)—,--.

Claim 4, column 211, line 11: "(i) aryl optionally substituted with one the same or dif-" should read --(i) aryl optionally substituted with the same or dif- --.

Claim 5, column 212, line 5:
"5-{[(4-[3-[1-(6-methylpyridin-2-yl)piperidin-4-yl]" should read
--5-{[(4-{3-[1-(6-methylpyridin-2-yl)piperidin-4-yl]--.

Claim 13, col. 212, line 41,
"54({4-[(E)-2-phenylvinyl]piperidin-1-yl}carbonyl)oxy]" should read
--5-[({4-[(E)-2-phenylvinyl]piperidin-1-yl}carbonyl)oxy]--.

Claim 14, column 212, line 46:
"5-{[(4-[3-[1-(6-methylpyridin-2-yl)piperidin-4-yl]" should read
--5-{[(4-{3-[1-(6-methylpyridin-2-yl)piperidin-4-yl]--.

Signed and Sealed this
Twenty-seventh Day of December, 2011

David J. Kappos
*Director of the United States Patent and Trademark Office*

SEQUENCE LISTING

```
<160> NUMBER OF SEQ ID NOS: 8

<210> SEQ ID NO 1
<211> LENGTH: 2063
<212> TYPE: DNA
<213> ORGANISM: Homo sapiens
<220> FEATURE:
```

```
<221> NAME/KEY: CDS
<222> LOCATION: (36)..(1772)

<400> SEQUENCE: 1
tgccgggcgg taggcagcag caggctgaag ggatc atg gtg cag tac gag ctg         53
                                      Met Val Gln Tyr Glu Leu
                                        1               5 tgg gcc gcg ctg cct ggc gcc tcc ggg gtc gcc ctg gcc tgc tgc ttc       101
Trp Ala Ala Leu Pro Gly Ala Ser Gly Val Ala Leu Ala Cys Cys Phe
         10                  15                  20 gtg gcg gcg gcc gtg gcc ctg cgc tgg tcc ggg cgc cgg acg gcg cgg       149
Val Ala Ala Ala Val Ala Leu Arg Trp Ser Gly Arg Arg Thr Ala Arg
 25                  30                  35 ggc gcg gtg gtc cgg gcg cga cag aag cag cga gcg ggc ctg gag aac       197
Gly Ala Val Val Arg Ala Arg Gln Lys Gln Arg Ala Gly Leu Glu Asn
 40                  45                  50 atg gac agg gcg gcg cag cgc ttc cgg ctc cag aac cca gac ctg gac       245
Met Asp Arg Ala Ala Gln Arg Phe Arg Leu Gln Asn Pro Asp Leu Asp
 55                  60                  65                  70 tca gag gcg ctg cta gcc ctg ccc ctg cct cag ctg gtg cag aag tta       293
Ser Glu Ala Leu Leu Ala Leu Pro Leu Pro Gln Leu Val Gln Lys Leu
                 75                  80                  85 cac agt aga gag ctg gcc cct gag gcc gtg ctc ttc acc tat gtg gga       341
His Ser Arg Glu Leu Ala Pro Glu Ala Val Leu Phe Thr Tyr Val Gly
             90                  95                 100 aag gcc tgg gaa gtg aac aaa ggg acc aac tgt gtg acc tcc tat ctg       389
Lys Ala Trp Glu Val Asn Lys Gly Thr Asn Cys Val Thr Ser Tyr Leu
        105                 110                 115 gct gac tgt gag act cag ctg tct cag gcc cca agg cag ggc ctg ctc       437
Ala Asp Cys Glu Thr Gln Leu Ser Gln Ala Pro Arg Gln Gly Leu Leu
    120                 125                 130 tat ggc gtc cct gtg agc ctc aag gag tgc ttc acc tac aag ggc cag       485
Tyr Gly Val Pro Val Ser Leu Lys Glu Cys Phe Thr Tyr Lys Gly Gln
135                 140                 145                 150 gac tcc acg ctg ggc ttg agc ctg aat gaa ggg gtg ccg gcg gag tgc       533
Asp Ser Thr Leu Gly Leu Ser Leu Asn Glu Gly Val Pro Ala Glu Cys
                155                 160                 165 gac agc gta gtg gtg cat gtg ctg aag ctg cag ggt gcc gtg ccc ttc       581
Asp Ser Val Val Val His Val Leu Lys Leu Gln Gly Ala Val Pro Phe
            170                 175                 180 gtg cac acc aat gtt cca cag tcc atg ttc agc tat gac tgc agt aac       629
Val His Thr Asn Val Pro Gln Ser Met Phe Ser Tyr Asp Cys Ser Asn
        185                 190                 195 ccc ctc ttt ggc cag acc gtg aac cca tgg aag tcc tcc aaa agc cca       677
Pro Leu Phe Gly Gln Thr Val Asn Pro Trp Lys Ser Ser Lys Ser Pro
    200                 205                 210 ggg ggc tcc tca ggg ggt gaa ggg gcc ctc atc ggg tct gga ggc tcc       725
Gly Gly Ser Ser Gly Gly Glu Gly Ala Leu Ile Gly Ser Gly Gly Ser
215                 220                 225                 230 ccc ctg ggc tta ggc act gat atc gga ggc agc atc cgc ttc ccc tcc       773
Pro Leu Gly Leu Gly Thr Asp Ile Gly Gly Ser Ile Arg Phe Pro Ser
                235                 240                 245 tcc ttc tgc ggc atc tgc ggc ctc aag ccc aca ggg aac cgc ctc agc       821
Ser Phe Cys Gly Ile Cys Gly Leu Lys Pro Thr Gly Asn Arg Leu Ser
            250                 255                 260 aag agt ggc ctg aag ggc tgt gtc tat gga cag gag gca gtg cgt ctc       869
Lys Ser Gly Leu Lys Gly Cys Val Tyr Gly Gln Glu Ala Val Arg Leu
        265                 270                 275 tcc gtg ggc ccc atg gcc cgg gac gtg gag agc ctg gca ctg tgc ctg       917
Ser Val Gly Pro Met Ala Arg Asp Val Glu Ser Leu Ala Leu Cys Leu
    280                 285                 290
```

| | | |
|---|---|---|
| cga gcc ctg ctg tgc gag gac atg ttc cgc ttg gac ccc act gtg cct<br>Arg Ala Leu Leu Cys Glu Asp Met Phe Arg Leu Asp Pro Thr Val Pro<br>295                        300                     305                   310 | | 965 |
| ccc ttg ccc ttc aga gaa gag gtc tac acc agc tct cag ccc ctg cgt<br>Pro Leu Pro Phe Arg Glu Glu Val Tyr Thr Ser Ser Gln Pro Leu Arg<br>                   315                     320                     325 | | 1013 |
| gtg ggg tac tat gag act gac aac tat acc atg ccc tcc ccg gcc atg<br>Val Gly Tyr Tyr Glu Thr Asp Asn Tyr Thr Met Pro Ser Pro Ala Met<br>                   330                     335                     340 | | 1061 |
| agg cgg gcc gtg ctg gag acc aaa cag agc ctt gag gct gcg ggg cac<br>Arg Arg Ala Val Leu Glu Thr Lys Gln Ser Leu Glu Ala Ala Gly His<br>345                        350                     355 | | 1109 |
| acg ctg gtt ccc ttc ttg cca agc aac ata ccc cat gct ctg gag acc<br>Thr Leu Val Pro Phe Leu Pro Ser Asn Ile Pro His Ala Leu Glu Thr<br>    360                     365                     370 | | 1157 |
| ctg tca aca ggt ggg ctc ttc agt gat ggt ggc cac acc ttc cta cag<br>Leu Ser Thr Gly Gly Leu Phe Ser Asp Gly Gly His Thr Phe Leu Gln<br>375                        380                     385                     390 | | 1205 |
| aac ttc aaa ggt gat ttc gtg gac ccc tgc ctg ggg gac ctg gtc tca<br>Asn Phe Lys Gly Asp Phe Val Asp Pro Cys Leu Gly Asp Leu Val Ser<br>                   395                     400                     405 | | 1253 |
| att ctg aag ctt ccc caa tgg ctt aaa gga ctg ctg gcc ttc ctg gtg<br>Ile Leu Lys Leu Pro Gln Trp Leu Lys Gly Leu Leu Ala Phe Leu Val<br>            410                     415                     420 | | 1301 |
| aag cct ctg ctg cca agg ctg tca gct ttc ctc agc aac atg aag tct<br>Lys Pro Leu Leu Pro Arg Leu Ser Ala Phe Leu Ser Asn Met Lys Ser<br>425                        430                     435 | | 1349 |
| cgt tcg gct gga aaa ctc tgg gaa ctg cag cac gag atc gag gtg tac<br>Arg Ser Ala Gly Lys Leu Trp Glu Leu Gln His Glu Ile Glu Val Tyr<br>    440                     445                     450 | | 1397 |
| cgc aaa acc gtg att gcc cag tgg agg gcg ctg gac ctg gat gtg gtg<br>Arg Lys Thr Val Ile Ala Gln Trp Arg Ala Leu Asp Leu Asp Val Val<br>455                        460                     465                   470 | | 1445 |
| ctg acc ccc atg ctg gcc cct gct ctg gac ttg aat gcc cca ggc agg<br>Leu Thr Pro Met Leu Ala Pro Ala Leu Asp Leu Asn Ala Pro Gly Arg<br>                   475                     480                     485 | | 1493 |
| gcc aca ggg gcc gtc agc tac act atg ctg tac aac tgc ctg gac ttc<br>Ala Thr Gly Ala Val Ser Tyr Thr Met Leu Tyr Asn Cys Leu Asp Phe<br>            490                     495                     500 | | 1541 |
| cct gca ggg gtg gtg cct gtc acc acg gtg act gct gag gac gag gcc<br>Pro Ala Gly Val Val Pro Val Thr Thr Val Thr Ala Glu Asp Glu Ala<br>505                        510                     515 | | 1589 |
| cag atg gaa cat tac agg ggc tac ttt ggg gat atc tgg gac aag atg<br>Gln Met Glu His Tyr Arg Gly Tyr Phe Gly Asp Ile Trp Asp Lys Met<br>520                        525                     530 | | 1637 |
| ctg cag aag ggc atg aag aag agt gtg ggg ctg ccg gtg gcc gtg cag<br>Leu Gln Lys Gly Met Lys Lys Ser Val Gly Leu Pro Val Ala Val Gln<br>535                        540                     545                     550 | | 1685 |
| tgt gtg gct ctg ccc tgg caa gaa gag ttg tgt ctg cgg ttc atg cgg<br>Cys Val Ala Leu Pro Trp Gln Glu Glu Leu Cys Leu Arg Phe Met Arg<br>                   555                     560                     565 | | 1733 |
| gag gtg gag cga ctg atg acc cct gaa aag cag tca tcc tgatggctct<br>Glu Val Glu Arg Leu Met Thr Pro Glu Lys Gln Ser Ser<br>            570                     575 | | 1782 |
| ggctccagag gacctgagac tcacactctc tgcagcccag cctagtcagg gcacagctgc | | 1842 |
| cctgctgcca cagcaaggaa atgtcctgca tggggcagag gcttccgtgt cctctccccc | | 1902 |
| aaccccctgc aagaagcgcc gactccctga gtctggacct ccatccctgc tctggtcccc | | 1962 |
| tctcttcgtc ctgatccctc caccccatg tggcagccca tgggtatgac ataggccaag | | 2022 |

```
gcccaactaa cagtcaagaa acaaaaaaaa aaaaaaaaa a                              2063
```

```
<210> SEQ ID NO 2
<211> LENGTH: 579
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Val | Gln | Tyr | Glu | Leu | Trp | Ala | Ala | Leu | Pro | Gly | Ala | Ser | Gly | Val |
| 1 | | | | 5 | | | | | 10 | | | | | 15 | |
| Ala | Leu | Ala | Cys | Cys | Phe | Val | Ala | Ala | Val | Ala | Leu | Arg | Trp | Ser | |
| | | | 20 | | | | | 25 | | | | | 30 | | |
| Gly | Arg | Arg | Thr | Ala | Arg | Gly | Ala | Val | Val | Arg | Ala | Arg | Gln | Lys | Gln |
| | | 35 | | | | | 40 | | | | | 45 | | | |
| Arg | Ala | Gly | Leu | Glu | Asn | Met | Asp | Arg | Ala | Ala | Gln | Arg | Phe | Arg | Leu |
| 50 | | | | | 55 | | | | | 60 | | | | | |
| Gln | Asn | Pro | Asp | Leu | Asp | Ser | Glu | Ala | Leu | Ala | Leu | Pro | Leu | Pro | |
| 65 | | | | 70 | | | | | 75 | | | | | 80 | |
| Gln | Leu | Val | Gln | Lys | Leu | His | Ser | Arg | Glu | Leu | Ala | Pro | Glu | Ala | Val |
| | | | | 85 | | | | | 90 | | | | | 95 | |
| Leu | Phe | Thr | Tyr | Val | Gly | Lys | Ala | Trp | Glu | Val | Asn | Lys | Gly | Thr | Asn |
| | | | 100 | | | | | 105 | | | | | 110 | | |
| Cys | Val | Thr | Ser | Tyr | Leu | Ala | Asp | Cys | Glu | Thr | Gln | Leu | Ser | Gln | Ala |
| | | | 115 | | | | | 120 | | | | | 125 | | |
| Pro | Arg | Gln | Gly | Leu | Leu | Tyr | Gly | Val | Pro | Val | Ser | Leu | Lys | Glu | Cys |
| | | 130 | | | | | 135 | | | | | 140 | | | |
| Phe | Thr | Tyr | Lys | Gly | Gln | Asp | Ser | Thr | Leu | Gly | Leu | Ser | Leu | Asn | Glu |
| 145 | | | | | 150 | | | | | 155 | | | | | 160 |
| Gly | Val | Pro | Ala | Glu | Cys | Asp | Ser | Val | Val | His | Val | Leu | Lys | Leu | |
| | | | | 165 | | | | | 170 | | | | | 175 | |
| Gln | Gly | Ala | Val | Pro | Phe | Val | His | Thr | Asn | Val | Pro | Gln | Ser | Met | Phe |
| | | | 180 | | | | | 185 | | | | | 190 | | |
| Ser | Tyr | Asp | Cys | Ser | Asn | Pro | Leu | Phe | Gly | Gln | Thr | Val | Asn | Pro | Trp |
| | | 195 | | | | | 200 | | | | | 205 | | | |
| Lys | Ser | Ser | Lys | Ser | Pro | Gly | Gly | Ser | Ser | Gly | Gly | Glu | Gly | Ala | Leu |
| | | 210 | | | | | 215 | | | | | 220 | | | |
| Ile | Gly | Ser | Gly | Gly | Ser | Pro | Leu | Gly | Leu | Gly | Thr | Asp | Ile | Gly | Gly |
| 225 | | | | | 230 | | | | | 235 | | | | | 240 |
| Ser | Ile | Arg | Phe | Pro | Ser | Ser | Phe | Cys | Gly | Ile | Cys | Gly | Leu | Lys | Pro |
| | | | | 245 | | | | | 250 | | | | | 255 | |
| Thr | Gly | Asn | Arg | Leu | Ser | Lys | Ser | Gly | Leu | Lys | Gly | Cys | Val | Tyr | Gly |
| | | | 260 | | | | | 265 | | | | | 270 | | |
| Gln | Glu | Ala | Val | Arg | Leu | Ser | Val | Gly | Pro | Met | Ala | Arg | Asp | Val | Glu |
| | | 275 | | | | | 280 | | | | | 285 | | | |
| Ser | Leu | Ala | Leu | Cys | Leu | Arg | Ala | Leu | Leu | Cys | Glu | Asp | Met | Phe | Arg |
| | | 290 | | | | | 295 | | | | | 300 | | | |
| Leu | Asp | Pro | Thr | Val | Pro | Pro | Leu | Pro | Phe | Arg | Glu | Glu | Val | Tyr | Thr |
| 305 | | | | | 310 | | | | | 315 | | | | | 320 |
| Ser | Ser | Gln | Pro | Leu | Arg | Val | Gly | Tyr | Tyr | Glu | Thr | Asp | Asn | Tyr | Thr |
| | | | | 325 | | | | | 330 | | | | | 335 | |
| Met | Pro | Ser | Pro | Ala | Met | Arg | Arg | Ala | Val | Leu | Glu | Thr | Lys | Gln | Ser |
| | | | 340 | | | | | 345 | | | | | 350 | | |
| Leu | Glu | Ala | Ala | Gly | His | Thr | Leu | Val | Pro | Phe | Leu | Pro | Ser | Asn | Ile |
| | | | | 355 | | | | | 360 | | | | | 365 | |

```
Pro His Ala Leu Glu Thr Leu Ser Thr Gly Gly Leu Phe Ser Asp Gly
    370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Leu Pro Arg Leu Ser Ala Phe
                420                 425                 430

Leu Ser Asn Met Lys Ser Arg Ser Ala Gly Lys Leu Trp Glu Leu Gln
                435                 440                 445

His Glu Ile Glu Val Tyr Arg Lys Thr Val Ile Ala Gln Trp Arg Ala
    450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
                485                 490                 495

Tyr Asn Cys Leu Asp Phe Pro Ala Gly Val Val Pro Val Thr Thr Val
                500                 505                 510

Thr Ala Glu Asp Glu Ala Gln Met Glu His Tyr Arg Gly Tyr Phe Gly
    515                 520                 525

Asp Ile Trp Asp Lys Met Leu Gln Lys Gly Met Lys Lys Ser Val Gly
530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser

<210> SEQ ID NO 3
<211> LENGTH: 3805
<212> TYPE: DNA
<213> ORGANISM: Mus musculus
<220> FEATURE:
<221> NAME/KEY: CDS
<222> LOCATION: (247)..(1983)

<400> SEQUENCE: 3
ggttccgcct gccttaaaac gctggcacgc caggaaccgg gccagaaggg gtctaggctt      60
gaccttgacc gttggagctg ctagcttggc tctcgctgcc gggcaacggc gcgctccccg     120
cgggcccgcg gctgcgcctg cccctccctc aagcggaatc gcgggcgatc caggccgggt     180
tttgcagcgg agctgttggt gtgcgcgtgc cgagtcctct cgggtggcgg tcggctgcag     240 gagatc atg gtg ctg agc gaa gtg tgg acc gcg ctg tct gga ctc tcc         288
       Met Val Leu Ser Glu Val Trp Thr Ala Leu Ser Gly Leu Ser
       1               5                   10 ggg gtt tgc cta gcc tgc agc ttg ctg tcg gcg gcg gtg gtc ctg cga        336
Gly Val Cys Leu Ala Cys Ser Leu Leu Ser Ala Ala Val Val Leu Arg
15                  20                  25                  30 tgg acc agg agc cag acc gcc cgg ggc gcg gtg acc agg gcg cgg cag        384
Trp Thr Arg Ser Gln Thr Ala Arg Gly Ala Val Thr Arg Ala Arg Gln
                35                  40                  45 aag cag cga gcc ggc ctg gag acc atg gac aag gcg gtg cag cgc ttc        432
Lys Gln Arg Ala Gly Leu Glu Thr Met Asp Lys Ala Val Gln Arg Phe
            50                  55                  60 cgg ctg cag aat cct gac ctg gat tca gag gcc ttg ctg gct ctg ccc        480
Arg Leu Gln Asn Pro Asp Leu Asp Ser Glu Ala Leu Leu Ala Leu Pro
        65                  70                  75
```

| | | | | | | | | | | | | | | | | |
|---|---|---|---|---|---|---|---|---|---|---|---|---|---|---|---|---|
| ctg | ctc | caa | ctg | gta | cag | aag | tta | cag | agt | ggg | gaa | ctg | tcc | cca | gaa | 528 |
| Leu | Leu | Gln | Leu | Val | Gln | Lys | Leu | Gln | Ser | Gly | Glu | Leu | Ser | Pro | Glu | |
| | | 80 | | | | 85 | | | | 90 | | | | | | |
| gct | gtg | ctc | ttt | acc | tac | ctg | gga | aag | gcc | tgg | gaa | gtg | aac | aaa | ggg | 576 |
| Ala | Val | Leu | Phe | Thr | Tyr | Leu | Gly | Lys | Ala | Trp | Glu | Val | Asn | Lys | Gly | |
| 95 | | | | | 100 | | | | | 105 | | | | | 110 | |
| acc | aac | tgt | gtg | acc | tcc | tat | ctg | act | gac | tgt | gag | act | cag | ctg | tcc | 624 |
| Thr | Asn | Cys | Val | Thr | Ser | Tyr | Leu | Thr | Asp | Cys | Glu | Thr | Gln | Leu | Ser | |
| | | | | 115 | | | | | 120 | | | | | 125 | | |
| cag | gcc | cca | cgg | cag | ggc | ctg | ctc | tat | ggc | gtc | ccc | gtg | agc | ctc | aag | 672 |
| Gln | Ala | Pro | Arg | Gln | Gly | Leu | Leu | Tyr | Gly | Val | Pro | Val | Ser | Leu | Lys | |
| | | 130 | | | | | 135 | | | | | 140 | | | | |
| gaa | tgc | ttc | agc | tac | aag | ggc | cat | gct | tcc | aca | ctg | gga | tta | agt | ttg | 720 |
| Glu | Cys | Phe | Ser | Tyr | Lys | Gly | His | Ala | Ser | Thr | Leu | Gly | Leu | Ser | Leu | |
| | | | 145 | | | | | 150 | | | | | 155 | | | |
| aac | gag | ggt | gtg | aca | tcg | gag | agt | gac | tgt | gtg | gtg | gtg | cag | gta | ctg | 768 |
| Asn | Glu | Gly | Val | Thr | Ser | Glu | Ser | Asp | Cys | Val | Val | Val | Gln | Val | Leu | |
| | 160 | | | | | 165 | | | | | 170 | | | | | |
| aag | ctg | cag | gga | gct | gtg | ccc | ttt | gtg | cac | acc | aac | gtc | ccc | cag | tcc | 816 |
| Lys | Leu | Gln | Gly | Ala | Val | Pro | Phe | Val | His | Thr | Asn | Val | Pro | Gln | Ser | |
| 175 | | | | | 180 | | | | | 185 | | | | | 190 | |
| atg | cta | agc | tat | gac | tgc | agt | aac | ccc | ctc | ttt | ggc | cag | acc | atg | aac | 864 |
| Met | Leu | Ser | Tyr | Asp | Cys | Ser | Asn | Pro | Leu | Phe | Gly | Gln | Thr | Met | Asn | |
| | | | | 195 | | | | | 200 | | | | | 205 | | |
| ccg | tgg | aag | ccc | tcc | aag | agt | cca | gga | ggt | tcc | tca | ggg | ggt | gag | ggg | 912 |
| Pro | Trp | Lys | Pro | Ser | Lys | Ser | Pro | Gly | Gly | Ser | Ser | Gly | Gly | Glu | Gly | |
| | | 210 | | | | | 215 | | | | | 220 | | | | |
| gct | ctc | att | gga | tct | gga | ggc | tcc | cct | ctg | ggt | tta | ggc | act | gac | atc | 960 |
| Ala | Leu | Ile | Gly | Ser | Gly | Gly | Ser | Pro | Leu | Gly | Leu | Gly | Thr | Asp | Ile | |
| | | | 225 | | | | | 230 | | | | | 235 | | | |
| ggc | ggc | agc | atc | cgg | ttc | cct | tct | gcc | ttc | tgt | ggc | atc | tgt | ggc | ctc | 1008 |
| Gly | Gly | Ser | Ile | Arg | Phe | Pro | Ser | Ala | Phe | Cys | Gly | Ile | Cys | Gly | Leu | |
| | 240 | | | | | 245 | | | | | 250 | | | | | |
| aag | cct | act | ggg | aac | cgc | ctc | agc | aag | agt | ggc | ctg | aag | agc | tgt | gtt | 1056 |
| Lys | Pro | Thr | Gly | Asn | Arg | Leu | Ser | Lys | Ser | Gly | Leu | Lys | Ser | Cys | Val | |
| 255 | | | | | 260 | | | | | 265 | | | | | 270 | |
| tat | gga | cag | aca | gca | gtg | cag | ctt | tct | gtt | ggc | ccc | atg | gca | cgg | gat | 1104 |
| Tyr | Gly | Gln | Thr | Ala | Val | Gln | Leu | Ser | Val | Gly | Pro | Met | Ala | Arg | Asp | |
| | | | 275 | | | | | 280 | | | | | 285 | | | |
| gtg | gat | agc | ctg | gca | ttg | tgc | atg | aaa | gcc | cta | ctt | tgt | gag | gat | ttg | 1152 |
| Val | Asp | Ser | Leu | Ala | Leu | Cys | Met | Lys | Ala | Leu | Leu | Cys | Glu | Asp | Leu | |
| | | | 290 | | | | | 295 | | | | | 300 | | | |
| ttc | cgc | ttg | gac | tcc | acc | atc | ccc | ccc | ttg | ccc | ttc | agg | gag | gag | atc | 1200 |
| Phe | Arg | Leu | Asp | Ser | Thr | Ile | Pro | Pro | Leu | Pro | Phe | Arg | Glu | Glu | Ile | |
| | | 305 | | | | | 310 | | | | | 315 | | | | |
| tac | aga | agt | tct | cga | ccc | ctt | cgt | gtg | gga | tac | tat | gaa | act | gac | aac | 1248 |
| Tyr | Arg | Ser | Ser | Arg | Pro | Leu | Arg | Val | Gly | Tyr | Tyr | Glu | Thr | Asp | Asn | |
| | 320 | | | | | 325 | | | | | 330 | | | | | |
| tac | acc | atg | ccc | act | cca | gcc | atg | agg | agg | gct | gtg | atg | gag | acc | aag | 1296 |
| Tyr | Thr | Met | Pro | Thr | Pro | Ala | Met | Arg | Arg | Ala | Val | Met | Glu | Thr | Lys | |
| 335 | | | | | 340 | | | | | 345 | | | | | 350 | |
| cag | agt | ctc | gag | gct | gct | ggc | cac | acg | ctg | gtc | ccc | ttc | tta | cca | aac | 1344 |
| Gln | Ser | Leu | Glu | Ala | Ala | Gly | His | Thr | Leu | Val | Pro | Phe | Leu | Pro | Asn | |
| | | | | 355 | | | | | 360 | | | | | 365 | | |
| aac | ata | cct | tat | gcc | ctg | gag | gtc | ctg | tcg | gca | ggt | ggg | ctg | ttc | agt | 1392 |
| Asn | Ile | Pro | Tyr | Ala | Leu | Glu | Val | Leu | Ser | Ala | Gly | Gly | Leu | Phe | Ser | |
| | | | 370 | | | | | 375 | | | | | 380 | | | |
| gat | ggt | ggc | tgc | tct | ttt | ctc | caa | aac | ttc | aaa | ggc | gac | ttt | gtg | gat | 1440 |
| Asp | Gly | Gly | Cys | Ser | Phe | Leu | Gln | Asn | Phe | Lys | Gly | Asp | Phe | Val | Asp | |
| | | | 385 | | | | | 390 | | | | | 395 | | | |

```
ccc tgc ttg ggg gac ctg gtc tta gtg ctg aag ctg ccc agg tgg ttt     1488
Pro Cys Leu Gly Asp Leu Val Leu Val Leu Lys Leu Pro Arg Trp Phe
    400                 405                 410 aaa aaa ctg ctg agc ttc ctg ctg aag cct ctg ttt cct cgg ctg gca     1536
Lys Lys Leu Leu Ser Phe Leu Leu Lys Pro Leu Phe Pro Arg Leu Ala
415                 420                 425                 430 gcc ttt ctc aac agt atg tgt cct cgg tca gcc gaa aag ctg tgg gaa     1584
Ala Phe Leu Asn Ser Met Cys Pro Arg Ser Ala Glu Lys Leu Trp Glu
                435                 440                 445 ctg cag cat gag att gag atg tat cgc cag tcc gtc att gcc cag tgg     1632
Leu Gln His Glu Ile Glu Met Tyr Arg Gln Ser Val Ile Ala Gln Trp
            450                 455                 460 aag gca atg aac ttg gac gtg gtg cta acc ccc atg ctg ggt cct gct     1680
Lys Ala Met Asn Leu Asp Val Val Leu Thr Pro Met Leu Gly Pro Ala
        465                 470                 475 ctg gat ttg aac gca ccg ggc aga gcc aca ggg gct atc agc tac act     1728
Leu Asp Leu Asn Ala Pro Gly Arg Ala Thr Gly Ala Ile Ser Tyr Thr
    480                 485                 490 gtt ctc tat aac tgc ctg gac ttc cct gcg ggg gtg gtg cct gtc acc     1776
Val Leu Tyr Asn Cys Leu Asp Phe Pro Ala Gly Val Val Pro Val Thr
495                 500                 505                 510 act gtg acc gct gag gac gat gcc cag atg gaa cac tac aaa ggc tac     1824
Thr Val Thr Ala Glu Asp Asp Ala Gln Met Glu His Tyr Lys Gly Tyr
                515                 520                 525 ttt ggg gat atg tgg gac aac att ctg aag aag ggc atg aaa aag ggt     1872
Phe Gly Asp Met Trp Asp Asn Ile Leu Lys Lys Gly Met Lys Lys Gly
            530                 535                 540 ata ggc ctg cct gtg gct gtg cag tgc gtg gct ctg ccc tgg cag gaa     1920
Ile Gly Leu Pro Val Ala Val Gln Cys Val Ala Leu Pro Trp Gln Glu
        545                 550                 555 gag ctg tgt ctg cgg ttc atg cgg gag gtg gaa cgg ctg atg acc cct     1968
Glu Leu Cys Leu Arg Phe Met Arg Glu Val Glu Arg Leu Met Thr Pro
    560                 565                 570 gaa aag cgg cca tct tgagggtcat tcatctgccc agctctggag gacctaaggc     2023
Glu Lys Arg Pro Ser
575 ccatgcgctc tgcactgcag ccccatctat tcaggatcct gccacccatg aggagatgcc     2083 cagcacggga agaggcaacc acctgccctc cctggactc ctacagaaac ccaggacatg      2143 ccctccataa ccaagtctgg accttgctcc cctttctggt ctactttcca tcctgacccc     2203 ctactctatg tgacagccca gcaggaacga cacgggccaa ggaccaccaa cagtcaaaaa     2263 aagcaatgtg tttctgtatt tttctgggta tttttctatt aggaccttgg aaccagagcc     2323 tgctgagagg gctgtgctgt ccctccagag ctggctgtaa tcatgtcact tcctgctcc      2383 aaagcctccc taggccatca cccacaaggt agacacaggg acatgtcctt ggcacttggc     2443 tcctgccctt ccttccttgt tcagattggc ccagctttg atggacaccg cccgggtctt      2503 cctccctcat tccacctctc tctcttctga cttggccttt ttacttctct agctgttgta     2563 gagaacaagg tttctctgtg tagccctggc tgtccaggat ctcactctgt agatcaggct     2623 ggctttcagc tcacaaggct gcctgcctgg gtgctggat taaaggcgtg tgttaccaga      2683 gtctggctgg ctgggatatc ttttagggtc atctctgtaa cccatttct acttacatat      2743 ccacaagtca gaacactgga ctgaggaagg actatgtcac cctggatacc tgtcagggaa     2803 cacttacaga gataccagtg tcatcaattt gagcttccca gccaaataag tctcctccag     2863 tctgtgtttg gttagcttgc cagtattgac ctggctcctg acggctcctc catgtaggtt     2923 gtactggcga cctaggatac cccttgtggt gagtgagtga gaccacttgt ggtctgggct     2983
```

-continued

```
ctgtaaggtt tatcatcaca tgcctagcac ccagcatgtt acctggcact tagtagatag    3043
ccagtcaggc ttgttggagg gatggcagat ttatttctag cgaatccatt ttggcacctc    3103
ccgattactt cctatgccat ccataatagg gaattttcag tttgcctctg acctgctacc    3163
tttatctaat ctacttaatt cactttgatt catgaccaca gggacaaata tctctttgtc    3223
tgtgatcaac gtagagcttc ctcctggtca agaaggctgc atgcatcaac ttctaccaac    3283
cctcagctcc tccatacttc ttccacccag cccacaagca cattgaattc ctcccactat    3343
gctcaggata agcaaacaga aacagcccct gcttgaatgg tttctcattc taccagcaac    3403
tgtgtattta cactgtaggt cacacaaatg ctataaagca gaagtccctg ggtatgatga    3463
catcaagcag gctacctggc ccgcaggtca tgtgtgcaag agtaggagta tcagggagtg    3523
ctctctgtgt gaagtgacat gtaagctgga aagctcacag ttaatgggag ccaaggaaca    3583
agtatttcaa gaagagtgga gtcgacttaa acgctgctga tgtaactgga taaggacaag    3643
tgaagggagg gatggagaac tccacctgcc atcattgaat cgagtgccta ctgtttgcca    3703
gacactttac caaaggctgc caaggtcctt gctcttaggg aactcgtttt ctagagagag    3763
ggcatgcaaa taagatcata aataaaataa tttatgctga tg                      3805
```

<210> SEQ ID NO 4
<211> LENGTH: 579
<212> TYPE: PRT
<213> ORGANISM: Mus musculus

<400> SEQUENCE: 4

```
Met Val Leu Ser Glu Val Trp Thr Ala Leu Ser Gly Leu Ser Gly Val
1               5                   10                  15

Cys Leu Ala Cys Ser Leu Leu Ser Ala Ala Val Val Leu Arg Trp Thr
            20                  25                  30

Arg Ser Gln Thr Ala Arg Gly Ala Val Thr Arg Ala Arg Gln Lys Gln
        35                  40                  45

Arg Ala Gly Leu Glu Thr Met Asp Lys Ala Val Gln Arg Phe Arg Leu
    50                  55                  60

Gln Asn Pro Asp Leu Asp Ser Glu Ala Leu Leu Ala Leu Pro Leu Leu
65                  70                  75                  80

Gln Leu Val Gln Lys Leu Gln Ser Gly Glu Leu Ser Pro Glu Ala Val
                85                  90                  95

Leu Phe Thr Tyr Leu Gly Lys Ala Trp Glu Val Asn Lys Gly Thr Asn
            100                 105                 110

Cys Val Thr Ser Tyr Leu Thr Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Ser Tyr Lys Gly His Ala Ser Thr Leu Gly Leu Ser Leu Asn Glu
145                 150                 155                 160

Gly Val Thr Ser Glu Ser Asp Cys Val Val Val Gln Val Leu Lys Leu
                165                 170                 175

Gln Gly Ala Val Pro Phe Val His Thr Asn Val Pro Gln Ser Met Leu
            180                 185                 190

Ser Tyr Asp Cys Ser Asn Pro Leu Phe Gly Gln Thr Met Asn Pro Trp
        195                 200                 205

Lys Pro Ser Lys Ser Pro Gly Gly Ser Gly Gly Glu Gly Ala Leu
    210                 215                 220

Ile Gly Ser Gly Gly Ser Pro Leu Gly Leu Gly Thr Asp Ile Gly Gly
225                 230                 235                 240
```

Ser Ile Arg Phe Pro Ser Ala Phe Cys Gly Ile Cys Gly Leu Lys Pro
            245                 250                 255

Thr Gly Asn Arg Leu Ser Lys Ser Gly Leu Lys Ser Cys Val Tyr Gly
            260                 265                 270

Gln Thr Ala Val Gln Leu Ser Val Gly Pro Met Ala Arg Asp Val Asp
            275                 280                 285

Ser Leu Ala Leu Cys Met Lys Ala Leu Leu Cys Glu Asp Leu Phe Arg
            290                 295                 300

Leu Asp Ser Thr Ile Pro Pro Leu Pro Phe Arg Glu Glu Ile Tyr Arg
305                 310                 315                 320

Ser Ser Arg Pro Leu Arg Val Gly Tyr Tyr Glu Thr Asp Asn Tyr Thr
            325                 330                 335

Met Pro Thr Pro Ala Met Arg Arg Ala Val Met Glu Thr Lys Gln Ser
            340                 345                 350

Leu Glu Ala Ala Gly His Thr Leu Val Pro Phe Leu Pro Asn Asn Ile
            355                 360                 365

Pro Tyr Ala Leu Glu Val Leu Ser Ala Gly Gly Leu Phe Ser Asp Gly
            370                 375                 380

Gly Cys Ser Phe Leu Gln Asn Phe Lys Gly Asp Phe Val Asp Pro Cys
385                 390                 395                 400

Leu Gly Asp Leu Val Leu Val Leu Lys Leu Pro Arg Trp Phe Lys Lys
            405                 410                 415

Leu Leu Ser Phe Leu Leu Lys Pro Leu Phe Pro Arg Leu Ala Ala Phe
            420                 425                 430

Leu Asn Ser Met Cys Pro Arg Ser Ala Glu Lys Leu Trp Glu Leu Gln
            435                 440                 445

His Glu Ile Glu Met Tyr Arg Gln Ser Val Ile Ala Gln Trp Lys Ala
            450                 455                 460

Met Asn Leu Asp Val Val Leu Thr Pro Met Leu Gly Pro Ala Leu Asp
465                 470                 475                 480

Leu Asn Ala Pro Gly Arg Ala Thr Gly Ala Ile Ser Tyr Thr Val Leu
            485                 490                 495

Tyr Asn Cys Leu Asp Phe Pro Ala Gly Val Val Pro Val Thr Thr Val
            500                 505                 510

Thr Ala Glu Asp Asp Ala Gln Met Glu His Tyr Lys Gly Tyr Phe Gly
            515                 520                 525

Asp Met Trp Asp Asn Ile Leu Lys Lys Gly Met Lys Lys Gly Ile Gly
            530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
            565                 570                 575

Arg Pro Ser

<210> SEQ ID NO 5
<211> LENGTH: 2472
<212> TYPE: DNA
<213> ORGANISM: Rattus norvegicus
<220> FEATURE:
<221> NAME/KEY: CDS
<222> LOCATION: (50)..(1786)

<400> SEQUENCE: 5
ggtttgtgcg agccgagttc tctcgggtgg cggtcggctg caggagatc atg gtg ctg     58
                                                    Met Val Leu
                                                     1

| | | |
|---|---|---|
| agc gaa gtg tgg acc acg ctg tct ggg gtc tcc ggg gtt tgc cta gcc<br>Ser Glu Val Trp Thr Thr Leu Ser Gly Val Ser Gly Val Cys Leu Ala<br>5         10        15 | | 106 |
| tgc agc ttg ttg tcg gcg gcg gtg gtc ctg cga tgg acc ggg cgc cag<br>Cys Ser Leu Leu Ser Ala Ala Val Val Leu Arg Trp Thr Gly Arg Gln<br>20        25        30        35 | | 154 |
| aag gcc cgg ggc gcg gcg acc agg gcg cgg cag aag cag cga gcc agc<br>Lys Ala Arg Gly Ala Ala Thr Arg Ala Arg Gln Lys Gln Arg Ala Ser<br>40        45        50 | | 202 |
| ctg gag acc atg gac aag gcg gtg cag cgc ttc cgg ctg cag aat cct<br>Leu Glu Thr Met Asp Lys Ala Val Gln Arg Phe Arg Leu Gln Asn Pro<br>55        60        65 | | 250 |
| gac ctg gac tcg gag gcc ttg ctg acc ctg ccc cta ctc caa ctg gta<br>Asp Leu Asp Ser Glu Ala Leu Leu Thr Leu Pro Leu Leu Gln Leu Val<br>70        75        80 | | 298 |
| cag aag tta cag agt gga gag ctg tcc cca gag gct gtg ttc ttt act<br>Gln Lys Leu Gln Ser Gly Glu Leu Ser Pro Glu Ala Val Phe Phe Thr<br>85        90        95 | | 346 |
| tac ctg gga aag gcc tgg gaa gtg aac aaa ggg acc aac tgc gtg acc<br>Tyr Leu Gly Lys Ala Trp Glu Val Asn Lys Gly Thr Asn Cys Val Thr<br>100       105       110       115 | | 394 |
| tcc tat ctg acc gac tgt gag act cag ctg tcc cag gcc cca cgg cag<br>Ser Tyr Leu Thr Asp Cys Glu Thr Gln Leu Ser Gln Ala Pro Arg Gln<br>120       125       130 | | 442 |
| ggc ctg ctc tat ggt gtc cct gtg agc ctc aag gaa tgc ttc agc tac<br>Gly Leu Leu Tyr Gly Val Pro Val Ser Leu Lys Glu Cys Phe Ser Tyr<br>135       140       145 | | 490 |
| aag ggc cac gac tcc aca ctg ggc ttg agc ctg aat gag ggc atg cca<br>Lys Gly His Asp Ser Thr Leu Gly Leu Ser Leu Asn Glu Gly Met Pro<br>150       155       160 | | 538 |
| tcg gaa tct gac tgt gtg gtg gtg caa gtg ttg aag ctg cag gga gct<br>Ser Glu Ser Asp Cys Val Val Val Gln Val Leu Lys Leu Gln Gly Ala<br>165       170       175 | | 586 |
| gtg ccc ttt gtg cat acc aat gtc ccc cag tcc atg tta agc ttt gac<br>Val Pro Phe Val His Thr Asn Val Pro Gln Ser Met Leu Ser Phe Asp<br>180       185       190       195 | | 634 |
| tgc agt aac cct ctc ttt ggc cag acc atg aac cca tgg aag tcc tcc<br>Cys Ser Asn Pro Leu Phe Gly Gln Thr Met Asn Pro Trp Lys Ser Ser<br>200       205       210 | | 682 |
| aag agc cca gga ggt tcc tca ggg ggt gag ggg gct ctc att gga tct<br>Lys Ser Pro Gly Gly Ser Ser Gly Gly Glu Gly Ala Leu Ile Gly Ser<br>215       220       225 | | 730 |
| gga ggt tcc cct ctg ggt tta ggc act gac att ggc ggc agc atc cgg<br>Gly Gly Ser Pro Leu Gly Leu Gly Thr Asp Ile Gly Gly Ser Ile Arg<br>230       235       240 | | 778 |
| ttc cct tct gcc ttc tgc ggc atc tgt ggc ctc aag cct act ggc aac<br>Phe Pro Ser Ala Phe Cys Gly Ile Cys Gly Leu Lys Pro Thr Gly Asn<br>245       250       255 | | 826 |
| cgc ctc agc aag agt ggc ctg aag ggc tgt gtc tat gga cag acg gca<br>Arg Leu Ser Lys Ser Gly Leu Lys Gly Cys Val Tyr Gly Gln Thr Ala<br>260       265       270       275 | | 874 |
| gtg cag ctt tct ctt ggc ccc atg gcc cgg gat gtg gag agc ctg gcg<br>Val Gln Leu Ser Leu Gly Pro Met Ala Arg Asp Val Glu Ser Leu Ala<br>280       285       290 | | 922 |
| cta tgc ctg aaa gct cta ctg tgt gag cac ttg ttc acc ttg gac cct<br>Leu Cys Leu Lys Ala Leu Leu Cys Glu His Leu Phe Thr Leu Asp Pro<br>295       300       305 | | 970 |
| acc gtg cct ccc ttg ccc ttc aga gag gag gtc tat aga agt tct aga<br>Thr Val Pro Pro Leu Pro Phe Arg Glu Glu Val Tyr Arg Ser Ser Arg<br>310       315       320 | | 1018 |

| | |
|---|---|
| ccc ctg cgt gtg ggg tac tat gag act gac aac tat acc atg ccc agc<br>Pro Leu Arg Val Gly Tyr Tyr Glu Thr Asp Asn Tyr Thr Met Pro Ser<br>325                          330                       335 | 1066 |
| cca gct atg agg agg gct ctg ata gag acc aag cag aga ctt gag gct<br>Pro Ala Met Arg Arg Ala Leu Ile Glu Thr Lys Gln Arg Leu Glu Ala<br>340                       345                       350                     355 | 1114 |
| gct ggc cac acg ctg att ccc ttc tta ccc aac aac ata ccc tac gcc<br>Ala Gly His Thr Leu Ile Pro Phe Leu Pro Asn Asn Ile Pro Tyr Ala<br>                        360                       365                     370 | 1162 |
| ctg gag gtc ctg tct gcg ggc ggc ctg ttc agt gac ggt ggc cgc agt<br>Leu Glu Val Leu Ser Ala Gly Gly Leu Phe Ser Asp Gly Gly Arg Ser<br>             375                       380                     385 | 1210 |
| ttt ctc caa aac ttc aaa ggt gac ttt gtg gat ccc tgc ttg gga gac<br>Phe Leu Gln Asn Phe Lys Gly Asp Phe Val Asp Pro Cys Leu Gly Asp<br>390                       395                          400 | 1258 |
| ctg atc tta att ctg agg ctg ccc agc tgg ttt aaa aga ctg ctg agc<br>Leu Ile Leu Ile Leu Arg Leu Pro Ser Trp Phe Lys Arg Leu Leu Ser<br>405                       410                       415 | 1306 |
| ctc ctg ctg aag cct ctg ttt cct cgg ctg gca gcc ttt ctc aac agt<br>Leu Leu Leu Lys Pro Leu Phe Pro Arg Leu Ala Ala Phe Leu Asn Ser<br>420                       425                       430                     435 | 1354 |
| atg cgt cct cgg tca gct gaa aag ctg tgg aaa ctg cag cat gag att<br>Met Arg Pro Arg Ser Ala Glu Lys Leu Trp Lys Leu Gln His Glu Ile<br>                        440                       445                     450 | 1402 |
| gag atg tat cgc cag tct gtg att gcc cag tgg aaa gcg atg aac ttg<br>Glu Met Tyr Arg Gln Ser Val Ile Ala Gln Trp Lys Ala Met Asn Leu<br>             455                       460                     465 | 1450 |
| gat gtg ctg ctg acc ccc atg ttg ggc cct gct ctg gat ttg aac aca<br>Asp Val Leu Leu Thr Pro Met Leu Gly Pro Ala Leu Asp Leu Asn Thr<br>470                       475                       480 | 1498 |
| ccg ggc aga gcc aca ggg gct atc agc tac acc gtt ctc tac aac tgc<br>Pro Gly Arg Ala Thr Gly Ala Ile Ser Tyr Thr Val Leu Tyr Asn Cys<br>485                       490                       495 | 1546 |
| ctg gac ttc cct gcg ggg gtg gtg cct gtc acc act gtg acc gcc gag<br>Leu Asp Phe Pro Ala Gly Val Val Pro Val Thr Thr Val Thr Ala Glu<br>500                       505                       510                     515 | 1594 |
| gac gat gcc cag atg gaa ctc tac aaa ggc tac ttt ggg gat atc tgg<br>Asp Asp Ala Gln Met Glu Leu Tyr Lys Gly Tyr Phe Gly Asp Ile Trp<br>                        520                       525                     530 | 1642 |
| gac atc atc ctg aag aag gcc atg aaa aat agt gtc ggt ctg cct gtg<br>Asp Ile Ile Leu Lys Lys Ala Met Lys Asn Ser Val Gly Leu Pro Val<br>             535                       540                     545 | 1690 |
| gct gtg cag tgc gtg gct ctg ccc tgg cag gaa gag ctg tgt ctg agg<br>Ala Val Gln Cys Val Ala Leu Pro Trp Gln Glu Glu Leu Cys Leu Arg<br>550                       555                       560 | 1738 |
| ttc atg cgg gag gtg gaa cag ctg atg acc cct caa aag cag cca tcg<br>Phe Met Arg Glu Val Glu Gln Leu Met Thr Pro Gln Lys Gln Pro Ser<br>565                       570                       575 | 1786 |
| tgagggtcgt tcatccgcca gctctggagg acctaaggcc catgcgctgt gcactgtagc | 1846 |
| cccatgtatt caggagccac cacccacgag ggaacgccca gcacagggaa gaggtgtcta | 1906 |
| cctgccctcc cctggactcc tgcagccaca accagtctg gaccttcctc cccgttatgg | 1966 |
| tctactttcc atcctgattc cctgcttttt atggcagcca gcaggaatga cgtgggccaa | 2026 |
| ggatcaccaa cattcaaaaa caatgcgttt atctattttc tgggtatctc cattagggcc | 2086 |
| ctgggaacca gagtgctggg aaggctgtcc agaccctcca gagctggctg taaccacatc | 2146 |
| actctcctgc tccaaagcct ccctagttct gtcacccaca agatagacac agggacatgt | 2206 |
| ccttggcact tgactcctgt ccttcctttc ttattcagat tgaccccagc cttgatggac | 2266 |

```
cctgccctg cacttccttc ctcagtccac ctctctgccg acacgccctt tttatggctc    2326
ctctatttgt tgtggagaca aggtttctct cagtagccct ggctgtccag gacctcactc    2386
tgtagatgag gctggctttc aactcacaag gctgcctgcc tgggtgctgg gattaaaggc    2446
gtatgccacc acaaagaaaa aaaaaa                                         2472
```

<210> SEQ ID NO 6
<211> LENGTH: 579
<212> TYPE: PRT
<213> ORGANISM: Rattus norvegicus

<400> SEQUENCE: 6

```
Met Val Leu Ser Glu Val Trp Thr Thr Leu Ser Gly Val Ser Gly Val
1               5                   10                  15

Cys Leu Ala Cys Ser Leu Leu Ser Ala Ala Val Val Leu Arg Trp Thr
                20                  25                  30

Gly Arg Gln Lys Ala Arg Gly Ala Ala Thr Arg Ala Arg Gln Lys Gln
            35                  40                  45

Arg Ala Ser Leu Glu Thr Met Asp Lys Ala Val Gln Arg Phe Arg Leu
    50                  55                  60

Gln Asn Pro Asp Leu Asp Ser Glu Ala Leu Leu Thr Leu Pro Leu Leu
65                  70                  75                  80

Gln Leu Val Gln Lys Leu Gln Ser Gly Glu Leu Ser Pro Glu Ala Val
                85                  90                  95

Phe Phe Thr Tyr Leu Gly Lys Ala Trp Glu Val Asn Lys Gly Thr Asn
            100                 105                 110

Cys Val Thr Ser Tyr Leu Thr Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Ser Tyr Lys Gly His Asp Ser Thr Leu Gly Leu Ser Leu Asn Glu
145                 150                 155                 160

Gly Met Pro Ser Glu Ser Asp Cys Val Val Gln Val Leu Lys Leu
                165                 170                 175

Gln Gly Ala Val Pro Phe Val His Thr Asn Val Pro Gln Ser Met Leu
            180                 185                 190

Ser Phe Asp Cys Ser Asn Pro Leu Phe Gly Gln Thr Met Asn Pro Trp
        195                 200                 205

Lys Ser Ser Lys Ser Pro Gly Gly Ser Gly Gly Glu Gly Ala Leu
    210                 215                 220

Ile Gly Ser Gly Gly Ser Pro Leu Gly Leu Gly Thr Asp Ile Gly Gly
225                 230                 235                 240

Ser Ile Arg Phe Pro Ser Ala Phe Cys Gly Ile Cys Gly Leu Lys Pro
                245                 250                 255

Thr Gly Asn Arg Leu Ser Lys Ser Gly Leu Lys Gly Cys Val Tyr Gly
            260                 265                 270

Gln Thr Ala Val Gln Leu Ser Leu Gly Pro Met Ala Arg Asp Val Glu
        275                 280                 285

Ser Leu Ala Leu Cys Leu Lys Ala Leu Leu Cys Glu His Leu Phe Thr
    290                 295                 300

Leu Asp Pro Thr Val Pro Pro Leu Pro Phe Arg Glu Glu Val Tyr Arg
305                 310                 315                 320

Ser Ser Arg Pro Leu Arg Val Gly Tyr Tyr Glu Thr Asp Asn Tyr Thr
                325                 330                 335
```

```
Met Pro Ser Pro Ala Met Arg Arg Ala Leu Ile Glu Thr Lys Gln Arg
            340                 345                 350

Leu Glu Ala Ala Gly His Thr Leu Ile Pro Phe Leu Pro Asn Asn Ile
            355                 360                 365

Pro Tyr Ala Leu Glu Val Leu Ser Ala Gly Gly Leu Phe Ser Asp Gly
    370                 375                 380

Gly Arg Ser Phe Leu Gln Asn Phe Lys Gly Asp Phe Val Asp Pro Cys
385                 390                 395                 400

Leu Gly Asp Leu Ile Leu Ile Leu Arg Leu Pro Ser Trp Phe Lys Arg
                405                 410                 415

Leu Leu Ser Leu Leu Lys Pro Leu Phe Pro Arg Leu Ala Ala Phe
            420                 425                 430

Leu Asn Ser Met Arg Pro Arg Ser Ala Glu Lys Leu Trp Lys Leu Gln
            435                 440                 445

His Glu Ile Glu Met Tyr Arg Gln Ser Val Ile Ala Gln Trp Lys Ala
            450                 455                 460

Met Asn Leu Asp Val Leu Leu Thr Pro Met Leu Gly Pro Ala Leu Asp
465                 470                 475                 480

Leu Asn Thr Pro Gly Arg Ala Thr Gly Ala Ile Ser Tyr Thr Val Leu
                485                 490                 495

Tyr Asn Cys Leu Asp Phe Pro Ala Gly Val Val Pro Val Thr Thr Val
            500                 505                 510

Thr Ala Glu Asp Asp Ala Gln Met Glu Leu Tyr Lys Gly Tyr Phe Gly
            515                 520                 525

Asp Ile Trp Asp Ile Ile Leu Lys Lys Ala Met Lys Asn Ser Val Gly
530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Gln Leu Met Thr Pro Gln Lys
                565                 570                 575

Gln Pro Ser

<210> SEQ ID NO 7
<211> LENGTH: 2300
<212> TYPE: DNA
<213> ORGANISM: Sus scrofa
<220> FEATURE:
<221> NAME/KEY: CDS
<222> LOCATION: (20)..(1756)

<400> SEQUENCE: 7
cggtcctcgg tgggagatc atg gtg cag gaa gaa ctg tgg gct gcg ttc tcc        52
                    Met Val Gln Glu Glu Leu Trp Ala Ala Phe Ser
                     1               5                  10 ggc ccc tcc ggg gtt gcc ctg gcc tgc tgc ttg gtg gca gcg gcc ttg        100
Gly Pro Ser Gly Val Ala Leu Ala Cys Cys Leu Val Ala Ala Ala Leu
         15                  20                  25 gcc ctg cgt tgg tcc agt cgc cgg atg gcg cgg ggc gcg gcg gcc cgg        148
Ala Leu Arg Trp Ser Ser Arg Arg Met Ala Arg Gly Ala Ala Ala Arg
     30                  35                  40 gcg cga cag agg cag caa gcg gcc ctg gag acc atg gac aag gcg gcg        196
Ala Arg Gln Arg Gln Gln Ala Ala Leu Glu Thr Met Asp Lys Ala Ala
 45                  50                  55 cag cgc ttc cgg ctc cag aac ccc gat ctg gac tcg gag atg ctg ctg        244
Gln Arg Phe Arg Leu Gln Asn Pro Asp Leu Asp Ser Glu Met Leu Leu
 60                  65                  70                  75 gcc ctg cca ctg cct cag ctg gta cag aag gta cga agt ggg gag ctg        292
Ala Leu Pro Leu Pro Gln Leu Val Gln Lys Val Arg Ser Gly Glu Leu
             80                  85                  90
```

-continued

```
                    80                  85                  90
tct cca gag gct gtg ctc ttt tcc tac ctg caa aag gcc tgg gaa gtg      340
Ser Pro Glu Ala Val Leu Phe Ser Tyr Leu Gln Lys Ala Trp Glu Val
        95                 100                 105 aac aga ggg acc aac tgc gtg acc acc tac ctg gca gac tgt gag gct      388
Asn Arg Gly Thr Asn Cys Val Thr Thr Tyr Leu Ala Asp Cys Glu Ala
            110                 115                 120 cag ctg tgc cag gcg ccc ggg cag ggc ctg ctc tac ggt gtc ccc gtc      436
Gln Leu Cys Gln Ala Pro Gly Gln Gly Leu Leu Tyr Gly Val Pro Val
        125                 130                 135 agc ctc aag gag tgc ttc agc tgc aag ggc cat gac tcc acg ctg ggc      484
Ser Leu Lys Glu Cys Phe Ser Cys Lys Gly His Asp Ser Thr Leu Gly
140                 145                 150                 155 ttg agc cgg aac cag ggg aca cca gca gaa tgt gac tgc gtg gtg gtg      532
Leu Ser Arg Asn Gln Gly Thr Pro Ala Glu Cys Asp Cys Val Val Val
            160                 165                 170 cag gtg ctg aaa ctg cag ggt gct gtg cct ttc gtg cac acc aac gtc      580
Gln Val Leu Lys Leu Gln Gly Ala Val Pro Phe Val His Thr Asn Val
        175                 180                 185 ccc cag tcc atg ttc agc tat gac tgc agt aac ccc ctc ttt ggc cag      628
Pro Gln Ser Met Phe Ser Tyr Asp Cys Ser Asn Pro Leu Phe Gly Gln
        190                 195                 200 acc acg aac cca tgg atg tcg tcc aag agc ccg ggc ggc tcc tcg gga      676
Thr Thr Asn Pro Trp Met Ser Ser Lys Ser Pro Gly Gly Ser Ser Gly
205                 210                 215 ggt gag ggg gcc ctc att gct gct gga ggc tcc cca ctg ggc tta ggc      724
Gly Glu Gly Ala Leu Ile Ala Ala Gly Gly Ser Pro Leu Gly Leu Gly
220                 225                 230                 235 acc gac atc ggg ggc agc atc cgc ttt ccc tcc gcc ttc tgt ggc atc      772
Thr Asp Ile Gly Gly Ser Ile Arg Phe Pro Ser Ala Phe Cys Gly Ile
            240                 245                 250 tgc ggc atc aaa ccc acg ggg aac cgc atc agc aag agt ggt ctg aag      820
Cys Gly Ile Lys Pro Thr Gly Asn Arg Ile Ser Lys Ser Gly Leu Lys
        255                 260                 265 ggc tct gtc tat gga cag gta gca gtg cag ctc tca gtg ggc ccc atg      868
Gly Ser Val Tyr Gly Gln Val Ala Val Gln Leu Ser Val Gly Pro Met
        270                 275                 280 gcg cgg gac gtg gag agc ctg gcc ctg tgc ctg cgt gcg ctg ctg tgc      916
Ala Arg Asp Val Glu Ser Leu Ala Leu Cys Leu Arg Ala Leu Leu Cys
285                 290                 295 gaa gac atg ttc cgc ctg gac ccc acg gtg cct ccc ctg ccc ttc aac      964
Glu Asp Met Phe Arg Leu Asp Pro Thr Val Pro Pro Leu Pro Phe Asn
300                 305                 310                 315 gag gag gtc tac gca agc tct cgg ccc ctg cgt gtc ggg tat tat gag     1012
Glu Glu Val Tyr Ala Ser Ser Arg Pro Leu Arg Val Gly Tyr Tyr Glu
            320                 325                 330 acc gac aac tac acc atg ccc acg ccg gcc atg agg cgg gcc ctg ctg     1060
Thr Asp Asn Tyr Thr Met Pro Thr Pro Ala Met Arg Arg Ala Leu Leu
        335                 340                 345 gag acc aag cgg agc ctt gag gct gcg ggc cac acg ctg att ccc ttc     1108
Glu Thr Lys Arg Ser Leu Glu Ala Ala Gly His Thr Leu Ile Pro Phe
        350                 355                 360 ctg ccg gcc aac ata ccc cac gct ctg gag gcc ctg tca acg ggc ggg     1156
Leu Pro Ala Asn Ile Pro His Ala Leu Glu Ala Leu Ser Thr Gly Gly
365                 370                 375 ctc ttc agt gat ggt ggg aag agg ttg cta cag aac ttc gaa ggc gat     1204
Leu Phe Ser Asp Gly Gly Lys Arg Leu Leu Gln Asn Phe Glu Gly Asp
380                 385                 390                 395 tac gtg gac tcc tgc tta ggg gac ctg atc tca att ctg agg ctg ccc     1252
Tyr Val Asp Ser Cys Leu Gly Asp Leu Ile Ser Ile Leu Arg Leu Pro
```

-continued

```
                    400                 405                 410
aaa tgg ctt aaa gga ctg ctg gct ttc atg ctg agg cct ctc cca       1300
Lys Trp Leu Lys Gly Leu Leu Ala Phe Met Leu Arg Pro Leu Leu Pro
            415                 420                 425 agg ttg gca ggc ttt ctc agc agc ctg agg cct cgg tcg gct gga aag   1348
Arg Leu Ala Gly Phe Leu Ser Ser Leu Arg Pro Arg Ser Ala Gly Lys
        430                 435                 440 ctc tgg gaa ctg cag cac gag att gag atg tac cgt cac tcc gtg att   1396
Leu Trp Glu Leu Gln His Glu Ile Glu Met Tyr Arg His Ser Val Ile
    445                 450                 455 gcc cag tgg cga gcg ctg gac ctg gat gtg gtg cta acc ccc atg ctg   1444
Ala Gln Trp Arg Ala Leu Asp Leu Asp Val Val Leu Thr Pro Met Leu
460                 465                 470                 475 agc cct gcc cta gac ttg aat gcc cca ggc aag gcc aca ggg gcc gtc   1492
Ser Pro Ala Leu Asp Leu Asn Ala Pro Gly Lys Ala Thr Gly Ala Val
                480                 485                 490 agc tac acg ctc ctc tac aac tgc ctg gac ttc ccc gcg ggg gtg gtg   1540
Ser Tyr Thr Leu Leu Tyr Asn Cys Leu Asp Phe Pro Ala Gly Val Val
            495                 500                 505 cct gtc acc acg gtg act gcc gag gac gag gcc cag atg gag cat tac   1588
Pro Val Thr Thr Val Thr Ala Glu Asp Glu Ala Gln Met Glu His Tyr
        510                 515                 520 aag ggc tac ttt ggg gac att tgg gac aag gtg gtg cag aag gcc atg   1636
Lys Gly Tyr Phe Gly Asp Ile Trp Asp Lys Val Val Gln Lys Ala Met
    525                 530                 535 aag agg agc gtg ggg ctg cct gtg gcc gtg cag tgt gtg gct ctg ccc   1684
Lys Arg Ser Val Gly Leu Pro Val Ala Val Gln Cys Val Ala Leu Pro
540                 545                 550                 555 tgg cag gag gag ctg tgt ttg cgg ttc atg cgg gag gtg gag cga ctg   1732
Trp Gln Glu Glu Leu Cys Leu Arg Phe Met Arg Glu Val Glu Arg Leu
                560                 565                 570 atg gct cct ggg cgg cag ccc tcc tgaccgctgc ccgcccggcc ccccaggacc  1786
Met Ala Pro Gly Arg Gln Pro Ser
            575 tgagacccac tggatccgcg cccagcggag tcaggacaca actgccaccg tgcaagaaaa  1846 tgttcaacct caggcagagg cttcccggtc tctccccctc gccccctgcca gaagcccaga  1906 accactgagt ctggaccttg ctcttcccgt ggtccctgct ctgccctgac ccgccaatg   1966 tggcagctag tgggtatgac atggcaaagg ccccccaacc gtcaaaaacc ggttcctggt  2026 ctccatactt tctggcagtc gttgttaggg cagtgggggt tggagacctg accttctgga  2086 acccgactcc agccatgtcc gtctcgtgct gcagaagctt ctctggtcct cgtcactcac  2146 gggcagacac cggcttctcc gagtgggcct tgcagcccag gacttcaccc cgccgccccc  2206 agcctaagcc ctactttgcg aggcattgtc ttctctcctg ccctctgctg agggtgccct  2266 ttctgctcct ctaccattaa atcctttgag gccc                             2300

<210> SEQ ID NO 8
<211> LENGTH: 579
<212> TYPE: PRT
<213> ORGANISM: Sus scrofa

<400> SEQUENCE: 8

Met Val Gln Glu Glu Leu Trp Ala Ala Phe Ser Gly Pro Ser Gly Val
1               5                   10                  15

Ala Leu Ala Cys Cys Leu Val Ala Ala Leu Ala Leu Arg Trp Ser
            20                  25                  30

Ser Arg Arg Met Ala Arg Gly Ala Ala Arg Ala Arg Gln Arg Gln
        35                  40                  45
```

```
Gln Ala Ala Leu Glu Thr Met Asp Lys Ala Ala Gln Arg Phe Arg Leu
         50                  55                  60
Gln Asn Pro Asp Leu Asp Ser Glu Met Leu Leu Ala Leu Pro Leu Pro
 65                  70                  75                  80
Gln Leu Val Gln Lys Val Arg Ser Gly Glu Leu Ser Pro Glu Ala Val
                 85                  90                  95
Leu Phe Ser Tyr Leu Gln Lys Ala Trp Glu Val Asn Arg Gly Thr Asn
                100                 105                 110
Cys Val Thr Thr Tyr Leu Ala Asp Cys Glu Ala Gln Leu Cys Gln Ala
                115                 120                 125
Pro Gly Gln Gly Leu Leu Tyr Gly Val Pro Val Ser Leu Lys Glu Cys
130                 135                 140
Phe Ser Cys Lys Gly His Asp Ser Thr Leu Gly Leu Ser Arg Asn Gln
145                 150                 155                 160
Gly Thr Pro Ala Glu Cys Asp Cys Val Val Gln Val Leu Lys Leu
                165                 170                 175
Gln Gly Ala Val Pro Phe Val His Thr Asn Val Pro Gln Ser Met Phe
                180                 185                 190
Ser Tyr Asp Cys Ser Asn Pro Leu Phe Gly Gln Thr Thr Asn Pro Trp
                195                 200                 205
Met Ser Ser Lys Ser Pro Gly Gly Ser Gly Gly Glu Gly Ala Leu
210                 215                 220
Ile Ala Ala Gly Gly Ser Pro Leu Gly Leu Gly Thr Asp Ile Gly Gly
225                 230                 235                 240
Ser Ile Arg Phe Pro Ser Ala Phe Cys Gly Ile Cys Gly Ile Lys Pro
                245                 250                 255
Thr Gly Asn Arg Ile Ser Lys Ser Gly Leu Lys Gly Ser Val Tyr Gly
                260                 265                 270
Gln Val Ala Val Gln Leu Ser Val Gly Pro Met Ala Arg Asp Val Glu
                275                 280                 285
Ser Leu Ala Leu Cys Leu Arg Ala Leu Leu Cys Glu Asp Met Phe Arg
290                 295                 300
Leu Asp Pro Thr Val Pro Pro Leu Pro Phe Asn Glu Glu Val Tyr Ala
305                 310                 315                 320
Ser Ser Arg Pro Leu Arg Val Gly Tyr Tyr Glu Thr Asp Asn Tyr Thr
                325                 330                 335
Met Pro Thr Pro Ala Met Arg Arg Ala Leu Leu Glu Thr Lys Arg Ser
                340                 345                 350
Leu Glu Ala Ala Gly His Thr Leu Ile Pro Phe Leu Pro Ala Asn Ile
                355                 360                 365
Pro His Ala Leu Glu Ala Leu Ser Thr Gly Gly Leu Phe Ser Asp Gly
370                 375                 380
Gly Lys Arg Leu Leu Gln Asn Phe Glu Gly Asp Tyr Val Asp Ser Cys
385                 390                 395                 400
Leu Gly Asp Leu Ile Ser Ile Leu Arg Leu Pro Lys Trp Leu Lys Gly
                405                 410                 415
Leu Leu Ala Phe Met Leu Arg Pro Leu Leu Pro Arg Leu Ala Gly Phe
                420                 425                 430
Leu Ser Ser Leu Arg Pro Arg Ser Ala Gly Lys Leu Trp Glu Leu Gln
                435                 440                 445
His Glu Ile Glu Met Tyr Arg His Ser Val Ile Ala Gln Trp Arg Ala
450                 455                 460

Leu Asp Leu Asp Val Val Leu Thr Pro Met Leu Ser Pro Ala Leu Asp
```

-continued

```
              465                 470                 475                 480
Leu Asn Ala Pro Gly Lys Ala Thr Gly Ala Val Ser Tyr Thr Leu Leu
                485                 490                 495
Tyr Asn Cys Leu Asp Phe Pro Ala Gly Val Val Pro Val Thr Thr Val
                500                 505                 510
Thr Ala Glu Asp Glu Ala Gln Met Glu His Tyr Lys Gly Tyr Phe Gly
                515                 520                 525
Asp Ile Trp Asp Lys Val Val Gln Lys Ala Met Lys Arg Ser Val Gly
                530                 535                 540
Leu Pro Val Ala Val Gln Cys Val Ala Leu Pro Trp Gln Glu Glu Leu
545                 550                 555                 560
Cys Leu Arg Phe Met Arg Glu Val Glu Arg Leu Met Ala Pro Gly Arg
                565                 570                 575
Gln Pro Ser
```